US012788822B2

(12) United States Patent
Hilderbrand et al.

(10) Patent No.: US 12,788,822 B2
(45) **Date of Patent: *Nov. 10, 2026**

(54) MUSCLE TARGETING COMPLEXES AND FORMULATIONS FOR TREATING MYOTONIC DYSTROPHY

(71) Applicant: Dyne Therapeutics, Inc., Waltham, MA (US)

(72) Inventors: Scott Hilderbrand, Waltham, MA (US); Timothy Weeden, Waltham, MA (US); John Najim, Waltham, MA (US); Stefano Zanotti, Waltham, MA (US); Romesh R. Subramanian, Framingham, MA (US); Mohammed T. Qatanani, Waltham, MA (US); Cody A. Desjardins, Waltham, MA (US); Kim Tang, Belmont, MA (US); Brendan Quinn, Waltham, MA (US)

(73) Assignee: Dyne Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/306,199

(22) Filed: Aug. 21, 2025

(65) Prior Publication Data

US 2026/0069704 A1 Mar. 12, 2026

Related U.S. Application Data

(60) Division of application No. 18/436,078, filed on Feb. 8, 2024, now Pat. No. 12,440,574, which is a division of application No. 18/303,506, filed on Apr. 19, 2023, now Pat. No. 11,931,421, which is a continuation of application No. PCT/US2023/065753, filed on Apr. 14, 2023.

(60) Provisional application No. 63/331,727, filed on Apr. 15, 2022.

(51) Int. Cl.

| | |
|---|---|
| ***A61K 47/68*** | (2017.01) |
| ***A61K 47/54*** | (2017.01) |
| ***A61P 21/00*** | (2006.01) |
| ***C07K 16/28*** | (2006.01) |
| ***C12N 15/113*** | (2010.01) |

(52) U.S. Cl.

CPC ........ *A61K 47/6807* (2017.08); *A61K 47/545* (2017.08); *A61K 47/548* (2017.08); *A61K 47/6849* (2017.08); *A61P 21/00* (2018.01); *C07K 16/2881* (2013.01); *C12N 15/1137* (2013.01); *C12Y 207/11001* (2013.01); *C07K 2317/55* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/335* (2013.01); *C12N 2310/3513* (2013.01)

(58) Field of Classification Search

CPC .................................................. A61K 47/6807

See application file for complete search history.

(56) References Cited

U.S. PATENT DOCUMENTS

| | | | |
|---|---|---|---|
| 2,631,173 | A | 3/1953 | Hillyer et al. |
| 6,214,345 | B1 | 4/2001 | Firestone et al. |
| 7,015,315 | B1 | 3/2006 | Cook et al. |
| 7,064,142 | B2 | 6/2006 | Sato et al. |
| 7,223,837 | B2 | 5/2007 | De Groot et al. |
| 7,265,131 | B2 | 9/2007 | Johnson et al. |
| 7,541,330 | B2 | 6/2009 | Santi et al. |
| 7,575,886 | B2 | 8/2009 | Venkataraman et al. |
| 7,968,586 | B2 | 6/2011 | Gangwar et al. |
| 8,409,573 | B2 | 4/2013 | Boumsell et al. |
| 8,580,756 | B2 | 11/2013 | Hansen et al. |
| 8,846,639 | B2 | 9/2014 | Swayze et al. |
| 8,859,629 | B2 | 10/2014 | van Delft et al. |
| 8,889,851 | B2 | 11/2014 | Leproust et al. |
| 8,927,485 | B2 | 1/2015 | Krantz et al. |
| 8,952,147 | B2 | 2/2015 | Bouchard et al. |
| 9,045,754 | B2 | 6/2015 | Bhanot et al. |
| 9,222,940 | B2 | 12/2015 | van Delft et al. |
| 9,260,371 | B2 | 2/2016 | Bertozzi et al. |
| 9,428,534 | B2 | 8/2016 | Christensen et al. |
| 9,447,416 | B2 | 9/2016 | Sazani et al. |
| 9,504,758 | B2 | 11/2016 | van Delft et al. |
| 9,550,834 | B2 | 1/2017 | Shirai et al. |

(Continued)

FOREIGN PATENT DOCUMENTS

| | | | |
|---|---|---|---|
| CN | 103443125 | A | 12/2013 |
| CN | 103732259 | A | 4/2014 |

(Continued)

OTHER PUBLICATIONS

[No Author Listed] GenBank: NP_001121620. transferrin receptor protein 1 isoform 1 [*Homo sapiens*]. Dec. 28, 2017. Retrieved from the internet Aug. 2, 2023: https://www.ncbi.nlm.nih.gov/protein/NP_001121620.1, 4 pages.

(Continued)

*Primary Examiner* — Vanessa L. Ford

*Assistant Examiner* — Sandra Carter

(74) *Attorney, Agent, or Firm* — Wolf, Greenfield & Sacks, P.C.

(57) ABSTRACT

Aspects of the disclosure relate to complexes and other aspects relate to formulations (e.g., aqueous, lyophilized forms) comprising such complexes comprising an oligonucleotide (e.g., useful for targeting DMPK) covalently linked to an antibody (e.g., anti-TfR1 antibody).

24 Claims, 11 Drawing Sheets

Specification includes a Sequence Listing.

(56) References Cited

U.S. PATENT DOCUMENTS

| | | | |
|---|---|---|---|
| 9,550,988 | B2 | 1/2017 | Swayze |
| 9,610,362 | B2 | 4/2017 | Armstrong |
| 9,617,540 | B2 | 4/2017 | Bhanot et al. |
| 9,695,418 | B2 | 7/2017 | Seth et al. |
| 9,708,406 | B2 | 7/2017 | Zhang et al. |
| 9,708,614 | B2 | 7/2017 | Christensen et al. |
| 9,765,338 | B2 | 9/2017 | Bennett et al. |
| 10,131,682 | B2 | 11/2018 | Zhao |
| 10,238,753 | B2 | 3/2019 | Armstrong |
| 10,239,807 | B2 | 3/2019 | van Delft et al. |
| 10,266,502 | B2 | 4/2019 | van Delft et al. |
| 10,413,615 | B2 | 9/2019 | Hutchins |
| 10,434,111 | B2 | 10/2019 | Bertozzi et al. |
| 10,493,092 | B2 | 12/2019 | Swayze |
| 10,550,188 | B2 | 2/2020 | Geall et al. |
| 10,881,743 | B2 | 1/2021 | Geall et al. |
| 11,111,309 | B2 | 9/2021 | Subramanian et al. |
| 11,116,843 | B2 | 9/2021 | Seth et al. |
| 11,168,141 | B2 | 11/2021 | Subramanian et al. |
| 11,179,472 | B2 | 11/2021 | Levin et al. |
| 11,208,458 | B2 | 12/2021 | Baik et al. |
| 11,230,605 | B2 * | 1/2022 | Launay ............. C07K 16/2881 |
| 11,248,056 | B1 | 2/2022 | Subramanian et al. |
| 11,286,305 | B2 | 3/2022 | Subramanian et al. |
| 11,311,627 | B1 | 4/2022 | Levin et al. |
| 11,369,689 | B2 | 6/2022 | Subramanian et al. |
| 11,390,682 | B2 | 7/2022 | Subramanian et al. |
| 11,400,163 | B2 | 8/2022 | Levin et al. |
| 11,497,814 | B2 | 11/2022 | Geall et al. |
| 11,497,815 | B2 | 11/2022 | Subramanian et al. |
| 11,518,816 | B2 | 12/2022 | Subramanian et al. |
| 11,576,980 | B2 | 2/2023 | Geall et al. |
| 11,633,496 | B2 | 4/2023 | Subramanian et al. |
| 11,633,498 | B2 | 4/2023 | Subramanian et al. |
| 11,638,761 | B2 | 5/2023 | Subramanian et al. |
| 11,648,318 | B2 | 5/2023 | Subramanian et al. |
| 11,672,872 | B2 | 6/2023 | Subramanian et al. |
| 11,679,161 | B2 | 6/2023 | Subramanian et al. |
| 11,759,525 | B1 | 9/2023 | Subramanian et al. |
| 11,771,776 | B2 | 10/2023 | Subramanian et al. |
| 11,787,869 | B2 | 10/2023 | Subramanian et al. |
| 11,795,233 | B2 | 10/2023 | Subramanian et al. |
| 11,795,234 | B2 | 10/2023 | Subramanian et al. |
| 11,833,217 | B2 | 12/2023 | Subramanian et al. |
| 11,839,660 | B2 | 12/2023 | Subramanian et al. |
| 11,844,843 | B2 | 12/2023 | Subramanian et al. |
| 11,911,484 | B2 | 2/2024 | Subramanian et al. |
| 11,931,421 | B2 | 3/2024 | Hilderbrand et al. |
| 11,969,475 | B2 | 4/2024 | Subramanian et al. |
| 11,986,537 | B2 | 5/2024 | Subramanian et al. |
| 12,005,124 | B2 | 6/2024 | Subramanian et al. |
| 12,012,460 | B2 | 6/2024 | Subramanian et al. |
| 12,018,087 | B2 | 6/2024 | Subramanian et al. |
| 12,064,483 | B2 | 8/2024 | Levin et al. |
| 12,097,263 | B2 | 9/2024 | Subramanian et al. |
| 12,102,687 | B2 | 10/2024 | Subramanian et al. |
| 12,128,109 | B2 | 10/2024 | Weeden et al. |
| 12,144,867 | B2 | 11/2024 | Subramanian et al. |
| 12,144,868 | B2 | 11/2024 | Subramanian et al. |
| 12,173,078 | B2 | 12/2024 | Subramanian et al. |
| 12,173,079 | B2 | 12/2024 | Subramanian et al. |
| 12,239,716 | B2 | 3/2025 | Subramanian et al. |
| 12,239,717 | B2 | 3/2025 | Subramanian et al. |
| 12,263,225 | B2 | 4/2025 | Subramanian et al. |
| 12,280,122 | B2 | 4/2025 | Subramanian et al. |
| 12,319,743 | B2 | 6/2025 | Subramanian et al. |
| 12,325,753 | B2 | 6/2025 | Subramanian et al. |
| 12,329,824 | B1 | 6/2025 | Subramanian et al. |
| 12,329,825 | B1 | 6/2025 | Subramanian et al. |
| 12,357,703 | B2 | 7/2025 | Subramanian et al. |
| 12,370,264 | B1 | 7/2025 | Subramanian et al. |
| 12,397,062 | B2 | 8/2025 | Subramanian et al. |
| 12,403,203 | B2 | 9/2025 | Subramanian et al. |
| 12,428,487 | B2 | 9/2025 | Subramanian et al. |
| 12,440,574 | B2 | 10/2025 | Hilderbrand et al. |
| 12,440,575 | B2 | 10/2025 | Subramanian et al. |
| 12,460,011 | B2 | 11/2025 | Subramanian et al. |
| 12,496,352 | B2 | 12/2025 | Subramanian et al. |
| 12,624,120 | B2 | 5/2026 | Subramanian et al. |
| 12,629,426 | B2 | 5/2026 | Subramanian et al. |
| 2004/0063654 | A1 | 4/2004 | Davis et al. |
| 2004/0191243 | A1 | 9/2004 | Chen et al. |
| 2005/0084906 | A1 | 4/2005 | Goetsch et al. |
| 2005/0282252 | A1 | 12/2005 | Siegel |
| 2006/0110782 | A1 | 5/2006 | Bertozzi et al. |
| 2006/0252107 | A1 | 11/2006 | Kubota et al. |
| 2010/0016215 | A1 | 1/2010 | Moulton et al. |
| 2011/0009471 | A1 | 1/2011 | Kaneko et al. |
| 2011/0250199 | A1 | 10/2011 | Fitzgerald et al. |
| 2011/0256157 | A1 | 10/2011 | Howard et al. |
| 2012/0122801 | A1 | 5/2012 | Platenburg |
| 2012/0201809 | A1 | 8/2012 | Bhat et al. |
| 2012/0225013 | A1 | 9/2012 | Dennis et al. |
| 2013/0028891 | A1 | 1/2013 | Penichet et al. |
| 2013/0066063 | A1 | 3/2013 | Berry et al. |
| 2013/0096282 | A1 | 4/2013 | Neville |
| 2013/0137763 | A1 | 5/2013 | van Delft et al. |
| 2013/0177579 | A1 | 7/2013 | Lin et al. |
| 2013/0237585 | A1 | 9/2013 | Bennett et al. |
| 2014/0105916 | A1 | 4/2014 | Brasel et al. |
| 2014/0193436 | A1 | 7/2014 | Prudent |
| 2014/0323552 | A1 | 10/2014 | Burghes et al. |
| 2015/0064181 | A1 | 3/2015 | Armstrong |
| 2015/0225722 | A1 | 8/2015 | Ozsolak |
| 2015/0258210 | A1 | 9/2015 | van Delft et al. |
| 2016/0015828 | A1 | 1/2016 | Torgov et al. |
| 2016/0090598 | A1 | 3/2016 | Oestergaard et al. |
| 2016/0107999 | A1 | 4/2016 | Debets et al. |
| 2016/0175460 | A1 | 6/2016 | Arathoon et al. |
| 2016/0235861 | A1 | 8/2016 | van Delft et al. |
| 2016/0237157 | A1 | 8/2016 | Dennis et al. |
| 2016/0250347 | A1 | 9/2016 | van Delft et al. |
| 2016/0272973 | A1 | 9/2016 | Shehadeh |
| 2016/0324979 | A1 | 11/2016 | De Roo et al. |
| 2016/0355599 | A1 | 12/2016 | Sagert et al. |
| 2017/0002012 | A1 | 1/2017 | van Delft et al. |
| 2017/0008858 | A1 | 1/2017 | van Delft et al. |
| 2017/0072068 | A1 | 3/2017 | Verkade et al. |
| 2017/0130256 | A1 | 5/2017 | van Berkel et al. |
| 2017/0226554 | A1 | 8/2017 | Wasiel et al. |
| 2017/0247450 | A1 | 8/2017 | Joutel et al. |
| 2017/0281795 | A1 | 10/2017 | Geall et al. |
| 2017/0342169 | A1 | 11/2017 | Akamatsu et al. |
| 2017/0348416 | A1 | 12/2017 | Hasler et al. |
| 2018/0002433 | A1 | 1/2018 | Zhang et al. |
| 2018/0021449 | A1 | 1/2018 | Armstrong |
| 2018/0134797 | A1 | 5/2018 | Zhang et al. |
| 2018/0216111 | A1 | 8/2018 | Wilton et al. |
| 2018/0369400 | A1 | 12/2018 | Levin et al. |
| 2019/0000986 | A1 | 1/2019 | Levin et al. |
| 2019/0038762 | A1 | 2/2019 | Veiby et al. |
| 2019/0038765 | A1 | 2/2019 | van Berkel et al. |
| 2019/0060488 | A1 | 2/2019 | Tadin-Strapps et al. |
| 2019/0092833 | A1 | 3/2019 | Lin et al. |
| 2019/0092870 | A1 | 3/2019 | Launay et al. |
| 2019/0119383 | A1 | 4/2019 | Bruenker et al. |
| 2019/0153083 | A1 | 5/2019 | Juste et al. |
| 2019/0177723 | A1 | 6/2019 | Dickson et al. |
| 2019/0211362 | A1 | 7/2019 | Lundberg et al. |
| 2019/0240346 | A1 | 8/2019 | Sugo et al. |
| 2019/0298847 | A1 | 10/2019 | Geall et al. |
| 2019/0336615 | A1 | 11/2019 | Thompson et al. |
| 2019/0338043 | A1 | 11/2019 | Sonoda et al. |
| 2020/0046742 | A1 | 2/2020 | Bertozzi et al. |
| 2020/0048174 | A1 | 2/2020 | van Delft et al. |
| 2020/0123267 | A1 | 4/2020 | Zhang et al. |
| 2020/0282074 | A1 | 9/2020 | Levin et al. |
| 2020/0325237 | A1 | 10/2020 | Darimont et al. |
| 2021/0038739 | A1 | 2/2021 | Takahashi et al. |
| 2021/0095283 | A1 | 4/2021 | Geall et al. |
| 2021/0130486 | A1 | 5/2021 | Darimont et al. |
| 2021/0187116 | A1 | 6/2021 | Geall et al. |
| 2021/0206868 | A1 | 7/2021 | Subramanian et al. |
| 2021/0220479 | A1 | 7/2021 | Subramanian et al. |

(56) References Cited

U.S. PATENT DOCUMENTS

2021/0228730 A1 7/2021 Subramanian et al.
2021/0230290 A1 7/2021 Subramanian et al.
2021/0261680 A1 8/2021 Subramanian et al.
2021/0308272 A1 10/2021 Subramanian et al.
2021/0308273 A1 10/2021 Subramanian et al.
2021/0308274 A1 10/2021 Subramanian et al.
2021/0317226 A1 10/2021 Subramanian et al.
2021/0322562 A1 10/2021 Subramanian et al.
2021/0322563 A1 10/2021 Subramanian et al.
2021/0324101 A1 10/2021 Subramanian et al.
2021/0380709 A1 12/2021 Subramanian et al.
2022/0025066 A1 1/2022 Subramanian et al.
2022/0143206 A1 5/2022 Subramanian et al.
2022/0169743 A1 6/2022 Subramanian et al.
2022/0193250 A1 6/2022 Subramanian et al.
2022/0194988 A1 6/2022 Gowans et al.
2022/0288220 A1 9/2022 Subramanian et al.
2022/0306685 A1 9/2022 Weeden et al.
2022/0324992 A1 10/2022 Subramanian et al.
2022/0378934 A1 12/2022 Subramanian et al.
2023/0001002 A1 1/2023 Subramanian et al.
2023/0044278 A1 2/2023 Subramanian et al.
2023/0045002 A1 2/2023 Subramanian et al.
2023/0045314 A1 2/2023 Subramanian et al.
2023/0047754 A1 2/2023 Geall et al.
2023/0049450 A1 2/2023 Subramanian et al.
2023/0050911 A1 2/2023 Subramanian et al.
2023/0051954 A1 2/2023 Subramanian et al.
2023/0088865 A1 3/2023 Subramanian et al.
2023/0103793 A1 4/2023 Subramanian et al.
2023/0111147 A1 4/2023 Subramanian et al.
2023/0111212 A1 4/2023 Subramanian et al.
2023/0113823 A1 4/2023 Subramanian et al.
2023/0117883 A1 4/2023 Subramanian et al.
2023/0118799 A1 4/2023 Subramanian et al.
2023/0144436 A1 5/2023 Subramanian et al.
2023/0203180 A1 6/2023 Subramanian et al.
2023/0203181 A1 6/2023 Subramanian et al.
2023/0226212 A1 7/2023 Subramanian et al.
2023/0227569 A1 7/2023 Subramanian et al.
2023/0256112 A1 8/2023 Subramanian et al.
2023/0256113 A1 8/2023 Subramanian et al.
2023/0270873 A1 8/2023 Subramanian et al.
2023/0272065 A1 8/2023 Subramanian et al.
2023/0285582 A1 9/2023 Subramanian et al.
2023/0285586 A1 9/2023 Subramanian et al.
2023/0287108 A1 9/2023 Subramanian et al.
2023/0321264 A1 10/2023 Subramanian et al.
2023/0330247 A1 10/2023 Hildebrand et al.
2023/0330562 A1 10/2023 Weeden et al.
2023/0346966 A1 11/2023 Subramanian et al.
2023/0346967 A1 11/2023 Subramanian et al.
2024/0016950 A1 1/2024 Weeden et al.
2024/0016952 A1 1/2024 Subramanian et al.
2024/0066139 A1 2/2024 Subramanian et al.
2024/0066140 A1 2/2024 Subramanian et al.
2024/0067743 A1 2/2024 Subramanian et al.
2024/0067744 A1 2/2024 Subramanian et al.
2024/0100177 A1 3/2024 Hildebrand et al.
2024/0110184 A1 4/2024 Brown et al.
2024/0117356 A1 4/2024 Subramanian et al.
2024/0148891 A1 5/2024 Subramanian et al.
2024/0197901 A1 6/2024 Subramanian et al.
2024/0197905 A1 6/2024 Subramanian et al.
2024/0207430 A1 6/2024 Subramanian et al.
2024/0209119 A1 6/2024 Subramanian et al.
2024/0216522 A1 7/2024 Subramanian et al.
2024/0238435 A1 7/2024 Subramanian et al.
2024/0252666 A1 8/2024 Hilderbrand et al.
2024/0287201 A1 8/2024 Subramanian et al.
2024/0293568 A1 9/2024 Subramanian et al.
2024/0294921 A1 9/2024 Subramanian et al.
2024/0301416 A1 9/2024 Tone et al.
2024/0309107 A1 9/2024 Subramanian et al.
2024/0318176 A1 9/2024 Desjardins et al.
2024/0318177 A1 9/2024 Desjardins et al.
2024/0325558 A1* 10/2024 Zanotti .............. C07K 16/2881
2024/0368296 A1 11/2024 Desjardins et al.
2024/0382513 A1 11/2024 Subramanian et al.
2024/0382605 A1 11/2024 Seth et al.
2024/0382609 A1 11/2024 Desjardins et al.
2024/0398967 A1 12/2024 Subramanian et al.
2024/0398968 A1 12/2024 Subramanian et al.
2024/0408227 A1 12/2024 Subramanian et al.
2025/0018050 A1 1/2025 Desjardins et al.
2025/0025570 A1 1/2025 Hsia et al.
2025/0032634 A1 1/2025 Subramanian et al.
2025/0057972 A1 2/2025 Subramanian et al.
2025/0066495 A1 2/2025 Subramanian et al.
2025/0066496 A1 2/2025 Subramanian et al.
2025/0099603 A9 3/2025 Subramanian et al.
2025/0152727 A1 5/2025 Subramanian et al.
2025/0177549 A1 6/2025 Subramanian et al.
2025/0242042 A1 7/2025 Subramanian et al.
2025/0249116 A1 8/2025 Weeden et al.
2025/0249117 A1 8/2025 Zanotti et al.
2025/0249119 A1 8/2025 Subramanian et al.
2025/0270340 A1 8/2025 Subramanian et al.
2025/0276073 A1 9/2025 Skynner et al.
2025/0276083 A1 9/2025 Subramanian et al.
2025/0297024 A1 9/2025 Subramanian et al.
2025/0304710 A1 10/2025 Subramanian et al.
2025/0339553 A1 11/2025 Hilderbrand et al.
2025/0367310 A1 12/2025 Hilderbrand et al.
2025/0382375 A1 12/2025 Subramanian et al.
2026/0053941 A1 2/2026 Weeden et al.
2026/0069704 A1 3/2026 Hilderbrand et al.

FOREIGN PATENT DOCUMENTS

CN 105142672 A 12/2015
CN 106999605 A 8/2017
CN 107001473 A 8/2017
CN 107849555 A 3/2018
CN 110381980 A 10/2019
CN 105358578 B 8/2021
EP 2149605 A2 2/2010
EP 2241331 A2 10/2010
EP 2410053 A1 1/2012
EP 2410054 A1 1/2012
EP 3031920 A1 6/2016
EP 3067421 A1 9/2016
EP 2623609 B1 1/2017
EP 3185889 A1 7/2017
EP 3202905 A1 8/2017
EP 3315606 A1 5/2018
EP 2922818 B1 9/2018
EP 3436588 A1 2/2019
EP 3473270 A1 4/2019
EP 3489360 A2 5/2019
EP 3560958 A1 10/2019
EP 3565577 A1 11/2019
EP 3684376 A1 7/2020
EP 3691657 A1 8/2020
EP 3720448 A1 10/2020
EP 3735252 A2 11/2020
EP 3898693 A1 10/2021
EP 3980436 A1 4/2022
EP 3980437 A1 4/2022
EP 4126066 A1 2/2023
EP 4146229 A1 3/2023
EP 4314298 A1 2/2024
IL 54795 A 10/1980
JP 2002-253259 A 9/2002
JP 2010-532168 A 10/2010
JP 2013-538560 A 1/2012
JP 2015-532264 A 11/2015
JP 2015-534996 A 12/2015
JP 2016-528258 A 9/2016
JP 2017-535526 A 11/2017
JP 2018-503357 A 2/2018
JP 2018-134095 A 8/2018
JP 2019-516664 A 6/2019
JP 2019-137675 A 8/2019

(56) References Cited

FOREIGN PATENT DOCUMENTS

| | | | | |
|---|---|---|---|---|
| JP | 2020-537497 | A | 12/2020 | |
| JP | 2018-502047 | A | 10/2021 | |
| KR | 10-2013-0106811 | A | 9/2013 | |
| KR | 10-2019-0099470 | A | 8/2019 | |
| WO | WO 1989/007970 | A1 | 9/1989 | |
| WO | WO 1991/004753 | A1 | 4/1991 | |
| WO | WO 2003/059951 | A2 | 7/2003 | |
| WO | WO 2003/074654 | A2 | 9/2003 | |
| WO | WO 2004/069991 | A2 | 8/2004 | |
| WO | WO 2005/023825 | A2 | 3/2005 | |
| WO | WO 2006/022688 | A1 | 3/2006 | |
| WO | WO 2006/050262 | A2 | 5/2006 | |
| WO | WO 2007/089612 | A2 | 8/2007 | |
| WO | WO 2008/018795 | A1 | 2/2008 | |
| WO | WO 2008/049085 | A1 | 4/2008 | |
| WO | WO 2009/005793 | A2 | 1/2009 | |
| WO | WO 2009/100194 | A2 | 8/2009 | |
| WO | WO 2009/144481 | A2 | 12/2009 | |
| WO | WO 2010/048586 | A1 | 4/2010 | |
| WO | WO 2010/050802 | A1 | 5/2010 | |
| WO | WO 2010/123369 | A1 | 10/2010 | |
| WO | WO 2011/136645 | A1 | 11/2011 | |
| WO | WO 2012/012443 | A2 | 1/2012 | |
| WO | WO 2012/012467 | A2 | 1/2012 | |
| WO | WO 2012/075037 | A1 | 6/2012 | |
| WO | WO 2012/144906 | A1 | 10/2012 | |
| WO | WO 2013/085550 | A2 | 6/2013 | |
| WO | WO 2013/126746 | A2 | 8/2013 | |
| WO | WO 2013/138662 | A1 | 9/2013 | |
| WO | WO 2013/162363 | A1 | 10/2013 | |
| WO | 2013/177062 | A2 | 11/2013 | |
| WO | WO 2014/052276 | A1 | 4/2014 | |
| WO | WO 2014/065661 | A1 | 5/2014 | |
| WO | 2014/130723 | A1 | 8/2014 | |
| WO | WO 2014/189973 | A2 | 11/2014 | |
| WO | WO 2015/021457 | A2 | 2/2015 | |
| WO | WO 2015/023937 | A1 | 2/2015 | |
| WO | WO 2015/042581 | A1 | 3/2015 | |
| WO | WO 2015/179741 | A1 | 11/2015 | |
| WO | WO 2016/046574 | A1 | 3/2016 | |
| WO | WO 2016/081643 | A1 | 5/2016 | |
| WO | WO 2016/081670 | A2 | 5/2016 | |
| WO | WO 2016/187425 | A1 | 11/2016 | |
| WO | 2016/207240 | A1 | 12/2016 | |
| WO | WO 2016/208695 | A1 | 12/2016 | |
| WO | WO 2017/062862 | A2 | 4/2017 | |
| WO | WO 2017/100467 | A2 | 6/2017 | |
| WO | WO 2017/106643 | A1 | 6/2017 | |
| WO | WO 2017/143156 | A1 | 8/2017 | |
| WO | WO 2017/173408 | A1 | 10/2017 | |
| WO | WO 2017/192679 | A1 | 11/2017 | |
| WO | WO 2017/205191 | A1 | 11/2017 | |
| WO | WO 2017/221883 | A1 | 12/2017 | |
| WO | WO 2018/124121 | A1 | 7/2018 | |
| WO | WO 2018/129384 | A1 | 7/2018 | |
| WO | WO 2018/226861 | A1 | 12/2018 | |
| WO | WO 2019/023257 | A1 | 1/2019 | |
| WO | WO 2019/060775 | A1 | 3/2019 | |
| WO | WO 2019/071028 | A1 | 4/2019 | |
| WO | WO 2019/075417 | A1 | 4/2019 | |
| WO | WO 2019/090242 | A1 | 5/2019 | |
| WO | WO 2019/113393 | A1 | 6/2019 | |
| WO | WO 2019/136180 | A2 | 7/2019 | |
| WO | WO 2019/151539 | A1 | 8/2019 | |
| WO | WO 2019/157224 | A1 | 8/2019 | |
| WO | WO 2019/215175 | A1 | 11/2019 | |
| WO | WO 2019/229658 | A1 | 12/2019 | |
| WO | WO 2020/028831 | A1 | 2/2020 | |
| WO | WO 2020/028832 | A1 | 2/2020 | |
| WO | WO 2020/028836 | A1 | 2/2020 | |
| WO | WO 2020/028840 | A1 | 2/2020 | |
| WO | WO 2020/028841 | A1 | 2/2020 | |
| WO | WO 2020/028842 | A1 | 2/2020 | |
| WO | WO 2020/028844 | A1 | 2/2020 | |
| WO | WO 2020/028857 | A1 | 2/2020 | |
| WO | WO 2020/028861 | A1 | 2/2020 | |
| WO | WO 2020/028864 | A1 | 2/2020 | |
| WO | WO 2020/084488 | A1 | 4/2020 | |
| WO | WO 2020/094670 | A1 | 5/2020 | |
| WO | WO 2020/132584 | A1 | 6/2020 | |
| WO | WO 2020/163817 | A1 | 8/2020 | |
| WO | WO 2020/209285 | A1 | 10/2020 | |
| WO | WO 2020/247738 | A1 | 12/2020 | |
| WO | WO 2020/247782 | A1 | 12/2020 | |
| WO | WO 2020/247818 | A1 | 12/2020 | |
| WO | WO 2021/076856 | A1 | 4/2021 | |
| WO | WO 2021/108640 | A1 | 6/2021 | |
| WO | WO 2021/142217 | A1 | 7/2021 | |
| WO | WO 2021/142227 | A1 | 7/2021 | |
| WO | WO 2021/142234 | A1 | 7/2021 | |
| WO | WO 2021/142260 | A1 | 7/2021 | |
| WO | WO 2021/142269 | A1 | 7/2021 | |
| WO | WO 2021/142275 | A1 | 7/2021 | |
| WO | WO 2021/142307 | A1 | 7/2021 | |
| WO | WO 2021/142313 | A1 | 7/2021 | |
| WO | WO 2021/142331 | A1 | 7/2021 | |
| WO | WO 2021/150382 | A1 | 7/2021 | |
| WO | WO 2021/154476 | A1 | 8/2021 | |
| WO | WO 2021/154477 | A1 | 8/2021 | |
| WO | WO 2022/020105 | A1 | 1/2022 | |
| WO | WO 2022/020106 | A1 | 1/2022 | |
| WO | WO 2022/020107 | A1 | 1/2022 | |
| WO | WO 2022/020108 | A1 | 1/2022 | |
| WO | WO 2022/020109 | A1 | 1/2022 | |
| WO | WO 2022/026152 | A1 | 2/2022 | |
| WO | WO 2022/051665 | A1 | 3/2022 | |
| WO | WO 2022/056266 | A2 | 3/2022 | |
| WO | WO 2022/120132 | A1 | 6/2022 | |
| WO | WO 2022/147207 | A1 | 7/2022 | |
| WO | WO-2022147209 | A1 * | 7/2022 | ......... C12N 15/1137 |
| WO | WO 2022/212886 | A1 | 10/2022 | |
| WO | WO 2022/213118 | A1 | 10/2022 | |
| WO | WO 2022/240758 | A1 | 11/2022 | |
| WO | WO 2022/270585 | A1 | 12/2022 | |
| WO | WO 2022/271543 | A2 | 12/2022 | |
| WO | WO 2022/271549 | A1 | 12/2022 | |
| WO | WO 2023/283531 | A2 | 1/2023 | |
| WO | WO 2023/283613 | A1 | 1/2023 | |
| WO | WO 2023/283614 | A2 | 1/2023 | |
| WO | WO 2023/283615 | A1 | 1/2023 | |
| WO | WO 2023/283619 | A2 | 1/2023 | |
| WO | WO 2023/283620 | A1 | 1/2023 | |
| WO | WO 2023/283623 | A1 | 1/2023 | |
| WO | WO 2023/283624 | A2 | 1/2023 | |
| WO | WO 2023/283629 | A1 | 1/2023 | |
| WO | WO 2023/022229 | A1 | 2/2023 | |
| WO | WO 2023/026994 | A1 | 3/2023 | |
| WO | WO 2023/044398 | A1 | 3/2023 | |
| WO | WO 2023/077120 | A1 | 5/2023 | |
| WO | WO 2023/086864 | A1 | 5/2023 | |
| WO | WO 2023/121444 | A1 | 6/2023 | |
| WO | WO 2023/121445 | A1 | 6/2023 | |
| WO | WO 2023/121446 | A1 | 6/2023 | |
| WO | WO 2023/168427 | A1 | 9/2023 | |
| WO | WO 2023/171820 | A1 | 9/2023 | |
| WO | WO 2023/196400 | A2 | 10/2023 | |
| WO | WO 2023/201318 | A1 | 10/2023 | |
| WO | WO 2023/201324 | A1 | 10/2023 | |
| WO | WO 2023/201332 | A1 | 10/2023 | |
| WO | WO 2024/011135 | A1 | 1/2024 | |
| WO | WO 2024/011150 | A1 | 1/2024 | |
| WO | WO 2024/097644 | A1 | 5/2024 | |
| WO | WO 2024/112809 | A2 | 5/2024 | |
| WO | WO 2024/149282 | A1 | 7/2024 | |
| WO | WO 2024/182358 | A1 | 9/2024 | |
| WO | WO 2025/076486 | A1 | 4/2025 | |
| WO | WO 2025/137547 | A1 | 6/2025 | |
| WO | WO 2025/147541 | A1 | 7/2025 | |
| WO | WO 2025/255283 | A1 | 12/2025 | |

(56) References Cited

FOREIGN PATENT DOCUMENTS

WO WO 2025/259503 A1 12/2025
WO WO 2025/265092 A1 12/2025

OTHER PUBLICATIONS

[No Author Listed] UniProtKB/Swiss-Prot P02786. Transferrin receptor protein 1. Jul. 18, 2018. Retrieved from the Internet Oct. 23, 2019: https://www.uniprot.org/uniprot/P02786.txt?version=225, 20 pages.
[No Author Listed] Wikipedia, Mannose 6-phosphate receptor, Mar. 23, 2018. Retrieved from the internet Nov. 6, 2019: https://en.wikipedia.org/w/index.php?title=Mannose_6-phosphate_receptor&oldid=832003836, 8 pages.
[No Author Listed] Wikipedia, Myotonic dystrophy, Sep. 8, 2017. Retrieved from the internet Nov. 5, 2019: https://en.wikipedia.org/w/index.php?title=Myotonic_dystrophy&oldid=799605783, 9 pages.
[No Author Listed], Baliforsen—Ionis Pharmaceuticals Drug Profile. Springer Nature Switzerland AG. Nov. 15, 2016. 9 pages.
[No Author Listed], Building the world's leading muscle disease company. Dyne Company Overview. Jun. 2021. 42 pages.
[No Author Listed], *Homo sapiens* transferrin receptor (TFRC), transcript variant X1, mRNA. NCBI Reference Sequence XM_011513112.1. Mar. 12, 2015. 2 pages.
[No Author Listed], IRDye® Peptide Labeling Application Guide. <https://licor.com/documents/nmekjs7iez6sw5p8fv7b7005chbrcog7> Published Apr. 2013. Retrieved Oct. 27, 2021. 8 pages.
[No Author Listed], Stn Database Printout for RN: 2725863-42-1 and 2725863-34-1. CN: Immunoglobulin IgG1 Fab fragment, anti-(human and Macaca fascicularis transferrin receptors type 1) (human-Mus musculus monoclonal F5298 γ-1 chain), disulfide with human-Mus musculus monoclonal F5298.kappa.-chain. Entered into STN Database Nov. 5, 2021. Last accessed Nov. 17, 2021. 2 pages.
[No Author Listed], Transferrin Receptor/CD71 Extracellular Domain (human, recombinant) 2021, retrieved from https://www.caymanchem.com/product/32031/transferrin-receptor-extracellular-domain-(human%2C-recombinant)#:-:text=Cayman's Transferrin Receptor%2FCD71 Extracellular,molecular weight of 103.6 kDa (Year: 2021). 3 pages.
[No_Author_Listed], Dyne Therapeutics Announces Positive Initial Clinical Data from ACHIEVE Trial in DM1 Patients and DELIVER Trial in DMD Patients Demonstrating Promise of the FORCE™ Platform in Developing Therapeutics for Rare Muscle Diseases. Press Release Jan. 3, 2024. Retrieved on Dec. 23, 2024, from: <<https://investors.dyne-tx.com/news-releases/news-release-details/dyne-therapeutics-announces-positive-initial-clinical-data>>. 4 pages.
Agard et al., A Comparative Study of Bioorthogonal Reactions with Azides. ACS Chem. Biol. 2006;1(10):644-8. Epub Oct. 20, 2006.
Agard et al., A Strain-Promoted [3+2] Azide-Alkyne Cycloaddition for Covalent Modification of Biomolecules in Living Systems. J. Am. Chem. Soc. Nov. 2004;126(46):15046-7.
Altshuler et al., Generation of recombinant antibodies and means for increasing their affinity. Biochemistry (Mosc). Dec. 2010:75(13):1584-605.
Anciaux et al., Transition-metal-catalyzed reactions of diazo compounds. 1. Cyclopropanation of double bonds. The Journal of Organic Chemistry. Feb. 1980;45(4):695-702.
Antony-Mayer et al., Bicyclo[6.1.0]nonynes. Chemische Berichte. Nov. 1988;121(11):2013-8.
Aoki et al., Challenges for antisense oligonucleotide-based therapeutics, in particular for exon 51-skipping in Duchenne muscular dystrophy, 2011 Fourth International Conference on Modeling, Simulation and Applied Optimization, 2011, 1-6, doi: 10.1109/ICMSAO.2011.5775520.
Arzumanov et al., A structure-activity study of the inhibition of HIV-1 Tat-dependent trans-activation by mixmer 2'-O-methyl oligoribonucleotides containing locked nucleic acid (LNA), alpha-L-LNA, or 2'-thio-LNA residues. Oligonucleotides. 2003;13(6):435-53. doi: 10.1089/154545703322860762.
Arzumanov et al., Inhibition of HIV-1 Tat-dependent trans activation by steric block chimeric 2'-O-methyl/LNA oligoribonucleotides. Biochemistry. Dec. 4, 2001;40(48):14645-54. doi: 10.1021/bi011279e.
Ast et al., Estergruppenhaltige Polyalkenylene durch Olefin-Metathese. Die Makromolekulare Chemie. May 1976;177(5):1349-55.
Barfield et al., A Novel HER2-targeted Antibody-drug Conjugate Offers the Possibility of Clinical Dosing at Trastuzumab-equivalent Exposure Levels. Mol Cancer Ther. Sep. 2020;19(9):1866-1874. doi: 10.1158/1535-7163.MCT-20-0190. Epub Jul. 10, 2020.
Barrientos et al., Metabolic Catastrophe in Mice Lacking Transferrin Receptor in Muscle. EBioMedicine. Oct. 4, 2015;2(11):1705-17. doi: 10.1016/j.ebiom.2015.09.041.eCollection Nov. 2015.
Baskin et al., Copper-free click chemistry for dynamic in vivo imaging. PNAS. Oct. 2007;104(43):16793-7.
Behlke, Chemical modification of siRNAs for in vivo use. Oligonucleotides. Dec. 2008;18(4):305-19.
Bennett et al., RNA targeting therapeutics: molecular mechanisms of antisense oligonucleotides as a therapeutic platform. Annu Rev Pharmacol Toxicol. 2010;50:259-93. Epub Oct. 19, 2009.
Beskrovnaya, FORCETM platform delivers exon skipping PMO, leads to durable increases in dystrophin protein in mdx mice and is well tolerated NHPs. Presented at Muscle Study Group Annual Scientific Meeting. Oct. 1, 2021. 29 pages.
Bien-Ly et al., Transferrin receptor (TfR) trafficking determines brain uptake of TfR antibody affinity variants. J Exp Med. Feb. 10, 2014;211(2):233-44. Epub Jan. 27, 2014.
Black, 9.13.4.1.1.3.2 Variation 2: C-Alkylation (and Arylation) by Carbenes and Free Radicals. Science of Synthesis. 2001;9:514.
Brown et al., Tolerance to single, but not multiple, amino acid replacements in antibody VH CDR 2: a means of minimizing B cell wastage from somatic hypermutation? J Immunol. May 1, 1996;156(9):3285-91.
Buntz et al., Quantitative fluorescence imaging determines the absolute number of locked nucleic acid oligonucleotides needed for suppression of target gene expression. Nucleic Acids Res. Jan. 25, 2019;47(2):953-969. doi: 10.1093/nar/gky1158.
Bushel et al., Blood gene expression signatures predict exposure levels. Proc Natl Acad Sci USA. Nov. 13, 2007;104(46):18211-6. doi: 10.1073/pnas.0706987104. Epub Nov. 2, 2007.
Candelaria et al., Antibodies Targeting the Transferrin Receptor 1 (TfR1) as Direct Anti-cancer Agents. Front Immunol. Mar. 17, 2021;12:607692.
Carrell et al., Dmpk gene deletion or antisense knockdown does not compromise cardiac or skeletal muscle function in mice. Hum Mol Genet. Oct. 1, 2016;25(19):4328-4338. doi: 10.1093/hmg/ddw266. Epub Aug. 13, 2016.
Casi et al., Antibody-drug conjugates: basic concepts, examples and future perspectives. J Control Release. Jul. 20, 2012;161(2):422-8. doi: 10.1016/j.jconrel.2012.01.026. Epub Jan. 28, 2012.
Cenik et al., Argonaute proteins. Curr Biol. Jun. 21, 2011;21(12):R446-9.
Cho et al., Myotonic dystrophy: emerging mechanisms for DM1 and DM2. Biochim Biophys Acta. Feb. 2007;1772(2):195-204. Epub Jun. 20, 2006.
Chothia et al., Canonical structures for the hypervariable regions of immunoglobulins. J Mol Biol. Aug. 20, 1987;196(4):901-17. doi: 10.1016/0022-2836(87)90412-8.
Clark et al., Increased brain uptake of targeted nanoparticles by adding an acid-cleavable linkage between transferrin and the nanoparticle core. PNAS. Oct. 2015;112(40):12486-91.
Codelli et al., Second-Generation Difluorinated Cyclooctynes for Copper-Free Click Chemistry. J. Am. Chem. Soc. 2008;130(34):11486-11493. Epub Aug. 5, 2008.
Coico et al., Immunology: A short course. 2008 (originally published 2003): 61-2. 8 pages (including English translation).
Crook et al., Enrichment of early fetal-liver hemopoietic stem cells of the rat using monoclonal antibodies against the transferrin receptor, Thy-1, and MRC-OX82. Dev Immunol. 1996;4(4):235-46. doi: 10.1155/1995/85036.
Crooke et al., Antisense research and applications. 1993. p. 15-35.

(56) References Cited

OTHER PUBLICATIONS

Crooke et al., Kinetic characteristics of *Escherichia coli* RNase H1: cleavage of various antisense oligonucleotide-RNA duplexes. Biochem J . Dec. 1, 1995;312(Pt 2):599-608. doi: 10.1042/bj3120599.

Crooke et al., The Effects of 2'-O-Methoxyethyl Oligonucleotides on Renal Function in Humans. Nucleic Acid Ther. Feb. 2018;28(1):10-22. doi: 10.1089/nat.2017.0693. Epub Nov. 29, 2017.

Cuellar et al., Systematic evaluation of antibody-mediated siRNA delivery using an industrial platform of THIOMAB-siRNA conjugates. Nucleic Acids Res. Jan. 2015;43(2):1189-203. Epub Dec. 30, 2014.

Curtius, Ueber die Einwirkung von salpetriger Säure auf salzsauren Glycocolläther. Berichte der deutschen chemischen Gesellschaft. Jul.-Dec. 1883;16(2):2230-1.

Danis et al., Potential therapeutic application of antisense oligonucleotides in the treatment of ocular diseases. Expert Opin Pharmacother. Feb. 2001;2(2):277-91.

Darimont et al., A novel antibody-oligonucleotide conjugate (AOC) platform enables efficient regulation of muscle targets in mice. Abstract. 8-05. J. Cach Sarcopen Musc. 2017; 8: 1065-66.

Davis et al., Improved targeting of miRNA with antisense oligonucleotides. Nucleic Acids Res. May 11, 2006;34(8):2294-304. doi: 10.1093/nar/gkl183. Print 2006.

Debets et al., Bioorthogonal labelling of biomolecules: new functional handles and ligation methods. Org Biomol Chem. Oct. 14, 2013;11(38):6439-55. Epub Aug. 23, 2013.

Demonceau et al., Novel Ruthenium-Based Catalyst Systems for the Ring-Opening Metathesis Polymerization of Low-Strain Cyclic Olefins. Macromolecules. 1997;30(11):3127-36. Epub Jun. 2, 1997.

Desjardins et al., Building a FORCETM platform-based DMD franchise for the treatment of individuals with mutations amenable to exon skipping. Neuromusc Dis. Oct. 2022; 32: S101-2. Abstract.

Desjardins et al., Building a ForceTM platform-based DMD franchise for the treatment of individuals with mutations amenable to exon skipping. Presented at 27th Int Hybrid Annual Congress of the World Muscle Society. Oct. 11-15, 2022. Poster. 1 page.

Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414.

Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414. Supplemental Figures and Figure Legends. 34 pages.

Desjardins et al., ForceTM platform achieves robust exon skipping, restores dystrophin at the sarcolemma and halts progression of fibrosis in the severe D2-mdx model of DMD. Abstract. Mar. 2023. 1 page.

Desjardins et al., ForceTM platform achieves robust exon skipping, restores dystrophin at the sarcolemma and halts progression of fibrosis in the severe D2-mdx model of DMD. Poster. Presented at The Muscular Dystrophy Association Clinical and Scientific Conference. Mar. 19-22, 2023. 1 page.

Dommerholt et al., Readily accessible bicyclononynes for bioorthogonal labeling and three-dimensional imaging of living cells. Angew Chem Int Ed. Dec. 3, 2010;49(49):9422-5.

Dommerholt et al., Strain-Promoted 1,3-Dipolar Cycloaddition of Cycloalkynes and Organic Azides. Top Curr Chem. Apr. 2016;374(2):16. doi: 10.1007/s41061-016-0016-4. Epub Mar. 22, 2016.

Doucet et al., Abstract 150—RNA-based gene therapy for myotonic dystrophy type 1 (DM1). The Ottawa Conference on New Directions in Biology & Disease of Skeletal Muscle. Ottawa, CA. May 5-8, 2010:67. 6 pages total.

Dovgan et al., Antibody-Oligonucleotide Conjugates as Therapeutic, Imaging, and Detection Agents. Bioconjug Chem. Oct. 16, 2019;30(10):2483-2501. doi: 10.1021/acs.bioconjchem.9b00306. Epub Jul. 24, 2019.

Efferth et al., Enhancement of cytotoxicity of artemisinins toward cancer cells by ferrous iron. Free Radic Biol Med. Oct. 1, 2004;37(7):998-1009. doi: 10.1016/j.freeradbiomed.2004.06.023.

Elangkovan et al., Gene Therapy for Duchenne Muscular Dystrophy. J Neuromuscul Dis. 2021;8(s2):S303-S316.

Fan, Research on humanized antibody-drug conjugates targeting prostate-specific membrane antigen. Chapter 7. Frontiers in Cancer Research. vol. 16. Xi'an Jiaotong University Press. Dec. 2016; 163-5. Chinese.

Fluiter et al., On the in vitro and in vivo properties of four locked nucleic acid nucleotides incorporated into an anti-H-Ras antisense oligonucleotide. Chembiochem. Jun. 2005;6(6):1104-9. doi: 10.1002/cbic.200400419.

Frazier, Antisense oligonucleotide therapies: the promise and the challenges from a toxicologic pathologist's perspective. Toxicol Pathol. Jan. 2015;43(1):78-89. doi: 10.1177/0192623314551840. Epub Nov. 9, 2014.

Friden et al., Anti-transferrin receptor antibody and antibody-drug conjugates cross the blood-brain barrier. Proc Natl Acad Sci U S A. Jun. 1, 1991;88(11):4771-5. doi: 10.1073/pnas.88.11.4771.

Frieden et al., Nuclease stability of LNA oligonucleotides and LNA-DNA chimeras. Nucleosides Nucleotides Nucleic Acids. May-Aug. 2003;22(5-8):1041-3. doi: 10.1081/NCN-120022731.

Furling et al., Abstract R.P.1.01 Therapeutic RNA strategies for myotonic dystrophy with CTG repeats. Neuromuscular Disorders. 2004;14:585. 2 pages total.

Furling et al., Viral vector producing antisense RNA restores myotonic dystrophy myoblast functions. Gene Ther. May 2003;10(9):795-802.

Gagnon et al., RNAi factors are present and active in human cell nuclei. Cell Rep. Jan. 16, 2014;6(1):211-21. Epub Jan. 2, 2014.

Galderisi et al., Myotonic dystrophy: antisense oligonucleotide inhibition of DMPK gene expression in vitro. Biochem Biophys Res Commun. Apr. 25, 1996;221(3):750-4.

Gao et al., Antisense oligonucleotides: rising stars in eliminating RNA toxicity in myotonic dystrophy. Hum Gene Ther. May 2013;24(5):499-507. doi: 10.1089/hum.2012.212. Epub Jan. 30, 2013.

Geary et al., Pharmacokinetics, biodistribution and cell uptake of antisense oligonucleotides. Adv Drug Deliv Rev. Jun. 29, 2015;87:46-51. doi: 10.1016/j.addr.2015.01.008. Epub Feb. 7, 2015.

Giles et al., Enhanced RNase H activity with methylphosphonodiester/phosphodiester chimeric antisense oligodeoxynucleotides. Anticancer Drug Des. Feb. 1992;7(1):37-48.

Girones et al. Comparison of the kinetics of cycling of the transferrin receptor in the presence or absence of bound diferric transferrin. Biochem J. Nov. 15, 1989;264(1):35-46.

Gong et al., Simple Method To Prepare Oligonucleotide-Conjugated Antibodies and Its Application in Multiplex Protein Detection in Single Cells. Bioconjug Chem. Jan. 20, 2016;27(1):217-25. doi: 10.1021/acs.bioconjchem.5b00613. Epub Jan. 4, 2016.

Gonzalez-Barriga et al., Intracellular Distribution and Nuclear Activity of Antisense Oligonucleotides After Unassisted Uptake in Myoblasts and Differentiated Myotubes In Vitro. Nucleic Acid Ther. Jun. 2017;27(3):144-158. doi: 10.1089/nat.2016.0641. Epub Apr. 4, 2017.

Gray et al., Combinatorial peptide libraries: mining for cell-binding peptides. Chem Rev. Jan. 22, 2014;114(2):1020-81.

Heemskerk et al., Preclinical PK and PD studies on 2'-O-methyl-phosphorothioate RNA antisense oligonucleotides in the mdx mouse model. Mol Ther. Jun. 2010;18(6):1210-7. doi: 10.1038/mt.2010.72. Epub Apr. 20, 2010.

Hein et al., Click chemistry, a powerful tool for pharmaceutical sciences. Pharm Res. Oct. 2008;25(10):2216-30. doi: 10.1007/s11095-008-9616-1. Epub May 29, 2008.

Helguera et al. An antibody recognizing the apical domain of human transferrin receptor 1 efficiently inhibits the entry of all new world hemorrhagic Fever arenaviruses. J Virol. Apr. 2012;86(7):4024-8. doi: 10.1128/JVI.06397-11. Epub Jan. 25, 2012.

Iwaki et al., Preparation of Chiral Stationary Phase via Activated Carbamate Intermediate for Liquid Chromatographic Optical Resolution. Chromatographia. Oct. 1987;23:727-30.

Jain et al., Current ADC Linker Chemistry. Pharm Res. Nov. 2015;32(11):3526-40. Epub Mar. 11, 2015.

(56) References Cited

OTHER PUBLICATIONS

Jauvin et al., Targeting DMPK with Antisense Oligonucleotide Improves Muscle Strength in Myotonic Dystrophy Type 1 Mice. Mol Ther Nucleic Acids. Jun. 16, 2017;7:465-474. Epub May 17, 2017.
Jearawiriyapaisarn et al., Sustained Dystrophin Expression Induced by Peptide-conjugated Morpholino Oligomers in the Muscles of mdx Mice. Mol Ther. Sep. 2008;16(9):1624-9. doi: 10.1038/mt.2008.120. Epub Jun. 10, 2008.
Jepsen et al., Locked nucleic acid: a potent nucleic acid analog in therapeutics and biotechnology. Oligonucleotides. 2004;14(2):130-46. doi: 10.1089/1545457041526317.
Juliano, The delivery of therapeutic oligonucleotides. Nucleic Acids Res. Aug. 19, 2016;44(14):6518-48. doi: 10.1093/nar/gkw236. Epub Apr. 15, 2016.
Kher et al., Antisense Oligonucleotides and RNA Interference. Challenges in Delivery of Therapeutic Genomics and Proteomics. Aug. 2011:325-86.
Kline et al., Methods to Make Homogenous Antibody Drug Conjugates. Pharm Res. Nov. 2015;32(11):3480-93. Epub Dec. 16, 2014.
Koshelev et al., Abstract 130—Therapeutic application for a cell culture model of myotonic dystrophy. New Directions in Biology & Disease of Skeletal Muscle. New Orleans, LA. Apr. 27-30, 2008:44. 10 pages total.
Koshelev et al., Heart-specific overexpression of CUGBP1 reproduces functional and molecular abnormalities of myotonic dystrophy type 1. Hum Mol Genet. Mar. 15, 2010;19(6):1066-75. Epub Jan. 5, 2010.
Kuran et al., Investigations on the Catalytic Systems Diethylzinc/Di- and Trihydroxybenzenes in the Copolymerization of Carbon Dioxide with Propylene Oxide. Makromol. Chem. 1976;177:1283-92.
Kurreck et al., Design of antisense oligonucleotides stabilized by locked nucleic acids. Nucleic Acids Res. May 1, 2002;30(9):1911-8. doi: 10.1093/nar/30.9.1911.
Kurreck, Antisense technologies. Improvement through novel chemical modifications. Eur J Biochem. Apr. 2003;270(8):1628-44.
Lai et al., Mechanism of action and spectrum of cell lines sensitive to a doxorubicin-transferrin conjugate. Cancer Chemother Pharmacol. 1998;41(2):155-60. doi: 10.1007/s002800050722.
Langlois et al., Abstract 831—Ribozyme and Antisense RNA-Based Gene Therapies for Myotonic Dystrophy. Molecular Therapy. May 2003;7(5, Part 2):S320.
Langlois et al., Cytoplasmic and nuclear retained DMPK mRNAs are targets for RNA interference in myotonic dystrophy cells. J Biol Chem. Apr. 29, 2005;280(17):16949-54. Epub Feb. 18, 2005.
Langlois et al., Hammerhead ribozyme-mediated destruction of nuclear foci in myotonic dystrophy myoblasts. Mol Ther. May 2003;7(5 Pt 1):670-80.
Lawrence et al., Crystal structure of the ectodomain of human transferrin receptor. Science. Oct. 22, 1999;286(5440):779-82. doi: 10.1126/science.286.5440.779.
Lee et al., Abstract—Targeted Degradation of Toxic RNA in Myotonic Dystrophy. RNA & Oligonucleotide Therapeutics. Cold Spring Harbor Laboratory. Cold Spring Harbor, NY. Apr. 7-10, 2010:35. 19 pages total.
Lee et al., RNase H-mediated degradation of toxic RNA in myotonic dystrophy type 1. Proc Natl Acad Sci U S A. Mar. 13, 2012;109(11):4221-6. doi: 10.1073/pnas.1117019109. Epub Feb. 27, 2012.
Lennox et al., Cellular localization of long non-coding RNAs affects silencing by RNAi more than by antisense oligonucleotides. Nucleic Acids Res. Jan. 29, 2016;44(2):863-77. doi: 10.1093/nar/gkv1206. Epub Nov. 17, 2015.
Lesley et al., Selection of cell lines resistant to anti-transferrin receptor antibody: evidence for a mutation in transferrin receptor. Mol Cell Biol. Sep. 1984;4(9):1675-81. doi: 10.1128/mcb.4.9.1675-1681.1984.
Levin, Targeting Therapeutic Oligonucleotides. N Engl J Med. Jan. 5, 2017;376(1):86-88. doi: 10.1056/NEJMcibr1613559.
Liang et al., RNase H1-Dependent Antisense Oligonucleotides Are Robustly Active in Directing RNA Cleavage in Both the Cytoplasm and the Nucleus. Mol Ther. Sep. 6, 2017;25(9):2075-2092. Epub Jun. 27, 2017.
Liang et al., Targeted delivery of plasmid DNA to myogenic cells via transferrin-conjugated peptide nucleic acid. Mol Ther. Mar. 2000;1(3):236-43. doi: 10.1006/mthe.2000.0043.
Lima et al., Structural requirements at the catalytic site of the heteroduplex substrate for human RNase H1 catalysis. J Biol Chem. Aug. 27, 2004;279(35):36317-26. doi: 10.1074/jbc.M405035200. Epub Jun. 17, 2004.
Lima et al., The positional influence of the helical geometry of the heteroduplex substrate on human RNase H1 catalysis. Mol Pharmacol. Jan. 2007;71(1):73-82. doi: 10.1124/mol.106.025429. Epub Oct. 6, 2006.
Liu, Exploring cell type-specific internalizing antibodies for targeted delivery of siRNA. Brief Funct Genomic Proteomic. Jun. 2007;6(2):112-9. doi: 10.1093/bfgp/elm015. Epub Jul. 31, 2007.
Luria-Perez et al., Antibody-mediated targeting of the transferrin receptor in cancer cells. Bol Med Hosp Infant Mex. Nov.-Dec. 2016;73(6):372-379. doi: 10.1016/j.bmhimx.2016.11.004. Epub Dec. 13, 2016.
Masters et al., Clinical toxicity of antibody drug conjugates: a meta-analysis of payloads. Invest New Drugs. Feb. 2018;36(1):121-135. doi: 10.1007/s10637-017-0520-6. Epub Oct. 13, 2017.
Meeuwissen et al., Cofactor regeneration in polymersome nanoreactors: Enzymatically catalysed Baeyer-Villiger reactions. Journal of Materials Chemistry. Dec. 2011;21(47):18923-6.
Mignon, Update on Ionis-DMPKRX Program. 2018 MDF Annual Conference. Nashville, TN. Sep. 14-15, 2018:22 pages.
Mojsov et al., A Quantitative Evaluation of Methods for Coupling Asparagine. The Journal of Organic Chemistry. Feb. 1980;45(4):555-60.
Monia et al., Evaluation of 2'-modified oligonucleotides containing 2'-deoxy gaps as antisense inhibitors of gene expression. J Biol Chem. Jul. 5, 1993;268(19):14514-22.
Mulders et al., Abstract S8-06—Chemically modified (CAG)n antisense oligonucleotides as molecular tools to silence toxic, expanded DMPK transcripts. 7th International Myotonic Dystrophy Consortium Meeting (IDMC-7). Wuerzburg, Germany. Sep. 9-12, 2009:421-2. 12 pages total.
Mulders et al., Molecular therapy in myotonic dystrophy: focus on RNA gain-of-function. Human Molecular Genetics. 2010;19(1):R90-7. Epub Apr. 20, 2010.
Mulders et al., Triplet-repeat oligonucleotide-mediated reversal of RNA toxicity in myotonic dystrophy. PNAS. Aug. 18, 2009;106(33):13915-20. Supporting information included. 13 pages.
Murray et al., Human Biochemistry. "Mir." Moscow. 1993; 1:34. 5 pages (including English translation).
Naylor et al., DELIVER, a randomized, double-blind, placebo controlled, multiple ascending dose study of DYNE-251 in boys with DMD amenable to Exon 51 skipping. Poster. Presented at The Muscular Dystrophy Association Clinical and Scientific Conference. Mar. 19-22, 2023. 1 page.
Naylor et al., DELIVER, a randomized, double-blind, placebo controlled, multiple ascending dose study of DYNE-251 in boys with DMD amenable to Exon 51 skipping. Abstract. Mar. 2023. 1 page.
Overby et al., RNA-mediated therapies in myotonic dystrophy. Drug Discov Today. Dec. 2018;23(12):2013-2022. Epub Aug. 4, 2018.
Padlan et al., A possible procedure for reducing the immunogenicity of antibody variable domains while preserving their ligand-binding properties. Molecular Immunology. Apr.-May 1991;28(4-5):489-98.
Pandey et al., Identification and characterization of modified antisense oligonucleotides targeting DMPK in mice and nonhuman primates for the treatment of myotonic dystrophy type 1. J Pharmacol Exp Ther. Nov. 2015;355(2):329-40. doi: 10.1124/jpet.115.226969. Epub Sep. 1, 2015.

(56) References Cited

OTHER PUBLICATIONS

Panowski et al., Site-specific antibody drug conjugates for cancer therapy. MAbs. Jan.-Feb. 2014;6(1):34-45.
Picariello et al., Dyne-101 achieves durable knockdown of toxic human nuclear DMPK RNA and correction of splicing in the hTfR1/DMSXL mouse model of DM1. Presented at The Muscular Dystrophy Association Clinical and Scientific Conference. Mar. 13-16, 2022. 1 page.
Piche-Nicholas et al., Changes in complementarity-determining regions significantly alter IgG binding to the neonatal Fc receptor (FcRn) and pharmacokinetics. MAbs. Jan. 2018;10(1):81-94. doi: 10.1080/19420862.2017.1389355. Epub Nov. 3, 2017.
Pradeepkumar, Chemically modified oligonucleotides: synthesis, physicochemical and biochemical properties of their duplexes with DNA and RNA. Comprehensive Summaries of Uppsala Disserations from the Faculty of Science and Technology. 2004; 973: 56 pages.
Qian et al., Targeted drug delivery via the transferrin receptor-mediated endocytosis pathway. Pharmacol Rev. Dec. 2002;54(4):561-87. doi: 10.1124/pr.54.4.561.
Ramasamy et al., Remarkable enhancement of binding affinity of Heterocycle-modified DNA to DNA and RNA. Synthesis, characterization and biophysical evaluation of N2-imidazolylpropylguanine and N2-imidazolylpropyl-2-aminoadenine modified oligonucleotides. Tetrahedron Let. 1994;35(2):215-18.
Roberts et al., Advances in oligonucleotide drug delivery. Nat Rev Drug Discov. Oct. 2020;19(10):673-694. doi: 10.1038/s41573-020-0075-7. Epub Aug. 11, 2020.
Roberts et al., The Halogenation of Ethylenes. J. Am. Chem. Soc. May 1937;59(5):947-8.
Rodriguez et al. Binding specificity and internalization properties of an antibody-avidin fusion protein targeting the human transferrin receptor. Journal of Controlled Release 124 (2007) 35-42. (2007).
Sahenk et al., The muscular dystrophies: distinct pathogenic mechanisms invite novel therapeutic approaches. Curr Rheumatol Rep. Jun. 2011;13(3):199-207.
Samoylova et al., Elucidation of muscle-binding peptides by phage display screening. Muscle Nerve. Apr. 1999;22(4):460-6.
Sansone et al., Initial data from the ACHIEVE trial of DYNE-101 in adults with myotonic dystrophy type 1 (DM1). 2024 MDA Clinical and Scientific Conference. Mar. 6, 2024. 19 pages.
Sansone et al., Initial data from the ACHIEVE trial of DYNE-101 in adults with myotonic dystrophy type 1 (DM1). 2024 MDA Clinical and Scientific Conference. Mar. 6, 2024. Poster. 3 pages.
Sazani et al., Systemically delivered antisense oligomers upregulate gene expression in mouse tissues. Nat Biotechnol. Dec. 2002;20(12):1228-33. doi: 10.1038/nbt759. Epub Nov. 11, 2002.
Scanlon, Anti-genes: siRNA, ribozymes and antisense. Curr Pharm Biotechnol. Oct. 2004;5(5):415-20.
Scherr et al., Detection of antisense and ribozyme accessible sites on native mRNAs: application to NCOA3 mRNA. Mol Ther. Nov. 2001;4(5):454-60.
Schneider et al., Structural features of the cell surface receptor for transferrin that is recognized by the monoclonal antibody OKT9. J Biol Chem. Jul. 25, 1982;257(14):8516-22.
Schnyder et al., Targeting of skeletal muscle in vitro using biotinylated immunoliposomes. Biochem J. Jan. 1, 2004;377(Pt 1):61-7. doi: 10.1042/BJ20031034.
Setten et al., The current state and future directions of RNAi-based therapeutics. Nat Rev Drug Discov. Jun. 2019;18(6):421-446. doi: 10.1038/s41573-019-0017-4.
Shen et al., Chemistry, mechanism and clinical status of antisense oligonucleotides and duplex RNAs. Nucleic Acids Res. Feb. 28, 2018;46(4):1584-1600.
Singh et al., Catalytic Enantioselective Cyclopropanation of Olefins Using Carbenoid Chemistry. Synthesis. Feb. 1997;137-49.
Stein, The experimental use of antisense oligonucleotides: a guide for the perplexed. J Clin Invest. Sep. 2001;108(5):641-4.
Stocki et al., Blood-brain barrier transport using a high affinity, brain-selective VNAR antibody targeting transferrin receptor 1. FASEB J. Feb. 2021;35(2):e21172. doi: 10.1096/fj.202001787R. Epub Nov. 25, 2020.
Strop et al., Location matters: site of conjugation modulates stability and pharmacokinetics of antibody drug conjugates. Chem Biol. Feb. 21, 2013;20(2):161-7.
Subramanian et al., Abstract 1074. Targeted delivery of oligonucleotide therapeutics to muscle demonstrates potential to treat duchenne muscular dystrophy. Abstract. Mol Ther. 28 (4S1): 465. (2020) 1 page.
Subramanian, Splice Correction and Reduction of Toxic DMPK RNA In Vitro and In Vivo Utilizing Novel Antibody Targeted Antisense Oligonucleotides. Presented at ASGST Annual Meeting; May 14, 2021. 19 pages.
Sugo et al., Development of antibody-siRNA conjugate targeted to cardiac and skeletal muscles. J Control Release. Sep. 10, 2016;237:1-13. doi: 10.1016/j.jconrel.2016.06.036. Epub Jun. 29, 2016.
Swayze et al., Antisense oligonucleotides containing locked nucleic acid improve potency but cause significant hepatotoxicity in animals. Nucleic Acids Res. 2007;35(2):687-700. doi: 10.1093/nar/gkl1071. Epub Dec. 19, 2006.
Swayze et al., The medicinal chemistry of oligonucleotides. In: Antisense Drug Technology, Second Edition. 2007. Crooke, Ed. Chapter 6: 143-182.
Thomas et al., Myotonic Dystrophy and Developmental Regulation of RNA Processing. Comprehensive Physiology. Apr. 2018;8(2):509-53. Epub Mar. 25, 2018.
Thornton et al., Abstract—Oligonucleotide Therapeutics in Myotonic Dystrophy. RNA & Oligonucleotide Therapeutics. Cold Spring Harbor Laboratory. Cold Spring Harbor, NY. Apr. 7-10, 2010:31. 19 pages total.
Thornton et al., Myotonic dystrophy: approach to therapy. Curr Opin Genet Dev. Jun. 2017;44:135-140. doi: 10.1016/j.gde.2017.03.007. Epub Apr. 1, 2017.
Tron et al., Click chemistry reactions in medicinal chemistry: applications of the 1,3-dipolar cycloaddition between azides and alkynes. Med Res Rev. Mar. 2008;28(2):278-308.
Trowbridge et al., Anti-transferrin receptor monoclonal antibody and toxin-antibody conjugates affect growth of human tumour cells. Nature. Nov. 12, 1981;294(5837):171-3. doi: 10.1038/294171a0.
Van Deutekom, Abstract—The Development of RNA-Modulating Therapies. RNA & Oligonucleotide Therapeutics. Cold Spring Harbor Laboratory. Cold Spring Harbor, NY. Apr. 7-10, 2010:3. 19 pages total.
Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.
Wagner et al., Transferrin-polycation conjugates as carriers for DNA uptake into cells. Proc Natl Acad Sci U S A. May 1990;87(9):3410-4. doi: 10.1073/pnas.87.9.3410.
Walder et al., Role of RNase H in hybrid-arrested translation by antisense oligonucleotides. Proc. Natl. Acad. Sci. Jul. 1988;85:5011-5.
Walker et al., Improved cellular delivery of antisense oligonucleotides using transferrin receptor antibody-oligonucleotide conjugates. Pharm Res. Oct. 1995;12(10):1548-53. doi: 10.1023/a:1016260110049.
Walles et al., ADME and Safety Aspects of Non-cleavable Linkers in Drug Discovery and Development. Curr Top Med Chem. 2017;17(32):3463-3475. doi: 10.2174/1568026618666180118153502.
Weeden et al., FORCE platform overcomes barriers of oligonucleotide delivery to muscle and corrects myotonic dystrophy features in preclinical models. Commun Med (Lond). Jan. 18, 2025;5(1):22.
Wheeler et al., Reversal of RNA dominance by displacement of protein sequestered on triplet repeat RNA. Science. Jul. 17, 2009;325(5938):336-9.
Wheeler et al., Targeting nuclear RNA for in vivo correction of myotonic dystrophy. Nature. Aug. 2, 2012;488(7409):111-5. doi: 10.1038/nature11362.
Wheeler, Myotonic dystrophy: therapeutic strategies for the future. Neurotherapeutics. Oct. 2008;5(4):592-600.

(56) References Cited

OTHER PUBLICATIONS

Wilton et al., Exon skipping and Duchenne muscular dystrophy: hope, hype and how feasible? Neurol India. Jul.-Sep. 2008;56(3):254-62. doi: 10.4103/0028-3886.43443.
Wolf et al., ACHIEVE trial, a randomized, placebo-controlled, multiple ascending dose study of Dyne-101 in individuals with myotonic dystrophy Type 1 (DM1). Abstract. Mar. 2023. 1 page.
Wolf et al., ACHIEVE trial, a randomized, placebo-controlled, multiple ascending dose study of Dyne-101 in individuals with myotonic dystrophy Type 1 (DM1). Presented at The Muscular Dystrophy Association Clinical and Scientific Conference. Poster. Mar. 19-22, 2023. 1 page.
Wolf et al., Initial Data from the ACHIEVE Trial of DYNE-101 in Adults with Myotonic Dystrophy Type 1 (DM1). 2024 World Muscle Society Annual Meeting P221. Oct. 12-14, 2024. Poster. Prague, Czechia.
Wu et al., Determination of the role of the human RNase H1 in the pharmacology of DNA-like antisense drugs. J Biol Chem. Apr. 23, 2004;279(17):17181-9. Epub Feb. 11, 2004.
Xia et al., Intravenous siRNA of brain cancer with receptor targeting and avidin-biotin technology. Pharm Res. Dec. 2007;24(12):2309-16. doi: 10.1007/s11095-007-9460-8. Epub Oct. 11, 2007.
Yao et al., Targeted Delivery of ASOs Demonstrates Potential to Treat Duchenne Muscular Dystrophy. Poster. Presented at ASGCT; May 12, 2020. 1 page.
Ye et al., Generation and functional characterization of the anti-transferrin receptor single-chain antibody-GAL4 (TfRscFv-GAL4) fusion protein. BMC Biotechnol. Nov. 28, 2012;12:91.
Yoshida et al., Evaluation of off-target effects of gapmer antisense oligonucleotides using human cells. Genes Cells. Dec. 2019;24(12):827-835. doi: 10.1111/gtc.12730. Epub Nov. 12, 2019.
Zanotti et al., Abstract 17. Repeat dosing with DYNE-101 is Well Tolerated and Leads to a Sustained Reduction of DMPK RNA expression in key muscles for DM1 pathology in hTfR1/DMSXL mice and NHPs. Abstract. Mol Ther. Apr. 2022; 30(4S1): 9.
Zanotti et al., Abstract 247. The ForceTM platform achieves robust knock down of toxic human nuclear DMPK RNA and foci reduction in DM1 cells and in newly developed hTfR1/DMSXL mouse model. Mol Ther. 29(4S1): 127. Apr. 2021. 1 page.
Zanotti et al., Abstract 82. The ForceTM platform delivers oligonucleotides to the brain in a DM1 mouse model and in NHPs. Mol Ther. Apr. 2023; 31(4S1): 44.
Zanotti et al., Abstract EP.233. The ForceTM platform achieves durable knockdown of toxic human nuclear Dmpk Rna and correction of splicing in the hTFR1/DMSXL mouse model. Neuromusc Disord. 2021; 31: S120.
Zanotti et al., DYNE-101 achieves durable knockdown of toxic human nuclear DMPK RNA and correction of splicing in the hTfR1/DMSXL mouse model of DM1. Abstract. Mar. 2022. 1 page.
Zanotti et al., The ForceTM platform achieves durable knockdown of toxic human nuclear DMPK RNA and correction of splicing in the hTFR1/DMSXL mouse model. Presented at WMS Meeting. Sep. 20-24, 2021. 1 page.
Zanotti, Repeat dosing with DYNE-101 is Well Tolerated and Leads to a Sustained Reduction of DMPK RNA expression in key muscles for DM1 pathology in hTfR1/DMSXL mice and NHPs. Presented at American Society of Gene & Cell Therapy Conference. May 16, 2022. 15 pages.
Zanotti, The ForceTM platform delivers oligonucleotides to the brain in a DM1 mouse model and in NHPs. Presented at American Society of Gene & Cell Therapy Conference. May 17, 2023. 16 pages.
Zanotti, The FORCE™ Platform Achieves Robust Knock Down of Toxic Human Nuclear DMPK RNA and Foci Reduction in DM1 Cells and in Newly Developed hTfR1/DMSXL Mouse Model. Presented at American Society of Gene & Cell Therapy Annual Meeting; May 14, 2021. 13 pages.
Bisset et al., Therapeutic impact of systemic AAV-mediated RNA interference in a mouse model of myotonic dystrophy. Hum Mol Genet. Sep. 1, 2015;24(17):4971-83. doi: 10.1093/hmg/ddv219. Epub Jun. 16, 2015.
Brun et al., Protocols for lysine conjugation. Methods Mol Biol. 2013;1045:173-87. doi: 10.1007/978-1-62703-541-5_10.
Deweid, Arming Antibodies for Cancer Therapy: 15 Transglutaminase-Mediated Toxin Conjugation, Dissertation, Retrieved from the Internet: URL:https://tuprints.ulb.tu-darmstadt.de/11441/1/Dissertation%20Luwig%20Lukas%20Deweid.pdf. [retrieved on Aug. 5, 2021].
Dovgan et al., Acyl Fluorides: Fast, Efficient, and Versatile Lysine-Based Protein Conjugation via Plug-and-Play Strategy. Bioconjug Chem. May 17, 2017;28(5):1452-1457. doi: 10.1021/acs.bioconjchem.7b00141. Epub 2017.
Hammond et al., Antibody-oligonucleotide conjugate achieves CNS delivery in animal models for spinal muscular atrophy. JCI Insight. Dec. 22, 2022;7(24):e154142. doi: 10.1172/jci.insight.154142.
Kanodia et al., Prospective Design of Anti-Transferrin Receptor Bispecific Antibodies for Optimal Delivery into the Human Brain. CPT Pharmacometrics Syst Pharmacol. May 2016;5(5):283-91. doi: 10.1002/psp4.12081. Epub May 17, 2016.
Karalė K, et al., Synthesis and stability studies of bicyclo[6.1.0]nonyne scaffolds for automated solid-phase oligonucleotide synthesis. RSC Adv. May 29, 2024;14(25):17406-17412. doi: 10.1039/d3ra08732h.
Karalė, K., Development and synthesis of oligonucleotide building blocks and conjugates for therapeutic applications. Thesis for Karolinska Institutet. 2022. 70 pages.
Matos et al., Quaternization of Vinyl/Alkynyl Pyridine Enables Ultrafast Cysteine-Selective Protein Modification and Charge Modulation. Angew Chem Int Ed Engl. May 13, 2019;58(20):6640-6644. doi: 10.1002/anie.201901405. Epub Apr. 9, 2019.
Mcdonagh et al., “Engineered antibody-drug conjugates with defined sites and stoichiometries of drug attachment”, Protein Engineering, Desigen & Selection, vol. 19, No. 7, Apr. 27, 2006, pp. 299-307, XP002774610, DOI: 10.1093/PROTEIN/GZL013.
Winkler J. Oligonucleotide conjugates for therapeutic applications. Ther Deliv. Jul. 2013;4(7):791-809. doi: 10.4155/tde.13.47.
Brumm et al., Form S-1 1-15 Registration Statement Under the Securities Act of 1933.
Nakamori et al., Splicing biomarkers of disease severity in myotonic dystrophy. Ann Neurol. Dec. 2013;74(6):862-72. doi: 10.1002/ana.23992.
Van Geel et al., Chemoenzymatic Conjugation of Toxic Payloads to the Globally Conserved N-Glycan of Native mAbs Provides Homogeneous and Highly Efficacious Antibody-Drug Conjugates. Bioconjug Chem. Nov. 18, 2015;26(11):2233-42. 2015.
Wiener et al., Scientific Reports 10: 1457 (2020).

* cited by examiner

MUSCLE TARGETING COMPLEXES AND FORMULATIONS FOR TREATING MYOTONIC DYSTROPHY

RELATED APPLICATION

This application is a division of U.S. application Ser. No. 18/436,078, filed Feb. 8, 2024, entitled "MUSCLE TARGETING COMPLEXES AND FORMULATIONS FOR TREATING MYOTONIC DYSTROPHY", which is a division of U.S. application Ser. No. 18/303,506, filed Apr. 19, 2023, entitled "MUSCLE TARGETING COMPLEXES AND FORMULATIONS FOR TREATING MYOTONIC DYSTROPHY", now U.S. Pat. No. 11,931,421, which is a continuation of International Patent Application No. PCT/US2023/065753, filed Apr. 14, 2023, entitled "MUSCLE TARGETING COMPLEXES AND FORMULATIONS FOR TREATING MYOTONIC DYSTROPHY", which claims the benefit under 35 U.S.C. § 119(e) of the filing date of U.S. Provisional Application No. 63/331,727, entitled "MUSCLE TARGETING COMPLEXES AND FORMULATIONS FOR TREATING MYOTONIC DYSTROPHY", filed Apr. 15, 2022; the contents of each of which are incorporated herein by reference in their entirety.

FIELD OF THE INVENTION

The present application relates to targeting complexes for delivering oligonucleotide molecular payloads to cells, formulations comprising such complexes, and uses thereof, particularly uses relating to treatment of disease.

REFERENCE TO AN ELECTRONIC SEQUENCE LISTING

The contents of the electronic sequence listing (D082470076US04-SEQ-CBD.xml; Size: 56,346 bytes; and Date of Creation: Aug. 19, 2025) are herein incorporated by reference in its entirety.

BACKGROUND

Myotonic dystrophy (DM) is a dominantly inherited genetic disease that is characterized by myotonia, muscle loss or degeneration, diminished muscle function, insulin resistance, cardiac arrhythmia, smooth muscle dysfunction, and neurological abnormalities. DM is the most common form of adult-onset muscular dystrophy, with a worldwide incidence of about 1 in 8000 people worldwide. Two types of the disease, myotonic dystrophy type 1 (DM1) and myotonic dystrophy type 2 (DM2), have been described. DM1, the more common form of the disease, results from a repeat expansion of a CTG trinucleotide repeat in the 3' non-coding region of DMPK on chromosome 19; DM2 results from a repeat expansion of a CCTG tetranucleotide repeat in the first intron of ZNF9 on chromosome 3. In DM1 patients, the repeat expansion of a CTG trinucleotide repeat, which may comprise greater than about 50 to about 3,000 or more total repeats, leads to generation of toxic RNA repeats capable of forming hairpin structures that bind essential intracellular proteins, e.g. muscleblind-like proteins, with high affinity resulting in protein sequestration and the loss-of-function phenotypes that are characteristic of the disease. Apart from supportive care and treatments to address the symptoms of the disease, no effective therapeutic for DM1 is currently available.

SUMMARY

According to some aspects, the present disclosure provides complexes and formulations comprising such complexes.

According to some aspects, a formulation provided herein comprises complexes that comprise an oligonucleotide covalently linked to an anti-transferrin receptor 1 (TfR1) antibody,

- wherein the anti-TfR1 antibody comprises: a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16,
- wherein the oligonucleotide comprises a 5'-X—Y—Z-3' configuration, wherein X and Z are flanking regions comprising one or more modified nucleosides and Y is a gap region comprising one or more 2'-deoxyribonucleosides,
- and wherein the complexes are formulated with tris(hydroxymethyl)aminomethane and sucrose.

According to some aspects, a formulation provided herein comprises complexes comprising a structure of formula (I): $[R^1]_{n1}$—$R^2$, wherein each $R^1$ independently comprises a group of the formula (Ia):

(Ia)

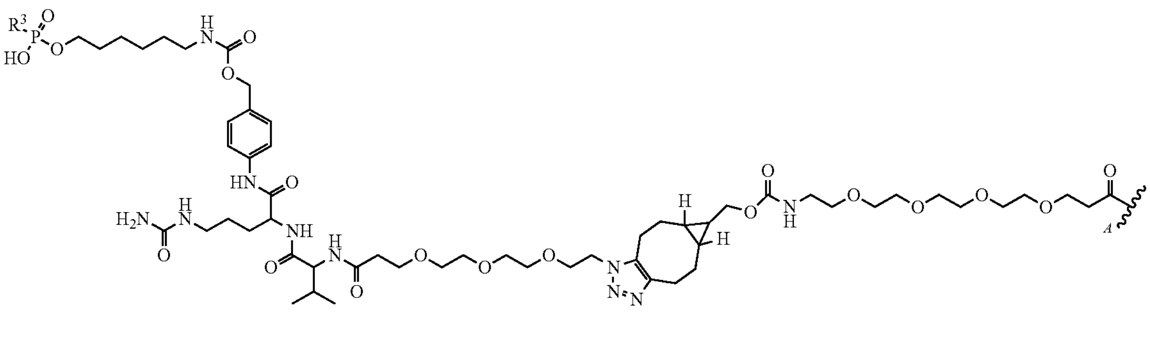, wherein $R^2$ comprises an antibody, and $R^3$ comprises an oligonucleotide comprising a 5'-X—Y—Z-3' configuration, wherein X and Z are flanking regions comprising one or more modified nucleosides and Y is a gap region comprising one or more 2'-deoxyribonucleosides;

wherein $R^1$ is covalently linked to $R^2$ at attachment point A; and wherein n1 is an integer representing the number of instances of $R^1$, wherein each instance of $R^1$ is covalently linked to a different amino acid residue of the antibody;

wherein the complexes are formulated with tris(hydroxymethyl)aminomethane and sucrose. In some embodiments, each different amino acid residue of the antibody is a lysine. In some embodiments, the antibody is an anti-TfR1 antibody.

In some embodiments, the antibody comprises a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16.

In some embodiments, the formulation is in a lyophilized form or a frozen solid form.

In some embodiments, the formulation is in an aqueous solution.

In some embodiments, the tris(hydroxymethyl)aminomethane is present in the aqueous solution at a concentration in the range of 5 mM to 50 mM.

In some embodiments, the sucrose is present in the aqueous solution at a concentration in the range of 5% to 15% weight per volume (w/v %).

In some embodiments, the aqueous solution has a pH in the range of 6.5 to 8.5.

In some embodiments, the tris(hydroxymethyl)aminomethane is present in the aqueous solution at a concentration of 25 mM and/or the sucrose is present in the aqueous solution at a concentration of 10 w/v % and/or the aqueous solution is at a pH of 7.5.

In some embodiments, the antibody is a Fab fragment, a full-length IgG, a Fab' fragment, a $F(ab')_2$ fragment, an scFv, or an Fv.

In some embodiments, the antibody is a Fab fragment.

In some embodiments, the antibody comprises a heavy chain variable region (VH) comprising an amino acid sequence at least 85% identical to SEQ ID NO: 17; and/or wherein the antibody comprises a light chain variable region (VL) comprising an amino acid sequence at least 85% identical to SEQ ID NO: 18. In some embodiments, the antibody comprises a VH comprising the amino acid sequence of SEQ ID NO: 17 and/or a VL comprising the amino acid sequence of SEQ ID NO: 18.

In some embodiments, the antibody comprises a heavy chain comprising an amino acid sequence at least 85% identical to SEQ ID NO: 19; and/or wherein the antibody comprises a light chain comprising an amino acid sequence at least 85% identical to SEQ ID NO: 20. In some embodiments, the antibody comprises a heavy chain comprising the amino acid sequence of SEQ ID NO: 19 and/or a light chain comprising the amino acid sequence of SEQ ID NO: 20.

In some embodiments, the oligonucleotide is 10-30 nucleotides in length. In some embodiments, the oligonucleotide comprises a nucleotide sequence having a region of complementarity of at least 8 consecutive nucleotides in length to SEQ ID NO: 22.

In some embodiments, the oligonucleotide comprises at least 8 consecutive nucleotides of a nucleotide sequence as set forth in SEQ ID NO: 21. In some embodiments, the oligonucleotide comprises the nucleotide sequence of SEQ ID NO: 21.

In some embodiments, each $R^1$ comprises a group of the formula (Ib):

(Ib)

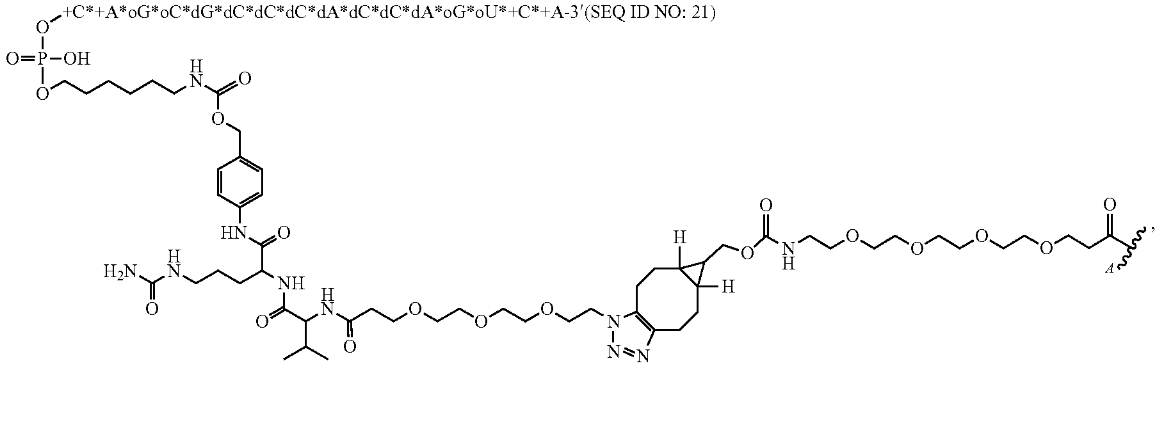

wherein +N represents an LNA (2'-4' methylene bridge) ribonucleoside, dN represents a 2'-deoxyribonucleoside, oN represents a 2'-O-methoxyethyl (MOE) modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, * represents a phosphorothioate internucleoside linkage, such that the oligonucleotide comprises a nucleobase sequence of CAGCGCCCACCAGUCA (SEQ ID NO: 21).

In some embodiments, each $R^1$ comprises a group of the formula (Ic):

(Ic)
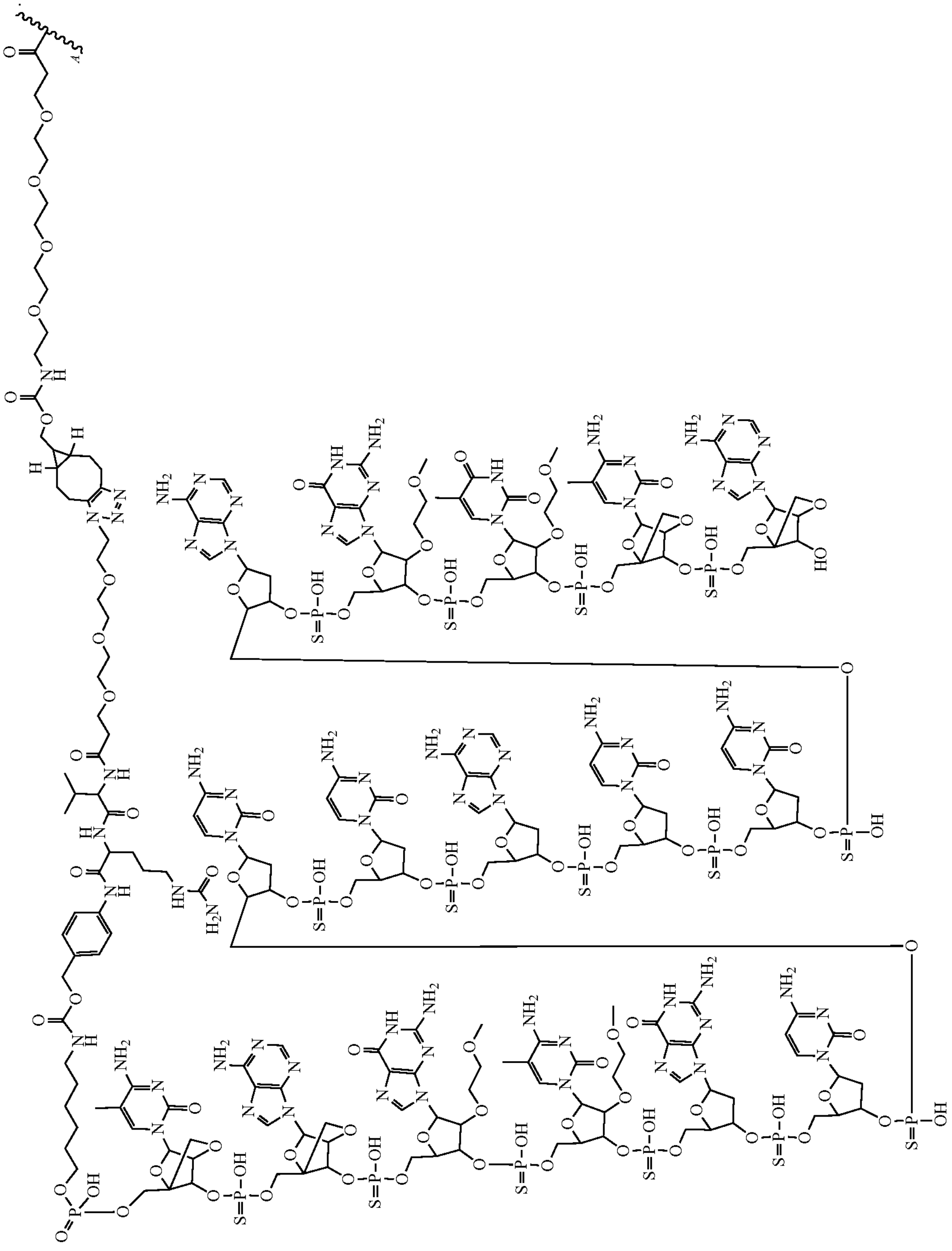

In some embodiments, the complexes are present in the formulation at a concentration in the range of 10 mg/mL to 50 mg/mL.

In some embodiments, the formulation further comprises one or more antibodies that are not covalently linked to an oligonucleotide.

In some embodiments, the average value of n1 of complexes in the formulation is in the range of 0.5 to 5.

According to some aspects, methods of reducing DMPK expression and/or treating myotonic dystrophy in a subject are provided herein, the method comprising administering to the subject an effective amount of a formulation provided herein.

In some embodiments, the subject has an expansion of a disease-associated repeat of a DMPK allele that is associated with myotonic dystrophy. In some embodiments, the disease-associated repeat comprises repeating units of a CTG trinucleotide sequence.

In some embodiments, the complexes reduce DMPK expression in the subject.

BRIEF DESCRIPTION OF THE DRAWINGS

FIG. 3A shows representative images of samples following in situ hybridization staining for DMPK foci and fluorescence staining of myofibers (inset panels). In the microscopy images shown in FIG. 3A, the light rounded shapes show cell nuclei, and the bright puncta within the nuclei show DMPK foci. FIG. 3B shows quantification of DMPK foci.

FIG. 10A shows concentration of the Fab of the conjugates in mg/ml. FIG. 10B shows concentration of the Fab of the conjugates in μM. FIG. 10C shows concentration of the oligonucleotide of the conjugates in μM.

FIG. 11B) for a lyophilized formulation of anti-TfR1 Fab-ASO conjugates after reconstitution at T0, T4w, and T8w, at 2-8° C.

FIG. 12A shows concentration of the Fab of the conjugates in mg/ml. FIG. 12B shows concentration of the Fab of the conjugates in μM. FIG. 12C shows concentration of the oligonucleotide of the conjugates in μM.

FIG. 13B) for a lyophilized formulation of anti-TfR1 Fab-ASO conjugates after reconstitution at T0, T2w, T4w, and T8w, at 25° C.

FIG. 14A shows concentration of the Fab of the conjugates in mg/ml. FIG. 14B shows concentration of the Fab of the conjugates in μM. FIG. 14C shows concentration of the oligonucleotide of the conjugates in μM.

FIG. 15B) of lyophilized anti-TfR1 Fab-ASO conjugates after reconstitution at T0, T2w, T4w, and T8w, at 40° C.

DETAILED DESCRIPTION OF INVENTION

Figure 1A:
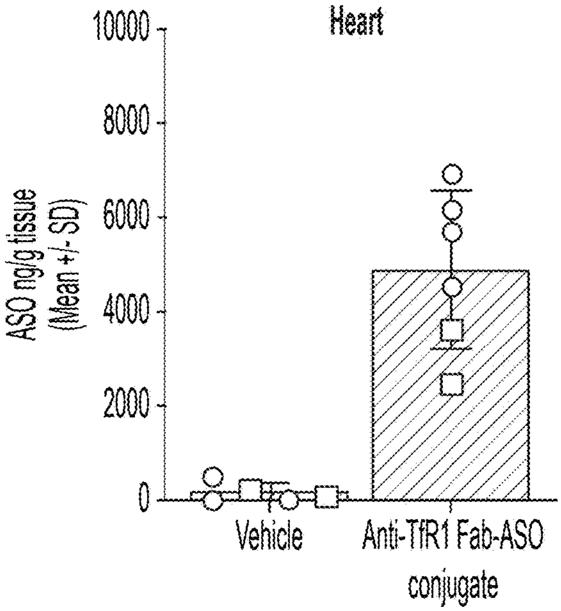
FIGS. 1A-1D show the amount of DMPK-targeting oligonucleotide (ASO) in the heart (FIG. 1A), diaphragm (FIG. 1B), gastrocnemius (FIG. 1C), or tibialis anterior (FIG. 1D), respectively, after administration of conjugates containing an anti-TfR1 Fab covalently linked to the ASO.
Figure 1B:
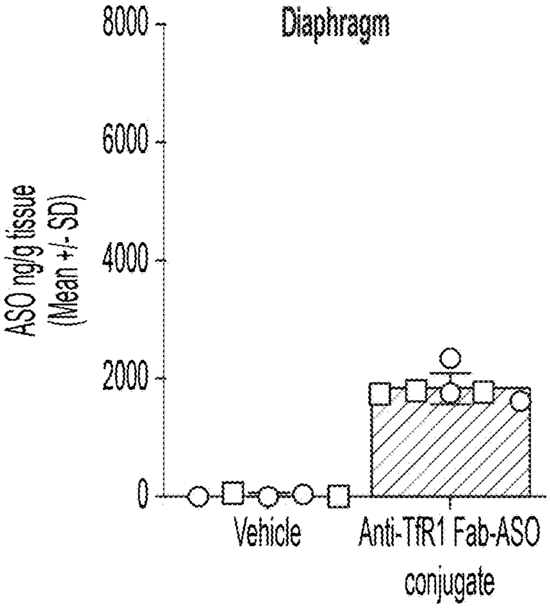
Figure 1C:
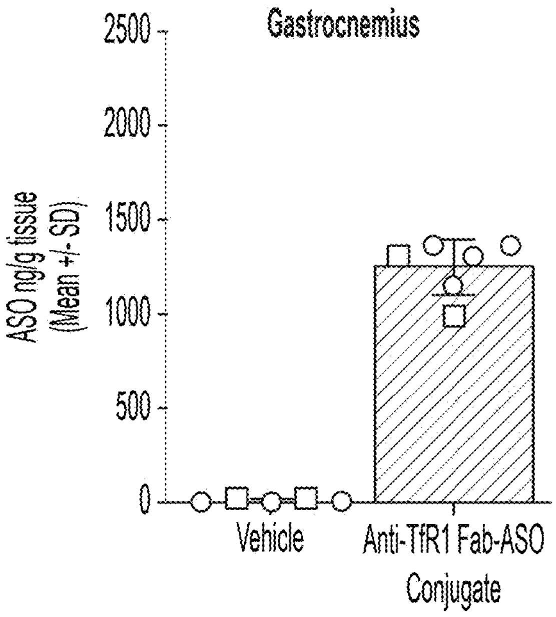
Figure 1D:
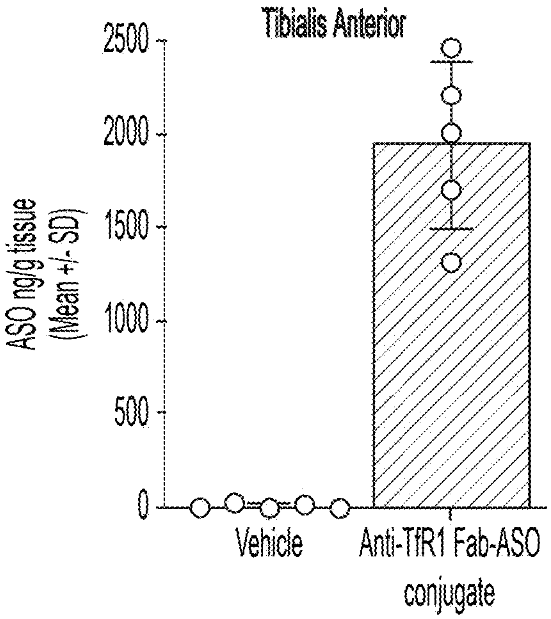

According to some aspects, the present disclosure provides complexes and formulations comprising such complexes. In some embodiments, the complexes are formulated with tris(hydroxymethyl)aminomethane and sucrose. In some embodiments, the complexes are formulated as aqueous or lyophilized (e.g., lyophilized powder) forms. In some embodiments, a complex comprises an oligonucleotide (e.g., an oligonucleotide comprising a 5'-X—Y—Z-3' configuration) covalently linked to an antibody. In some embodiments, a complex comprises a muscle-targeting complex comprising an oligonucleotide (e.g., an oligonucleotide comprising a 5'-X—Y—Z-3' configuration) covalently linked to an anti-transferrin receptor 1 (TfR1) antibody. In some embodiments, a complex comprises a muscle-targeting complex comprising an oligonucleotide (e.g., an oligonucleotide comprising a 5'-X—Y—Z-3' configuration) covalently linked to the anti-transferrin receptor 1 (TfR1) antibody provided in Table 2. Also provided are methods of using the complexes and formulations described herein for treating a subject having a myotonic dystrophy (e.g., DM1) and/or methods of reducing the expression or activity of DMPK (e.g., a DMPK RNA) in a cell.

Further aspects of the disclosure, including a description of defined terms, are provided below.

Definitions

Administering: As used herein, the terms "administering" or "administration" means to provide a complex to a subject in a manner that is physiologically and/or (e.g., and) pharmacologically useful (e.g., to treat a condition in the subject).

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable domain or at least one antigenic determinant, e.g., paratope that specifically binds to an antigen. In some embodiments, an antibody is a full-length antibody. In some embodiments, an antibody is a chimeric antibody. In some embodiments, an antibody is a humanized antibody. However, in some embodiments, an antibody is a Fab fragment, a Fab' fragment, a $F(ab')_2$ fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as VH), and/or (e.g., and) a light (L) chain variable region (abbreviated herein as VL). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha (α), delta (Δ), epsilon (ε), gamma (γ) or mu (μ) heavy chain. In some embodiments, the heavy chain of an antibody described herein can comprise a human alpha (α), delta (Δ), epsilon (ε), gamma (γ) or mu (μ) heavy chain. In a particular embodiment, an antibody described herein comprises a human gamma 1 CH1, CH2, and/or (e.g., and) CH3 domain. In some embodiments, the amino acid sequence of the VH domain comprises the amino acid sequence of a human gamma (γ) heavy chain constant region, such as any known in the art. Non-limiting examples of human constant region sequences have been described in the art, e.g., see U.S. Pat. No. 5,693,780 and Kabat E A et al., (1991) supra. In some embodiments, the VH domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or (e.g., and) methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or (e.g., and) phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

CDR: As used herein, the term "CDR" refers to the complementarity determining region within antibody variable sequences. A typical antibody molecule comprises a heavy chain variable region (VH) and a light chain variable region (VL), which are usually involved in antigen binding. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the IMGT definition, the Chothia definition, the AbM definition, and/or (e.g., and) the contact definition, all of which are well known in the art. Sec, e.g., Kabat, E. A., et al. (1991) Sequences of Proteins of Immunological Interest, Fifth Edition, U.S. Department of Health and Human Services, NIH Publication No. 91-3242; IMGT®, the international ImMunoGeneTics Information System® http://www.imgt.org, Lefranc, M.-P. et al., Nucleic Acids Res., 27:209-212 (1999); Ruiz, M. et al., Nucleic Acids Res., 28:219-221 (2000); Lefranc, M.-P., Nucleic Acids Res., 29:207-209 (2001); Lefranc, M.-P., Nucleic Acids Res., 31:307-310 (2003); Lefranc, M.-P. et al., In Silico Biol., 5, 0006 (2004) [Epub], 5:45-60 (2005); Lefranc, M.-P. et al., Nucleic Acids Res., 33:D593-597 (2005); Lefranc, M.-P. et al., Nucleic Acids Res., 37: D1006-1012 (2009); Lefranc, M.-P. et al., Nucleic Acids Res., 43:D413-422 (2015); Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs. As used herein, a CDR may refer to the CDR defined by any method known in the art. Two antibodies having the same CDR means that the two antibodies have the same amino acid sequence of that CDR as determined by the same method, for example, the IMGT definition.

There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262 (5): 732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems. Examples of CDR definition systems are provided in Table 1.

TABLE 1

| CDR Definitions | | | |
|---|---|---|---|
| | IMGT[1] | Kabat[2] | Chothia[3] |
| CDR-H1 | 27-38 | 31-35 | 26-32 |
| CDR-H2 | 56-65 | 50-65 | 53-55 |
| CDR-H3 | 105-116/117 | 95-102 | 96-101 |
| CDR-L1 | 27-38 | 24-34 | 26-32 |
| CDR-L2 | 56-65 | 50-56 | 50-52 |
| CDR-L3 | 105-116/117 | 89-97 | 91-96 |

[1]IMGT ®, the international ImMunoGeneTics information system ®, imgt.org, Lefranc, M.-P. et al., Nucleic Acids Res., 27: 209-212 (1999)
[2]Kabat et al. (1991) Sequences of Proteins of Immunological Interest, Fifth Edition, U.S. Department of Health and Human Services, NIH Publication No. 91-3242
[3]Chothia et al., J. Mol. Biol. 196: 901-917 (1987))

Complementary: As used herein, the term "complementary" refers to the capacity for precise pairing between two nucleotides or two sets of nucleotides. In particular, complementary is a term that characterizes an extent of hydrogen bond pairing that brings about binding between two nucleotides or two sets of nucleotides. For example, if a base at one position of an oligonucleotide is capable of hydrogen bonding with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

Covalently linked: As used herein, the term “covalently linked” refers to a characteristic of two or more molecules being linked together via at least one covalent bond. In some embodiments, two molecules can be covalently linked together by a single bond, e.g., a disulfide bond or disulfide bridge, that serves as a linker between the molecules. However, in some embodiments, two or more molecules can be covalently linked together via a molecule that serves as a linker that joins the two or more molecules together through multiple covalent bonds. In some embodiments, a linker may be a cleavable linker. However, in some embodiments, a linker may be a non-cleavable linker.

Disease-associated-repeat: As used herein, the term “disease-associated-repeat” refers to a repeated nucleotide sequence at a genomic location for which the number of units of the repeated nucleotide sequence is correlated with and/or (e.g., and) directly or indirectly contributes to, or causes, genetic disease. Each repeating unit of a disease associated repeat may be 2, 3, 4, 5 or more nucleotides in length. For example, in some embodiments, a disease associated repeat is a dinucleotide repeat. In some embodiments, a disease associated repeat is a trinucleotide repeat. In some embodiments, a disease associated repeat is a tetranucleotide repeat. In some embodiments, a disease associated repeat is a pentanucleotide repeat. In some embodiments, the disease-associated-repeat comprises CAG repeats, CTG repeats, CUG repeats, CGG repeats, CCTG repeats, or a nucleotide complement of any thereof. In some embodiments, a disease-associated-repeat is in a non-coding portion of a gene. However, in some embodiments, a disease-associated-repeat is in a coding region of a gene. In some embodiments, a disease-associated-repeat is expanded from a normal state to a length that directly or indirectly contributes to, or causes, genetic disease. In some embodiments, a disease-associated-repeat is in RNA (e.g., an RNA transcript). In some embodiments, a disease-associated-repeat is in DNA (e.g., a chromosome, a plasmid). In some embodiments, a disease-associated-repeat is expanded in a chromosome of a germline cell. In some embodiments, a disease-associated-repeat is expanded in a chromosome of a somatic cell. In some embodiments, a disease-associated-repeat is expanded to a number of repeating units that is associated with congenital onset of disease. In some embodiments, a disease-associated-repeat is expanded to a number of repeating units that is associated with childhood onset of disease. In some embodiments, a disease-associated-repeat is expanded to a number of repeating units that is associated with adult onset of disease. In DM1, the DMPK gene comprises a disease-associated repeat of CTG units.

DMPK: As used herein, the term “DMPK” refers to a gene that encodes myotonin-protein kinase (also known as myotonic dystrophy protein kinase or dystrophia myotonica protein kinase), a serine/threonine protein kinase. Substrates for this enzyme may include myogenin, the beta-subunit of the L-type calcium channels, and phospholemman. In some embodiments, DMPK may be a human (Gene ID: 1760), non-human primate (e.g., Gene ID: 456139, Gene ID: 715328, Gene ID: 102125829), or rodent gene (e.g., Gene ID: 13400). In humans, a CTG repeat expansion in the 3' non-coding, untranslated region of DMPK is associated with myotonic dystrophy type I (DM1). In addition, multiple human transcript variants (e.g., as annotated under GenBank RefSeq Accession Numbers: NM_001081563.2, NM_004409.4, NM_001081560.2, NM_001081562.2, NM_001288764.1, NM_001288765.1, and NM_001288766.1) have been characterized that encode different protein isoforms.

DMPK allele: As used herein, the term “DMPK allele” refers to any one of alternative forms (e.g., wild-type or mutant forms) of a DMPK gene. In some embodiments, a DMPK allele may encode for wild-type myotonin-protein kinase that retains its normal and typical functions. In some embodiments, a DMPK allele may comprise one or more disease-associated-repeat expansions. In some embodiments, normal subjects have two DMPK alleles comprising in the range of 5 to 37 repeat units. In some embodiments, the number of CTG repeat units in subjects having DM1 is in the range of about 50 to about 3,000 or more, with higher numbers of repeats leading to an increased severity of disease. In some embodiments, mildly affected DM1 subjects have at least one DMPK allele having in the range of 50 to 150 repeat units. In some embodiments, subjects with classic DM1 have at least one DMPK allele having in the range of 100 to 1,000 or more repeat units. In some embodiments, subjects having DM1 with congenital onset may have at least one DMPK allele comprising more than 2,000 repeat units.

Framework: As used herein, the term “framework” or “framework sequence” refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In one embodiment, the acceptor sequences known in the art may be used in the antibodies disclosed herein.

Human antibody: The term “human antibody”, as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term “human antibody”, as used herein, is not intended to include antibodies in which CDR sequences derived from the germline of another mammalian species, such as a mouse, have been grafted onto human framework sequences.

Humanized antibody: The term “humanized antibody” refers to antibodies which comprise heavy and light chain variable region sequences from a non-human species (e.g., a mouse) but in which at least a portion of the VH and/or (e.g., and) VL sequence has been altered to be more “human-like”, i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-transferrin receptor antibodies and antigen binding portions are provided. Such antibodies may be generated by obtaining murine anti-transferrin receptor monoclonal antibodies using traditional hybridoma technology followed by humanization using in vitro genetic engineering, such as those disclosed in Kasaian et al PCT publication No. WO 2005/123126 A2.

Kabat numbering: The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

Myotonic dystrophy (DM): As used herein, the term "Myotonic dystrophy (DM)" refers to a genetic disease caused by mutations in the DMPK gene or CNBP (ZNF9) gene that is characterized by muscle loss, muscle weakening, and muscle function. Two types of the disease, myotonic dystrophy type 1 (DM1) and myotonic dystrophy type 2 (DM2), have been described. DM1 is associated with an expansion of a CTG trinucleotide repeat in the 3' non-coding region of DMPK. DM2 is associated with an expansion of a CCTG tetranucleotide repeat in the first intron of ZNF9. In both DM1 and DM2, the nucleotide expansions lead to toxic RNA repeats capable of forming hairpin structures that bind critical intracellular proteins, e.g., muscleblind-like proteins, with high affinity. Myotonic dystrophy, the genetic basis for the disease, and related symptoms are described in the art (see, e.g. Thornton, C. A., "Myotonic Dystrophy" Neurol Clin. (2014), 32 (3): 705-719; and Konieczny et al. "Myotonic dystrophy: candidate small molecule therapeutics" Drug Discovery Today (2017), 22:11). In some embodiments, subjects are born with a variation of DM1 called congenital myotonic dystrophy. Symptoms of congenital myotonic dystrophy are present from birth and include weakness of all muscles, breathing problems, clubfeet, developmental delays and intellectual disabilities. DM1 is associated with Online Mendelian Inheritance in Man (OMIM) Entry #160900. DM2 is associated with OMIM Entry #602668.

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, gapmers, mixmers, phosphorodiamidate morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleosides (e.g., 2'-O-methyl sugar modifications, purine or pyrimidine modifications). In some embodiments, an oligonucleotide may comprise one or more modified internucleoside linkage. In some embodiments, an oligonucleotide may comprise one or more phosphorothioate linkages, which may be in the Rp or Sp stereochemical conformation.

Region of complementarity: As used herein, the term "region of complementarity" refers to a nucleotide sequence, e.g., of an oligonucleotide, that is sufficiently complementary to a cognate nucleotide sequence, e.g., of a target nucleic acid, such that the two nucleotide sequences are capable of annealing to one another under physiological conditions (e.g., in a cell). In some embodiments, a region of complementarity is fully complementary to a cognate nucleotide sequence of target nucleic acid. However, in some embodiments, a region of complementarity is partially complementary to a cognate nucleotide sequence of target nucleic acid (e.g., at least 80%, 90%, 95% or 99% complementarity). In some embodiments, a region of complementarity contains 1, 2, 3, or 4 mismatches compared with a cognate nucleotide sequence of a target nucleic acid.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to the transferrin receptor, e.g., an epitope of the apical domain of transferrin receptor.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having a disease resulting from a disease-associated-repeat expansion, e.g., in a DMPK allele.

Transferrin receptor: As used herein, the term, "transferrin receptor" (also known as TFRC, CD71, p90, TFR, or TFR1) refers to an internalizing cell surface receptor that binds transferrin to facilitate iron uptake by endocytosis. In some embodiments, a transferrin receptor may be of human (NCBI Gene ID 7037), non-human primate (e.g., NCBI Gene ID 711568 or NCBI Gene ID 102136007), or rodent (e.g., NCBI Gene ID 22042) origin. In addition, multiple human transcript variants have been characterized that encoded different isoforms of the receptor (e.g., as annotated under GenBank RefSeq Accession Numbers: NP_001121620.1, NP_003225.2, NP_001300894.1, and NP_001300895.1).

2'-modified nucleoside: As used herein, the terms "2'-modified nucleoside" and "2'-modified ribonucleoside" are used interchangeably and refer to a nucleoside having a sugar moiety modified at the 2' position. In some embodiments, the 2'-modified nucleoside is a 2'-4' bicyclic nucleoside, where the 2' and 4' positions of the sugar are bridged (e.g., via a methylene, an ethylene, or a (S)-constrained ethyl bridge). In some embodiments, the 2'-modified nucleoside is a non-bicyclic 2'-modified nucleoside, e.g., where the 2' position of the sugar moiety is substituted. Non-limiting examples of 2'-modified nucleosides include: 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminocthyl (2'-O-DMAOE), 2'-O-dimethylaminopropyl (2'-O-DMAP), 2'-O-dimethylaminoethyloxyethyl (2'-O-DMAEOE), 2'-O—N-methylacetamido (2'-O-NMA), locked nucleic acid (LNA, methylene-bridged nucleic acid), ethylene-bridged nucleic acid (ENA), and (S)-constrained ethyl-bridged nucleic acid (cEt). In some embodiments, the 2'-modified nucleosides described herein are high-affinity modified nucleotides and oligonucleotides comprising the 2'-modified nucleosides have increased affinity to a target sequences, relative to an unmodified oligonucleotide. Examples of structures of 2'-modified nucleosides are provided below:

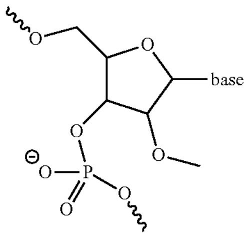

2′-O-methyl

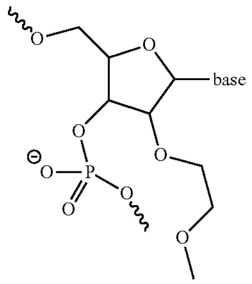

2′-O-methoxyethyl
(MEO)

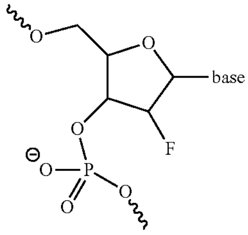

2′-fluoro

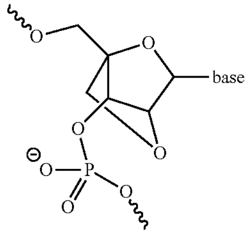

locked nucleic acid
(LNA)

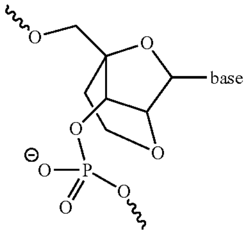

ethylene-bridged
nucleic acid (ENA)

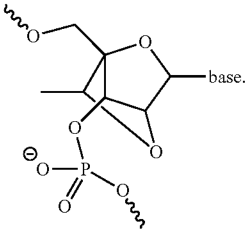

(S)-constrained
ethyl (cET)

These examples are shown with phosphate groups, but any internucleoside linkages are contemplated between 2'-modified nucleosides.

Ranges: All ranges provided in the present disclosure are inclusive of the end points.

Complexes

Provided herein are complexes that comprise a targeting agent, e.g., an antibody, covalently linked to an oligonucleotide. In some embodiments, a complex comprises a muscle-targeting antibody covalently linked to one or more oligonucleotides. In some embodiments, the oligonucleotide is an antisense oligonucleotide that targets a DMPK RNA to reduce expression or activity of DMPK (e.g., reduce the level of a mutant or wild-type DMPK RNA, or the activity of a DMPK gene product).

Complexes described herein generally comprise a linker that covalently links an antibody (e.g., an anti-TfR1 antibody) described herein to an oligonucleotide (e.g., an oligonucleotide comprising a 5'-X—Y—Z-3' configuration). A linker comprises at least one covalent bond.

In some embodiments, complexes described herein comprise a structure of formula (I): $[R^1]_{n1}$—$R^2$, in which each $R^1$ independently comprises a compound comprising an oligonucleotide (e.g., an oligonucleotide comprising a 5'-X—Y—Z-3' configuration) and $R^2$ comprises an antibody (e.g., an anti-TfR1 antibody), and wherein in each complex n1 is independently an integer (e.g., one or greater) representing the number of instances of $R^1$ in each complex. In some embodiments, each $R^1$ independently comprises a group comprising an oligonucleotide. In some embodiments, each $R^1$ independently comprises a group that comprises additional elements in addition to an oligonucleotide. In some embodiments, $R^2$ comprises an antibody (e.g., an anti-TfR1 antibody) comprising a heavy chain comprising a heavy chain variable region (VH) and a heavy chain constant region, and a light chain comprising a light chain variable region (VL) and a light chain constant region. In some embodiments, each $R^1$ of a complex is independently covalently linked to a different amino acid residue (e.g., lysine or cysteine) of $R^2$.

In some embodiments, in each complex n1 is independently an integer (e.g., one or greater). In some embodiments, the antibody comprises a sequence as set forth in Table 2. For example, in some embodiments, the antibody comprises a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprises a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NO: 6 or 16. In some embodiments, the antibody comprises a heavy chain variable region (VH) comprising an amino acid sequence at least 85% (e.g., at least 95%) identical to SEQ ID NO: 17 and/or comprises a light chain variable region (VL) comprising an amino acid sequence at least 85% (e.g., at least 95%) identical to SEQ ID NO: 18. In some embodiments, the antibody comprises a VH comprising the amino acid sequence of SEQ ID NO: 17 and/or comprises a VL comprising the amino acid sequence of SEQ ID NO: 18. In some embodiments, the antibody comprises a heavy chain comprising an amino acid sequence at least 85% (e.g., at least 95%) identical to SEQ ID NO: 19 and/or comprises a light chain comprising an amino acid sequence at least 85% (e.g., at least 95%) identical to SEQ ID NO: 20. In some embodiments, the antibody comprises a heavy chain comprising the amino acid sequence of SEQ ID NO: 19 and/or comprises a light chain comprising the amino acid sequence of SEQ ID NO: 20. In some embodiments, the antibody is a Fab fragment, a full-length IgG, a Fab' fragment, a F(ab') 2 fragment, an scFv, or an Fv. In some embodiments, the antibody is a Fab fragment.

In some embodiments, the value of n1 of each or any complex (e.g., any complex in any of the compositions or formulations disclosed herein) is an integer up to the number of amino acid residues in the antibody to which conjugation is desired or targeted (e.g., the number of lysine residues). In some embodiments, in each complex the value of n1 is independently selected from 1, 2, 3, 4, 5, 6, 7, 8, 9, 10, 11, 12, 13, 14, 15, 16, 17, 18, 19, 20, 21, 22, 23, 24, 25, 26, and 27. In some embodiments, in each complex the value of n1 is independently selected from 1, 2, 3, 4, 5, 6, 7, 8, 9, 10, 11, 12, 13, 14, 15, 16, 17, 18, 19, 20, 21, 22, 23, 24, 25 and 26. In some embodiments, in each complex the value of n1 is independently in the range of 1-27, 1-26, 1-10, 1-5, or 1-3. In some embodiments, the average value of n1 of complexes of the composition is in the range of 1 to 5 (e.g., 1-5, 1-4, 1-3, 3-5, or 1-2). In some embodiments, compositions described herein comprise complexes that comprise a structure of formula (I): $[R^1]_{n1}$—$R^2$, wherein n1 is 0. In some embodiments, the average value of n1 of complexes of the composition is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, in each complex type n1 is independently an integer of one or greater representing the number of instances of $R^1$ in each complex of the complex type, and in which the different complex types of the composition are characterized by having different n1 values (e.g., n1 values in the range of 1-27, 1-26, 1-25, 1-20, 1-15, 1-10, 1-5, or 1-3).

In some embodiments, compositions are provided (e.g., formulations comprising tris(hydroxymethyl)aminomethane and/or sucrose, as described herein) that comprise a plurality of different complexes. In some embodiments, the plurality of different complexes comprise a common targeting agent (e.g. an antibody) and a common oligonucleotide (e.g., an oligonucleotide comprising a 5'-X—Y—Z-3' configuration, such as a DMPK-targeting oligonucleotide). In such embodiments, different complex types are characterized by having different numbers of oligonucleotides covalently linked to an antibody. For example, in some embodiments, compositions are provided that comprise a plurality of complexes comprising a structure of formula (I): $[R^1]_{n1}$—$R^2$, in which each $R^1$ independently comprises a compound comprising an oligonucleotide (e.g., a DMPK-targeting oligonucleotide) and $R^2$ comprises an antibody (e.g., anti-TfR1 antibody), and in which n1 is an integer representing the number of instances of $R^1$ in a complex, and in which different complexes of the composition may have different n1 values (e.g., n1 values in the range of 1-27, 1-26, 1-10, 1-5, or 1-3). In some embodiments, in complexes of a composition n1 is independently an integer. In some embodiments, the average value of n1 of complexes of the composition is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, compositions described herein comprise complexes in which n1 is 0.

In some embodiments, a composition described herein comprises antibody that is not conjugated to an oligonucleotide (e.g., in trace amounts) and antibody conjugated to one or more oligonucleotides. In some embodiments, antibody that is not conjugated to an oligonucleotide may be referred to as a compound comprising a structure of formula (I): $[R^1]_{n1}$—$R^2$, for which n1 is zero. Accordingly, in some embodiments, a composition for administration to a subject in the methods described herein comprises compounds (e.g., complexes) comprising a structure of formula (I): $[R^1]_{n1}$—$R^2$, for which each $R^1$ independently comprises a group comprising an oligonucleotide, $R^2$ comprises an antibody and n1 is independently an integer of zero or greater that reflects the number of instances of $R^1$ in each compound (e.g., complex). In some embodiments, the fraction of compounds comprising a structure of formula (I): $[R^1]_{n1}$—$R^2$, in a composition, for which n1 is zero, compared with all compounds of that structure in the composition for which n1 is one or greater, is less than 10%, less than 5%, less than 1% less than 0.5%, less than 0.1%, less than 0.05%, or less than 0.01%. As such, in some embodiments, the average value of n1 of complexes in a composition disclosed herein is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2).

In some embodiments, each instance of $R^1$ in a complex is covalently linked to a different amino acid residue of the antibody. In some embodiments, an amino acid to which $R^1$ is covalently linked comprises an ε-amino group (e.g., lysine, arginine). However, in some embodiments, an amino acid to which $R^1$ is covalently linked is a cysteine. In some embodiments, $R^1$ is directly covalently linked to an amino acid residue of the antibody. However, in some embodiments, $R^1$ is indirectly covalently linked to an amino acid of the antibody, e.g., covalently linked to a glycosylation site on the amino acid. In some embodiments, $R^1$ is not covalently linked to an amino acid residue residing in a CDR region of the antibody.

In some embodiments, complexes provided herein (e.g., in compositions or formulations described herein) comprise a structure of formula (I): $[R^1]_{n1}$—$R^2$, in which each instance of $R^1$ independently comprises a group of the formula (Ia):

(Ia)

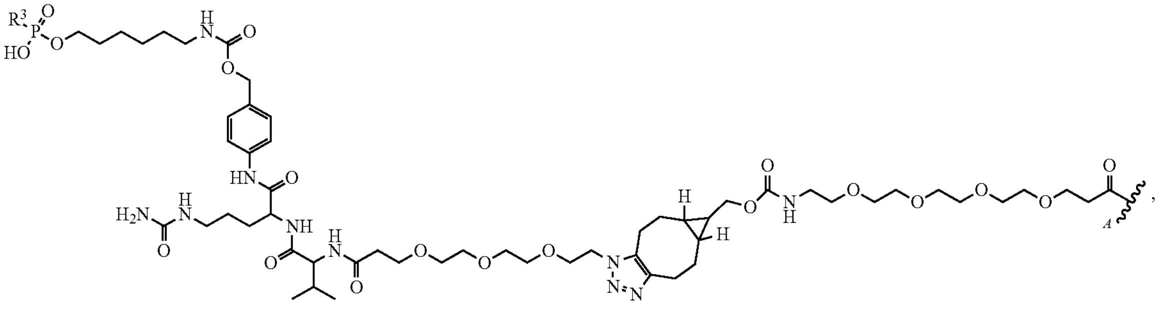

in which $R^3$ comprises an oligonucleotide, e.g., an oligonucleotide comprising a 5'-X—Y—Z-3' configuration; and $R^1$ is covalently linked (e.g., indirectly or directly linked, e.g., directly linked) to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a F(ab') 2 fragment, an scFv, or an Fv. In some embodiments, $R^3$ comprises an oligonucleotide comprising a nucleobase sequence of CAGCGCCCACCA-GUCA (SEQ ID NO: 21). In some embodiments, $R^3$ comprises an oligonucleotide comprising a structure of +C*+A*OG*oC*dG*dC*dC*dC*dA*dC*dC*dA*oG*OU*+C*+A (SEQ ID NO: 21), wherein +N represents an LNA (2'-4' methylene bridge) ribonucleoside, dN represents a 2'-deoxyribonucleoside, oN represents a 2'-MOE modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, and * represents a phosphorothioate internucleoside linkage.

In some embodiments, complexes provided herein (e.g., in compositions or formulations described herein) comprise a structure of formula (I): $[R^1]_{n1}$—$R^2$, in which each $R^1$ comprises a group of the formula (Ib):

(Ib)

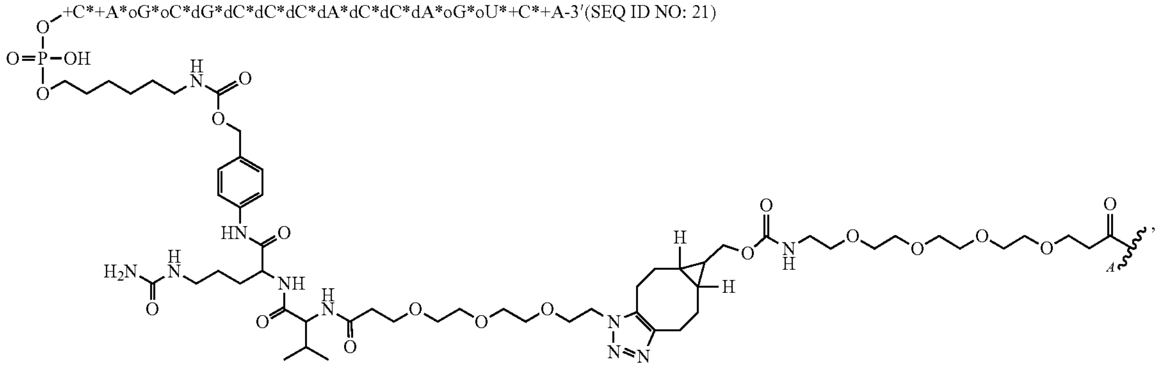

wherein +N represents an LNA (2'-4' methylene bridge) ribonucleoside, dN represents a 2'-deoxyribonucleoside, oN represents a 2'-O-methoxyethyl (MOE) modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, * represents a phosphorothioate internucleoside linkage, and wherein the oligonucleotide comprises a nucleobase sequence of CAGCGCCCACCAGUCA (SEQ ID NO: 21), wherein n1 is an integer (e.g., one or greater) representing the number of instances of $R^1$ in each complex, and each $R^1$ is covalently linked to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv.

In some embodiments, complexes provided herein (e.g., in compositions or formulations described herein) comprise a structure of formula (I): $[R^1]_{n1}$—$R^2$, in which each $R^1$ comprises a group of the formula (Ic):

(Ic)
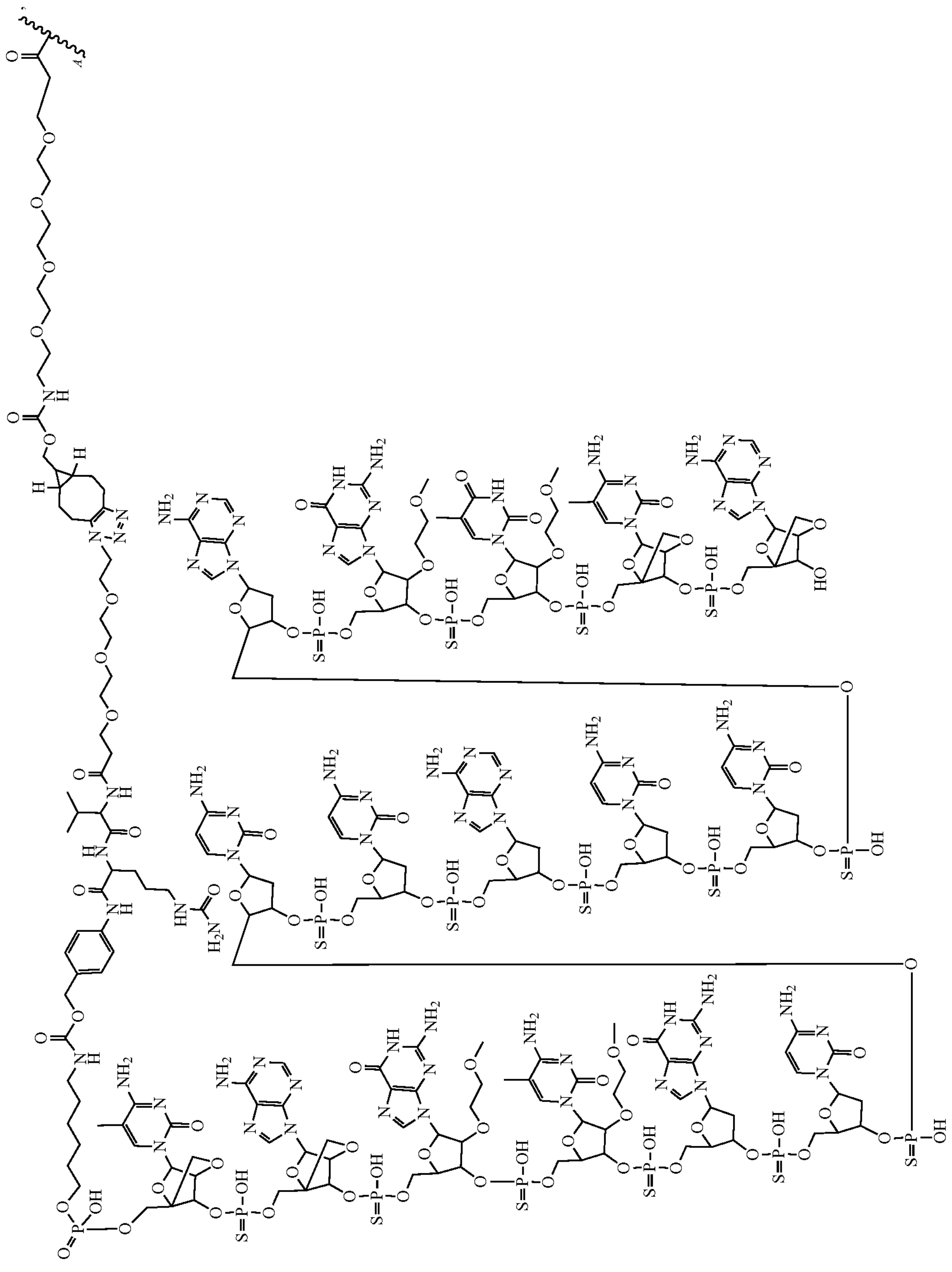

wherein $R^1$ is covalently linked to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv.

In some embodiments, complexes provided herein (e.g., in compositions or formulations described herein) comprise a structure of the formula (Id):

(Id)

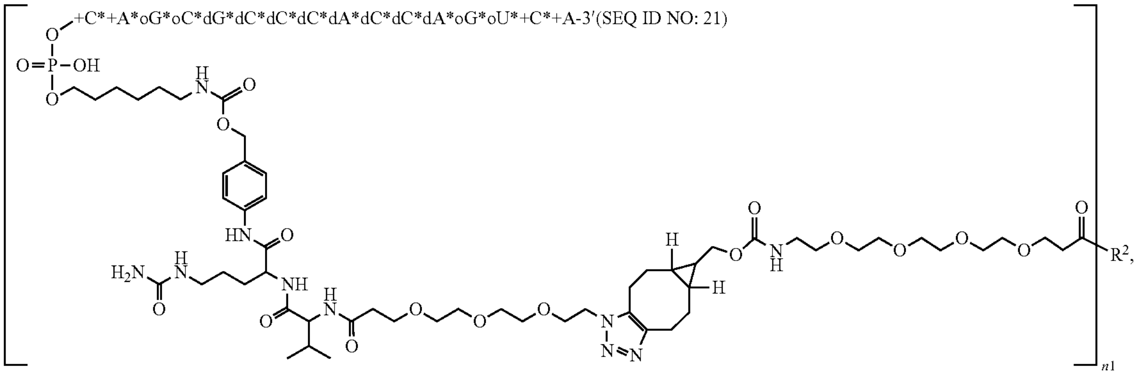

wherein +N represents an LNA (2'-4' methylene bridge) ribonucleoside, dN represents a 2'-deoxyribonucleoside, oN represents a 2'-O-methoxyethyl (MOE) modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, * represents a phosphorothioate internucleoside linkage, and wherein the oligonucleotide comprises a nucleobase sequence of CAGCGCCCACCAGUCA (SEQ ID NO: 21); wherein $R^2$ comprises an antibody comprising a sequence as set forth in Table 2; wherein n1 is an integer (e.g., one or greater) representing the number of instances of the group enclosed by square brackets, wherein each instance of the group enclosed by square brackets is covalently linked to a different amino acid residue of the antibody, optionally wherein each different amino acid residue is a lysine. In some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv.

In some embodiments, complexes described herein comprise a structure of formula (A):

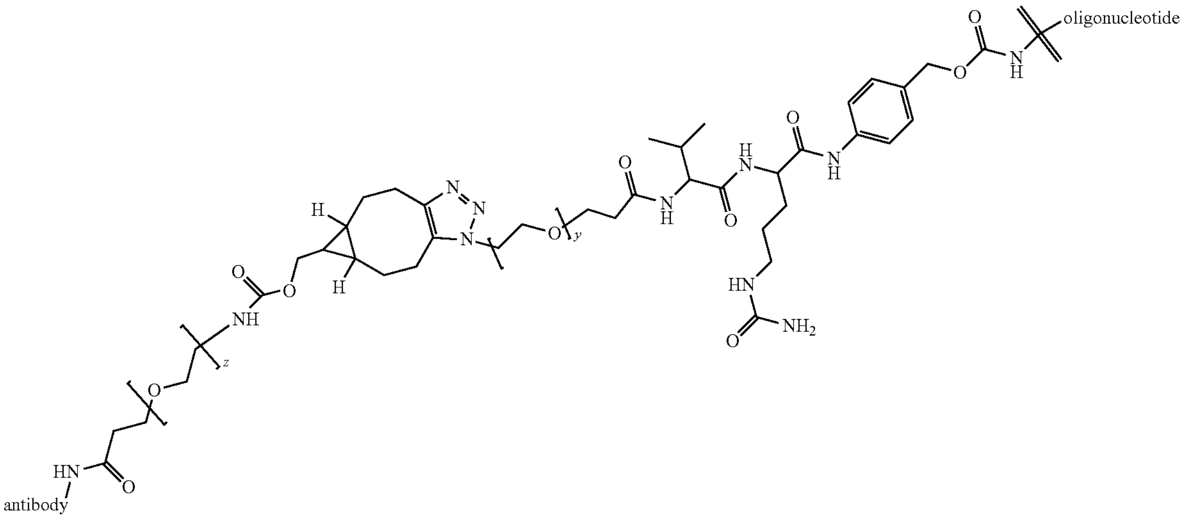

(A), wherein y is 0-15 (e.g., 3) and z is 0-15 (e.g., 4). In some embodiments, the amide shown adjacent the antibody (e.g., anti-TfR1 antibody) in the structure (A) results from a reaction with an amine of the antibody, such as a lysine epsilon amine. In some embodiments, a complex described herein comprises an anti-TfR1 antibody (e.g., an anti-TfR1 Fab) covalently linked via a lysine of the antibody to the 5' end of an oligonucleotide (e.g., an oligonucleotide comprising a 5'-X—Y—Z-3' configuration). In some embodiments, the antibody comprises a sequence as set forth in Table 2. For example, in some embodiments, the antibody comprises a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprises a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, the antibody comprises a heavy chain variable region (VH) comprising an amino acid sequence at least 85% (e.g., at least 95%) identical to SEQ ID NO: 17 and/or comprises a light chain variable region (VL) comprising an amino acid sequence at least 85% (e.g., at least 95%) identical to SEQ ID NO: 18. In some embodiments, the antibody comprises a VH comprising the amino acid sequence of SEQ ID NO: 17 and/or comprises a VL comprising the amino acid sequence of SEQ ID NO: 18. In some embodiments, the antibody comprises a heavy chain comprising an amino acid sequence at least 85% (e.g., at least 95%) identical to SEQ ID NO: 19 and/or comprises a light chain comprising an amino acid sequence at least 85% (e.g., at least 95%) identical to SEQ ID NO: 20. In some embodiments, the antibody comprises a heavy chain comprising the amino acid sequence of SEQ ID NO: 19 and/or comprises a light chain comprising the amino acid sequence of SEQ ID NO: 20. In some embodiments, the antibody is a Fab fragment, a full-length IgG, a Fab' fragment, a F(ab') 2 fragment, an scFv, or an Fv.

Antibodies

In some embodiments, complexes described herein comprise an antibody that binds human transferrin receptor 1 (TfR1). An example human TfR1 amino acid sequence, corresponding to NCBI sequence NP_003225.2 (transferrin receptor protein 1 isoform 1, *Homo sapiens*) is as follows:

```
                                        (SEQ ID NO: 23)
MMDQARSAFSNLFGGEPLSYTRFSLARQVDGDNSHVEMKLAVDEEENAD

NNTKANVTKPKRCSGSICYGTIAVIVFFLIGFMIGYLGYCKGVEPKTEC

ERLAGTESPVREEPGEDFPAARRLYWDDLKRKLSEKLDSTDFTGTIKLL

NENSYVPREAGSQKDENLALYVENQFREFKLSKVWRDQHFVKIQVKDSA

QNSVIIVDKNGRLVYLVENPGGYVAYSKAATVTGKLVHANFGTKKDFED

LYTPVNGSIVIVRAGKITFAEKVANAESLNAIGVLIYMDQTKFPIVNAE

LSFFGHAHLGTGDPYTPGFPSFNHTQFPPSRSSGLPNIPVQTISRAAAE

KLFGNMEGDCPSDWKTDSTCRMVTSESKNVKLTVSNVLKEIKILNIFGV

IKGFVEPDHYVVVGAQRDAWGPGAAKSGVGTALLLKLAQMFSDMVLKDG

FQPSRSIIFASWSAGDFGSVGATEWLEGYLSSLHLKAFTYINLDKAVLG

TSNFKVSASPLLYTLIEKTMQNVKHPVTGQFLYQDSNWASKVEKLTLDN

AAFPFLAYSGIPAVSFCFCEDTDYPYLGTTMDTYKELIERIPELNKVAR

AAAEVAGQFVIKLTHDVELNLDYERYNSQLLSFVRDLNQYRADIKEMGL

SLOWLYSARGDFFRATSRLTTDFGNAEKTDRFVMKKLNDRVMRVEYHFL

SPYVSPKESPFRHVFWGSGSHTLPALLENLKLRKQNNGAFNETLFRNQL

ALATWTIQGAANALSGDVWDIDNEF.
```

Table 2 provides examples of sequences of an anti-TfR1 antibody useful in the complexes provided herein.

TABLE 2

Examples of anti-TfR1 antibody sequences

| Feature | IMGT | Kabat | Chothia |
|---|---|---|---|
| CDR-H1 | GYSITSGYY (SEQ ID NO: 1) | SGYYWN (SEQ ID NO: 7) | GYSITSGY (SEQ ID NO: 12) |
| CDR-H2 | ITFDGAN (SEQ ID NO: 2) | YITFDGANNYNPSL KN (SEQ ID NO: 8) | FDG (SEQ ID NO: 13) |
| CDR-H3 | TRSSYDYDVL DY (SEQ ID NO: 3) | SSYDYDVLDY (SEQ ID NO: 9) | SYDYDVLD (SEQ ID NO: 14) |
| CDR-L1 | QDISNF (SEQ ID NO: 4) | RASQDISNFLN (SEQ ID NO: 10) | SQDISNF (SEQ ID NO: 15) |
| CDR-L2 | YTS (SEQ ID NO: 5) | YTSRLHS (SEQ ID NO: 11) | YTS (SEQ ID NO: 5) |
| CDR-L3 | QQGHTLPYT (SEQ ID NO: 6) | QQGHTLPYT (SEQ ID NO: 6) | GHTLPY (SEQ ID NO: 16) |
| VH | QVQLQESGPGLVKPSQTLSLTCTVTGYSITSGYYWNWIRQPPGKGLEWI GYITFDGANNYNPSLKNRVSISRDTSKNQFSLKLSSVTAEDTATYYCTR SSYDYDVLDYWGQGTTVTVSS (SEQ ID NO: 17) | | |
| VL | DIQMTQSPSSLSASVGDRVTITCRASQDISNFLNWYQQKPGQPVKLLIY YTSRLHSGVPSRFSGSGSGTDFTLTISSLQPEDFATYYCQQGHTLPYTFG QGTKLEIK (SEQ ID NO: 18) | | |
| Fab HC | QVQLQESGPGLVKPSQTLSLTCTVTGYSITSGYYWNWIRQPPGKGLEWI GYITFDGANNYNPSLKNRVSISRDTSKNQFSLKLSSVTAEDTATYYCTR SSYDYDVLDYWGQGTTVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDKTHT (SEQ ID NO: 19) | | |
| Fab LC | DIQMTQSPSSLSASVGDRVTITCRASQDISNFLNWYQQKPGQPVKLLIY YTSRLHSGVPSRFSGSGSGTDFTLTISSLQPEDFATYYCQQGHTLPYTFG QGTKLEIKRTVAAPSVFIFPPSDEQLKSGTASVVCLLNNFYPREAKVQW KVDNALQSGNSQESVTEQDSKDSTYSLSSTLTLSKADYEKHKVYACEV THQGLSSPVTKSFNRGEC (SEQ ID NO: 20) | | |

In some embodiments, the anti-TfR1 antibody of the present disclosure comprises a heavy chain complementarity determining region 1 (CDR-H1) of SEQ ID NO: 1 (according to the IMGT definition system), a heavy chain complementarity determining region 2 (CDR-H2) of SEQ ID NO: 2 (according to the IMGT definition system), a heavy chain complementarity determining region 3 (CDR-H3) of SEQ ID NO: 3 (according to the IMGT definition system), a light chain complementarity determining region 1 (CDR-L1) of SEQ ID NO: 4 (according to the IMGT definition system), a light chain complementarity determining region 2 (CDR-L2) of SEQ ID NO: 5 (according to the IMGT definition system), and a light chain complementarity determining region 3 (CDR-L3) of SEQ ID NO: 6 (according to the IMGT definition system).

In some embodiments, the anti-TfR1 antibody of the present disclosure comprises a heavy chain complementarity determining region 1 (CDR-H1) of SEQ ID NO: 7 (according to the Kabat definition system), a heavy chain complementarity determining region 2 (CDR-H2) of SEQ ID NO: 8 (according to the Kabat definition system), a heavy chain complementarity determining region 3 (CDR-H3) of SEQ ID NO: 9 (according to the Kabat definition system), a light chain complementarity determining region 1 (CDR-L1) of SEQ ID NO: 10 (according to the Kabat definition system), a light chain complementarity determining region 2 (CDR-L2) of SEQ ID NO: 11 (according to the Kabat definition system), and a light chain complementarity determining region 3 (CDR-L3) of SEQ ID NO: 6 (according to the Kabat definition system).

In some embodiments, the anti-TfR1 antibody of the present disclosure comprises a heavy chain complementarity determining region 1 (CDR-H1) of SEQ ID NO: 12 (according to the Chothia definition system), a heavy chain complementarity determining region 2 (CDR-H2) of SEQ ID NO: 13 (according to the Chothia definition system), a heavy chain complementarity determining region 3 (CDR-H3) of SEQ ID NO: 14 (according to the Chothia definition system), a light chain complementarity determining region 1 (CDR-L1) of SEQ ID NO: 15 (according to the Chothia definition system), a light chain complementarity determining region 2 (CDR-L2) of SEQ ID NO: 5 (according to the Chothia definition system), and a light chain complementarity determining region 3 (CDR-L3) of SEQ ID NO: 16 (according to the Chothia definition system).

In some embodiments, the anti-TfR1 antibody of the present disclosure comprises a heavy chain variable region (VH) containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH comprising the amino acid sequence of SEQ ID NO: 17. Alternatively or in addition (e.g., in addition), the anti-TfR1 antibody of the present disclosure comprises a light chain variable region (VL) containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL comprising the amino acid sequence of SEQ ID NO: 18.

In some embodiments, the anti-TfR1 antibody of the present disclosure comprises a VH comprising an amino acid sequence that is at least 75% (e.g., 75%, 80%, 85%, 90%, 95%, 98%, or 99%) identical in the framework regions to the VH comprising the amino acid sequence of SEQ ID NO: 17. Alternatively or in addition (e.g., in addition), in some embodiments, the anti-TfR1 antibody of the present disclosure comprises a VL comprising an amino acid sequence that is at least 75% (e.g., 75%, 80%, 85%, 90%, 95%, 98%, or 99%) identical in the framework regions to the VL comprising the amino acid sequence of SEQ ID NO: 18.

In some embodiments, the anti-TfR1 antibody of the present disclosure comprises a VH comprising the amino acid sequence of SEQ ID NO: 17. Alternatively or in addition (e.g., in addition), in some embodiments, the anti-TfR1 antibody of the present disclosure comprises a VL comprising the amino acid sequence of SEQ ID NO: 18.

In some embodiments, the anti-TfR1 antibody of the present disclosure comprises a heavy chain comprising an amino acid sequence least 75% (e.g., 75%, 80%, 85%, 90%, 95%, 98%, or 99%) identical to the amino acid sequence of SEQ ID NO: 19. Alternatively or in addition (e.g., in addition), the anti-TfR1 antibody of the present disclosure comprises a light chain comprising an amino acid sequence least 75% (e.g., 75%, 80%, 85%, 90%, 95%, 98%, or 99%) identical to the amino acid sequence of SEQ ID NO: 20. In some embodiments, the anti-TfR1 antibody of the present disclosure is a Fab that comprises a heavy chain comprising an amino acid sequence least 75% (e.g., 75%, 80%, 85%, 90%, 95%, 98%, or 99%) identical to the amino acid sequence of SEQ ID NO: 19. Alternatively or in addition (e.g., in addition), the anti-TfR1 antibody of the present disclosure is a Fab that comprises a light chain comprising an amino acid sequence least 75% (e.g., 75%, 80%, 85%, 90%, 95%, 98%, or 99%) identical to the amino acid sequence of SEQ ID NO: 20.

In some embodiments, the anti-TfR1 antibody of the present disclosure comprises a heavy chain comprising the amino acid sequence of SEQ ID NO: 19. Alternatively or in addition (e.g., in addition), the anti-TfR1 antibody of the present disclosure comprises a light chain comprising the amino acid sequence of SEQ ID NO: 20. In some embodiments, the anti-TfR1 antibody of the present disclosure is a Fab that comprises a heavy chain comprising an amino acid sequence of SEQ ID NO: 19. Alternatively or in addition (e.g., in addition), the anti-TfR1 antibody of the present disclosure is a Fab that comprises a light chain comprising the amino acid sequence of SEQ ID NO: 20.

In some embodiments, the anti-TfR1 antibody provided herein may have one or more post-translational modifications. In some embodiments, N-terminal cyclization, also called pyroglutamate formation (pyro-Glu), may occur in the antibody at N-terminal Glutamate (Glu) and/or Glutamine (Gln) residues during production. As such, it should be appreciated that an antibody specified as having a sequence comprising an N-terminal glutamate or glutamine residue encompasses antibodies that have undergone pyroglutamate formation resulting from a post-translational modification. In some embodiments, pyroglutamate formation occurs in a heavy chain sequence. In some embodiments, pyroglutamate formation occurs in a light chain sequence.

Oligonucleotides

In some embodiments, an oligonucleotide of the complexes described herein is a single stranded oligonucleotide. In some embodiments, the oligonucleotide is useful for targeting DMPK (e.g., for reducing expression or activity of a DMPK RNA, such as the level of a mutant or wild-type DMPK RNA). In some embodiments, an oligonucleotide that is useful for targeting DMPK RNAs. (e.g., for reducing expression or activity of a DMPK RNA, such as the level of a mutant or wild-type DMPK RNA). In some embodiments, the oligonucleotide comprises a region of complementarity to a DMPK RNA. In some embodiments, the oligonucleotide is useful for reducing levels of toxic DMPK having disease-associated repeat expansions, e.g., in a subject having or suspected of having myotonic dystrophy. In some embodiments, the oligonucleotide is designed to direct RNAse H mediated degradation of the target DMPK RNA residing in the nucleus of cells, e.g., muscle cells (e.g., myotubes) or cells of the nervous system (e.g., central nervous system (CNS) cells). In some embodiments, the oligonucleotide is designed to have desirable bioavailability and/or serum-stability properties. In some embodiments, the oligonucleotide is designed to have desirable binding affinity properties. In some embodiments, the oligonucleotide is designed to have desirable toxicity profiles. In some embodiments, the oligonucleotide is designed to have low-complement activation and/or cytokine induction properties.

In some embodiments, DMPK-targeting oligonucleotides described herein are designed to caused RNase H mediated degradation of DMPK mRNA. It should be appreciated that, in some embodiments, oligonucleotides in one format (e.g., antisense oligonucleotides) may be suitably adapted to another format (e.g., siRNA oligonucleotides) by incorporating functional sequences (e.g., antisense strand sequences) from one format to the other format.

Examples of oligonucleotides useful for targeting DMPK are provided in US Patent Application Publication 20100016215A1, published on Jan. 1, 2010, entitled *Compound And Method For Treating Myotonic Dystrophy*; US Patent Application Publication 20130237585A1, published Jul. 19, 2010, *Modulation Of Dystrophia Myotonica-Protein Kinase* (*DMPK*) *Expression*; US Patent Application Publication 20150064181A1, published on Mar. 5, 2015, entitled "*Antisense Conjugates For Decreasing Expression Of Dmpk*"; US Patent Application Publication 20150238627A1, published on Aug. 27, 2015, entitled "*Peptide-Linked Morpholino Antisense Oligonucleotides For Treatment Of Myotonic Dystrophy*"; and US Patent Application Publication 20160304877A1, published on Oct. 20, 2016, entitled "*Compounds And Methods For Modulation Of Dystrophia Myotonica-Protein Kinase* (*Dmpk*) *Expression*," the contents of each of which are incorporated herein in their entireties.

In some embodiments, oligonucleotides may comprise a region of complementarity to a sequence set forth as follows, which is an example human DMPK gene sequence (Gene ID 1760; NM_001081560.2):

```
                                     (SEQ ID NO: 24)
AGGGGGGCTGGACCAAGGGGTGGGGAGAAGGGGAGGAGGCCTCGGCCGG

CCGCAGAGAGAAGTGGCCAGAGAGGCCCAGGGGACAGCCAGGGACAGGC

AGACATGCAGCCAGGGCTCCAGGGCCTGGACAGGGGCTGCCAGGCCCTG

TGACAGGAGGACCCCGAGCCCCCGGCCCGGGGAGGGGCCATGGTGCTGC

CTGTCCAACATGTCAGCCGAGGTGCGGCTGAGGCGGCTCCAGCAGCTGG

TGTTGGACCCGGGCTTCCTGGGGCTGGAGCCCCTGCTCGACCTTCTCCT

GGGCGTCCACCAGGAGCTGGGCGCCTCCGAACTGGCCCAGGACAAGTAC

GTGGCCGACTTCTTGCAGTGGGCGGAGCCCATCGTGGTGAGGCTTAAGG
```

-continued

AGGTCCGACTGCAGAGGGACGACTTCGAGATTCTGAAGGTGATCGGACG
CGGGGCGTTCAGCGAGGTAGCGGTAGTGAAGATGAAGCAGACGGGCCAG
GTGTATGCCATGAAGATCATGAACAAGTGGGACATGCTGAAGAGGGGCG
AGGTGTCGTGCTTCCGTGAGGAGAGGGACGTGTTGGTGAATGGGGACCG
GCGGTGGATCACGCAGCTGCACTTCGCCTTCCAGGATGAGAACTACCTG
TACCTGGTCATGGAGTATTACGTGGGCGGGGACCTGCTGACACTGCTGA
GCAAGTTTGGGGAGCGGATTCCGGCCGAGATGGCGCGCTTCTACCTGGC
GGAGATTGTCATGGCCATAGACTCGGTGCACCGGCTTGGCTACGTGCAC
AGGGACATCAAACCCGACAACATCCTGCTGGACCGCTGTGGCCACATCC
GCCTGGCCGACTTCGGCTCTTGCCTCAAGCTGCGGGCAGATGGAACGGT
GCGGTCGCTGGTGGCTGTGGGCACCCCAGACTACCTGTCCCCCGAGATC
CTGCAGGCTGTGGGCGGTGGGCCTGGGACAGGCAGCTACGGGCCCGAGT
GTGACTGGTGGGCGCTGGGTGTATTCGCCTATGAAATGTTCTATGGGCA
GACGCCCTTCTACGCGGATTCCACGGCGGAGACCTATGGCAAGATCGTC
CACTACAAGGAGCACCTCTCTCTGCCGCTGGTGGACGAAGGGGTCCCTG
AGGAGGCTCGAGACTTCATTCAGCGGTTGCTGTGTCCCCCGGAGACACG
GCTGGGCCGGGGTGGAGCAGGCGACTTCCGGACACATCCCTTCTTCTTT
GGCCTCGACTGGGATGGTCTCCGGGACAGCGTGCCCCCCTTTACACCGG
ATTTCGAAGGTGCCACCGACACATGCAACTTCGACTTGGTGGAGGACGG
GCTCACTGCCATGGAGACACTGTCGGACATTCGGGAAGGTGCGCCGCTA
GGGGTCCACCTGCCTTTTGTGGGCTACTCCTACTCCTGCATGGCCCTCA
GGGACAGTGAGGTCCCAGGCCCCACACCCATGGAACTGGAGGCCGAGCA
GCTGCTTGAGCCACACGTGCAAGCGCCCAGCCTGGAGCCCTCGGTGTCC
CCACAGGATGAAACAGCTGAAGTGGCAGTTCCAGCGGCTGTCCCTGCGG
CAGAGGCTGAGGCCGAGGTGACGCTGCGGGAGCTCCAGGAAGCCCTGGA
GGAGGAGGTGCTCACCCGGCAGAGCCTGAGCCGGGAGATGGAGGCCATC
CGCACGGACAACCAGAACTTCGCCAGTCAACTACGCGAGGCAGAGGCTC
GGAACCGGGACCTAGAGGCACACGTCCGGCAGTTGCAGGAGCGGATGGA
GTTGCTGCAGGCAGAGGGAGCCACAGCTGTCACGGGGGTCCCCAGTCCC
CGGGCCACGGATCCACCTTCCCATCTAGATGGCCCCCCGGCCGTGGCTG
TGGGCCAGTGCCCGCTGGTGGGGCCAGGCCCCATGCACCGCCGCCACCT
GCTGCTCCCTGCCAGGGTCCCTAGGCCTGGCCTATCGGAGGCGCTTTCC
CTGCTCCTGTTCGCCGTTGTTCTGTCTCGTGCCGCCGCCCTGGGCTGCA
TTGGGTTGGTGGCCCACGCCGGCCAACTCACCGCAGTCTGGCGCCGCCC
AGGAGCCGCCCGCGCTCCCTGAACCCTAGAACTGTCTTCGACTCCGGGG
CCCCGTTGGAAGACTGAGTGCCCGGGGCACGGCACAGAAGCCGCGCCCA
CCGCCTGCCAGTTCACAACCGCTCCGAGCGTGGGTCTCCGCCCAGCTCC
AGTCCTGTGATCCGGGCCCGCCCCCTAGCGGCCGGGGAGGGAGGGGCCG
GGTCCGCGGCCGGCGAACGGGGCTCGAAGGGTCCTTGTAGCCGGGAATG
CTGCTGCTGCTGCTGCTGCTGCTGCTGCTGCTGCTGCTGCTGCTGCTGC
TGCTGCTGCTGGGGGGATCACAGACCATTTCTTTCTTTCGGCCAGGCTG
AGGCCCTGACGTGGATGGGCAAACTGCAGGCCTGGGAAGGCAGCAAGCC
GGGCCGTCCGTGTTCCATCCTCCACGCACCCCCACCTATCGTTGGTTCG
CAAAGTGCAAAGCTTTCTTGTGCATGACGCCCTGCTCTGGGGAGCGTCT
GGCGCGATCTCTGCCTGCTTACTCGGGAAATTTGCTTTTGCCAAACCCG
CTTTTTCGGGGATCCCGCGCCCCCCTCCTCACTTGCGCTGCTCTCGGAG
CCCCAGCCGGCTCCGCCCGCTTCGGCGGTTTGGATATTTATTGACCTCG
TCCTCCGACTCGCTGACAGGCTACAGGACCCCCAACAACCCCAATCCAC
GTTTTGGATGCACTGAGACCCCGACATTCCTCGGTATTTATTGTCTGTC
CCCACCTAGGACCCCCACCCCCGACCCTCGCGAATAAAAGGCCCTCCAT
CTGCCCAAAGCTCTGGA.

In some embodiments, oligonucleotides may comprise a region of complementarity to a sequence set forth as follows, which is an example mouse DMPK gene sequence (Gene ID 13400; NM_001190490.1).

(SEQ ID NO: 25)
GAACTGGCCAGAGAGACCCAAGGGATAGTCAGGGACGGGCAGACATGCA
GCTAGGGTTCTGGGGCCTGGACAGGGGCAGCCAGGCCCTGTGACGGGAA
GACCCCGAGCTCCGGCCCGGGGAGGGGCCATGGTGTTGCCTGCCCAACA
TGTCAGCCGAAGTGCGGCTGAGGCAGCTCCAGCAGCTGGTGCTGGACCC
AGGCTTCCTGGGACTGGAGCCCCTGCTCGACCTTCTCCTGGGCGTCCAC
CAGGAGCTGGGTGCCTCTCACCTAGCCCAGGACAAGTATGTGGCCGACT
TCTTGCAGTGGGTGGAGCCCATTGCAGCAAGGCTTAAGGAGGTCCGACT
GCAGAGGGATGATTTTGAGATTTTGAAGGTGATCGGGCGTGGGGCGTTC
AGCGAGGTAGCGGTGGTGAAGATGAAACAGACGGGCCAAGTGTATGCCA
TGAAGATTATGAATAAGTGGGACATGCTGAAGAGAGGCGAGGTGTCGTG
CTTCCGGGAAGAAAGGGATGTATTAGTGAAAGGGGACCGGCGCTGGATC
ACACAGCTGCACTTTGCCTTCCAGGATGAGAACTACCTGTACCTGGTCA
TGGAATACTACGTGGGCGGGGACCTGCTAACGCTGCTGAGCAAGTTTGG
GGAGCGGATCCCCGCCGAGATGGCTCGCTTCTACCTGGCCGAGATTGTC
ATGGCCATAGACTCCGTGCACCGGCTGGGCTACGTGCACAGGGACATCA
AACCAGATAACATTCTGCTGGACCGATGTGGGCACATTCGCCTGGCAGA
CTTCGGCTCCTGCCTCAAACTGCAGCCTGATGGAATGGTGAGGTCGCTG
GTGGCTGTGGGCACCCCGGACTACCTGTCTCCTGAGATTCTGCAGGCCG
TTGGTGGAGGGCCTGGGGCAGGCAGCTACGGGCCAGAGTGTGACTGGTG
GGCACTGGGCGTGTTCGCCTATGAGATGTTCTATGGGCAGACCCCCTTC
TACGCGGACTCCACAGCCGAGACATATGCCAAGATTGTGCACTACAGGG
AACACTTGTCGCTGCCGCTGGCAGACACAGTTGTCCCCGAGGAAGCTCA
GGACCTCATTCGTGGGCTGCTGTGTCCTGCTGAGATAAGGCTAGGTCGA
GGTGGGGCAGACTTCGAGGGTGCCACGGACACATGCAATTTCGATGTGG
TGGAGGACCGGCTCACTGCCATGGTGAGCGGGGGCGGGGAGACGCTGTC
AGACATGCAGGAAGACATGCCCCTTGGGGTGCGCCTGCCCTTCGTGGGC

-continued

```
TACTCCTACTGCTGCATGGCCTTCAGAGACAATCAGGTCCCGGACCCCA

CCCCTATGGAACTAGAGGCCCTGCAGTTGCCTGTGTCAGACTTGCAAGG

GCTTGACTTGCAGCCCCCAGTGTCCCCACCGGATCAAGTGGCTGAAGAG

GCTGACCTAGTGGCTGTCCCTGCCCCTGTGGCTGAGGCAGAGACCACGG

TAACGCTGCAGCAGCTCCAGGAAGCCCTGGAAGAAGAGGTTCTCACCCG

GCAGAGCCTGAGCCGCGAGCTGGAGGCCATCCGGACCGCCAACCAGAAC

TTCTCCAGCCAACTACAGGAGGCCGAGGTCCGAAACCGAGACCTGGAGG

CGCATGTTCGGCAGCTACAGGAACGGATGGAGATGCTGCAGGCCCCAGG

AGCCGCAGCCATCACGGGGGTCCCCAGTCCCCGGGCCACGGATCCACCT

TCCCATCTAGATGGCCCCCCGGCCGTGGCTGTGGGCCAGTGCCCGCTGG

TGGGGCCAGGCCCCATGCACCGCCGTCACCTGCTGCTCCCTGCCAGGAT

CCCTAGGCCTGGCCTATCCGAGGCGCGTTGCCTGCTCCTGTTCGCCGCT

GCTCTGGCTGCTGCCGCCACACTGGGCTGCACTGGGTTGGTGGCCTATA

CCGGCGGTCTCACCCCAGTCTGGTGTTTCCCGGGAGCCACCTTCGCCCC

CTGAACCCTAAGACTCCAAGCCATCTTTCATTTAGGCCTCCTAGGAAGG

TCGAGCGACCAGGGAGCGACCCAAAGCGTCTCTGTGCCCATCGCGCCCC

CCCCCCCCCCCCACCGCTCCGCTCCACACTTCTGTGAGCCTGGGTCCCC

ACCCAGCTCCGCTCCTGTGATCCAGGCCTGCCACCTGGCGGCCGGGGAG

GGAGGAACAGGGCTCGTGCCCAGCACCCCTGGTTCCTGCAGAGCTGGTA

GCCACCGCTGCTGCAGCAGCTGGGCATTCGCCGACCTTGCTTTACTCAG

CCCCGACGTGGATGGGCAAACTGCTCAGCTCATCCGATTTCACTTTTTC

ACTCTCCCAGCCATCAGTTACAAGCCATAAGCATGAGCCCCCTATTTCC

AGGGACATCCCATTCCCATAGTGATGGATCAGCAAGACCTCTGCCAGCA

CACACGGAGTCTTTGGCTTCGGACAGCCTCACTCCTGGGGGTTGCTGCA

ACTCCTTCCCCGTGTACACGTCTGCACTCTAACAACGGAGCCACAGCTG

CACTCCCCCCTCCCCCAAAGCAGTGTGGGTATTTATTGATCTTGTTATC

TGACTCACTGACAGACTCCGGGACCCACGTTTTAGATGCATTGAGACTC

GACATTCCTCGGTATTTATTGTCTGTCCCCACCTACGACCTCCACTCCC

GACCCTTGCGAATAAAATACTTCTGGTCTGCCCTAAA.
```

In some embodiments, an oligonucleotide may comprise a region of complementarity to DMPK gene sequences of multiple species, e.g., selected from human, mouse and non-human species (e.g., cynomolgus monkey).

In some embodiments, the oligonucleotide may comprise a region of complementarity to a mutant form of DMPK, for example, a mutant form as reported in Botta A. et al. "The CTG repeat expansion size correlates with the splicing defects observed in muscles from myotonic dystrophy type 1 patients." J Med Genet. 2008 October; 45(10):639-46; and Machuca-Tzili L. et al. "Clinical and molecular aspects of the myotonic dystrophies: a review." Muscle Nerve. 2005 July; 32(1):1-18; the contents of each of which are incorporated herein by reference in their entireties.

In some embodiments, an oligonucleotide provided herein is an antisense oligonucleotide targeting DMPK. In some embodiments, the oligonucleotide targeting DMPK is any one of the antisense oligonucleotides targeting DMPK as described in US Patent Application Publication US20160304877A1, published on Oct. 20, 2016, entitled "Compounds And Methods For Modulation Of Dystrophia Myotonica-Protein Kinase (DMPK) Expression," incorporated herein by reference). In some embodiments, the DMPK targeting oligonucleotide targets a region of the DMPK gene sequence as set forth in Genbank accession No. NM_001081560.2 (SEQ ID NO: 24) or as set forth in Genbank accession No. NG_009784.1 (SEQ ID NO: 26).

In some embodiments, a DMPK targeting oligonucleotide provided herein comprises a nucleotide sequence comprising a region complementary to a target region that is at least 8 continuous nucleotides (e.g., at least 8, at least 9, at least 10, at least 12, at least 14, at least 16, at least 18, at least 20 or more continuous nucleotides) of SEQ ID NO: 24.

In some embodiments, a DMPK targeting oligonucleotide provided herein is 10-35 (e.g., 10-35, 10-30, 10-25, 10-20, 10-15, 15-35, 15-30, 15-25, 15-20, 20-35, 20-30, 13-18, 14-17, 15-18, 20-30, 15-17, 27-30, 25-35, or 30-35) nucleotides in length. In some embodiments, a DMPK targeting oligonucleotide provided herein is 10, 11, 12, 13, 14, 15, 16, 17, 18, 19, 20, 21, 22, 23, 24, 25, 26, 27, 28, 29, or 30 nucleotides in length, optionally 15-30, or 16 nucleotides in length. In some embodiments, a DMPK targeting oligonucleotide provided herein is 16 nucleotides in length.

In some embodiments, a DMPK targeting oligonucleotide provided herein comprises a region of complementarity of at least 8 (e.g., at least 8, 9, 10, 11, 12, 13, 14, 15, 16, 17, 18, 19, 20, 21, 22, 23, 24, 25, 26, 27, 28, 29, 30, or more) consecutive nucleotides to a DMPK RNA.

In some embodiments, a DMPK targeting oligonucleotide provided herein comprises a region of complementarity of at least 8 (e.g., at least 8, 9, 10, 11, 12, 13, 14, 15, 16, 17, 18, 19, 20, 21, 22, 23, 24, 25, 26, 27, 28, 29, 30, or more) consecutive nucleotides to a DMPK sequence as set forth in SEQ ID NO: 24 or 25.

In some embodiments, a DMPK targeting oligonucleotide provided herein comprises a region of complementarity of at least 8 (e.g., at least 8, 9, 10, 11, 12, 13, 14, 15, or 16) consecutive nucleotides to a target sequence as set forth in SEQ ID NO: 22 (TGACTGGTGGGCGCTG). In some embodiments, an oligonucleotide useful for targeting DMPK comprises at least 8 (e.g., at least 8, 9, 10, 11, 12, 13, 14, 15, or 16) consecutive nucleotides of a sequence as set forth in SEQ ID NO: 21 (CAGCGCCCACCAGUCA). In some embodiments, an oligonucleotide useful for targeting DMPK comprises the nucleotide sequence of SEQ ID NO: 21.

In some embodiments, the DMPK targeting oligonucleotide comprises a 5'-X—Y—Z-3' configuration. An oligonucleotide comprising a 5'-X—Y—Z-3' configuration can refer to a chimeric antisense compound in which a gap region having a plurality of nucleosides that support RNase H cleavage is positioned between flanking regions having one or more nucleosides, wherein the nucleosides comprising the gap region are chemically distinct from the nucleoside or nucleosides comprising the flanking regions. In some embodiments, an oligonucleotide described herein (e.g., a DMPK-targeting oligonucleotide described herein) comprises a 5'-X—Y—Z-3' configuration, with X and Z as flanking regions around a gap region Y. In some embodiments, the gap region Y comprises one or more 2'-deoxyribonucleosides. In some embodiments, each nucleoside in the gap region Y is a 2'-deoxyribonucleoside, and neither the flanking region X nor the flanking region Z contains any 2'-deoxyribonucleosides.

In some embodiments, the gap region Y comprises a continuous stretch of 6 or more 2'-deoxyribonucleosides, which are capable of recruiting an RNAse, such as RNAse H. In some embodiments, the oligonucleotide binds to the target nucleic acid, at which point an RNAse is recruited and can then cleave the target nucleic acid. In some embodiments, the flanking regions X and Z each comprise one or more modified nucleosides. In some embodiments, flanking regions X and Z each comprise one or more high-affinity modified nucleosides, e.g., one to six high-affinity modified nucleosides. Examples of high affinity modified nucleosides include, but are not limited to, 2'-modified nucleosides (e.g., 2'-MOE, 2'-O-Me, 2'-F) or 2'-4' bicyclic nucleosides (e.g., LNA, cEt, ENA). In some embodiments, the flanking regions X and Z may be of 1-20 nucleotides, 1-8 nucleotides, or 1-5 nucleotides in length. The flanking regions X and Z may be of similar length or of dissimilar lengths. In some embodiments, the gap region Y may comprise a nucleotide sequence of 5-20 nucleotides, 5-15 nucleotides, 5-12 nucleotides, or 6-10 nucleotides in length.

In some embodiments, the gap region Y comprises one or more unmodified internucleoside linkages. In some embodiments, one or both flanking regions X and Z each independently comprise phosphorothioate internucleoside linkages (e.g., phosphorothioate internucleoside linkages or other linkages) between at least two, at least three, at least four, at least five or more nucleotides. In some embodiments, the gap region Y and two flanking regions X and Z each independently comprise modified internucleoside linkages (e.g., phosphorothioate internucleoside linkages or other linkages) between at least two, at least three, at least four, at least five or more nucleotides.

In some embodiments, the gap region Y in the gapmer is 5-20 nucleosides in length. For example, the gap region Y may be 5-20, 5-15, 5-10, 10-20, 10-15, or 15-20 nucleosides in length. In some embodiments, the gap region Y is 5, 6, 7, 8, 9, 10, 11, 12, 13, 14, 15, 16, 17, 18, 19, or 20 nucleosides in length. In some embodiments, each nucleoside in the gap region Y is a 2'-deoxyribonucleoside. In some embodiments, all nucleosides in the gap region Y are 2'-deoxyribonucleosides. In some embodiments, one or more of the nucleosides in the gap region Y is a modified nucleoside (e.g., a 2' modified nucleoside such as those described herein). In some embodiments, one or more cytosines in the gap region Y are optionally 5-methyl-cytosines. In some embodiments, each cytosine in the gap region Y is a 5-methyl-cytosine.

In some embodiments, the flanking region X of the oligonucleotide (X in the 5'-X—Y—Z-3' configuration) and the flanking region Z of the oligonucleotide (Z in the 5'-X—Y—Z-3' configuration) are independently 1-20 nucleosides long. For example, the flanking region X of the oligonucleotide and the flanking region Z of the oligonucleotide may be independently 1-20, 1-15, 1-10, 1-7, 1-5, 1-3, 1-2, 2-5, 2-7, 3-5, 3-7, 5-20, 5-15, 5-10, 10-20, 10-15, or 15-20 nucleosides long. In some embodiments, the flanking region X of the oligonucleotide and the flanking region Z of the oligonucleotide are independently 1, 2, 3, 4, 5, 6, 7, 8, 9, 10, 11, 12, 13, 14, 15, 16, 17, 18, 19, or 20 nucleosides long. In some embodiments, the flanking region X of the oligonucleotide and the flanking region Z of the oligonucleotide are of the same length. In some embodiments, the flanking region X of the oligonucleotide and the flanking region Z of the oligonucleotide are of different lengths. In some embodiments, the flanking region X of the oligonucleotide is longer than the flanking region Z of the oligonucleotide. In some embodiments, the flanking region X of the oligonucleotide is shorter than the flanking region Z of the oligonucleotide.

In some embodiments, an oligonucleotide described herein (e.g., a DMPK targeting oligonucleotide) comprises a 5'-X—Y—Z-3' configuration of 5-10-5, 4-12-4, 3-14-3, 2-16-2, 1-18-1, 3-10-3, 2-10-2, 1-10-1, 2-8-2, 4-6-4, 3-6-3, 2-6-2, 4-7-4, 3-7-3, 2-7-2, 4-8-4, 3-8-3, 2-8-2, 1-8-1, 2-9-2, 1-9-1, 2-10-2, 1-10-1, 1-12-1, 1-16-1, 2-15-1, 1-15-2, 1-14-3, 3-14-1, 2-14-2, 1-13-4, 4-13-1, 2-13-3, 3-13-2, 1-12-5, 5-12-1, 2-12-4, 4-12-2, 3-12-3, 1-11-6, 6-11-1, 2-11-5, 5-11-2, 3-11-4, 4-11-3, 1-17-1, 2-16-1, 1-16-2, 1-15-3, 3-15-1, 2-15-2, 1-14-4, 4-14-1, 2-14-3, 3-14-2, 1-13-5, 5-13-1, 2-13-4, 4-13-2, 3-13-3, 1-12-6, 6-12-1, 2-12-5, 5-12-2, 3-12-4, 4-12-3, 1-11-7, 7-11-1, 2-11-6, 6-11-2, 3-11-5, 5-11-3, 4-11-4, 1-18-1, 1-17-2, 2-17-1, 1-16-3, 1-16-3, 2-16-2, 1-15-4, 4-15-1, 2-15-3, 3-15-2, 1-14-5, 5-14-1, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 1-11-8, 8-11-1, 2-11-7, 7-11-2, 3-11-6, 6-11-3, 4-11-5, 5-11-4, 1-18-1, 1-17-2, 2-17-1, 1-16-3, 3-16-1, 2-16-2, 1-15-4, 4-15-1, 2-15-3, 3-15-2, 1-14-5, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 1-11-8, 8-11-1, 2-11-7, 7-11-2, 3-11-6, 6-11-3, 4-11-5, 5-11-4, 1-19-1, 1-18-2, 2-18-1, 1-17-3, 3-17-1, 2-17-2, 1-16-4, 4-16-1, 2-16-3, 3-16-2, 1-15-5, 2-15-4, 4-15-2, 3-15-3, 1-14-6, 6-14-1, 2-14-5, 5-14-2, 3-14-4, 4-14-3, 1-13-7, 7-13-1, 2-13-6, 6-13-2, 3-13-5, 5-13-3, 4-13-4, 1-12-8, 8-12-1, 2-12-7, 7-12-2, 3-12-6, 6-12-3, 4-12-5, 5-12-4, 2-11-8, 8-11-2, 3-11-7, 7-11-3, 4-11-6, 6-11-4, 5-11-5, 1-20-1, 1-19-2, 2-19-1, 1-18-3, 3-18-1, 2-18-2, 1-17-4, 4-17-1, 2-17-3, 3-17-2, 1-16-5, 2-16-4, 4-16-2, 3-16-3, 1-15-6, 6-15-1, 2-15-5, 5-15-2, 3-15-4, 4-15-3, 1-14-7, 7-14-1, 2-14-6, 6-14-2, 3-14-5, 5-14-3, 4-14-4, 1-13-8, 8-13-1, 2-13-7, 7-13-2, 3-13-6, 6-13-3, 4-13-5, 5-13-4, 2-12-8, 8-12-2, 3-12-7, 7-12-3, 4-12-6, 6-12-4, 5-12-5, 3-11-8, 8-11-3, 4-11-7, 7-11-4, 5-11-6, 6-11-5, 1-21-1, 1-20-2, 2-20-1, 1-20-3, 3-19-1, 2-19-2, 1-18-4, 4-18-1, 2-18-3, 3-18-2, 1-17-5, 2-17-4, 4-17-2, 3-17-3, 1-16-6, 6-16-1, 2-16-5, 5-16-2, 3-16-4, 4-16-3, 1-15-7, 7-15-1, 2-15-6, 6-15-2, 3-15-5, 5-15-3, 4-15-4, 1-14-8, 8-14-1, 2-14-7, 7-14-2, 3-14-6, 6-14-3, 4-14-5, 5-14-4, 2-13-8, 8-13-2, 3-13-7, 7-13-3, 4-13-6, 6-13-4, 5-13-5, Jan. 12, 2010, 10-12-1, 2-12-9, 9-12-2, 3-12-8, 8-12-3, 4-12- 7, 7-12-4, 5-12-6, 6-12-5, 4-11-8, 8-11-4, 5-11-7, 7-11-5, 6-11-6, 1-22-1, 1-21-2, 2-21-1, 1-21-3, 3-20-1, 2-20-2, 1-19-4, 4-19-1, 2-19-3, 3-19-2, 1-18-5, 2-18-4, 4-18-2, 3-18-3, 1-17-6, 6-17-1, 2-17-5, 5-17-2, 3-17-4, 4-17-3, 1-16-7, 7-16-1, 2-16-6, 6-16-2, 3-16-5, 5-16-3, 4-16-4, 1-15-8, 8-15-1, 2-15-7, 7-15-2, 3-15-6, 6-15-3, 4-15-5, 5-15-4, 2-14-8, 8-14-2, 3-14-7, 7-14-3, 4-14-6, 6-14-4, 5-14-5, 3-13-8, 8-13-3, 4-13-7, 7-13-4, 5-13-6, 6-13-5, 4-12-8, 8-12-4, 5-12-7, 7-12-5, 6-12-6, 5-11-8, 8-11-5, 6-11-7, or 7-11-6. The numbers indicate the number of nucleosides in X, Y, and Z regions, respectively, in an oligonucleotide comprising the 5'-X—Y—Z-3' configuration.

In some embodiments, one or more nucleosides in the flanking region X of the oligonucleotide (X in the 5'-X—Y—Z-3' configuration) or the flanking region Z of the oligonucleotide (Z in the 5'-X—Y—Z-3' configuration) are modified nucleosides (e.g., high-affinity modified nucleosides). In some embodiments, the modified nucleoside (e.g., high-affinity modified nucleosides) is a 2'-modified nucleoside. In some embodiments, the 2'-modified nucleoside is a 2'-4' bicyclic nucleoside or a non-bicyclic 2'-modified nucleoside. In some embodiments, the high-affinity modified nucleoside is a 2'-4' bicyclic nucleoside (e.g., LNA, cEt, or ENA) or a non-bicyclic 2'-modified nucleoside (e.g., 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA)).

In some embodiments, an oligonucleotide described herein (e.g., a DMPK targeting oligonucleotide described herein) comprises a 5'-X—Y—Z-3' configuration, wherein X and Z are independently 2-7 (e.g., 2, 3, 4, 5, 6, or 7) nucleosides in length and Y is 6-10 (e.g., 6, 7, 8, 9, or 10) nucleosides in length, wherein at least one but not all (e.g., 1, 2, 3, 4, 5, or 6) of positions 1, 2, 3, 4, 5, 6, or 7 in X (the 5'-most position is position 1) is a non-bicyclic 2'-modified nucleoside (e.g., 2'-MOE or 2'-O-Me), wherein the rest of the nucleosides in both X and Z are 2'-4' bicyclic nucleosides (e.g., LNA or cEt), and wherein each nucleoside in Y is a 2' deoxyribonucleoside. In some embodiments, an oligonucleotide described herein (e.g., a DMPK targeting oligonucleotide described herein) comprises a 5'-X—Y—Z-3' configuration, wherein X and Z are independently 2-7 (e.g., 2, 3, 4, 5, 6, or 7) nucleosides in length and Y is 6-10 (e.g., 6, 7, 8, 9, or 10) nucleosides in length, wherein at least one but not all (e.g., 1, 2, 3, 4, 5, or 6) of positions 1, 2, 3, 4, 5, 6, or 7 in Z (the 5'-most position is position 1) is a non-bicyclic 2'-modified nucleoside (e.g., 2'-MOE or 2'-O-Me), wherein the rest of the nucleosides in both X and Z are 2'-4' bicyclic nucleosides (e.g., LNA or cEt), and wherein each nucleoside in Y is a 2' deoxyribonucleoside. In some embodiments, an oligonucleotide described herein (e.g., a DMPK targeting oligonucleotide described herein) comprises a 5'-X—Y—Z-3' configuration, wherein X and Z are independently 2-7 (e.g., 2, 3, 4, 5, 6, or 7) nucleosides in length and Y is 6-10 (e.g., 6, 7, 8, 9, or 10) nucleosides in length, wherein at least one but not all (e.g., 1, 2, 3, 4, 5, or 6) of positions 1, 2, 3, 4, 5, 6, or 7 in X and at least one of positions but not all (e.g., 1, 2, 3, 4, 5, or 6) of positions 1, 2, 3, 4, 5, 6, or 7 in Z (the 5'-most position is position 1) is a non-bicyclic 2'-modified nucleoside (e.g., 2'-MOE or 2'-O-Me), wherein the rest of the nucleosides in both X and Z are 2'-4' bicyclic nucleosides (e.g., LNA or cEt), and wherein each nucleoside in Y is a 2' deoxyribonucleoside.

In some embodiments, an oligonucleotide described herein (e.g., a DMPK targeting oligonucleotide) is 10-20 nucleosides (e.g., 10, 11, 12, 13, 14, 15, 16, 17, 18, 19, or 20 nucleosides) in length, comprises a region of complementarity to at least 8 consecutive nucleosides (e.g., at least 8, at least 9, at least 10, at least 11, at least 12, at least 13, at least 14, at least 15, or 16 consecutive nucleosides) of SEQ ID NO: 22 (TGACTGGTGGGCGCTG), and comprises a 5'-X—Y—Z-3' configuration, wherein X comprises 3-5 (e.g., 3, 4, or 5) linked nucleosides, wherein at least one of the nucleosides in X is a 2'-modified nucleoside (e.g., 2'-MOE modified nucleoside, 2'-O-Me modified nucleoside, LNA, cEt, or ENA); Y comprises 6-10 (e.g., 6, 7, 8, 9, or 10) linked 2'-deoxyribonucleosides, wherein each cytosine in Y is optionally and independently a 5-methyl-cytosine; and Z comprises 3-5 (e.g., 3, 4, or 5) linked nucleosides, wherein at least one of the nucleosides in Z is a 2'-modified nucleoside (e.g., 2'-MOE modified nucleoside, 2'-O-Me modified nucleoside, LNA, cEt, or ENA).

In some embodiments, an oligonucleotide described herein (e.g., a DMPK targeting oligonucleotide described herein) comprises at least 8 consecutive nucleosides (e.g., at least 8, at least 9, at least 10, at least 11, at least 12, at least 13, at least 14, at least 15, or 16 consecutive nucleosides consecutive nucleosides) of the nucleotide sequence of SEQ ID NO: 21 (CAGCGCCCACCAGUCA), and comprises a 5'-X—Y—Z-3' configuration, wherein X comprises 3-5 (e.g., 3, 4, or 5) linked nucleosides, wherein at least one of the nucleosides in X is a 2'-modified nucleoside (e.g., 2'-MOE modified nucleoside, 2'-O-Me modified nucleoside, LNA, cEt, or ENA); Y comprises 6-10 (e.g., 6, 7, 8, 9, or 10) linked 2'-deoxyribonucleosides, wherein each cytosine in Y is optionally and independently a 5-methyl-cytosine; and Z comprises 3-5 (e.g., 3, 4, or 5) linked nucleosides, wherein at least one of the nucleosides in Z is a 2'-modified nucleoside (e.g., 2'-MOE modified nucleoside, 2'-O-Me modified nucleoside, LNA, cEt, or ENA). In some embodiments, each thymine base (T) of the nucleotide sequence of the antisense oligonucleotide may independently and optionally be replaced with a uracil base (U), and each U may independently and optionally be replaced with a T.

In some embodiments, an oligonucleotide described herein (e.g., a DMPK targeting oligonucleotide described herein) comprises the nucleotide sequence of SEQ ID NO: 21 and comprises a 5'-X—Y—Z-3' configuration, wherein X comprises 3-5 (e.g., 3, 4, or 5) linked nucleosides, wherein at least one of the nucleosides in X is a 2'-modified nucleoside (e.g., 2'-MOE modified nucleoside, 2'-O-Me modified nucleoside, LNA, cEt, or ENA); Y comprises 6-10 (e.g., 6, 7, 8, 9, or 10) linked 2'-deoxyribonucleosides, wherein each cytosine in Y is optionally and independently a 5-methyl-cytosine; and Z comprises 3-5 (e.g., 3, 4, or 5) linked nucleosides, wherein at least one of the nucleosides in Z is a 2'-modified nucleoside (e.g., 2'-MOE modified nucleoside, 2'-O-Me modified nucleoside, LNA, cEt, or ENA). In some embodiments, each thymine base (T) of the nucleotide sequence of the antisense oligonucleotide may independently and optionally be replaced with a uracil base (U), and each U may independently and optionally be replaced with a T.

In some embodiments, X comprises at least one 2'-4' bicyclic nucleoside (e.g., LNA, cEt, or ENA) and at least one non-bicyclic 2'-modified nucleoside e.g., 2'-MOE modified nucleoside or 2'-O-Me modified nucleoside, and/or (e.g., and) Z comprises at least one 2'-4' bicyclic nucleoside (e.g., LNA, cEt, or ENA) and at least one non-bicyclic 2'-modified nucleoside (e.g., 2'-MOE modified nucleoside or 2'-O-Me modified nucleoside).

In some embodiments, the 2'-4' bicyclic nucleoside is selected from LNA, cEt, and ENA nucleosides. In some embodiments, the non-bicyclic 2'-modified nucleoside is a 2'-MOE modified nucleoside or a 2'-OMe modified nucleoside.

In some embodiments, the nucleosides of the oligonucleotides are joined together by phosphorothioate internucleoside linkages, phosphodiester internucleoside linkages or a combination thereof. In some embodiments, the oligonucleotide comprises only phosphorothioate internucleoside linkages joining each nucleoside (i.e., the oligonucleotide comprises a fully phosphorothioate backbone). In some embodiments, the oligonucleotide comprises at least one phosphorothioate internucleoside linkage. In some embodiments, the oligonucleotide comprises a mix of phosphorothioate and phosphodiester internucleoside linkages. In some embodiments, the oligonucleotide comprises only phosphorothioate internucleoside linkages joining each pair of 2'-deoxyribonucleosides and a mix of phosphorothioate and phosphodiester internucleoside linkages joining the remaining nucleosides.

In some embodiments, the oligonucleotide comprises a 5'-X—Y—Z-3' configuration of LLEE-$(D)_8$-EELL, wherein "E" is a 2'-MOE modified ribonucleoside; "L" is LNA; "D" is a 2'-deoxyribonucleoside; and "10" or "8" is the number of 2'-deoxyribonucleosides in Y, and wherein the oligonucleotide comprises phosphorothioate internucleoside linkages, phosphodiester internucleoside linkages or a combination thereof.

In some embodiments, each cytidine (e.g., a 2'-modified cytidine) in X and/or Z of the oligonucleotide is optionally 2'-MOE-uridine, * represents a phosphorothioate internucleoside linkage.

In some embodiments, an oligonucleotide described herein (e.g., a DMPK targeting oligonucleotide described herein) comprises a structure of the formula (Ie):

(Ie)

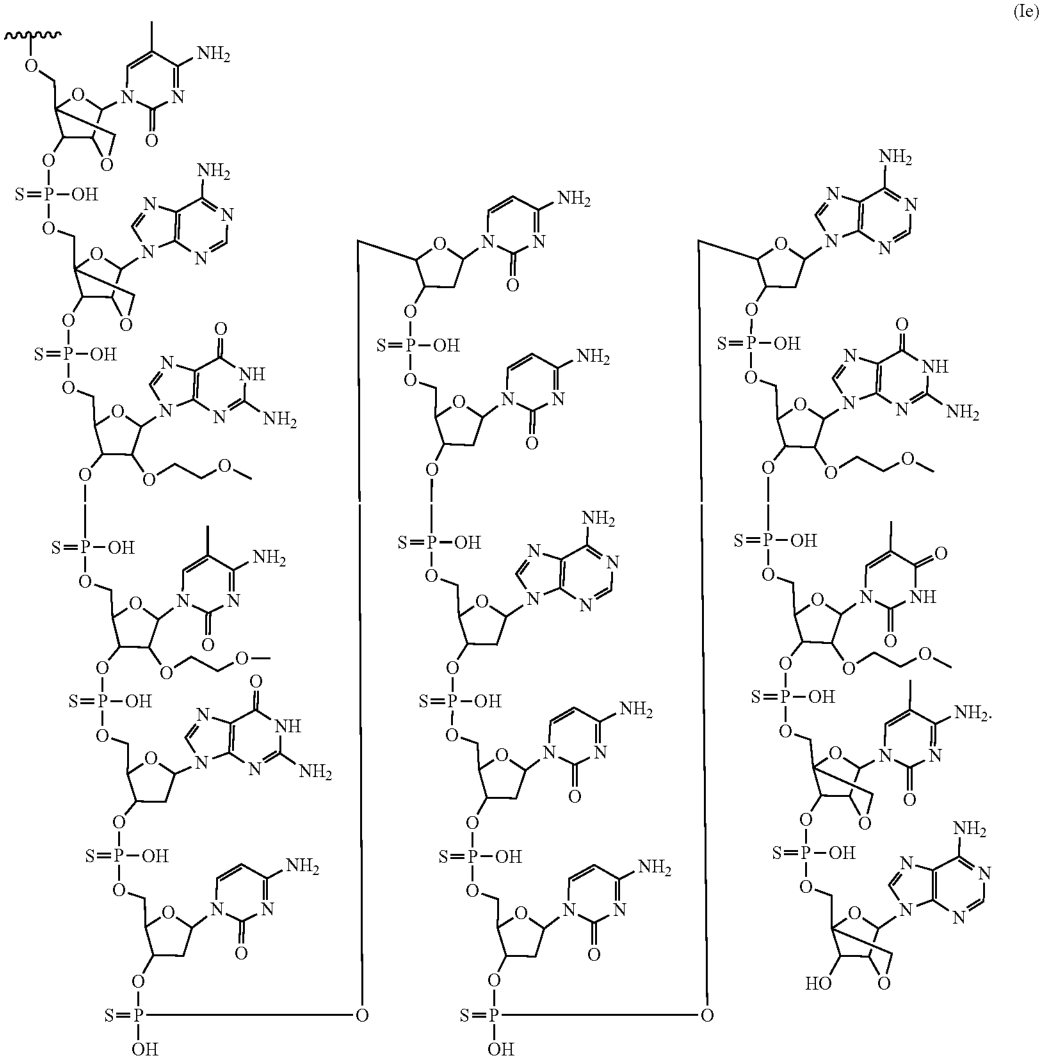

and independently a 5-methyl-cytidine, and/or each uridine (e.g., a 2'-modified uridine) in X and/or Z is optionally and independently a 5-methyl-uridine.

In some embodiments, an oligonucleotide described herein (e.g., a DMPK targeting oligonucleotide described herein) comprises a 5'-X—Y—Z-3' configuration and comprises a nucleobase sequence of CAGCGCCCACCAGUCA (SEQ ID NO: 21). In some embodiments, an oligonucleotide described herein (e.g., a DMPK targeting oligonucleotide described herein) comprises a structure of +C*+A*OG*oC*dG*dC*dC*dC*dA*dC*dC*dA*OG*OU*+C*+A (SEQ ID NO: 21), wherein +N represents an LNA (2'-4' methylene bridge) ribonucleoside, dN represents a 2'-deoxyribonucleoside, oN represents a 2'-O-methoxyethyl (MOE) modified ribonucleoside, oC represents a 5-methyl-2'-MOE-cytidine, +C represents a 5-methyl-2'-4'-bicyclic-cytidine (2'-4' methylene bridge), oU represents a 5-methyl- In some embodiments, an oligonucleotide described herein (e.g., a DMPK targeting oligonucleotide described herein) can be in salt form, e.g., as sodium, potassium, or magnesium salts.

In some embodiments, the 5' or 3' nucleoside (e.g., terminal nucleoside) of the oligonucleotide is conjugated to an amine group, optionally via a spacer. In some embodiments, the spacer comprises an aliphatic moiety. In some embodiments, the spacer comprises a polyethylene glycol moiety. In some embodiments, a phosphodiester linkage is present between the spacer and the 5' or 3' nucleoside of the oligonucleotide. In some embodiments, the 5' or 3' nucleoside (e.g., terminal nucleoside) of an oligonucleotide described herein is covalently linked to a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, —O—, —$N(R^A)$—, —S—, —C(═O)—, —C(═O)O—, —C(═O)$NR^A$—, —$NR^A$C(═O)—, —$NR^A$C(═O)$R^A$—, —C(═O)$R^A$—, —$NR^A$C(═O)O—, —$NR^A$C(═O)$N(R^A)$—, —OC(═O)—, —OC(═O)O—, —OC(═O)$N(R^A)$—, —$S(O)_2NR^A$—, —$NR^AS(O)_2$—, or a combination thereof; each $R^A$ is independently hydrogen or substituted or unsubstituted alkyl. In certain embodiments, the spacer is a substituted or unsubstituted alkylene, substituted or unsubstituted heterocyclylene, substituted or unsubstituted heteroarylene, —O—, —$N(R^A)$—, or —C(═O)N $(R^A)_2$, or a combination thereof.

In some embodiments, the 5' or 3' nucleoside of the oligonucleotide is conjugated to a compound of the formula —$NH_2$—$(CH_2)_n$—, wherein n is an integer from 1 to 12. In some embodiments, n is 6, 7, 8, 9, 10, 11, or 12. In some embodiments, a phosphodiester linkage is present between the compound of the formula $NH_2$—$(CH_2)_n$— and the 5' or 3' nucleoside of the oligonucleotide. In some embodiments, a compound of the formula $NH_2$—$(CH_2)_6$— is conjugated to the oligonucleotide via a reaction between 6-amino-1-hexanol ($NH_2$—$(CH_2)_6$—OH) and the 5' phosphate of the oligonucleotide.

In some embodiments, the oligonucleotide is conjugated to a targeting agent, e.g., a muscle targeting agent such as an anti-TfR1 antibody, e.g., via an amine group of a lysine of the targeting agent.

In some embodiments, it should be appreciated that methylation of the nucleobase uracil at the C5 position forms thymine. Thus, in some embodiments, a nucleotide or nucleoside having a C5 methylated uracil (or 5-methyluracil) may be equivalently identified as a thymine nucleotide or nucleoside.

In some embodiments, any one or more of the thymine bases (T's) in any one of the oligonucleotides provided herein may independently and optionally be uracil bases (U's), and/or any one or more of the U's in the oligonucleotides provided herein (e.g., the oligonucleotide as set forth in SEQ ID NO: 21) may independently and optionally be T's.

Compositions

In some embodiments, compositions described herein comprise complexes (i.e., a plurality of complexes), each of which complex comprises an antibody (e.g., anti-TFR1 antibody) covalently linked to one or more oligonucleotides (e.g., a DMPK-targeting oligonucleotide described herein), wherein the antibody comprises a heavy chain comprising a heavy chain variable region (VH) and a heavy chain constant region, and a light chain comprising a light chain variable region (VL) and a light chain constant region. In some embodiments, the antibody of such complexes comprises a CDR-H1, CDR-H2, CDR-H3, CDR-L1, CDR-L2, and CDR-L3 as set forth in Table 2. Complexes of a composition described herein can comprise any structure provided herein, e.g., a structure of formula (I) (e.g., comprising a group of the formula (Ia), formula (Ib), formula (Ic), or formula (Id)) or formula (A).

In some embodiments, compositions described herein comprise complexes (i.e., a plurality of complexes) wherein each complex comprises a structure of formula (I): $[R^1]_{n1}$—$R^2$, in which each $R^1$ independently comprises a compound comprising an oligonucleotide (e.g., a DMPK-targeting oligonucleotide described herein) and is covalently linked to $R^2$, wherein $R^2$ comprises an antibody (e.g., anti-TfR1 antibody) comprising a heavy chain comprising a heavy chain variable region (VH) and a heavy chain constant region, and a light chain comprising a light chain variable region (VL) and a light chain constant region. In some embodiments, each $R^1$ of a complex is independently covalently linked to a different amino acid residue (e.g., lysine or cysteine) of $R^2$.

In some embodiments, the value of n1 of complexes in the composition is independently and optionally an integer from one up to the number of amino acid residues to which conjugation is desired or targeted (e.g., the number of lysine residues) in the antibody (e.g., an antibody comprised within $R^2$). In some embodiments, the value of n1 of each complex in the composition is independently and optionally selected from 1, 2, 3, 4, 5, 6, 7, 8, 9, 10, 11, 12, 13, 14, 15, 16, 17, 18, 19, 20, 21, 22, 23, 24, 25, 26, and 27. In some embodiments, the value of n1 of each complex in the composition is independently and optionally selected from 1, 2, 3, 4, 5, 6, 7, 8, 9, 10, 11, 12, 13, 14, 15, 16, 17, 18, 19, 20, 21, 22, 23, 24, 25 and 26. In some embodiments, the value of n1 of each complex in the composition is independently selected and optionally from an integer in the range of 1 to 27, 1 to 26, 1 to 10, 1 to 5, or 1 to 3. In some embodiments, the average value of n1 of complexes of the composition is in the range of 1 to 2, 1 to 3, 1 to 5, 1 to 10, 1 to 26, or 1 to 27. In some embodiments, compositions described herein comprise complexes in which the value of n1 is 0. In some embodiments, the average value of n1 of complexes of the composition is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2).

In some embodiments, a composition described herein comprises antibody that is not conjugated to an oligonucleotide (e.g., in trace amounts) and antibody conjugated to one or more oligonucleotides. In some embodiments, antibody that is not conjugated to an oligonucleotide may be referred to as a compound comprising a structure of formula (I): $[R^1]_{n1}$—$R^2$, for which n1 is zero. Accordingly, in some embodiments, a composition for administration to a subject in the methods described herein comprises compounds (e.g., complexes) comprising a structure of formula (I): $[R^1]_{n1}$—$R^2$, for which each $R^1$ independently comprises a group comprising an oligonucleotide, $R^2$ comprises an antibody and n1 is independently an integer of zero or greater that reflects the number of instances of $R^1$ in each compound (e.g., complex). In some embodiments, the fraction of compounds comprising a structure of formula (I): $[R^1]_{n1}$—$R^2$, in a composition, for which n1 is zero, compared with all compounds of that structure in the composition for which n1 is one or greater, is less than 10%, less than 5%, less than 1% less than 0.5%, less than 0.1%, less than 0.05%, or less than 0.01%. As such, in some embodiments, the average value of n1 of complexes in a composition disclosed herein is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2).

Formulations

Complexes provided herein are formulated in a manner suitable for pharmaceutical use. In some embodiments, complexes can be delivered to a subject using a formulation that minimizes degradation, facilitates delivery and/or (e.g., and) uptake, or provides another beneficial property to complexes in the formulation. Accordingly, in some embodiments, it has been found that formulating complexes (e.g., complexes comprising an oligonucleotide covalently linked with a Fab) with tris(hydroxymethyl)aminomethane (also known as tromethamine or THAM) and/or sucrose is particularly advantageous for pharmaceutical use, e.g., as described herein. Thus, in some embodiments, provided herein are formulations (e.g., aqueous solutions, lyophilized forms, or frozen forms) comprising complexes together with tris(hydroxymethyl)aminomethane and/or sucrose. Such formulations can be suitably prepared such that when administered to a subject, either into the immediate environment of a target cell or systemically, a sufficient amount of the complexes enter target muscle cells.

In some embodiments, formulations are provided herein that comprise complexes (i.e., a plurality of complexes) that comprise an oligonucleotide (e.g., an oligonucleotide comprising a 5'-X—Y—Z-3' configuration) covalently linked to an antibody. In some embodiments, provided herein is a formulation comprising complexes, in which each complex comprises an oligonucleotide (e.g., an oligonucleotide comprising a 5'-X—Y—Z-3' configuration) covalently linked to an anti-TfR1 antibody, optionally wherein the antibody of such complexes comprises a CDR-H1, CDR-H2, CDR-H3, CDR-L1, CDR-L2, and CDR-L3 as set forth in Table 2, and further, in some embodiments, wherein the complexes are formulated with tris(hydroxymethyl)aminomethane and sucrose. In some embodiments, the antibody is an anti-TfR1 antibody.

In some embodiments, formulations are provided that comprise complexes comprising a structure of formula (I): $[R^1]_{n1}$—$R^2$, in which each $R^1$ independently comprises a compound comprising an oligonucleotide (e.g., e.g., an oligonucleotide comprising a 5'-X—Y—Z-3' configuration) and $R^2$ comprises an antibody (e.g., anti-TfR1 antibody), and in which n1 is an integer representing the number of instances of $R^1$ in the complex.

In some embodiments, formulations described herein comprise complexes comprising an antibody that comprises a CDR-H1, CDR-H2, CDR-H3, CDR-L1, CDR-L2, and CDR-L3 as set forth in Table 2. In some embodiments, the antibody comprises a VH comprising the amino acid sequence of SEQ ID NO: 17 and a VL comprising the amino acid sequence of SEQ ID NO: 18. In some embodiments, the antibody is a Fab and comprises a heavy chain comprising the amino acid sequence of SEQ ID NO: 19 and a light chain comprising the amino acid sequence of SEQ ID NO: 20.

In some embodiments, a formulation described herein comprises complexes described herein at a concentration of between 1-50 mg of the complex per mL of the formulation. In some embodiments, a formulation described herein comprises complexes at a concentration of 10-50 mg/ml or 20-35 mg/mL (e.g., 15-45 mg/mL, 20-40 mg/mL, 25-35 mg/mL, 25.5-34.5 mg/mL, 26-34 mg/mL, 27-33 mg/mL, 28-32 mg/mL, 29-31 mg/mL, 29.5-30.5 mg/mL, 10-40 mg/mL, 15-35 mg/mL, 20-30 mg/mL, 21-29 mg/mL, 21.2-28.8 mg/mL, 22-28 mg/mL, 23-27 mg/mL, 24-26 mg/mL, or 24.5-25.5 mg/mL). In some embodiments, a formulation described herein comprises complexes at a concentration of approximately 25 mg/mL (e.g., 25 mg/mL). In some embodiments, a formulation described herein comprises complexes at a concentration of approximately 30 mg/mL (e.g., 30 mg/mL). In some embodiments, the concentration of complexes in a formulation may vary by up to 20% (e.g., +/−up to 20%, +/−up to 15%, +/−up to 10%, or +/−up to 5%) of a set value. For example, in some embodiments, the concentration of complexes in the formulation is 30 mg/mL+/−up to 15% (e.g., 30+/−4.5 mg/mL). In some embodiments, the concentration of complexes in the formula is 25 mg/mL+/−up to 15% (e.g., 25+/−3.8 mg/mL).

In some embodiments, any one or a plurality of the complexes described herein is formulated with tris(hydroxymethyl)aminomethane and sucrose in an aqueous solution. In some embodiments, the tris(hydroxymethyl)aminomethane is present in the aqueous solution at a concentration in the range of 5-50 mM (e.g., 5-40 mM, 5-35 mM, 5-30 mM, 10-50 mM, 15-45 mM, 10-40 mM, 20-40 mM, 20-35 mM, 20-30 mM, 21-29 mM, 22-28 mM, 23-27 mM, 24-26 mM). In some embodiments, the tris(hydroxymethyl)aminomethane is present in the aqueous solution at a concentration of approximately 25 mM (e.g., 25 mM). In some embodiments, the sucrose is present in the aqueous solution at a concentration in the range of 5% to 15% weight per volume (w/v %), for example, 7-13 w/v %, 8-15% w/v %, 9-15% w/v %, 9-11% w/v %, 9.5-11% w/v %, or for example, in the range of 9-10 w/v %, 10-11 w/v %, 10-12 w/v %, or 8-12 w/v %. In some embodiments, the sucrose is present in the aqueous solution at a concentration in the range of 7-13 w/v %, 8-12 w/v %, or 9-11 w/v %. In some embodiments, the sucrose is present in the aqueous solution at a concentration of approximately 10 w/v % (e.g., 10 w/v %). In some embodiments, the aqueous solution has a pH in the range of 6.5 to 8.5, for example, 6.5-6.5, 6.7-6.9, 6.9-7.1, 7.1-7.3, 7.2-7.8, 7.3-7.5, 7.4-7.5, 7.4-7.6, 7.5-7.6; for example, 7.0-8.0, or for example, in the pH range of 7.0-7.3, 7.2-7.8, 7.3-7.5, 7.4-7.6, 7.5-7.6, 7.5-7.7, 7.7-7.9, 7.9-8.0, 8.0-8.2, 8.2-8.4, 8.3-8.4, 8.4-8.5, 8.5-8.6, or 7.3-7.7. In some embodiments, the aqueous solution has a pH in the range of 7.0-8.0 (e.g., 7.0-7.8, 7.1-7.8, 7.2-7.8, 7.3-7.7, 7.3-7.5, 7.3-7.6, 7.4-7.6, or 7.4-7.8). In some embodiments, the aqueous solution has a pH of approximately 7.5 (e.g., 7.5). In some embodiments, the aqueous solution has a pH in the range of 7.4-7.7. In some embodiments, the aqueous solution has a pH in the range of 7.4-7.6 (e.g., 7.5, or about 7.5).

In some embodiments, any one of the formulations described herein is an aqueous solution, wherein tris(hydroxymethyl)aminomethane is present in the aqueous solution at a concentration of approximately 25 mM (e.g., 25 mM), wherein sucrose is present in the aqueous solution at a concentration of approximately 10 w/v % (e.g., 10 w/v %), and wherein the aqueous solution is at a pH of approximately 7.5 (e.g., 7.5).

In some embodiments, any one of the formulations described herein is an aqueous solution, wherein tris(hydroxymethyl)aminomethane is present in the aqueous solution at a concentration of approximately 25 mM (e.g., 25 mM), wherein sucrose is present in the aqueous solution at a concentration of approximately 10 w/v % (e.g., 10 w/v %), wherein complexes are present in the aqueous solution at a concentration of approximately 20-35 mg/ml (e.g., 25 mg/ml or 30 mg/ml) and wherein the aqueous solution is at a pH of approximately 7.5 (e.g., 7.5).

In some embodiments, any one or a plurality of the complexes described herein is formulated with tris(hydroxymethyl)aminomethane and sucrose in a lyophilized form (e.g., lyophilized powder). In some embodiments, the lyophilized form (e.g., lyophilized powder) is obtained by lyophilization of any one of the aqueous solutions described herein.

In some embodiments, a lyophilized form is a lyophilized cake. In some embodiments, a lyophilized cake comprises a plurality of complexes provided herein, tris(hydroxymethyl) aminomethane, and sucrose. In some embodiments, a lyophilized cake comprises $1\times10^{-2}$ mg-1.5 mg (e.g., $1\times10^{-2}$ mg-1.5 mg, $4.02\times10^{-2}$ mg-1.21 mg, $6\times10^{-2}$ mg-1 mg, $8\times10^{-2}$ mg-1 mg, 0.1 mg-1 mg, 0.05 mg-0.2 mg, 0.05 mg-0.3 mg, 0.05 mg-0.4 mg, 0.1 mg-0.2 mg, 0.1 mg-0.3 mg, 0.1 mg-0.4 mg, 0.1 mg-0.5 mg, 0.2 mg-0.3 mg, 0.2 mg-0.4 mg, 0.2 mg-0.4 mg, 0.3 mg-0.4 mg, or 0.3 mg-0.5 mg) tris(hydroxymethyl)aminomethane per g of cake. In some embodiments, a lyophilized cake comprises 900 mg-1100 mg (e.g., 900 mg-1100 mg, 989 mg-999 mg, 950 mg-1000 mg, 980 mg-1000 mg, 980 mg-990 mg, 990 mg-1000 mg, 995 mg-1000 mg, 992 mg-998 mg, 994 mg-999 mg) sucrose per g of cake. In some embodiments, a lyophilized cake comprises 0.5 mg-10 mg (e.g., 0.5 mg-10 mg, 0.5 mg-1.5 mg, 1 mg-2 mg, 1.5 mg-3 mg, 1 mg-8 mg, 0.5 mg-6 mg, 0.5 mg-5 mg, 1.5 mg-3.5 mg, 1.5 mg-4 mg, 1.5 mg-5 mg, 2 mg-5 mg, 2.5 mg-5 mg, 2 mg-3 mg, 3 mg-4 mg, 4 mg-5 mg) of complexes per g of cake.

In some embodiments, a lyophilized cake comprises 0.303 mg tris(hydroxymethyl)aminomethane per g of cake, 998.6 mg sucrose per g of cake, and/or (e.g., and) 0.999 mg complexes per g of cake. In some embodiments, a lyophilized cake comprises 0.302 mg tris(hydroxymethyl)aminomethane per g of cake, 997.7 mg sucrose per g of cake, and/or (e.g., and) 1.995 mg complexes per g of cake. In some embodiments, a lyophilized cake comprises 0.302 mg tris(hydroxymethyl)aminomethane per g of cake, 997.2 mg sucrose per g of cake, and/or (e.g., and) 2.49 mg complexes per g of cake. In some embodiments, a lyophilized cake comprises 0.302 mg tris(hydroxymethyl)aminomethane per g of cake, 996.7 mg sucrose per g of cake, and/or (e.g., and) 2.99 mg complexes per g of cake. In some embodiments, a lyophilized cake comprises 0.302 mg tris(hydroxymethyl) aminomethane per g of cake, 995.7 mg sucrose per g of cake, and/or (e.g., and) 3.98 mg complexes per g of cake. In some embodiments, a lyophilized cake comprises 0.301 mg tris (hydroxymethyl)aminomethane per g of cake, 994.7 mg sucrose per g of cake, and/or (e.g., and) 4.97 mg complexes per g of cake.

In some embodiments, reconstitution of a lyophilized cake (e.g., with water) results in a solution comprising tris(hydroxymethyl)aminomethane at a concentration of 5 to 50 mM, sucrose at a concentration of 5 w/v % to 15 w/v %, and/or (e.g., and) complexes at a concentration of 10 mg/mL to 50 mg/mL. In some embodiments, reconstitution of 10.053 g of a lyophilized cake with a solvent (e.g., water) to form 1 mL of reconstituted solution results in a solution comprising tris(hydroxymethyl)aminomethane at a concentration of 5 to 50 mM (optionally 25 mM), sucrose at a concentration of 5 w/v % to 15 w/v % (optionally 10 w/v %), and/or (e.g., and) complexes at a concentration of 10 mg/mL to 50 mg/mL. In some embodiments, reconstitution of about 10 g of a lyophilized cake with a solvent (e.g., water) to form 1 mL of reconstituted solution results in a solution comprising tris(hydroxymethyl)aminomethane at a concentration of 5 to 50 mM (optionally 25 mM), sucrose at a concentration of 5 w/v % to 15 w/v % (optionally 10 w/v %), and/or (e.g., and) complexes at a concentration of 10 mg/mL to 50 mg/mL.

In some embodiments, any one or a plurality of the complexes described herein is formulated with tris(hydroxymethyl)aminomethane and sucrose in a frozen form (e.g., a frozen aqueous solid). In some embodiments, the frozen form (e.g., frozen aqueous solid) is obtained by freezing of any one of the aqueous solutions described herein. A frozen form may be frozen to a temperature of less than −20° C. (e.g., less than −20° C., less than −30° C., less than −40° C., less than −50° C., less than −60° C., less than −70° C., less than −80° C., or lower).

In some embodiments, the value of n1 of each complex in the formulation is independently and optionally an integer from zero up to the number of amino acid residues to which conjugation is desired or targeted (e.g., the number of lysine residues) in the antibody ($R^2$). In some embodiments, the value of n1 of each complex in the formulation is independently and optionally selected from 0, 1, 2, 3, 4, 5, 6, 7, 8, 9, 10, 11, 12, 13, 14, 15, 16, 17, 18, 19, 20, 21, 22, 23, 24, 25, 26, and 27. In some embodiments, the value of n1 of each complex in the formulation is independently and optionally selected from 0, 1, 2, 3, 4, 5, 6, 7, 8, 9, 10, 11, 12, 13, 14, 15, 16, 17, 18, 19, 20, 21, 22, 23, 24, 25 and 26. In some embodiments, the value of n1 of each complex in the formulation is independently selected and optionally from an integer in the range of 1 to 27, 1 to 26, 1 to 10, 1 to 5, or 1 to 3. In some embodiments, the average value of n1 of complexes in the formulation is in the range of 1 to 2, 1 to 3, 1 to 5, 1 to 10, 1 to 26 or 1 to 27. In some embodiments, formulations described herein comprise complexes that comprise a structure of formula (I): $[R^1]_{n1}$—$R^2$, wherein n1 is 0. In some embodiments, the average value of n1 of complexes of the formulation is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2).

In some embodiments, each instance of $R^1$ in a complex herein (e.g., a complex of a formulation provided herein) is conjugated to a different amino acid residue of the antibody. In some embodiments, each different amino acid comprises an ε-amino group (e.g., lysine, arginine). However, in some embodiments, each different amino acid to which $R^1$ is covalently linked is a cysteine. In some embodiments, $R^1$ is directly covalently linked to an amino acid residue of the antibody. However, in some embodiments, $R^1$ is indirectly covalently linked to an amino acid of the antibody, e.g., covalently linked to a glycosylation site on the amino acid. In some embodiments, formulations are provided in which complexes for which $R^1$ is covalently linked to an amino acid residue residing in a CDR region of the antibody are present in only trace amounts, or in undetectable amount, or not at all. In some embodiments, formulations are provided in which complexes for which $R^1$ is covalently linked to an amino acid residue residing in a CDR region of the antibody are not detectable in the formulation using standard detection techniques.

In some embodiments, formulations provided herein comprise complexes that comprise a structure of formula (I): $[R^1]_{n1}$—$R^2$, in which each instance of $R^1$ independently comprises a group of the formula (Ia):

(Ia)

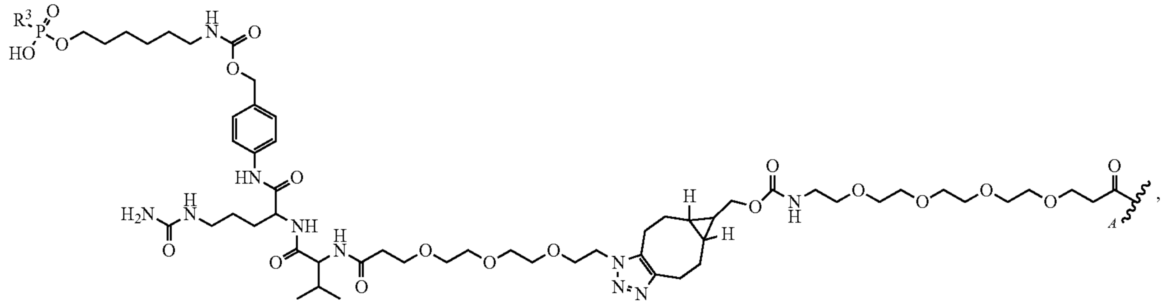

in which $R^3$ comprises an oligonucleotide, e.g., an oligonucleotide comprising a 5'-X—Y—Z-3' configuration; and $R^1$ is covalently linked to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, $R^3$ comprises an oligonucleotide comprising a nucleobase sequence of CAGCGCCCACCAGUCA (SEQ ID NO: 21). In some embodiments, $R^3$ comprises an oligonucleotide comprising a structure of +C*+A*OG*oC*dG*dC*dC*dC*dA*dC*dC*dA*G*OU*+C*+A (SEQ ID NO: 21), wherein +N represents an LNA (2'-4' methylene bridge) ribonucleoside, dN represents a 2'-deoxyribonucleoside, oN represents a 2'-MOE modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, and * represents a phosphorothioate internucleoside linkage. In some embodiments, in each complex n1 is independently an integer (e.g., an integer in the range of 1-27, 1-26, 1-10, 1-5, or 1-3). In some embodiments, formulations described herein further comprise complexes that comprise a structure of formula (I): $[R^1]_{n1}—R^2$, wherein n1 is 0. In some embodiments, the average value of n1 of complexes of the composition is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, formulations further comprise tris(hydroxymethyl)aminomethane and sucrose. In some embodiments, formulations comprise tris(hydroxymethyl)aminomethane at a concentration of 25 mM and/or (e.g., and) sucrose at a concentration of 10 w/v %, optionally wherein the formulation has a pH of 7.5. In some embodiments, formulations comprise complexes at a concentration of 30 mg/mL.

In some embodiments, formulations provided herein comprise complexes that comprise a structure of formula (I): $[R^1]_{n1}—R^2$, in which each instance of $R^1$ in a complex of a formulation provided herein comprises a group of the formula (Ib):

(Ib)

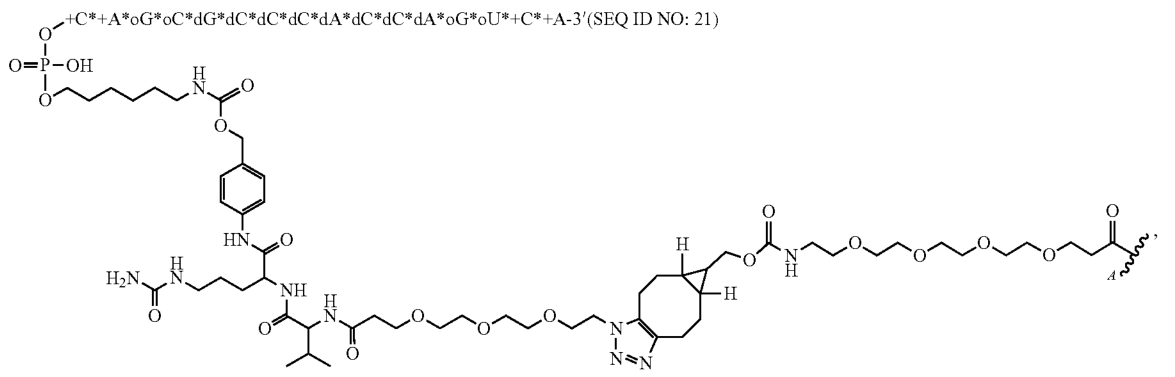

wherein +N represents an LNA (2'-4' methylene bridge) ribonucleoside, dN represents a 2'-deoxyribonucleoside, oN represents a 2'-O-methoxyethyl (MOE) modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, * represents a phosphorothioate internucleoside linkage, and wherein the oligonucleotide comprises a nucleobase sequence of CAGCGCCCACCAGUCA (SEQ ID NO: 21), wherein n1 is an integer (e.g., one or greater) representing the number of instances of $R^1$ in each complex, and each $R^1$ is covalently linked to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, formulations described herein further comprise complexes that comprise a structure of formula (I): $[R^1]_{n1}$—$R^2$, wherein n1 is 0. In some embodiments, the average value of n1 of complexes of the composition is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, formulations further comprise tris(hydroxymethyl)aminomethane and sucrose. In some embodiments, formulations comprise tris(hydroxymethyl)aminomethane at a concentration of 25 mM and/or (e.g., and) sucrose at a concentration of 10 w/v %, optionally wherein the formulation has a pH of 7.5. In some embodiments, formulations comprise complexes at a concentration of 30 mg/mL.

In some embodiments, formulations provided herein comprise complexes that comprise a structure of formula (I): $[R^1]_{n1}$—$R^2$, in which each $R^1$ comprises a group of the formula (Ic):

(Ie)

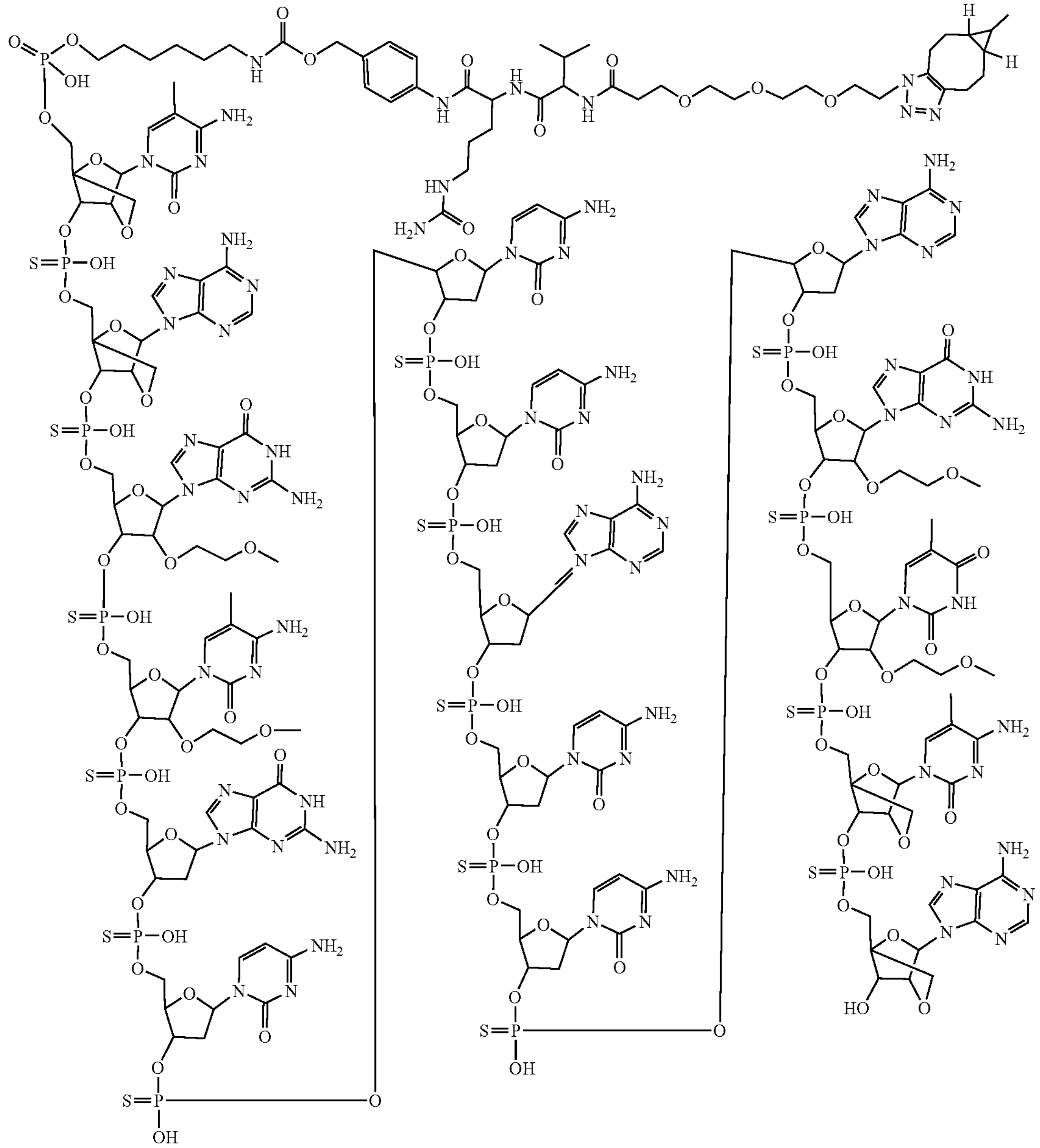

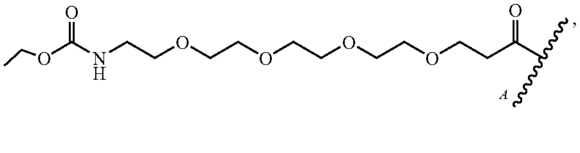

wherein $R^1$ is covalently linked to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, formulations described herein further comprise complexes that comprise a structure of formula (I): $[R^1]_{n1}$—$R^2$, wherein n1 is 0. In some embodiments, the average value of n1 of complexes of the composition is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, formulations further comprise tris(hydroxymethyl)aminomethane and sucrose. In some embodiments, formulations comprise tris(hydroxymethyl)aminomethane at a concentration of 25 mM and/or (e.g., and) sucrose at a concentration of 10 w/v %, optionally wherein the formulation has a pH of 7.5. In some embodiments, formulations comprise complexes at a concentration of 30 mg/mL.

In some embodiments, formulations provided herein comprise complexes that comprise a structure of the formula (Id):

(Id)

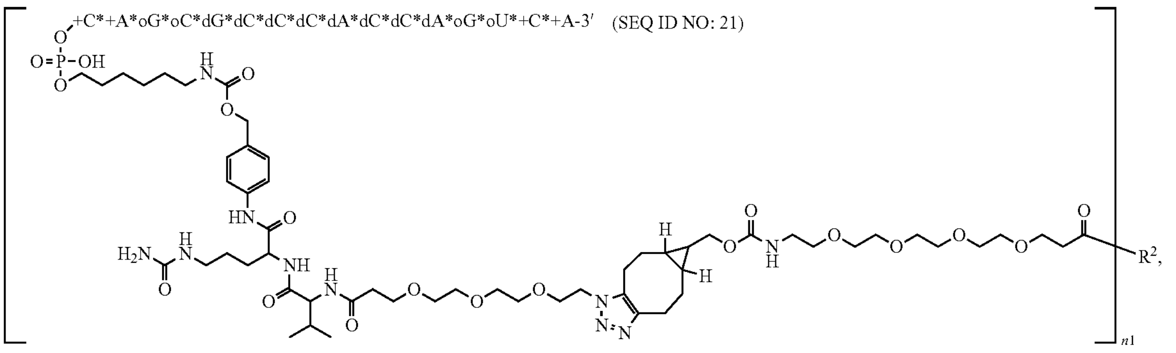

wherein +N represents an LNA (2'-4' methylene bridge) ribonucleoside, dN represents a 2'-deoxyribonucleoside, oN represents a 2'-O-methoxyethyl (MOE) modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, * represents a phosphorothioate internucleoside linkage, and wherein the oligonucleotide comprises a nucleobase sequence of CAGCGCCCACCAGUCA (SEQ ID NO: 21); wherein $R^2$ comprises an antibody comprising a sequence as set forth in Table 2; wherein n1 is an integer (e.g., one or greater) representing the number of instances of the group enclosed by square brackets, wherein each instance of the group enclosed by square brackets is covalently linked to a different amino acid residue of the antibody, optionally wherein each different amino acid residue is a lysine. In some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, formulations described herein further comprise complexes in which n1 is 0. In some embodiments, the average value of n1 of complexes of the composition is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, formulations further comprise tris(hydroxymethyl)aminomethane and sucrose. In some embodiments, formulations comprise tris(hydroxymethyl)aminomethane at a concentration of 25 mM and/or (e.g., and) sucrose at a concentration of 10 w/v %, optionally wherein the formulation has a pH of 7.5. In some embodiments, formulations comprise complexes at a concentration of 30 mg/mL.

In some embodiments, complexes provided in the formulations described herein comprise a structure of formula (A):

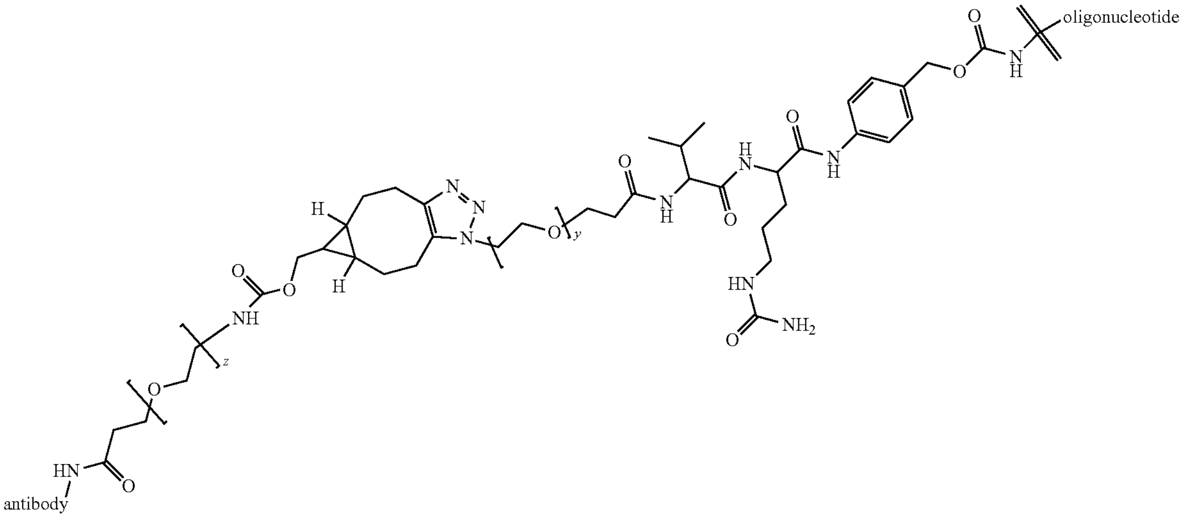

(A), wherein y is 0-15 (e.g., 3) and z is 0-15 (e.g., 4). In some embodiments, the amide shown adjacent the antibody (e.g., anti-TfR1 antibody) in the structure (A) results from a reaction with an amine of the antibody, such as a lysine epsilon amine. In some embodiments, a complex described herein comprises an anti-TfR1 antibody (e.g., an anti-TfR1 Fab) covalently linked via a lysine of the antibody to the 5' end of an oligonucleotide (e.g., an oligonucleotide comprising a 5'-X—Y—Z-3' configuration). In some embodiments, the antibody comprises a sequence as set forth in Table 2. For example, in some embodiments, the antibody comprises a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprises a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, the antibody comprises a heavy chain variable region (VH) comprising an amino acid sequence at least 85% (e.g., at least 95%) identical to SEQ ID NO: 17 and/or comprises a light chain variable region (VL) comprising an amino acid sequence at least 85% (e.g., at least 95%) identical to SEQ ID NO: 18. In some embodiments, the antibody comprises a VH comprising the amino acid sequence of SEQ ID NO: 17 and/or comprises a VL comprising the amino acid sequence of SEQ ID NO: 18. In some embodiments, the antibody comprises a heavy chain comprising an amino acid sequence at least 85% (e.g., at least 95%) identical to SEQ ID NO: 19 and/or comprises a light chain comprising an amino acid sequence at least 85% (e.g., at least 95%) identical to SEQ ID NO: 20. In some embodiments, the antibody comprises a heavy chain comprising the amino acid sequence of SEQ ID NO: 19 and/or comprises a light chain comprising the amino acid sequence of SEQ ID NO: 20. In some embodiments, the antibody is a Fab fragment, a full-length IgG, a Fab' fragment, a $F(ab')_2$ fragment, an scFv, or an Fv. In some embodiments, the antibody is a Fab fragment. In some embodiments, formulations further comprise tris(hydroxymethyl)aminomethane and sucrose. In some embodiments, formulations comprise tris(hydroxymethyl)aminomethane at a concentration of 25 mM and/or (e.g., and) sucrose at a concentration of 10 w/v %, optionally wherein the formulation has a pH of 7.5. In some embodiments, formulations comprise complexes at a concentration of 30 mg/mL.

As described herein, in some embodiments, formulations provided herein comprise sucrose. In some embodiments, sucrose serves at least in part as a lyoprotectant. In some embodiments, the sucrose is from a plant, e.g., grass, fruit, or vegetable (e.g., root vegetable) source (e.g., beet (e.g., sugar beet, for example, *Saccharum* spp.)), sugarcane (e.g., *Beta vulgaris*), dates, sugar maple, sweet sorghum, apples, oranges, carrots, molasses, maple syrup, corn sweeteners) or animal product (e.g., honey). In some embodiments, the sucrose is from beet or sugarcane (e.g., beet sucrose, sugarcane sucrose). In some embodiments, a lyoprotectant other than sucrose may be used, e.g., trehalose, mannitol, lactose, polyethylene glycol, or polyvinyl pyrrolidone. However, in some embodiments, a collapse temperature modifier (e.g., dextran, ficoll, or gelatin) may be provided in a formulation.

In some embodiments, provided is a product (e.g., lyophilized formulation described herein), produced by a process comprising lyophilizing an aqueous solution of a formulation (e.g., aqueous form) described herein.

In some embodiments, a pharmaceutical composition is formulated to be compatible with its intended route of administration. Examples of routes of administration include parenteral, e.g., intravenous, intradermal, subcutaneous, administration. Typically, the route of administration is intravenous or subcutaneous.

Methods of Use/Treatment

Complexes comprising an anti-TfR1 antibody (e.g., a Fab) covalently linked to a molecular payload (e.g., a DMPK targeting oligonucleotide) as described herein are effective in treating a subject having a myotonic dystrophy, e.g., DM1. In some embodiments, complexes comprise a molecular payload that is an oligonucleotide, e.g., an oligonucleotide that facilitates reduced expression or activity of DMPK (e.g., reduced level of a mutant or wild-type DMPK RNA).

In some embodiments, a subject may be a human subject, a non-human primate subject, a rodent subject, or any suitable mammalian subject. In some embodiments, a subject may have myotonic dystrophy. In some embodiments, a subject has a DMPK allele, which may optionally contain a disease-associated repeat, e.g., a CTG trinucleotide repeat expansion. In some embodiments, a subject may have a DMPK allele with an expanded disease-associated-repeat that comprises about 2-10 repeat units, about 2-50 repeat units, about 2-100 repeat units, about 50-1,000 repeat units, about 50-500 repeat units, about 50-250 repeat units, about 50-100 repeat units, about 500-10,000 repeat units, about 500-5,000 repeat units, about 500-2,500 repeat units, about 500-1,000 repeat units, or about 1,000-10,000 repeat units. In some embodiments, a subject may have myotonic dystrophy, such as DM1. In some embodiments, a subject is suffering from symptoms of DM1, e.g. muscle atrophy, muscle loss, excessive daytime sleepiness or cognitive delay. In some embodiments, a subject is not suffering from symptoms of DM1. In some embodiments, subjects have congenital myotonic dystrophy. In some embodiments, a subject is ambulant. In some embodiments, a subject is non-ambulant.

An aspect of the disclosure includes methods involving administering to a subject a formulation comprising an effective amount of complex(es) as described herein. In some embodiments, an effective amount of a pharmaceutical composition that comprises complex(es) comprising an antibody (e.g., Fab) described herein covalently linked to an oligonucleotide (e.g., a DMPK targeting oligonucleotide) described herein can be administered to a subject in need of treatment. In some embodiments, a pharmaceutical composition comprising complex(es) as described herein may be administered by a suitable route, which may include intravenous administration, e.g., as a bolus or by continuous infusion over a period of time. In some embodiments, administration may be performed by intravenous, intramuscular, intraperitoneal, intracerebrospinal, subcutaneous, intra-articular, intrasynovial, or intrathecal routes. In some embodiments, a pharmaceutical composition may be in solid form, aqueous form, or a liquid form. In some embodiments, an aqueous or liquid form may be nebulized or lyophilized. In some embodiments, a lyophilized form may be reconstituted with an aqueous or liquid solution.

In some embodiments, provided are methods of and/or uses for treating a subject having a DMPK allele, which may optionally contain a disease-associated repeat, comprising administering to the subject a formulation described herein that comprises an effective amount of complex(es) described herein. In some embodiments, provided are methods of and/or uses for reducing the expression or activity of DMPK (e.g., reducing the level of a mutant or wild-type DMPK RNA, or the activity of a DMPK gene product) in a cell (e.g., a muscle cell), the methods comprising contacting the cell with a formulation described herein comprising an effective amount of complex(es) described herein. In some embodiments, the method comprises administering a lyophilized form (e.g., lyophilized powder) of the formulation described herein, comprising reconstituting a lyophilized form of the formulation in an aqueous solution, and administering the aqueous solution of the formulation to a subject in need thereof. For example, in some embodiments, a lyophilized form of the formulation is shipped and/or stored in the lyophilized form, reconstituted at a location for administering the aqueous solution of the formulation (e.g., healthcare provider location), and administered in the reconstituted form (e.g., as an aqueous solution) by injection or intravenously, e.g., by infusion.

In some embodiments, a pharmaceutical composition is administered via site-specific or local delivery techniques. Examples of these techniques include implantable depot sources of the complex, local delivery catheters, site specific carriers, direct injection, or direct application.

In some embodiments, a pharmaceutical composition that comprises a complex comprising a an anti-TfR1 antibody (e.g., a fab) covalently linked to a molecular payload (e.g., a DMPK targeting oligonucleotide) is administered at an effective concentration that confers therapeutic effect on a subject. Effective amounts vary, as recognized by those skilled in the art, depending on the severity of the disease, unique characteristics of the subject being treated, e.g. age, physical conditions, health, or weight, the duration of the treatment, the nature of any concurrent therapies, the route of administration and related factors. These related factors are known to those in the art and may be addressed with no more than routine experimentation. In some embodiments, an effective concentration is the maximum dose that is considered to be safe for the patient. In some embodiments, an effective concentration will be the lowest possible concentration that provides maximum efficacy.

Empirical considerations, e.g. the half-life of the complex(es) in a subject, generally will contribute to determination of the concentration of pharmaceutical composition that is used for treatment. The frequency of administration may be empirically determined and adjusted to maximize the efficacy of the treatment. The efficacy of treatment may be assessed using any suitable methods. In some embodiments, the efficacy of treatment may be assessed by evaluation or observation of symptoms associated with a myotonic dystrophy, e.g. muscle atrophy or muscle weakness, through measures of a subject's self-reported outcomes, e.g. mobility, self-care, usual activities, pain/discomfort, and anxiety/depression, or by quality-of-life indicators, e.g. lifespan. In some embodiments, a pharmaceutical composition that comprises a complex comprising a muscle-targeting agent covalently linked to a molecular payload described herein is administered to a subject at an effective concentration sufficient to modulate activity or expression of a target gene by at least 10%, at least 20%, at least 30%, at least 40%, at least 50%, at least 60%, at least 70%, at least 80%, at least 90% or at least 95% relative to a control, e.g. baseline level of gene expression prior to treatment.

EXAMPLES

Example 1. In Vivo Tissue Distribution of Conjugates Containing Anti-TfR1 Fab Conjugated to a DMPK-Targeting Oligonucleotide in DM1 Mouse Model Conjugates comprising an anti-TfR1 Fab conjugated to a DMPK-targeting oligonucleotide (ASO) were tested in a mouse model that expresses both human TfR1 and a human DMPK mutant that harbors expanded CUG repeats. The anti-TfR1 Fab used has the VH/VL sequences provided in Table 2. The Fab was covalently linked (through lysine conjugation) via a linker comprising a valine-citrulline sequence to a DMPK targeting oligonucleotide comprising a nucleobase sequence of SEQ ID NO: 21. The conjugate comprises a structure of formula (Id):

+C*+A*oG*oC*dG*dC*dC*dC*dA*dC*dC*dA*oG*oU*+C*+A-3′ (SEQ ID NO: 21)

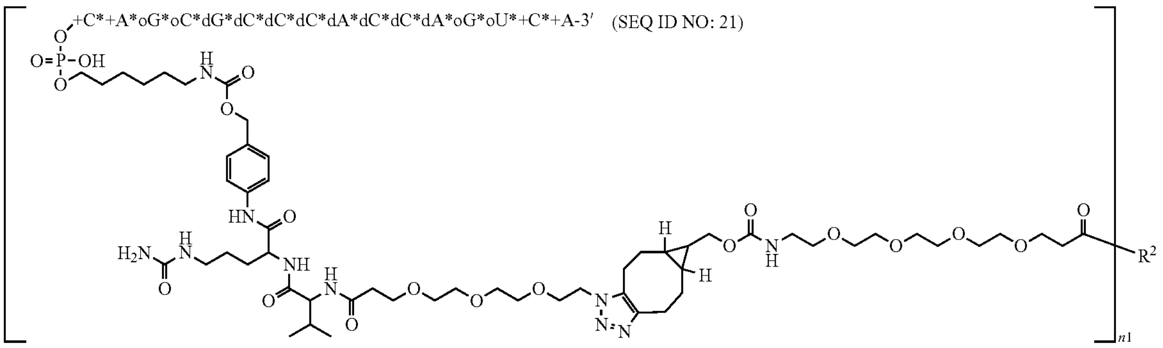

(Id), wherein +N represents an LNA (2'-4' methylene bridge) ribonucleoside, dN represents a 2'-deoxyribonucleoside, oN represents a 2'-O-methoxyethyl (MOE) modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, * represents a phosphorothioate internucleoside linkage, and wherein the oligonucleotide comprises a nucleobase sequence of CAGCGCCCACCAGUCA (SEQ ID NO: 21), and in which $R^2$ comprises the anti-TfR1 antibody provided in Table 2, and wherein in each conjugate n1 is independently an integer of 1-3.

The conjugates were administered intravenously to the mice at day 0 and day 7, each time at a dose equivalent to 9.7 mg/kg of the ASO. The tissue exposure of the ASO was tested by hybridization ELISA (Burki et al., Nucleic Acid Ther. 2015 October; 25 (5): 275-84, incorporated herein by reference), and the levels of ASO in the tissue were graphed. FIGS. 1A, 1B, 1C, and 1D show the amount of ASO in the heart, diaphragm, gastrocnemius, or tibialis anterior, respectively, two weeks after the first injection. These results demonstrate that conjugates comprising an anti-TfR1 antibody (e.g., an anti-TfR1 Fab having the VH and VL sequences provided in Table 2) are capable of delivering an oligonucleotide (e.g., a DMPK-targeting ASO) to various muscle tissues following intravenous administration.

Example 2. Sustained Knockdown of Toxic Human DMPK in hTfR1/DMSXL Homozygous Mice at 4 Weeks after Repeat Dosing of Anti-TfR1 Fab-ASO Conjugates Conjugates (labeled in this Example as "Anti-TfR1 Fab-ASO conjugate") as described in Example 1, containing an anti-TfR1 Fab covalently linked to a DMPK-targeting oligonucleotide (ASO) were tested in a mouse model that expresses both human TfR1 and two copies of a mutant human DMPK transgene that harbors expanded CUG repeats (hTfR1/DMSXL mice). Mice were administered either vehicle control (PBS) or 10 mg/kg ASO-equivalent dose of anti-TfR1 Fab-ASO conjugate at days 0 and 7. Mice were sacrificed at day 28 (four weeks following administration of the first dose of anti-TfR1 Fab-ASO conjugate), and tissues were collected. RNA was extracted and selected tissue samples were fixed, paraffin embedded and sectioned, then subjected to in situ hybridization. Reverse transcription-quantitative polymerase chain reaction (RT-qPCR) of the RNA samples was performed to measure human DMPK and mouse Ppib (peptidylprolyl isomerase) as an internal control. DMPK expression is shown in FIGS. 2A-2D as geometric means+/−standard deviation (n=6-9). Significance was assessed by Student's t-test (****P<0.0001).

Figures 2A, 2B, 2C, 2D:
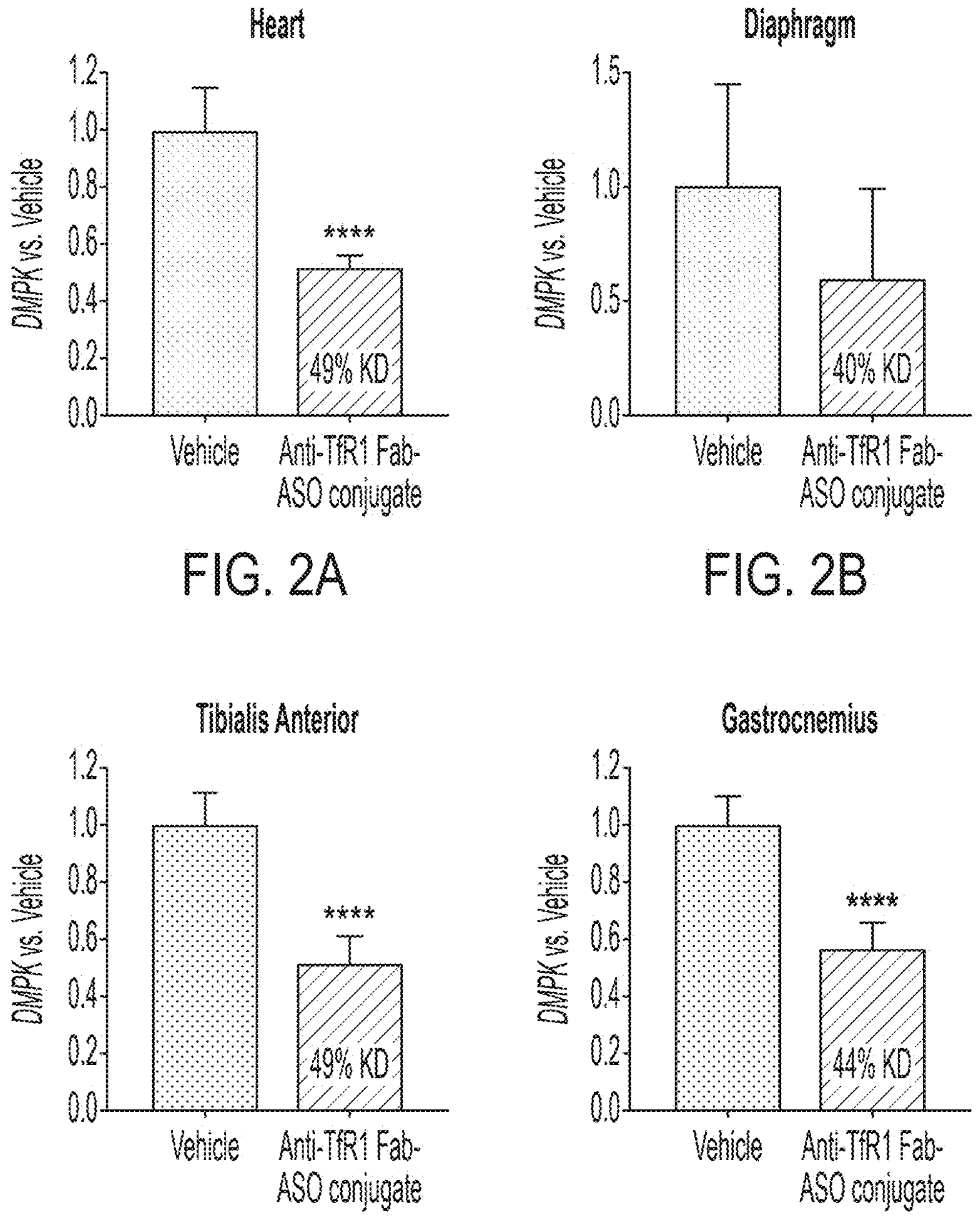
FIGS. 2A-2D show the ability of conjugates containing an anti-TfR1 Fab conjugated to a DMPK-targeting oligonucleotide (ASO) to knock down human DMPK RNA in the heart (FIG. 2A), diaphragm (FIG. 2B), tibialis anterior (FIG. 2C) and gastrocnemius (FIG. 2D) of mice expressing both human TfR1 and two copies of a mutant human DMPK transgene that harbors expanded CTG repeats.

FIG. 2A shows that anti-TfR1 Fab-ASO conjugate knocked down DMPK expression in heart by 49% relative to PBS-treated mice. FIG. 2B shows that anti-TfR1 Fab-ASO conjugate knocked down DMPK expression in diaphragm by 40% relative to PBS-treated mice. FIG. 2C shows that anti-TfR1 Fab-ASO conjugate knocked down DMPK expression in tibialis anterior by 49% relative to PBS-treated mice. FIG. 2D shows that anti-TfR1 Fab-ASO conjugate knocked down DMPK expression in gastrocnemius by 44% relative to PBS-treated mice.

Figure 3A:
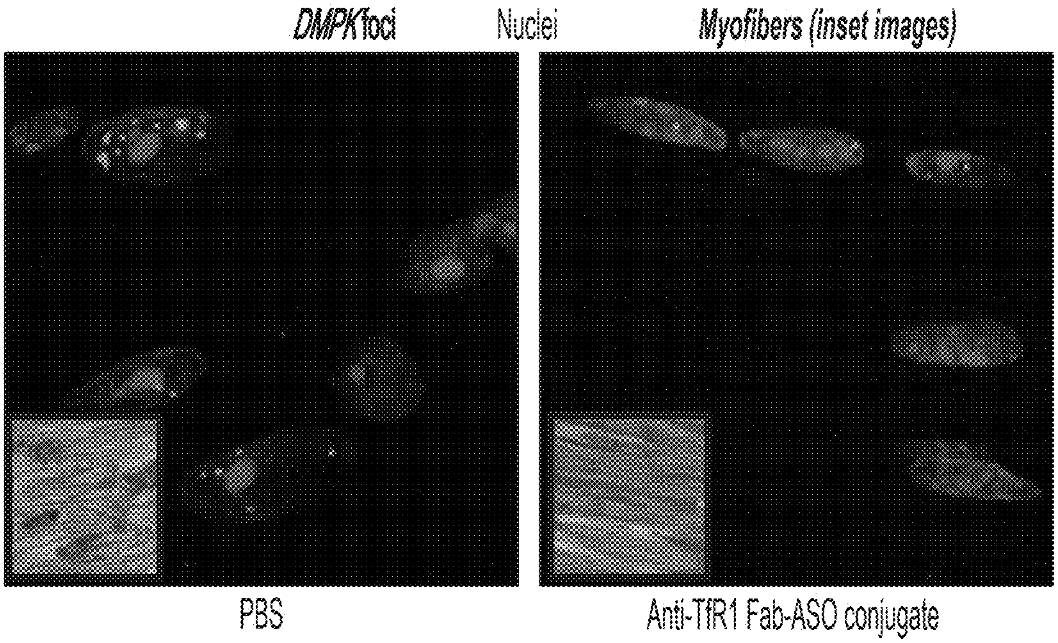
FIGS. 3A-3B show reduced DMPK foci in nuclei of cardiac muscle fibers in mice expressing both human TfR1 and two copies of a mutant human DMPK transgene that harbors expanded CTG repeats and treated with anti-TfR1 Fab conjugated to DMPK-targeting oligonucleotide (ASO).
Figure 3B:
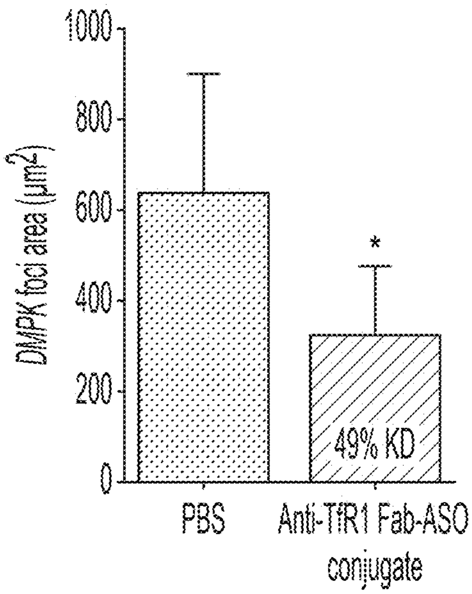

FIGS. 3A and 3B show that anti-TfR1 Fab-ASO conjugate reduced DMPK foci within nuclei of myofibers. FIG. 3A shows reduced DMPK foci by in situ hybridization, and FIG. 3B shows quantification of DMPK foci in fluorescent microscopy images, demonstrating the conjugate reduced foci area by 49%. Data are presented as mean+/−standard deviation (n=7). Significance was assessed by t-test (*P<0.05).

These results demonstrate that administration of anti-TfR1 Fab-ASO conjugate leads to robust, sustained knockdown of human toxic DMPK in cardiac and skeletal muscle.

Example 3. Correction of Splicing Defects in hTfR1/DMSXL Homozygous Mice by Anti-TfR1 Fab-ASO Conjugates Conjugates (labeled in this Example as "Anti-TfR1 Fab-ASO conjugate") as described in Example 1, containing an anti-TfR1 Fab covalently linked to a DMPK-targeting oligonucleotide (ASO) were tested in a mouse model ("hTfR1/DMSXL") that expresses both human TfR1 and two copies of a mutant human DMPK transgene that harbors expanded CUG repeats. These mice are known to display splicing defects that are consistent with those observed in patients afflicted with DM1 (Huguet, et al. (2012) *PLOS Genetics* 8(11): e1003043). Mice were administered either vehicle control ("hTfR1/DMSXL—PBS") or 10 mg/kg ASO-equivalent dose of anti-TfR1 Fab-ASO conjugate ("hTfR1/DMSXL—Conjugate") on days 0 and 7. Mice expressing only the human TfR1 but not the mutant human DMPK transgene (hTfR1 mice) and treated with PBS ("hTfR1—PBS") were used as another control to define the extent of the splicing phenotype in hTfR1/DMSXL mice and assess the magnitude of the effect of the conjugate on splicing. Mice were sacrificed on day 28 (four weeks following administration of the first dose of anti-TfR1 Fab-ASO conjugate), tissues were collected, and RNA was extracted. Reverse transcription-quantitative polymerase chain reaction (RT-qPCR) was performed to measure exon inclusion in a set of RNAs known to be mis-spliced during DM1 progression in humans and mice (Nakamori, et al. (2013) *Ann. Neurol.* 74 (6): 862-872; Huguet, et al. (2012) *PLOS Genetics* 8(11):e1003043). Exon inclusion was calculated as normalized percent spliced in (PSI) for each splicing RNA marker, and composite splicing indices were calculated using the normalized PSI values from splicing markers in heart (FIG. 4), diaphragm (FIG. 5), tibialis anterior (FIG. 6), and gastrocnemius (FIG. 7). Composite splicing indices were calculated as previously described (Tanner M K, et al. (2021) *Nucleic Acids Res.* 49:2240-2254), and are shown as mean+/−standard deviation.

Figure 4:
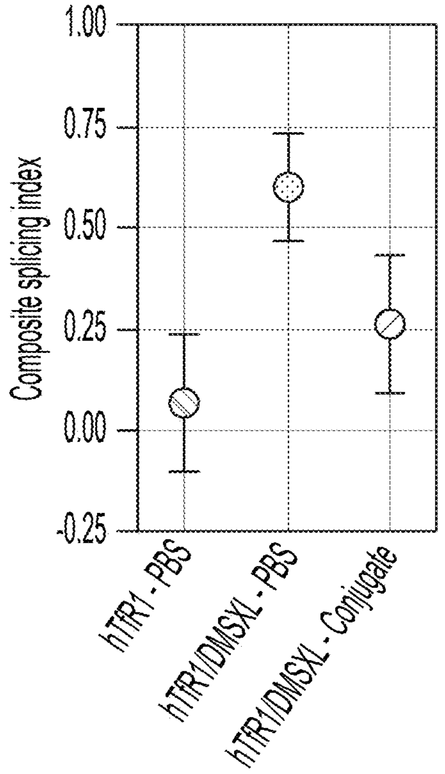
FIG. 4 shows the splicing correction activity of conjugates containing an anti-TfR1 Fab covalently linked to a DMPK-targeting oligonucleotide (ASO) in the heart of mice expressing both human TfR1 and two copies of a mutant human DMPK transgene that harbors expanded CTG repeats (hTfR1/DMSXL mice). Composite splicing indices based on splicing of Ldb3 exon 11, Mbnl2 exon 6, and Nfix exon 7 are shown for control mice treated with vehicle control ("hTfR1—PBS"), hTfR1/DMSXL mice treated with vehicle control ("hTfR1/DMSXL—PBS"), and hTfR1/DMSXL mice treated with anti-TfR1 Fab-ASO conjugate ("hTfR1/DMSXL—Conjugate").

FIG. 4 shows that anti-TfR1 Fab-ASO conjugate corrected splicing in heart tissue of hTfR1/DMSXL mice, as demonstrated by composite splicing index data. The normalized PSI values used to generate the composite splicing index data showed correction of Mbnl2 exon 6 (E6) and Nfix E7 splicing in heart tissue of hTfR1/DMSXL mice by treatment with anti-TfR1 Fab-ASO conjugate, but did not show correction of Ldb3 E11 splicing. Composite splicing index data shown in FIG. 4 were based on Ldb3 E11, Mbnl2 E6, and Nfix E7 splicing data; Bin1 E11, Dtna E12, Insr E11, and Mbnl2 E5 were not included because their normalized PSI values in heart tissue were not changed in hTfR1/DMSXL mice relative to hTfR1 mice under the experimental conditions tested.

Figure 5:
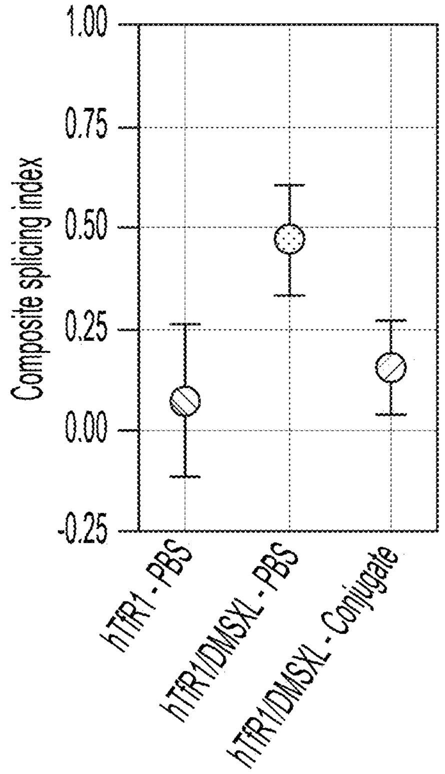
FIG. 5 shows the splicing correction activity of conjugates containing an anti-TfR1 Fab covalently linked to a DMPK-targeting oligonucleotide (ASO) in the diaphragm of mice expressing both human TfR1 and two copies of a mutant human DMPK transgene that harbors expanded CTG repeats (hTfR1/DMSXL mice). Composite splicing indices based on splicing of Bin1 exon 11, Insr exon 11, Ldb3 exon 11 and Nfix exon 7 are shown for control mice treated with vehicle control ("hTfR1—PBS"), hTfR1/DMSXL mice treated with vehicle control ("hTfR1/DMSXL—PBS"), and hTfR1/DMSXL mice treated with anti-TfR1 Fab-ASO conjugate ("hTfR1/DMSXL—Conjugate").

FIG. 5 shows that anti-TfR1 Fab-ASO conjugate corrected splicing in diaphragm tissue of hTfR1/DMSXL mice, as demonstrated by composite splicing index data. The normalized PSI values used to generate the composite splicing index data showed correction of Bin1 E11, Insr E11, Ldb3 E11 and Nfix E7 splicing in diaphragm tissue of hTfR1/DMSXL mice by treatment with anti-TfR1 Fab-ASO conjugate. Composite splicing index data shown in FIG. 5 were based on Bin1 E11, Insr E11, Ldb3 E11 and Nfix E7 splicing data; Dtna E12, Mbnl2 E5, Mbnl2 E6, and Ttn E313 were not included because their normalized PSI values in diaphragm tissue were not changed in hTfR1/DMSXL mice relative to hTfR1 mice under the experimental conditions tested.

Figure 6:
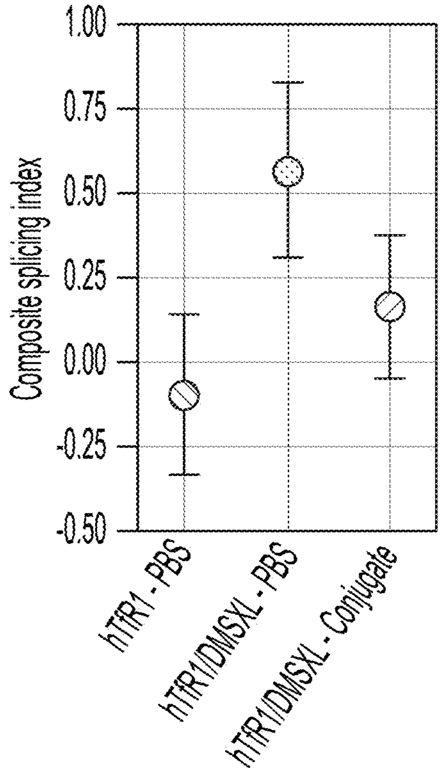
FIG. 6 shows the splicing correction activity of conjugates containing an anti-TfR1 Fab covalently linked to a DMPK-targeting oligonucleotide (ASO) in the tibialis anterior of mice expressing both human TfR1 and two copies of a mutant human DMPK transgene that harbors expanded CTG repeats (hTfR1/DMSXL mice). Composite splicing indices based on splicing of Bin1 exon 11, Ldb3 exon 11, Mbnl2 exon 6, and Nfix exon 7 are shown for control mice treated with vehicle control ("hTfR1—PBS"), hTfR1/DMSXL mice treated with vehicle control ("hTfR1/DMSXL—PBS"), and hTfR1/DMSXL mice treated with anti-TfR1 Fab-ASO conjugate ("hTfR1/DMSXL—Conjugate").
Figure 7:
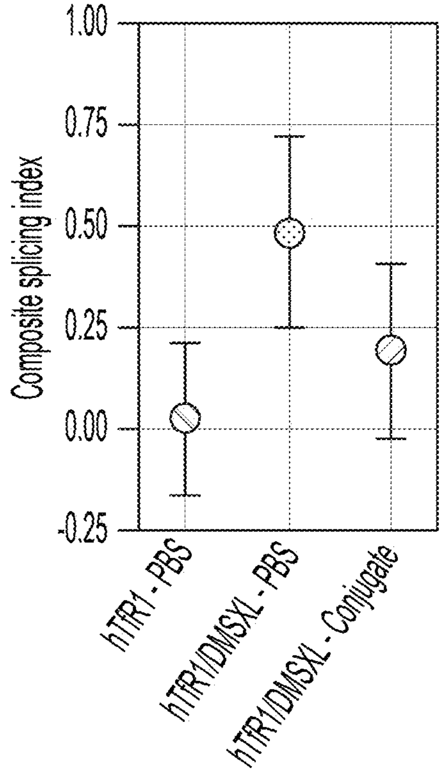
FIG. 7 shows the splicing correction activity of conjugates containing an anti-TfR1 Fab covalently linked to a DMPK-targeting oligonucleotide (ASO) in the gastrocnemius of mice expressing both human TfR1 and two copies of a mutant human DMPK transgene that harbors expanded CTG repeats (hTfR1/DMSXL mice). Composite splicing indices based on splicing of Mbnl2 exon 6, Nfix exon 7, and Tin exon 313 are shown for control mice treated with vehicle control ("hTfR1—PBS"), hTfR1/DMSXL mice treated with vehicle control ("hTfR1/DMSXL—PBS"), and hTfR1/DMSXL mice treated with anti-TfR1 Fab-ASO conjugate ("hTfR1/DMSXL—Conjugate").

FIG. 6 shows that anti-TfR1 Fab-ASO conjugate corrected splicing in tibialis anterior tissue of hTfR1/DMSXL mice, as demonstrated by composite splicing index data. The normalized PSI values used to generate the composite splicing index data showed correction of Bin1 E11, Ldb3 E11, and Nfix E7 splicing in tibialis anterior tissue of hTfR1/DMSXL mice by treatment with anti-TfR1 Fab-ASO conjugate, but did not show correction of Mbnl2 E6 splicing. Composite splicing index data shown in FIG. 6 were based on Bin1 E11, Ldb3 E11, Mbnl2 E6, and Nfix E7 splicing data; Dtna E12, Insr E11, Mbnl2 E5, and Tin E313 were not included because their normalized PSI values in tibialis anterior tissue were not changed in hTfR1/DMSXL mice relative to hTfR1 mice under the experimental conditions tested.

FIG. 7 shows that anti-TfR1 Fab-ASO conjugate corrected splicing in gastrocnemius tissue of hTfR1/DMSXL mice, as demonstrated by composite splicing index data. The normalized PSI values used to generate the composite splicing index data showed correction of Mbnl2 E6, Nfix E7, and Ttn E313 splicing in gastrocnemius tissue of hTfR1/DMSXL mice by treatment with anti-TfR1 Fab-ASO conjugate. Composite splicing index data shown in FIG. 7 were based on Mbnl2 E6, Nfix E7, and Ttn E313 splicing data; Bin1 E11, Dtna E12, Insr E11, Ldb3 E11, and Mbnl2 E5 were not included because their normalized PSI values in gastrocnemius tissue were not changed in hTfR1/DMSXL mice relative to hTfR1 mice under the experimental conditions tested.

These results demonstrate that administration of anti-TfR1 Fab-ASO conjugate facilitates correction of DM1 splicing defects in cardiac and skeletal muscle.

Example 4. DMPK Knockdown in Non-Human Primate and DM1 Patient Myotubes

Conjugates (labeled in this Example as "Anti-TfR1 Fab-ASO conjugate") as described in Example 1, containing an anti-TfR1 Fab covalently linked to a DMPK-targeting oligonucleotide (ASO) were tested in human DM1 patient myotubes (32F cells) and in non-human primate (NHP) myotubes. The DM1 patient myotubes used express both a mutant DMPK mRNA containing 380 CUG repeats and a wild-type DMPK mRNA. The NHP myotubes used express only wild-type DMPK.

DM1 patient cells or NHP cells were seeded at a density of 50,000 cells per well in 96 well plates in growth medium and were allowed to recover overnight. The following day, the growth medium was changed to a low-serum differentiation medium and the cells were treated with conjugates at a concentration equivalent to 125 nM, 250 nM, or 500 nM ASO. The cells were incubated for ten days, then cDNA was synthesized using the Cells-to-Ct kit with crude cell lysates as the source of total RNA.

cDNA was used to assess total DMPK knockdown using Taqman PCR. The data was normalized to PPIB expression and the $2^{-\Delta\Delta Ct}$ method was used to determine DMPK knock down compared to a PBS-treated control ("Vehicle"). Data shown in FIG. 8 are presented as mean DMPK expression relative to species-matched vehicle control+standard deviation (n=4 replicates per condition).

Figure 8:
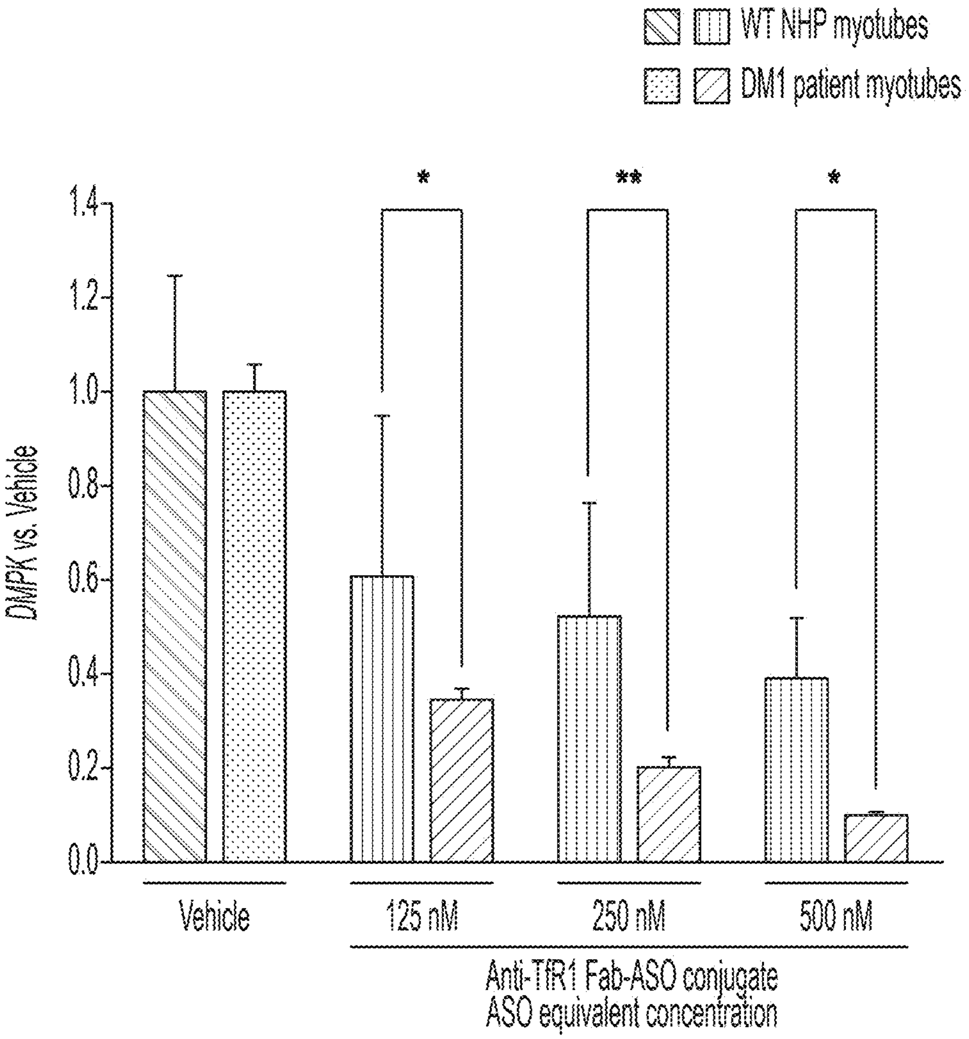
FIG. 8 shows DMPK knockdown in DM1 patient myotubes and wild-type non-human primate (NHP) myotubes resulting from incubation with conjugates containing an anti-TfR1 Fab covalently linked to a DMPK-targeting oligonucleotide (ASO). Results are shown normalized to expression in DM1 patient myotubes or NHP myotubes treated with vehicle only. Data are shown as mean+standard deviation for n=4 replicates per condition. Statistics were calculated by one-way ANOVA (*, $P<0.05$, **, $P<0.01$).

The results show that the anti-TfR1 Fab-ASO conjugates achieved knockdown of DMPK expression in both normal NHP myotubes and DM1 patient myotubes, with greater knockdown of DMPK expression in DM1 patient cells (expressing both DMPK mRNA containing 380 CUG repeats and wild-type DMPK mRNA) compared to NHP cells (expressing only wild-type DMPK mRNA) when treated at physiologically relevant concentrations (FIG. 8). At an ASO-equivalent concentration of 125 nM, the conjugates achieved approximately 40% DMPK knockdown relative to vehicle-only control in NHP myotubes, and approximately 65% DMPK knockdown in DM1 patient myotubes. At an ASO-equivalent concentration of 250 nM, the conjugates achieved approximately 45% DMPK knockdown relative to vehicle-only control in NHP myotubes, and approximately 80% DMPK knockdown in DM1 patient myotubes. At an ASO-equivalent concentration of 500 nM, the conjugates achieved approximately 60% DMPK knockdown relative to vehicle-only control in NHP myotubes, and approximately 90% DMPK knockdown in DM1 patient myotubes.

These results indicate that conjugates containing anti-TfR1 Fab covalently linked to a DMPK-targeting oligonucleotide can achieve greater knockdown of DMPK in human myotubes expressing both wild-type DMPK mRNA and mutant DMPK mRNA (with expanded CUG repeats) relative to cynomolgus monkey myotubes expressing wild-type DMPK.

Example 5. Comparison of Thermal Stability of Different Exemplary Formulations Formulations comprising conjugates as described in Example 1, containing an anti-TfR1 Fab covalently linked to a DMPK-targeting oligonucleotide (ASO) were prepared. The anti-TfR1 Fab-oligonucleotide conjugates starting material ("SM") was at a concentration of 33 mg/mL in a buffer containing 100 mM sodium phosphate and 100 mM sodium chloride at pH 7.4. For stability testing, the anti-TfR1 Fab-oligonucleotide conjugates were formulated in different buffers at a concentration of approximately 40 mg/mL. The buffer conditions in each of the four formulations were as follows:

Formulation buffer 1:25 mM succinate, 10% (w/v) sucrose, pH 5.2.

Formulation buffer 2:25 mM succinate, 10% (w/v) sucrose, pH 6.0.

Formulation buffer 3:25 mM tris(hydroxymethyl)aminomethane, 10% (w/v) sucrose, pH 7.5.

Formulation buffer 4:100 mM sodium phosphate, 100 mM sodium chloride, pH 7.4.

The formulation drug substance (formulation with conjugates described herein) was buffer exchanged into formulation buffers 1~4 as provided above using Vivaspin® 6 centrifugal membrane filters (30 kDa molecular weight cutoff). Following buffer exchange, the anti-TfR1 Fab-oligonucleotide conjugates were concentrated to approximately 40 mg/ml. Aliquots of approximately 150 μL from each of the concentrated samples were used to study thermal stability of the conjugates in each formulation. The samples were incubated for 1 week ("T1"), 2 weeks ("T2"), 4 weeks ("T4"), or 8 weeks ("T8") at −20° C., 2-8° C., 25° C., or 40° C. in glass vials. No change in color, appearance, or pH was observed in any of the test samples at any temperature or time point tested.

The thermal stability of each formulation was first tested by measuring the concentration of the conjugates in the various samples at T0 (week 0), T4 and T8, and at the specified temperatures. Standard BCA (Bicinchoninic Acid) analysis was used to measure the concentration. BCA assay was carried out using standard procedure:

1) Working Reagent (WR) was prepared by thoroughly mixing 20 mL of BCA reagent A with 200 μL BCA reagent B.
2) A standard curve and dilution curves for the test samples were prepared. The test samples were first diluted 1:4, then 20 μL of each test sample or standard was thoroughly mixed with 200 μL of WR and incubated at 60° C. for 10 minutes. The resulting solution was added to the first row of a 96-well plate and serially diluted. A 6-point standard curve was prepared.
3) Absorbance at 480 nm was measured on a plate reader.
4) The standard curve was used to determine the protein concentration of each test sample. Five dilutions were measured for each test sample.

The results of the concentration measurements of the thermal stability study are shown in Table 3 below.

TABLE 3

| | | Measured average concentration of conjugates (mg/mL)† | | | |
|---|---|---|---|---|---|
| Time point | Temp. (° C.) | Formulation 1 | Formulation 2 | Formulation 3 | Formulation 4 |
| T0 | N/A | 36.90 | 42.44 | 44.28 | 44.29 |
| T4 | −20 | 32.16 | 43.72 | 43.50 | 43.28 |
| | 2-8 | 31.70 | 42.62 | 39.31 | 40.42 |
| | 25 | 34.52 | 40.02 | 42.69 | 41.94 |
| | 40 | 41.00 | 41.40 | 42.60 | 42.03 |

TABLE 3-continued

| | | Measured average concentration of conjugates (mg/mL)† | | | |
|---|---|---|---|---|---|
| Time point | Temp. (° C.) | Formulation 1 | Formulation 2 | Formulation 3 | Formulation 4 |
| T8 | −20 | 32.43 | 42.15 | 42.01 | 42.67 |
| | 2-8 | 32.83 | 41.18 | 41.49 | 42.09 |
| | 25 | 34.23 | 43.80 | 42.16 | 43.15 |
| | 40 | 42.90 | 45.40 | 42.37 | 43.32 |

†Concentrations shown were calculated from the average of measurements of 5 serial dilutions of each test sample.

The results in Table 3 show that the concentrations of the Fab-oligonucleotide conjugates in Formulations 2, 3, and 4 are consistent at T0, T4, and T8. The concentration of the Fab-oligonucleotide conjugates in Formulation 1 at T4 and T8 showed reduced concentration at the lower storage temperatures compared to the TO measurement.

Thermal stability of the Fab-oligonucleotide conjugates was further studied by measurement of aggregate formation at a concentration of 40 mg/mL. After dilution to 1 mg/mL, T0, T1, T2, T4, and T8 samples incubated at various specified temperatures were the analyzed by size exclusion chromatography (SEC-UV) using a Waters ACQUITY UPLC Protein BEH SEC Column (125 Å, 1.7 μm, 4.6×150 mm) with a mobile phase of 0.2 M potassium phosphate pH 6.8, 0.2 M potassium chloride isocratic elution, 15% isopropyl alcohol. The column temperature was 30° C., and 10 μg injections were used. The flow rate was 0.35 mL/min, and analysis was conducted at a wavelength of 280 nm.

Percentages of high molecular weight (HMW) species, Fab-oligonucleotide conjugate monomers, and low molecular weight (LMW) species were measured in the SEC thermal stability analysis for each sample. The results are shown in Table 4 below. The values for the starting material (SM) are shown in the top row for comparison.

TABLE 4

| Time point | Temp. (° C.) | % HMW species | % monomer | % LMW species |
|---|---|---|---|---|
| SM | | 10.0 | 89.9 | 0.2 |
| | | Formulation 1 | | |
| T0 | N/A | 7.6 | 92.0 | 0.4 |
| T1 | −20 | 5.7 | 93.6 | 0.7 |
| | 2-8 | 4.4 | 94.8 | 0.8 |
| | 25 | 4.8 | 94.0 | 1.2 |
| | 40 | 4.4 | 94.0 | 1.6 |
| T2 | −20 | 7.5 | 91.8 | 0.7 |
| | 2-8 | 7.5 | 91.8 | 0.7 |
| | 25 | 7.5 | 90.5 | 2.0 |
| | 40 | 6.6 | 91.2 | 2.1 |
| T4 | −20 | 7.5 | 92.4 | 0.1 |
| | 2-8 | 8.1 | 91.5 | 0.5 |
| | 25 | 7.2 | 90.7 | 2.1 |
| | 40 | 6.6 | 88.3 | 5.1 |
| T8 | −20 | 8.8 | 90.7 | 0.5 |
| | 2-8 | 8.9 | 90.3 | 0.8 |
| | 25 | 8.6 | 89.2 | 2.2 |
| | 40 | 8.3 | 85.8 | 5.9 |
| | | Formulation 2 | | |
| T0 | N/A | 10.0 | 89.7 | 0.2 |
| T1 | −20 | 9.8 | 90.0 | 0.2 |
| | 2-8 | 9.9 | 89.9 | 0.2 |
| | 25 | 9.3 | 90.2 | 0.6 |
| | 40 | 8.6 | 89.9 | 1.5 |
| T2 | −20 | 9.3 | 90.4 | 0.3 |
| | 2-8 | 9.4 | 90.2 | 0.4 |
| | 25 | 9.1 | 90.0 | 0.9 |
| | 40 | 8.4 | 89.2 | 2.3 |

TABLE 4-continued

| Time point | Temp. (° C.) | % HMW species | % monomer | % LMW species |
|---|---|---|---|---|
| T4 | −20 | 9.1 | 90.8 | 0.1 |
| | 2-8 | 9.4 | 90.4 | 0.2 |
| | 25 | 8.3 | 90.6 | 1.1 |
| | 40 | 7.9 | 89.7 | 2.4 |
| T8 | −20 | 9.5 | 90.3 | 0.2 |
| | 2-8 | 9.6 | 89.9 | 0.5 |
| | 25 | 8.7 | 89.4 | 1.9 |
| | 40 | 8.8 | 87.0 | 4.2 |
| | | Formulation 3 | | |
| T0 | N/A | 9.8 | 89.8 | 0.5 |
| T1 | −20 | 10.1 | 89.6 | 0.3 |
| | 2-8 | 9.8 | 89.8 | 0.4 |
| | 25 | 9.2 | 89.8 | 1.0 |
| | 40 | 8.7 | 89.6 | 1.7 |
| T2 | −20 | 9.5 | 90.1 | 0.4 |
| | 2-8 | 9.3 | 90.1 | 0.6 |
| | 25 | 8.5 | 90.2 | 1.3 |
| | 40 | 8.8 | 89.2 | 2.0 |
| T4 | −20 | 8.7 | 91.1 | 0.2 |
| | 2-8 | 7.8 | 90.9 | 1.3 |
| | 25 | 7.9 | 90.8 | 1.3 |
| | 40 | 8.8 | 88.7 | 2.5 |
| T8 | −20 | 8.9 | 90.6 | 0.5 |
| | 2-8 | 8.5 | 90.7 | 0.8 |
| | 25 | 8.6 | 89.8 | 1.6 |
| | 40 | 11.0 | 86.0 | 3.0 |
| | | Formulation 4 | | |
| T0 | N/A | 9.6 | 90.2 | 0.2 |
| T1 | −20 | 9.1 | 90.8 | 0.2 |
| | 2-8 | 9.7 | 90.1 | 0.2 |
| | 25 | 9.2 | 90.2 | 0.7 |
| | 40 | 9.2 | 88.9 | 1.9 |
| T2 | −20 | 9.5 | 90.2 | 0.3 |
| | 2-8 | 9.6 | 90.0 | 0.4 |
| | 25 | 9.6 | 89.3 | 1.2 |
| | 40 | 9.2 | 88.4 | 2.5 |
| T4 | −20 | 8.5 | 91.4 | 0.1 |
| | 2-8 | 8.7 | 91.0 | 0.2 |
| | 25 | 8.9 | 89.8 | 1.3 |
| | 40 | 9.0 | 87.4 | 3.6 |

TABLE 4-continued

| Time point | Temp. (° C.) | % HMW species | % monomer | % LMW species |
|---|---|---|---|---|
| T8 | −20 | 9.7 | 90.0 | 0.3 |
| | 2-8 | 9.7 | 89.8 | 0.5 |
| | 25 | 9.9 | 88.3 | 1.8 |
| | 40 | 11.1 | 83.8 | 5.1 |

The results showed no significant change in percent monomer with increasing temperature or over time, and a slight increase in LMW species was observed over time with increasing temperature.

Overall, the SEC analysis indicated that Formulations 1, 2, and 3 provided slightly improved stability with respect to % monomer at the 8-week time point, compared to formulation 4. Formulation 3 showed the best stability with respect to changes in % LMW species.

Thermal stability of the Fab-oligonucleotide conjugates at 40 mg/mL was further studied by non-reduced protein express assay using capillary electrophoresis (CE-SDS). For analysis by this method, samples were diluted to 1 mg/mL, then mixed 1:1 with 10 mM N-ethylmaleimide in PBS. 5 μL of each of these samples was then added to 7 μL of sample buffer (Protein Express Reagent Kit, Perkin Elmer CLS960008) in a 96-well plate. Samples were incubated at 70° C. for 10 minutes, then cooled on ice for 5 minutes. 32 μL of water was added to each sample well, and the plate was centrifuged at 1200 g for 2 minutes prior to analysis. Samples were analyzed on an HT Protein Express LabChip (Perkin Elmer 760499), using a LabChip GXII Touch HT (Perkin Elmer), using measurement method HT High Sensitivity Antibody Analysis 200.

Results of the non-reduced CE-SDS analysis are shown in Table 5 below. For comparison, the starting material showed a size of 62.4 kDa with 100.0% purity.

TABLE 5

| | | Size† and % purity | | | |
|---|---|---|---|---|---|
| Time point | Temp.(° C.) | Formulation 1 | Formulation 2 | Formulation 3 | Formulation 4 |
| T0 | N/A | 65.0 (100.0) | 63.5 (100.0) | 63.3 (100.0) | 62.6 (100.0) |
| T1 | −20 | 66.0 (100.0) | 64.3 (100.0) | 65.1 (100.0) | 64.2 (100.0) |
| | 2-8 | 66.2 (100.0) | 65.4 (100.0) | 64.0 (100.0) | 63.7 (100.0) |
| | 25 | 66.3 (98.4) | 64.1 (98.9) | 64.1 (98.8) | 63.3 (98.7) |
| | 40 | 65.1 (97.4) | 63.1 (97.8) | 62.9 (97.9) | 63.2 (96.8) |
| T2 | −20 | 66.0 (100.0) | 64.6 (100.0) | 63.5 (100.0) | 63.2 (100.0) |
| | 2-8 | 66.4 (100.0) | 64.6 (100.0) | 63.0 (100.0) | 63.3 (100.0) |
| | 25 | 66.1 (97.7) | 64.0 (98.8) | 63.3 (98.8) | 63.4 (98.5) |
| | 40 | 66.3 (95.7) | 64.3 (97.5) | 63.3 (97.9) | 63.5 (96.7) |
| T4 | −20 | 66.6 (100.0) | 63.7 (100.0) | 63.5 (100.0) | 64.9 (100.0) |
| | 2-8 | 67.0 (100.0) | 63.7 (100.0) | 63.2 (100.0) | 64.0 (100.0) |
| | 25 | 66.2 (97.0) | 63.5 (98.5) | 63.8 (98.6) | 64.7 (98.2) |
| | 40 | 66.0 (84.1) | 64.1 (96.6) | 63.7 (97.1) | 64.3 (95.9) |
| T8 | −20 | 66.4 (100.0) | 65.9 (100.0) | 65.4 (100.0) | 64.2 (100.0) |
| | 2-8 | 66.7 (100.0) | 65.9 (100.0) | 65.7 (100.0) | 64.2 (100.0) |
| | 25 | 67.1 (96.9) | 64.6 (98.8) | 64.9 (98.2) | 63.7 (97.7) |
| | 40 | 67.4 (74.8) | 65.9 (95.0) | 64.7 (96.4) | 64.1 (94.9) |

†Size is shown in kDa. Values in parentheses represent the percent purity.

The results showed that the percent purity of conjugates in Formulation 1 gradually decreased at 25° C. and 40° C. from T1 to T8, and the formation of new species was observed, suggesting that conjugates in Formulation 1 are less stable at higher temperatures. The results also showed that conjugates had good percent purity in Formulations 2, 3, and 4 at all temperatures and time points tested. The high percent purity of conjugates in Formulation 3 at higher temperatures suggests that they have improved stability in Formulation 3 relative to the other formulations.

Thermal stability of the Fab-oligonucleotide conjugates at 40 mg/mL was further studied by reduced protein express assay using capillary electrophoresis (CE-SDS). For analysis by this method, samples were diluted with PBS to 0.5 mg/mL. Samples were next mixed with denaturing solution: 24.5 μL of 14.2 M β-mercaptoethanol (BME) was added to 700 μL of Protein Express Sample Buffer (Protein Express Reagent Kit, Perkin Elmer CLS960008), and then 5 μL of each of the diluted samples was added to 7 μL of the sample denaturing solution in a 96-well plate. Samples were incubated at 70° C. for 10 minutes, then cooled on ice for 5 minutes. 32 μL of water was added to each sample well, and the plate was centrifuged at 1200 g for 2 minutes prior to analysis. Samples were analyzed on an HT Protein Express LabChip (Perkin Elmer 760499), using a LabChip GXII Touch HT (Perkin Elmer), using measurement method HT High Sensitivity Antibody Analysis 200.

Results of the reduced CE-SDS analysis are shown in Table 6 below. Values for the starting material (SM) are shown for comparison in the top row.

TABLE 6

| Time point | Temp. (° C.) | LC Fragment Size† | % LC Fragment | Fab H/L Fragment Size† | % Fab H/L Fragment | Other Fragment Size† | % Other Fragment |
|---|---|---|---|---|---|---|---|
| SM | | 28.4 | 3.0 | 34.9 | 87.3 | 41.7 | 9.7 |
| Formulation 1 | | | | | | | |
| T0 | N/A | 27.7 | 15.3 | 35.6 | 79.9 | 41.7 | 5.2 |
| T1 | −20 | 27.0 | 3.9 | 34.2 | 89.8 | 41.0 | 6.4 |
| | 2-8 | 26.9 | 3.9 | 33.8 | 89.9 | 40.7 | 6.3 |
| | 25 | 27.8 | 4.0 | 34.9 | 89.7 | 42.0 | 6.3 |
| | 40 | 27.8 | 4.4 | 34.9 | 89.0 | 42.1 | 6.6 |
| T2 | −20 | 27.6 | 3.9 | 34.4 | 44.9 | 42.4 | 5.6 |
| | 2-8 | 27.4 | 4.0 | 34.1 | 45.8 | 42.0 | 5.6 |
| | 25 | 27.5 | 4.3 | 34.0 | 46.7 | 42.1 | 5.3 |
| | 40 | 27.4 | 4.9 | 33.9 | 45.3 | 41.8 | 5.2 |
| T4 | −20 | 27.1 | 3.7 | 33.7 | 48.0 | 41.5 | 6.2 |
| | 2-8 | 27.2 | 3.8 | 33.8 | 46.9 | 41.9 | 6.1 |
| | 25 | 26.9 | 4.4 | 33.4 | 47.2 | 41.3 | 5.4 |
| | 40 | 27.3 | 5.6 | 33.7 | 50.0 | 41.6 | 4.5 |
| T8 | −20 | 27.3 | 3.1 | 34.3 | 48.1 | 41.8 | 5.0 |
| | 2-8 | 27.6 | 3.4 | 34.3 | 46.1 | 42.2 | 5.1 |
| | 25 | 27.3 | 3.8 | 34.0 | 47.1 | 41.7 | 4.8 |
| | 40 | 27.5 | 6.4 | 33.9 | 53.9 | 41.7 | 4.3 |
| Formulation 2 | | | | | | | |
| T0 | N/A | 28.2 | 3.0 | 34.8 | 87.5 | 41.4 | 9.4 |
| T1 | −20 | 27.3 | 3.8 | 33.8 | 87.0 | 40.9 | 9.2 |
| | 2-8 | 27.1 | 3.7 | 33.5 | 86.5 | 40.6 | 8.8 |
| | 25 | 27.6 | 4.0 | 34.4 | 87.5 | 41.8 | 8.4 |
| | 40 | 28.1 | 4.3 | 34.8 | 87.4 | 42.3 | 8.3 |
| T2 | −20 | 27.5 | 4.5 | 34.3 | 87.5 | 42.0 | 8.0 |
| | 2-8 | 27.4 | 4.2 | 34.1 | 88.2 | 41.8 | 7.6 |
| | 25 | 26.7 | 4.7 | 33.2 | 87.0 | 40.9 | 7.3 |
| | 40 | 26.8 | 5.3 | 33.3 | 87.7 | 40.9 | 7.0 |
| T4 | −20 | 27.1 | 4.3 | 33.8 | 87.7 | 41.3 | 8.0 |
| | 2-8 | 27.0 | 4.2 | 33.7 | 88.2 | 41.2 | 7.6 |
| | 25 | 27.4 | 4.7 | 34.1 | 86.9 | 41.8 | 7.2 |
| | 40 | 27.0 | 5.1 | 33.6 | 85.8 | 41.1 | 6.6 |
| T8 | −20 | 27.5 | 3.7 | 34.3 | 89.1 | 41.8 | 7.2 |
| | 2-8 | 27.2 | 3.8 | 34.0 | 89.3 | 41.5 | 6.9 |
| | 25 | 27.1 | 6.3 | 33.7 | 87.7 | 41.1 | 6.0 |
| | 40 | 27.2 | 4.6 | 34.0 | 88.7 | 41.4 | 6.7 |
| Formulation 3 | | | | | | | |
| T0 | N/A | 28.3 | 3.1 | 34.8 | 87.6 | 41.4 | 9.4 |
| T1 | −20 | 27.2 | 3.8 | 33.7 | 87.0 | 41.1 | 9.2 |
| | 2-8 | 27.3 | 4.0 | 33.8 | 86.9 | 41.1 | 9.2 |
| | 25 | 28.0 | 4.1 | 34.7 | 87.0 | 42.2 | 8.8 |
| | 40 | 28.0 | 4.5 | 34.7 | 87.3 | 42.0 | 8.2 |
| T2 | −20 | 26.8 | 4.6 | 33.4 | 87.5 | 40.9 | 8.0 |
| | 2-8 | 27.2 | 4.6 | 33.8 | 87.5 | 41.4 | 7.9 |
| | 25 | 26.6 | 5.1 | 33.2 | 86.3 | 40.6 | 7.7 |
| | 40 | 26.8 | 5.5 | 33.2 | 82.4 | 40.6 | 6.1 |
| T4 | −20 | 26.9 | 4.4 | 33.5 | 87.5 | 41.0 | 8.1 |
| | 2-8 | 26.8 | 4.9 | 33.4 | 86.8 | 40.9 | 8.3 |
| | 25 | 27.2 | 4.9 | 33.8 | 86.7 | 41.4 | 7.4 |
| | 40 | 27.3 | 6.0 | 33.9 | 84.6 | 41.5 | 6.8 |

TABLE 6-continued

| Time point | Temp. (° C.) | LC Fragment Size† | % LC Fragment | Fab H/L Fragment Size† | % Fab H/L Fragment | Other Fragment Size† | % Other Fragment |
|---|---|---|---|---|---|---|---|
| T8 | −20 | 26.9 | 4.2 | 33.5 | 88.0 | 41.0 | 7.8 |
| | 2-8 | 27.0 | 4.3 | 33.6 | 88.4 | 41.0 | 7.3 |
| | 25 | 27.0 | 5.1 | 33.7 | 88.5 | 41.1 | 7.0 |
| | 40 | 27.2 | 6.3 | 33.8 | 84.3 | 41.3 | 5.7 |
| Formulation 4 | | | | | | | |
| T0 | N/A | 28.0 | 3.0 | 34.5 | 87.6 | 41.1 | 9.4 |
| T1 | −20 | 27.1 | 3.7 | 33.6 | 87.6 | 40.9 | 8.7 |
| | 2-8 | 27.1 | 3.8 | 33.7 | 87.4 | 40.9 | 8.8 |
| | 25 | 27.6 | 3.9 | 34.2 | 87.4 | 41.6 | 8.7 |
| | 40 | 27.4 | 4.9 | 34.1 | 87.0 | 41.5 | 8.1 |
| T2 | −20 | 27.0 | 4.3 | 33.6 | 87.3 | 41.2 | 8.1 |
| | 2-8 | 27.4 | 4.4 | 33.9 | 87.6 | 41.4 | 8.0 |
| | 25 | 27.0 | 4.7 | 33.7 | 87.8 | 41.2 | 7.5 |
| | 40 | 26.8 | 5.9 | 33.5 | 86.9 | 40.8 | 7.2 |
| T4 | −20 | 27.2 | 3.8 | 33.8 | 89.1 | 41.4 | 7.1 |
| | 2-8 | 26.7 | 4.3 | 33.8 | 88.0 | 40.6 | 7.7 |
| | 25 | 27.1 | 4.9 | 33.7 | 87.8 | 41.3 | 7.3 |
| | 40 | 27.2 | 6.3 | 33.8 | 86.8 | 41.4 | 6.7 |
| T8 | −20 | 26.9 | 4.2 | 33.5 | 87.7 | 40.9 | 8.1 |
| | 2-8 | 26.8 | 4.1 | 33.5 | 88.6 | 40.8 | 7.3 |
| | 25 | 26.7 | 5.1 | 33.4 | 88.0 | 40.7 | 5.4 |
| | 40 | 26.8 | 6.8 | 33.4 | 87.7 | 40.7 | 5.4 |

†Sizes are shown in kDa.

In Formulation 1, there were two additional peaks including one additional HC peak observed in all samples at T2, T4, and T8, indicating instability of the conjugates in this formulation. There were no significant differences in overall stability of the conjugates in formulations 2, 3, and 4 observed by the reduced CE-SDS.

Overall, the results of the various thermal stability tests presented herein suggest that Formulation 3 provided the best stability for the Fab-oligonucleotide conjugates.

Example 6. Comparison of Freeze/Thaw Stability of Different Exemplary Formulations Formulations comprising conjugates as described in Example 1, containing an anti-TfR1 Fab covalently linked to a DMPK-targeting oligonucleotide (ASO) were prepared. The anti-TfR1 Fab-oligonucleotide conjugates starting material ("SM") was at a concentration of 33 mg/mL in a buffer containing 100 mM sodium phosphate and 100 mM sodium chloride at pH 7.4. For freeze/thaw stability testing, the anti-TfR1 Fab-oligonucleotide conjugates were formulated in different buffers at a concentration of approximately 40 mg/mL. The buffer conditions in each of the four formulations were as follows:

Formulation buffer 1:25 mM succinate, 10% (w/v) sucrose, pH 5.2.

Formulation buffer 2:25 mM succinate, 10% (w/v) sucrose, pH 6.0.

Formulation buffer 3:25 mM tris(hydroxymethyl)aminomethane, 10% (w/v) sucrose, pH 7.5.

Formulation buffer 4:100 mM sodium phosphate, 100 mM sodium chloride, pH 7.4.

To test freeze/thaw stability of the conjugates in each formulation, aliquots were prepared and subjected to 0, 1, 3, or 5 freeze/thaw cycles, after which time visual appearance, protein concentration, and aggregate/fragment formation were assessed.

For each of formulations 1, 2, 3, and 4, visual appearance assessment showed the solutions were clear, colorless, and with no visible aggregates after 0, 1, 3, and 5 freeze/thaw cycles.

BCA analysis of each formulation, conducted as described in Example 5, suggested that there were no significant changes in the concentration of the complexes over 5 freeze/thaw ("F/T") cycles. The results are shown in Table 7 below. Values for the starting material (SM) are shown for comparison in the top row.

TABLE 7

| F/T cycles | Concentration (mg/mL) Formulation 1 | Formulation 2 | Formulation 3 | Formulation 4 |
|---|---|---|---|---|
| 0 | 34.4 | 42.4 | 40.6 | 44.2 |
| 1 | 35.5 | 42.3 | 41.9 | 44.7 |
| 3 | 35.4 | 42.1 | 43.3 | 43.2 |
| 5 | 36.4 | 42.5 | 42.9 | 44.1 |

Size exclusion chromatography (SEC) analysis of each formulation, conducted as described in Example 5, suggested that there were no significant differences between the four formulations with respect to low molecular weight (LMW) species, monomer, and high molecular weight (HMW) species over 5 freeze/thaw ("F/T") cycles. The results are shown in Table 8 below. Values for the starting material (SM) are shown for comparison in the top row.

TABLE 8

| F/T cycles | % HMW species | % monomer | % LMW species |
|---|---|---|---|
| SM | 9.48 | 89.70 | 0.83 |
| Formulation 1 | | | |
| 0 | 8.15 | 89.99 | 1.86 |
| 1 | 7.68 | 91.20 | 1.11 |
| 3 | 7.62 | 90.83 | 1.55 |
| 5 | 7.68 | 91.08 | 1.25 |

TABLE 8-continued

| F/T cycles | % HMW species | % monomer | % LMW species |
|---|---|---|---|
| Formulation 2 | | | |
| 0 | 9.50 | 89.66 | 0.84 |
| 1 | 9.45 | 89.71 | 0.84 |
| 3 | 9.49 | 89.68 | 0.82 |
| 5 | 9.55 | 89.67 | 0.78 |
| Formulation 3 | | | |
| 0 | 8.61 | 90.03 | 1.36 |
| 1 | 8.73 | 89.81 | 1.46 |
| 3 | 8.76 | 89.74 | 1.50 |
| 5 | 8.77 | 89.77 | 1.46 |
| Formulation 4 | | | |
| 0 | 9.73 | 89.24 | 1.03 |
| 1 | 9.63 | 89.46 | 0.92 |
| 3 | 9.56 | 89.45 | 1.00 |
| 5 | 9.48 | 89.52 | 0.99 |

Example 7. Evaluation of Stability of Lyophilized Formulations of Conjugates

Conjugates (labeled in this Example as "Anti-TfR1 Fab-ASO conjugate") as described in Example 1, containing an anti-TfR1 Fab covalently linked to a DMPK-targeting oligonucleotide (ASO) were prepared and lyophilized with tris(hydroxymethyl)aminomethane (25 mM), sucrose (10% (w/v)), at a pH of 7.5 and tested for stability. Prior to reconstitution all samples at all timepoints and temperatures were visually identified as a white cake and uniform in shape. Additionally, the samples reconstituted in less than 1 minute, and became clear and colorless with fewer than 10 particles. All samples were considered stable by visual analysis pre- and post-reconstitution up to 40° for at least 8 weeks.

X-ray diffraction analysis was performed to evaluate the crystallographic structure of the lyophilized composition. Approximately 20 mg of lyophilized anti-TfR1 Fab-ASO conjugates was placed in a plastic sample holder and flattened with a glass slide to ensure a flat surface. When performing this analysis, a Proto AXRD® Benchtop Power X-ray Diffractometer was used with a fine focus Cu-anode metal/ceramic construction 1500-Watt x-ray tube.

Figure 9:
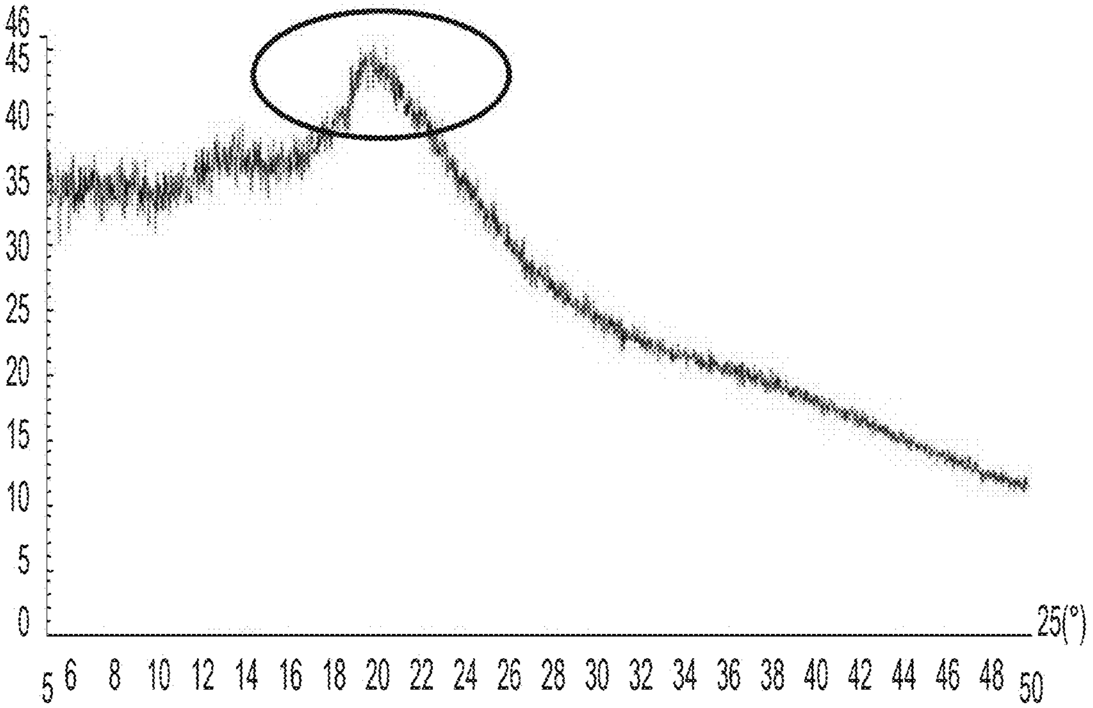
FIG. 9 shows x-ray diffraction (XRD) pattern of a lyophilized formulation of anti-TfR1 Fab-ASO conjugates.

The diffraction pattern was measured (FIG. 9), and a broad "halo" (circled in FIG. 9) was identified, which indicates that the material is amorphous at time 0 (T0).

To test the absorbance of the samples, the lyophilized anti-TfR1 Fab-ASO conjugates were first reconstituted with water and then diluted using formulation buffer (25 mM tris(hydroxymethyl)aminomethane, 10% (w/v) sucrose, pH 7.5) to a concentration of 0.2 mg/ml. Absorbance was measured at 260 nm and 280 nm using a DeNovix DS11+ spectrophotometer. Readings were performed in triplicate and averaged. These results were used to calculate the concentration (Fab (mg/mL and µM) and oligonucleotide (µM)), percent recovery, and Drug Antibody Ratio (DAR), at multiple timepoints. For all protein concentrations, percent recovery, and DAR testing, bovine serum albumin (BSA) was used as a positive control, PBS was used as a blank and negative control for BSA, and formulation buffer was used as a blank and negative control for the conjugates samples.

Figure 10A:
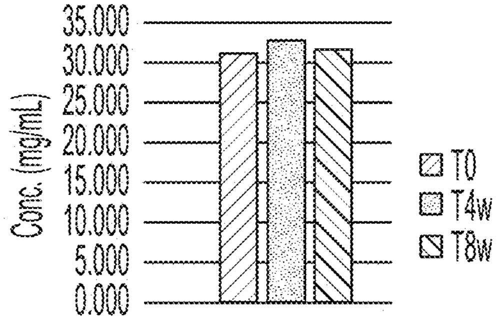
FIGS. 10A-10C show protein concentrations calculated from absorbance data of a lyophilized formulation of anti-TfR1 Fab-ASO conjugates after reconstitution at 0 weeks (TO), 4 weeks (T4w), and 8 weeks (T8w), at 2-8° C.
Figure 10B:
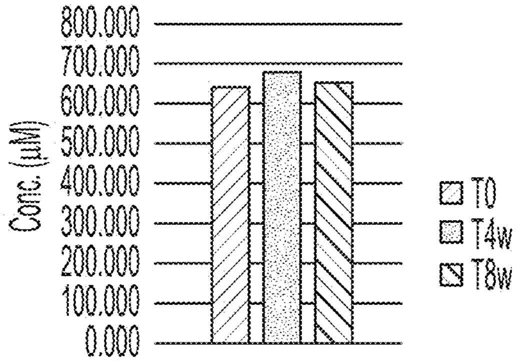
Figure 10C:
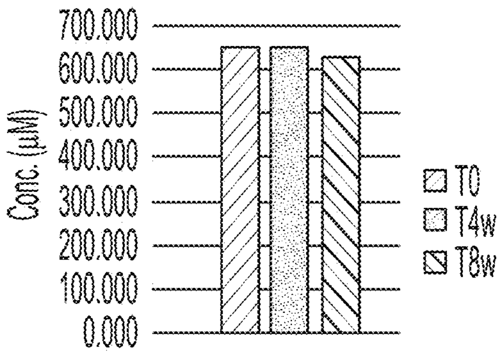
Figure 11A:
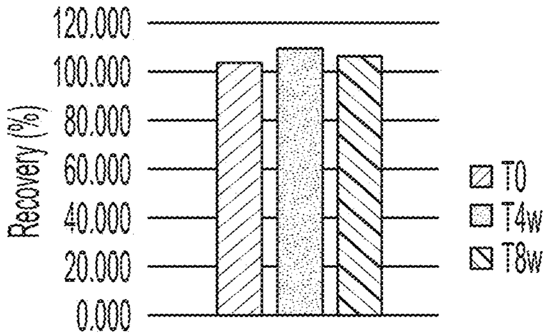
FIGS. 11A-11B show the average percent recovery (FIG. 11A) and Drug Antibody Ratio (DAR.
Figure 11B:
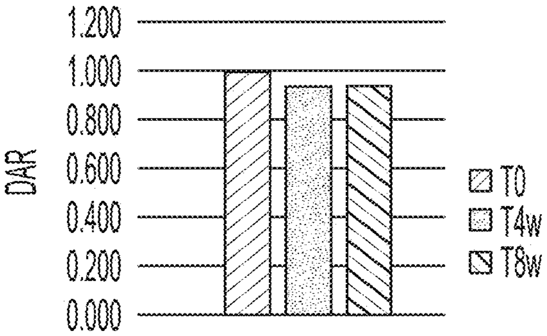

At 2-8° C. the average concentration of the replicates for Fab (FIG. 10A and FIG. 10B) showed no significant change from time 0 (T0), when compared to 4 weeks (T4w) or 8 weeks (T8w). Additionally, there was no significant change when comparing the 4 week and 8-week timepoints. At 2-8° C. the average concentration of the replicates for oligonucleotide concentration (FIG. 10C) showed no significant difference when comparing T0, T4w, and T8w. At 2-8° C. the average percent recovery (FIG. 11A) was close to 100% for all samples at all time points. At 2-8° C. the average DAR (FIG. 11B) was close to 1.0 at all timepoints.

Figure 12A:
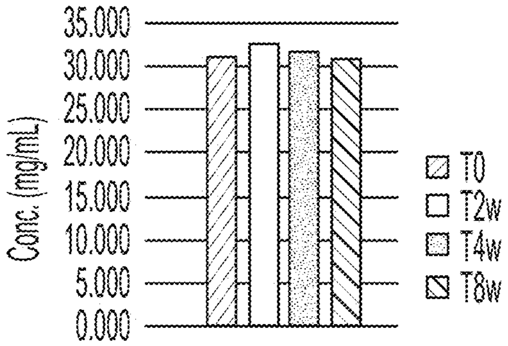
FIGS. 12A-12C show protein concentrations calculated from absorbance data of a lyophilized formulation of anti-TfR1 Fab-ASO conjugates after reconstitution at 0 weeks (T0), 2 weeks (T2w), 4 weeks (T4w), and 8 weeks (T8w), at 25° C.
Figure 12B:
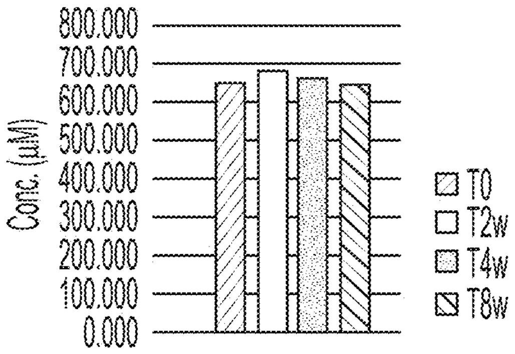
Figure 12C:
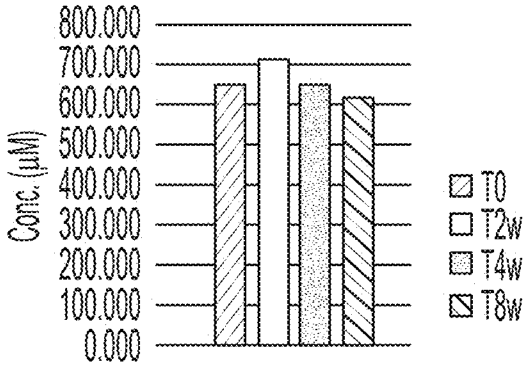
Figure 13A:
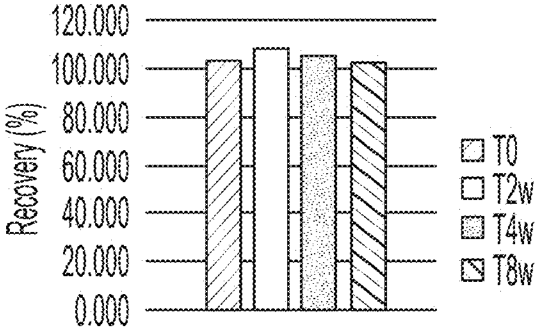
FIGS. 13A-13B show the average percent recovery (FIG. 13A) and Drug Antibody Ratio (DAR.
Figure 13B:
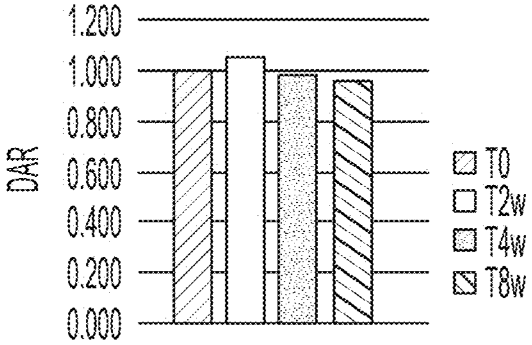

At 25° C. the average concentration of the replicates for Fab (FIG. 12A and FIG. 12B) showed no significant change from time 0 (T0), when compared to 2 weeks (T2w), 4 weeks (T4w), or 8 weeks (T8w) and there was no significant change when comparing T2w, T4w, and T8w to one another. At 25° C. the average concentration of the replicates for the oligonucleotide (FIG. 12C) did not show significant change over time. At 25° C. the average percent recovery (FIG. 13A) was close to 100% for all timepoints. At 25° C. the average DAR (FIG. 13B) was close to 1.0 at all timepoints.

Figure 14A:
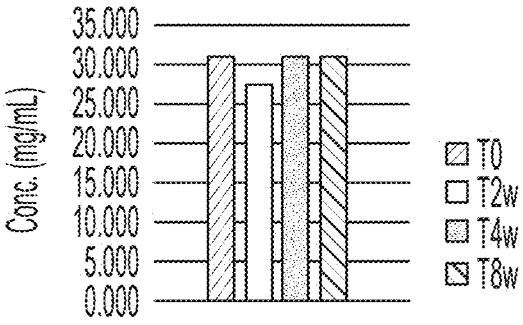
FIGS. 14A-14C show protein concentrations calculated from absorbance data of a lyophilized formulation of anti-TfR1 Fab-ASO conjugates after reconstitution at T0, T2w, T4w, and T8w, at 40° C.
Figure 14B:
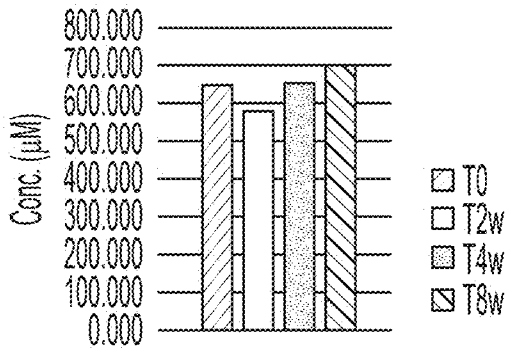
Figure 14C:
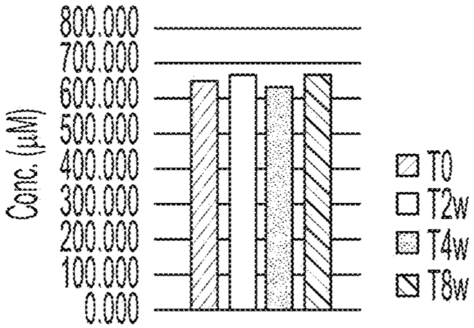
Figure 15A:
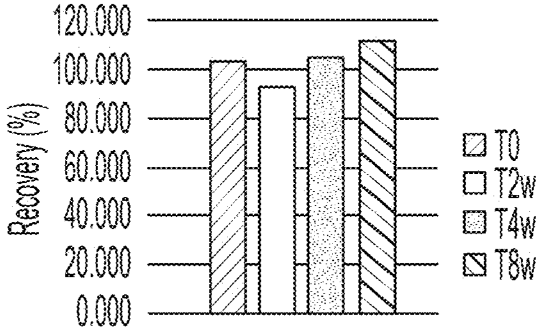
FIGS. 15A-15B show the average percent recovery (FIG. 15A) and Drug Antibody Ratio (DAR.
Figure 15B:
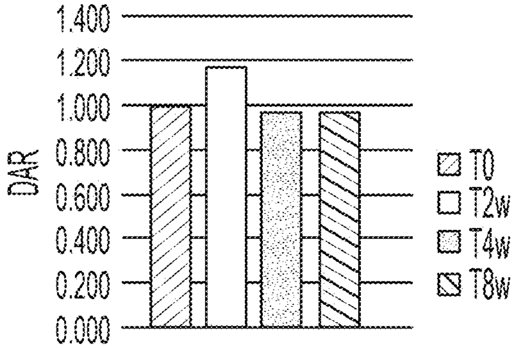

At 40° C. the average concentration of the replicates for Fab (FIG. 14A and FIG. 14B) showed no significant change from T0, when compared to T2w, T4w, or T8w. At 40° C. the average concentration of the replicates for oligonucleotide concentration (FIG. 10C) showed no significant change at any of the timepoints. At 40° C. the average percent recovery (FIG. 15A) was close to 100% for all samples at all time points. At 40° C. the average DAR (FIG. 15B) was close to 1.0 at all timepoints.

Next, the anti-TfR1 Fab-ASO conjugates were analyzed using size-exclusion chromatograph (SEC). All samples were diluted to a concentration of 1.0 mg/ml using formulation buffer (25 mM tris(hydroxymethyl)aminomethane, 10% (w/v) sucrose, pH 7.5) prior to analysis. For the mobile phase of the chromatographic conditions an isocratic elution was used containing potassium phosphate (200 mM), potassium chloride (200 mM), 5% (v/v) isopropanol (IPA) at a pH of 6.8, at a flow rate of 0.250 ml/min using a 20 minute run time. The wavelength used for measurements was 280 nm. The high-performance liquid chromatography system used was the Dionex Ultimate 3000 UPLC System, with a Waters BEH SEC column (200 Å, 300×4.6 mm, 1.7 µm, P/N 186005226).

Figure 16A:
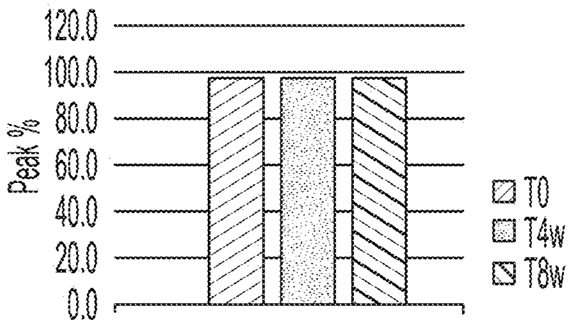
FIGS. 16A-16B show the sum of the relative area of peaks 1 and 2 (FIG. 16A) and peaks 3 and 4 (FIG. 16B) measured using size-exclusion chromatography (SEC) of lyophilized anti-TfR1 Fab-ASO conjugates after reconstitution at T0, T4w, and T8w, at 2-8° C.
Figure 16B:
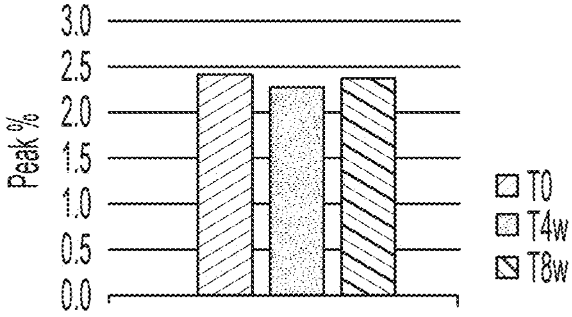

At 2-8° C. the sum of the relative area of the first and second (main) peaks (FIG. 16A) show no significant difference when comparing T0, T4w, and T8w. Further, the sum of the relative area of the third and fourth (high molecular weight species (HMWS)) peaks (FIG. 16B) also show no significant difference when comparing T0, T4w, and T8w.

Figure 17A:
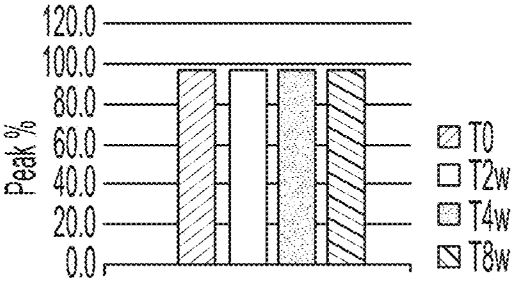
FIGS. 17A-17B show the sum of the relative area of peaks 1 and 2 (FIG. 17A) and peaks 3 and 4 (FIG. 17B) measured using size-exclusion chromatography (SEC) of lyophilized anti-TfR1 Fab-ASO conjugates after reconstitution at T0, T2w, T4w, and T8w, at 25° C.
Figure 17B:
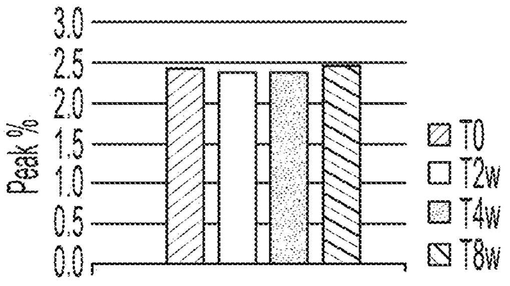

At 25° C. the sum of the relative area of the first and second (main) peaks (FIG. 17A) show no significant difference when comparing T0, T2w, T4w, and T8w. Further, the sum of the relative area of the third and fourth (HMWS) peaks (FIG. 17B) also show no significant difference when comparing T0, T2w, T4w, and T8w.

Figure 18A:
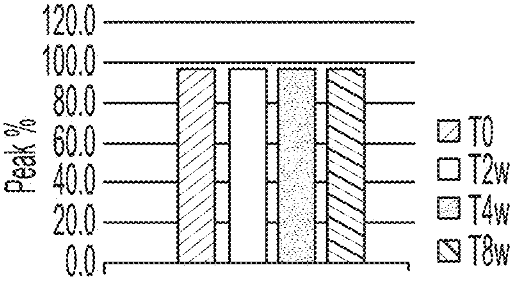
FIGS. 18A-18B show the sum of the relative area of peaks 1 and 2 (FIG. 18A) and peaks 3 and 4 (FIG. 18B) measured using size-exclusion chromatography (SEC) of lyophilized anti-TfR1 Fab-ASO conjugates after reconstitution at T0, T2w, T4w, T8w, at 40° C.
Figure 18B:
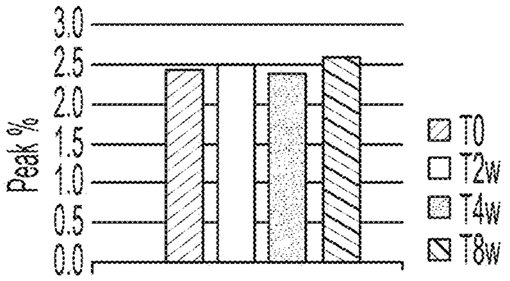

At 40° C. the sum of the relative area of the first and second (main) peaks (FIG. 18A) show no significant difference when comparing T0, T2w, T4w, and T8w. Further, the sum of the relative area of the third and fourth (HMWS) peaks (FIG. 18B) also show no significant difference when comparing T0, T2w, T4w, and T8w.

To conduct non-reduced capillary electrophoresis sodium dodecyl sulfate (CE-SDS) analysis, samples were diluted to 1 mg/ml in phosphate buffered saline (PBS). The diluted samples were then further diluted 1:1 with 10 mM N-ethylmaleimide (NEM) in PBS. 5.0 µl of the resulting solution was then added to 7.0 µl sample buffer. The samples were then incubated at 70° C. for 10 minutes. After incubation, 32 µl of water was added and the samples were centrifuged at 1200 g for 2 minutes. The samples were then analyzed using HT High Sensitivity Antibody Analysis 200, using HT Protein Express LabChip (Perkin Elmer, 760499) with Protein Express Reagent Kit (Perkin Elmer, CLS960008). Analysis was performed on a LabChip GXII Touch HT (Perkin Elmer).

Figure 19:
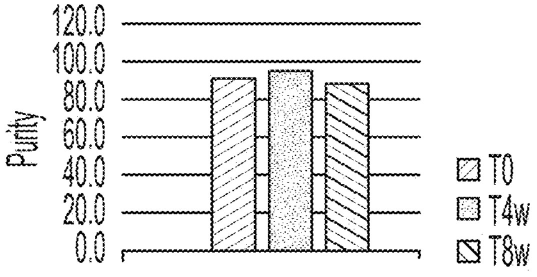
FIG. 19 shows percent purity of the main peak of lyophilized anti-TfR1 Fab-ASO conjugates after reconstitution measured using capillary electrophoresis (CE-SDS) at T0, T4w, and T8w, at 2-8° C.
Figure 20:
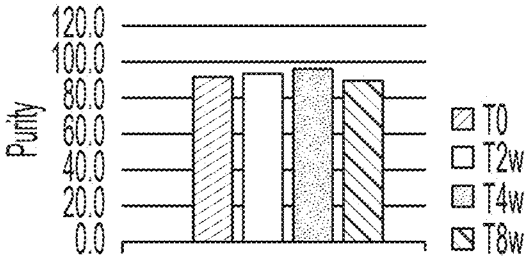
FIG. 20 shows percent purity of the main peak of lyophilized anti-TfR1 Fab-ASO conjugates after reconstitution measured using CE-SDS at T0, T2w, T4w, and T8w, at 25° C.
Figure 21:
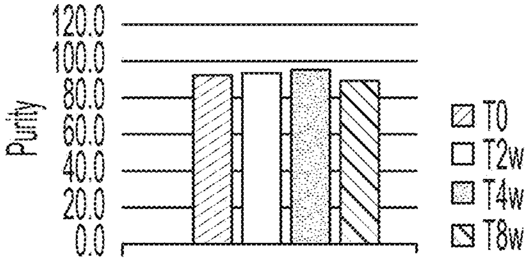
FIG. 21 shows percent purity of the main peak of lyophilized anti-TfR1 Fab-ASO conjugates after reconstitution measured using CE-SDS at T0, T2w, T4w, and T8w, at 40° C.

At 2-8° C. (FIG. 19), the purity of the main peak showed no significant change between T0, T4w, and T8w. At 25° C. (FIG. 20) and 40° C. (FIG. 21), the purity of the main peak showed no significant change between T0, T2w, T4w, and T8w.

To conduct reduced CE-SDS analysis, samples were diluted to 0.5 mg/ml in PBS. 5.0 μl of the diluted sample was added to 7.0 μl of sample denaturing solution (24.5 μL of 1M dithiothreitol (DTT) added to 700 μL Protein Express Sample Buffer). The samples were then incubated at 70° C. for 10 minutes. After incubation, 32 μl of water was added and the samples were centrifuged at 1200 g for 2 minutes. The samples were then analyzed using HT High Sensitivity Antibody Analysis 200, using HT Protein Express LabChip (Perkin Elmer, 760499) with Protein Express Reagent Kit (Perkin Elmer, CLS960008). Analysis was performed on a LabChip GXII Touch HT (Perkin Elmer).

At 2-8° C. (Table 9), the purity of the peaks 1, 2, 3, and 4 showed no significant change between T0, T4w, and T8w. At 25° C. (Table 10) and 40° C. (Table 11), the purity of the peaks 1, 2, 3, and 4 showed no significant change between T0, T2w, T4w, and T8w.

Overall, these results demonstrate that lyophilized anti-TfR1 Fab-ASO conjugates are stable at all temperatures and timepoints tested.

TABLE 9

Capillary electrophoresis sodium dodecyl sulfate (CE-SDS) results (reduced) at 2-8° C.

| Time point | Peak 1 (%) | Peak 2 (%) | Peak 3 (%) | Total (%) |
|---|---|---|---|---|
| T0 | 3.05 | 89.97 | 6.09 | 99.11 |
| T4w | 2.87 | 88.40 | 8.42 | 99.69 |
| T8w | 4.12 | 85.15 | 8.41 | 97.68 |

TABLE 10

Capillary electrophoresis sodium dodecyl sulfate (CE-SDS) results (reduced) at 25° C.

| Time point | Peak 1 (%) | Peak 2 (%) | Peak 3 (%) | Total (%) |
|---|---|---|---|---|
| T0 | 3.05 | 89.97 | 6.09 | 99.11 |
| T2w | 3.21 | 88.94 | 7.31 | 99.46 |
| T4w | 2.87 | 87.62 | 9.09 | 99.58 |
| T8w | 4.12 | 85.22 | 8.38 | 97.72 |

TABLE 11

Capillary electrophoresis sodium dodecyl sulfate (CE-SDS) results (reduced) at 40° C.

| Time point | Peak 1 (%) | Peak 2 (%) | Peak 3 (%) | Total (%) |
|---|---|---|---|---|
| T0 | 3.05 | 89.97 | 6.09 | 99.11 |
| T2w | 3.21 | 88.80 | 7.34 | 99.35 |
| T4w | 2.91 | 87.80 | 8.75 | 99.46 |
| T8w | 4.14 | 85.20 | 8.41 | 97.75 |

ADDITIONAL EMBODIMENTS

1. A formulation comprising complexes that comprise an oligonucleotide covalently linked to an anti-transferrin receptor 1 (TfR1) antibody, wherein the anti-TfR1 antibody comprises: a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16, wherein the oligonucleotide comprises a 5'-X—Y—Z-3' configuration, wherein X and Z are flanking regions comprising one or more modified nucleosides and Y is a gap region comprising one or more 2'-deoxyribonucleosides, and wherein the complexes are formulated with tris (hydroxymethyl)aminomethane and sucrose.

2. A formulation comprising complexes comprising a structure of formula (I): $[R^1]_{n1}$—$R^2$, wherein each $R^1$ independently comprises a group of the formula (Ia):

(Ia)

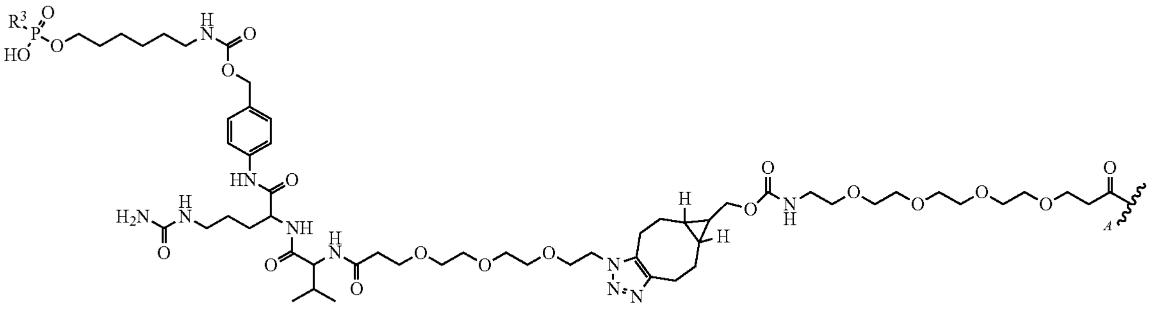, wherein $R^2$ comprises an antibody, and $R^3$ comprises an oligonucleotide comprising a 5'-X—Y—Z-3' configuration, wherein X and Z are flanking regions comprising one or more modified nucleosides and Y is a gap region comprising one or more 2'-deoxyribonucleosides;

wherein $R^1$ is covalently linked to $R^2$ at attachment point A; and wherein n1 is an integer representing the number of instances of $R^1$, wherein each instance of $R^1$ is covalently linked to a different amino acid residue of the antibody, optionally wherein each different amino acid residue is a lysine;

wherein the complexes are formulated with tris(hydroxymethyl)aminomethane and sucrose, optionally wherein the antibody is an anti-TfR1 antibody.

3. The formulation of embodiment 2, wherein the antibody comprises:

a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16.

4. The formulation of any one of embodiments 1 to 3, wherein the formulation is in a lyophilized form.

5. The formulation of any one of embodiments 1 to 3, wherein the formulation is in a frozen solid form.

6. The formulation of any one of embodiments 1 to 3, wherein the formulation is in an aqueous solution.

7. The formulation of embodiment 6, wherein the tris (hydroxymethyl)aminomethane is present in the aqueous solution at a concentration in the range of 5 mM to 50 mM.

8. The formulation of embodiment 6 or 7, wherein the sucrose is present in the aqueous solution at a concentration in the range of 5% to 15% weight per volume (w/v %).

9. The formulation of any one of embodiments 6 to 8, wherein the aqueous solution has a pH in the range of 6.5 to 8.5.

10. The formulation of any one of embodiments 6 to 9, wherein the tris(hydroxymethyl)aminomethane is present in the aqueous solution at a concentration of 25 mM and/or the sucrose is present in the aqueous solution at a concentration of 10 w/v % and/or the aqueous solution is at a pH of 7.5.

11. The formulation of any one of embodiments 1-10, wherein the antibody is a Fab fragment, a full-length IgG, a Fab' fragment, a $F(ab')_2$ fragment, an scFv, or an Fv.

12. The formulation of embodiment 11, wherein the antibody is a Fab fragment.

13. The formulation of any one of embodiments 1-12, wherein the antibody comprises a heavy chain variable region (VH) comprising an amino acid sequence at least 85% identical to SEQ ID NO: 17; and/or wherein the antibody comprises a light chain variable region (VL) comprising an amino acid sequence at least 85% identical to SEQ ID NO: 18, optionally wherein the antibody comprises a VH comprising the amino acid sequence of SEQ ID NO: 17 and/or a VL comprising the amino acid sequence of SEQ ID NO: 18.

14. The formulation of any one of embodiments 1-13, wherein the antibody comprises a heavy chain comprising an amino acid sequence at least 85% identical to SEQ ID NO: 19; and/or wherein the antibody comprises a light chain comprising an amino acid sequence at least 85% identical to SEQ ID NO: 20, optionally wherein the antibody comprises a heavy chain comprising the amino acid sequence of SEQ ID NO: 19 and/or a light chain comprising the amino acid sequence of SEQ ID NO: 20.

15. The formulation of any one of embodiments 1-14, wherein the oligonucleotide is 10-30 nucleotides in length.

16. The formulation of any one of embodiments 1-15, wherein the oligonucleotide comprises a nucleotide sequence having a region of complementarity of at least 8 consecutive nucleotides in length to SEQ ID NO: 22.

17. The formulation of any one of embodiments 1-16, wherein the oligonucleotide comprises at least 8 consecutive nucleotides of a nucleotide sequence as set forth in SEQ ID NO: 21, optionally wherein the oligonucleotide comprises the nucleotide sequence of SEQ ID NO: 21.

18. The formulation of any one of embodiments 2-17, wherein each $R^1$ comprises a group of the formula (Ib):

(Ib)

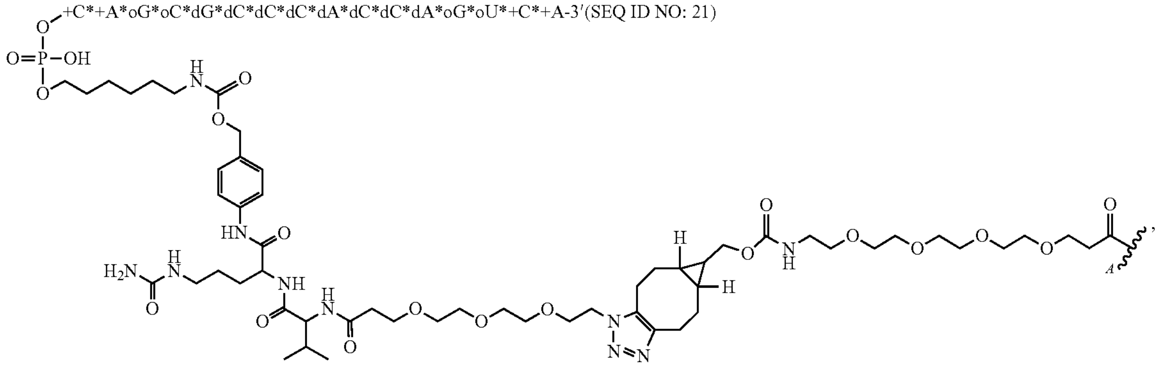

wherein +N represents an LNA (2'-4' methylene bridge) ribonucleoside, dN represents a 2'-deoxyribonucleoside, oN represents a 2'-O-methoxyethyl (MOE) modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, * represents a phosphorothioate internucleoside linkage, such that the oligonucleotide comprises a nucleobase sequence of CAGCGCCCACCAGUCA (SEQ ID NO: 21).

19. The formulation of any one of embodiments 2-17, wherein each $R^1$ comprises a group of the formula (Ic):

20. The formulation of any one of embodiments 1-19, wherein the complexes are present in the formulation at a concentration in the range of 10 mg/mL to 50 mg/mL.

21. The formulation of any one of embodiments 1-20, further comprising one or more antibodies that are not covalently linked to an oligonucleotide.

22. The formulation of embodiment 21, wherein the average value of n1 of complexes in the formulation is in the range of 0.5 to 5.

23. A method of reducing DMPK expression in a subject, the method comprising administering to the subject an effective amount of the formulation of any one of embodiments 1-22.

(Ic)

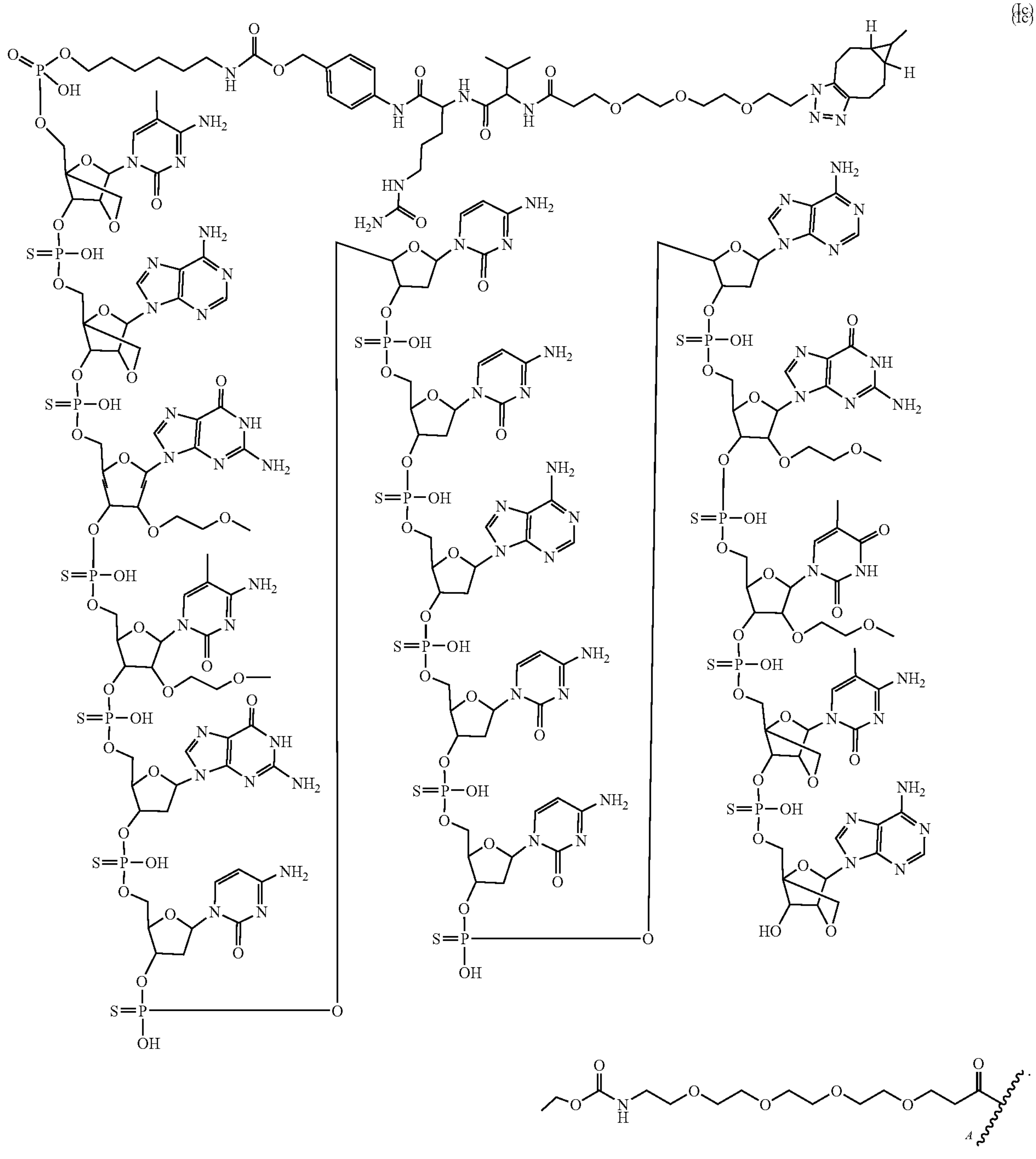

24. A method of treating myotonic dystrophy in a subject, the method comprising administering to the subject an effective amount of the formulation of any one of embodiments 1-22.

25. The method of embodiment 23 or embodiment 24, wherein the subject has an expansion of a disease-associated repeat of a DMPK allele that is associated with myotonic dystrophy.

26. The method of embodiment 25, wherein the disease-associated repeat comprises repeating units of a CTG trinucleotide sequence.

27. The method of any one of embodiments 23-26, wherein the complexes reduce DMPK expression in the subject.

28. A complex comprising a structure of formula (I): $[R^1]_{n1}$—$R^2$, wherein each $R^1$ comprises a group of the formula (Ia):

(Ia)

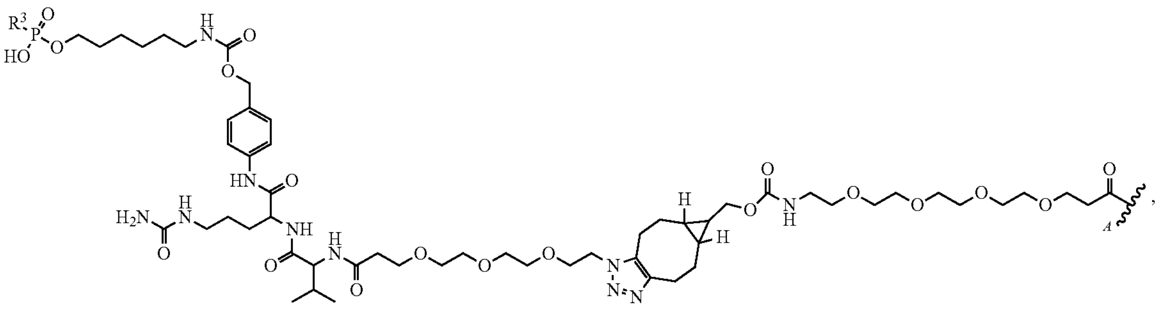

wherein $R^3$ comprises an oligonucleotide comprising a structure of +C*+A*OG*oC*dG*dC*dC*dC*dA*dC*dC*dA*OG*OU*+C*+A (SEQ ID NO: 21), wherein +N represents an LNA (2'-4' methylene bridge) ribonucleoside, dN represents a 2'-deoxyribonucleoside, oN represents a 2'-MOE modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, and * represents a phosphorothioate internucleoside linkage;

wherein $R^2$ comprises a Fab, and wherein the Fab comprises a CDR-H1, a CDR-H2, a CDR-H3, a CDR-L1, a CDR-L2, and a CDR-L3 selected from Table 2, optionally wherein the Fab comprises a VH comprising the amino acid sequence of SEQ ID NO: 17 and a VL comprising the amino acid sequence of SEQ ID NO: 18, further optionally wherein the Fab comprises a heavy chain comprising the amino acid sequence of SEQ ID NO: 19 and a light chain comprising the amino acid sequence of SEQ ID NO: 20;

wherein $R^1$ is covalently linked to $R^2$ at attachment point A; and wherein n1 is an integer representing the number of instances of $R^1$, wherein each instance of $R^1$ is covalently linked to a different amino acid residue of the Fab, optionally wherein each different amino acid residue is a lysine.

29. A complex comprising a structure of formula (I): $[R^1]_{n1}$—$R^2$, wherein each $R^1$ comprises a group of the formula (Ib):

(Ib)

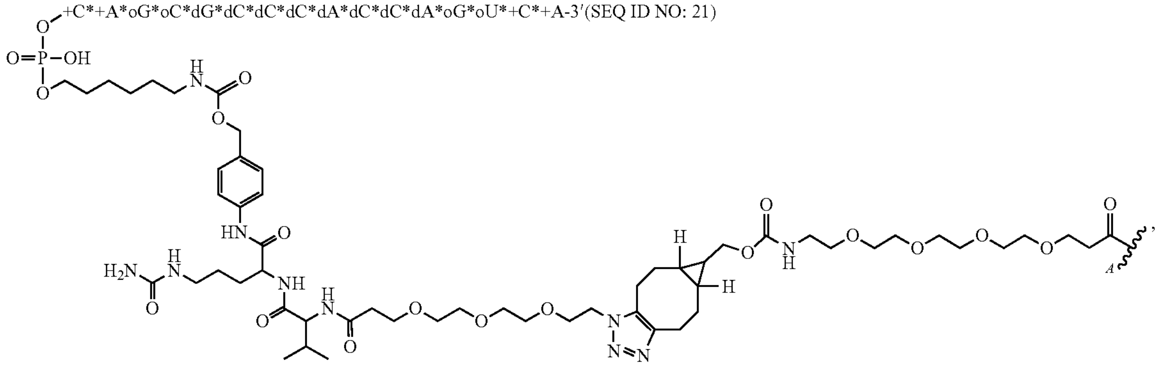

wherein +N represents an LNA (2'-4' methylene bridge) ribonucleoside, dN represents a 2'-deoxyribonucleoside, oN represents a 2'-O-methoxyethyl (MOE) modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, * represents a phosphorothioate internucleoside linkage, such that the oligonucleotide comprises a nucleobase sequence of CAGCGCC-CACCAGUCA (SEQ ID NO: 21);

wherein $R^2$ comprises a Fab, and wherein the Fab comprises a CDR-H1, a CDR-H2, a CDR-H3, a CDR-L1, a CDR-L2, and a CDR-L3 selected from Table 2, optionally wherein the Fab comprises a VH comprising the amino acid sequence of SEQ ID NO: 17 and a VL comprising the amino acid sequence of SEQ ID NO: 18, further optionally wherein the Fab comprises a heavy chain comprising the amino acid sequence of SEQ ID NO: 19 and a light chain comprising the amino acid sequence of SEQ ID NO: 20;

wherein $R^1$ is covalently linked to $R^2$ at attachment point A; and wherein n1 is an integer representing the number of instances of $R^1$, wherein each instance of $R^1$ is covalently linked to a different amino acid residue of the Fab, optionally wherein each different amino acid residue is a lysine.

30. A complex comprising a structure of formula (I): $[R^1]_{n1}$—$R^2$, wherein $R^1$ comprises a group of the formula (Ic):

(Ic)
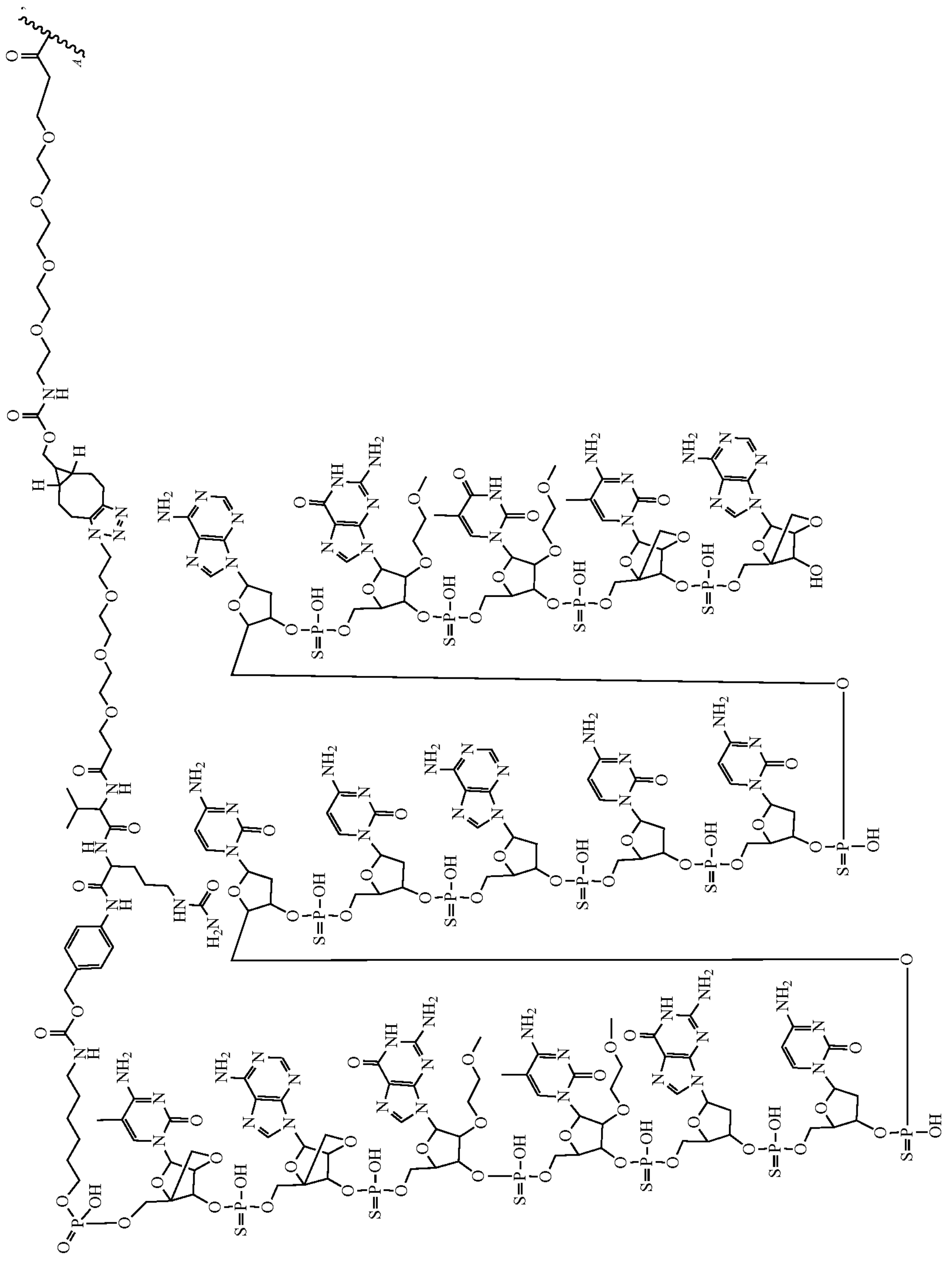

wherein $R^2$ comprises a Fab comprising a CDR-H1, a CDR-H2, a CDR-H3, a CDR-L1, a CDR-L2, and a CDR-L3 selected from Table 2, optionally wherein $R^2$ comprises a Fab comprising a VH comprising the amino acid sequence of SEQ ID NO: 17 and a VL comprising the amino acid sequence of SEQ ID NO: 18, further optionally wherein $R^2$ comprises a Fab comprising a heavy chain comprising the amino acid sequence of SEQ ID NO: 19 and a light chain comprising the amino acid sequence of SEQ ID NO: 20; wherein $R^1$ is covalently linked to $R^2$ at attachment point A;

wherein n1 is an integer representing the number of instances of $R^1$, wherein each instance of $R^1$ is covalently linked to a different amino acid residue of the Fab, optionally wherein each different amino acid residue is a lysine.

31. A complex comprising a structure of the formula (Id):

8.5, optionally wherein the plurality of complexes are at a concentration of 10 mg/mL to 50 mg/mL.

33. A lyophilized form of the formulation of embodiment 32.

34. A product produced by a process comprising lyophilizing the formulation of embodiment 32.

35. A frozen form of the formulation of embodiment 32.

36. A product produced by a process comprising freezing the formulation of embodiment 32.

37. A formulation comprising a plurality of complexes of any one of embodiments 28-31, and tris(hydroxymethyl) aminomethane at a concentration of 5 to 50 mM, and sucrose at a concentration of 5 w/v % to 15 w/v %, wherein the formulation is an aqueous solution and is at a pH of 6.5 to 8.5, optionally wherein the plurality of complexes are at a concentration of 10 mg/mL to 50 mg/mL.

38. A formulation comprising a plurality of complexes of any one of embodiments 28-31, and tris(hydroxymethyl) aminomethane at a concentration of 25 mM, and sucrose at (Id)

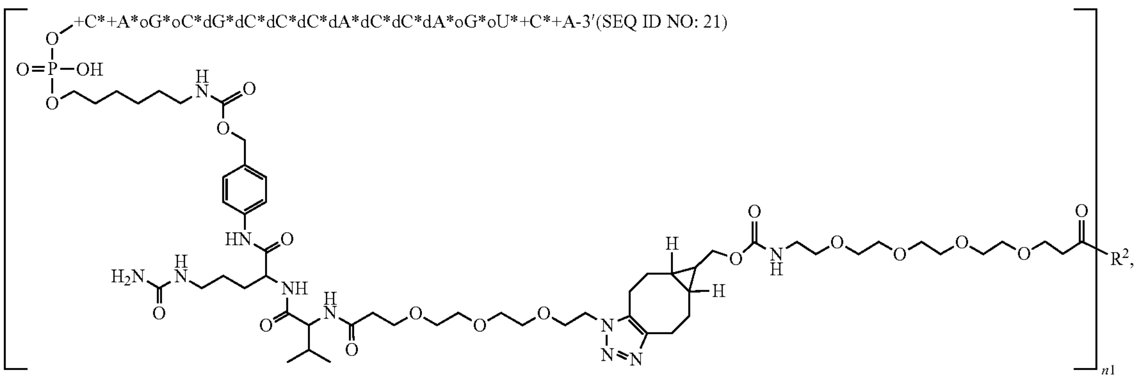

wherein +N represents an LNA (2'-4' methylene bridge) ribonucleoside, dN represents a 2'-deoxyribonucleoside, oN represents a 2'-O-methoxyethyl (MOE) modified ribonucleoside, oC represents a 5-methyl-2'-MOE-cytidine, +C represents a 5-methyl-2'-4'-bicyclic-cytidine (2'-4' methylene bridge), oU represents a 5-methyl-2'-MOE-uridine, * represents a phosphorothioate internucleoside linkage;

wherein $R^2$ comprises a Fab, and wherein the Fab comprises a CDR-H1, a CDR-H2, a CDR-H3, a CDR-L1, a CDR-L2, and a CDR-L3 selected from Table 2, optionally wherein the Fab comprises a VH comprising the amino acid sequence of SEQ ID NO: 17 and a VL comprising the amino acid sequence of SEQ ID NO: 18, further optionally wherein the Fab comprises a heavy chain comprising the amino acid sequence of SEQ ID NO: 19 and a light chain comprising the amino acid sequence of SEQ ID NO: 20;

wherein n1 is an integer representing the number of instances of the group enclosed by square brackets, wherein each instance of the group enclosed by square brackets is covalently linked to a different amino acid residue of the Fab, optionally wherein each different amino acid residue is a lysine.

32. A formulation comprising a plurality of complexes of any one of embodiments 28-31, and tris(hydroxymethyl) aminomethane at a concentration of 5 to 50 mM, and sucrose at a concentration of 5 w/v % to 10 w/v %, wherein the formulation is an aqueous solution and is at a pH of 6.5 to a concentration of 10 w/v %, wherein the formulation is an aqueous solution and is at a pH of 7.5, optionally wherein the plurality of complexes are at a concentration of 10 mg/mL to 50 mg/mL.

39. The formulation of any one of embodiments 32, 37 and 38, further comprising one or more antibodies that are not covalently linked to an oligonucleotide.

40. The formulation of embodiment 39, wherein the average value of n1 of complexes in the formulation is in the range of 0.5 to 5.

41. A lyophilized form of the formulation of any one of embodiments 37-40.

42. A lyophilized cake comprising a plurality of complexes of any one of embodiments 28-31, tris(hydroxymethyl) aminomethane, and sucrose.

43. The lyophilized cake of embodiment 42, comprising $4.02\times10^{-2}$ mg-1.21 mg tris(hydroxymethyl)aminomethane per g of cake; 989 mg-999 mg sucrose per g of cake; and/or 0.666 mg-9.90 mg complexes per g of cake;

optionally wherein the lyophilized cake comprises:

(i) 0.303 mg tris(hydroxymethyl)aminomethane per g of cake, 998.6 mg sucrose per g of cake, and/or 0.999 mg complexes per g of cake;

(ii) 0.302 mg tris(hydroxymethyl)aminomethane per g of cake, 997.7 mg sucrose per g of cake, and/or 1.995 mg complexes per g of cake;

(iii) 0.302 mg tris(hydroxymethyl)aminomethane per g of cake, 997.2 mg sucrose per g of cake, and/or 2.49 mg complexes per g of cake;

(iv) 0.302 mg tris(hydroxymethyl)aminomethane per g of cake, 996.7 mg sucrose per g of cake, and/or 2.99 mg complexes per g of cake;

(v) 0.302 mg tris(hydroxymethyl)aminomethane per g of cake, 995.7 mg sucrose per g of cake, and/or 3.98 mg complexes per g of cake; or (vi) 0.301 mg tris(hydroxymethyl)aminomethane per g of cake, 994.7 mg sucrose per g of cake, and/or 4.97 mg complexes per g of cake.

44. The lyophilized cake of embodiment 42 or embodiment 43, wherein when about 10 g of the lyophilized cake are reconstituted in water to produce 1 mL of a solution, the solution comprises tris(hydroxymethyl)aminomethane at a concentration of 5 to 50 mM, sucrose at a concentration of 5 w/v % to 15 w/v %, and complexes at a concentration of 10 mg/mL to 50 mg/mL, optionally wherein the tris(hydroxymethyl)aminomethane is at a concentration of 25 mM and/or the sucrose is at a concentration of 10 w/v %.

EQUIVALENTS AND TERMINOLOGY

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or (e.g., and) one or more modified nucleotides and/or (e.g., and) one or more modified internucleoside linkages and/or (e.g., and) one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. Unless otherwise indicated, ranges of values herein are inclusive of their endpoints (e.g., a range of X to Y is inclusive of the values X and Y). It should be understood that recitations herein of a value from X to Y indicates that the specified value falls in the range of X to Y. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. A complex comprising a structure of formula (I): $[R^1]_{n1}$—$R^2$, wherein each $R^1$ comprises a group of the formula (Ia):

(Ia)

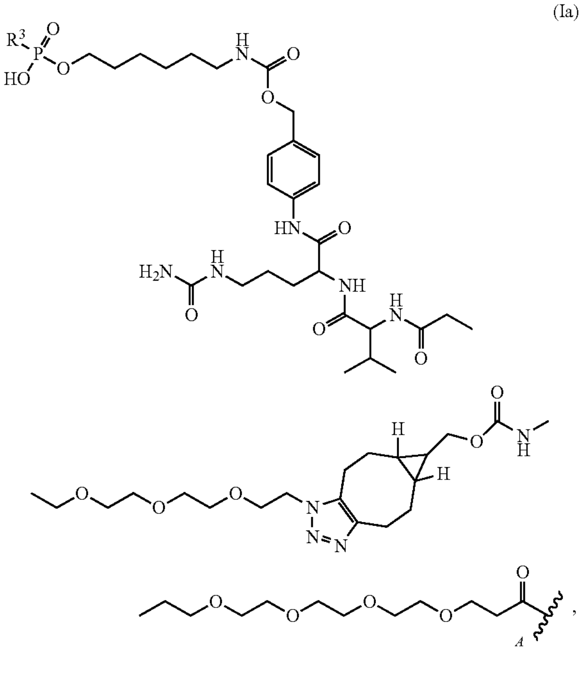

wherein $R^3$ comprises an oligonucleotide comprising a structure of +C*+A*OG*oC*dG*dC*dC*dC*dA*dC*dC*dA*OG*OU*+C*+A (SEQ ID NO: 21), wherein for each nucleoside, N, of the oligonucleotide, +N represents an LNA ribonucleoside, dN represents a 2'-deoxyribonucleoside, oN represents a 2'-O-methoxyethyl (MOE) modified ribonucleoside, oC represents a 5-methyl-2'-MOE-cytidine, +C represents a 5-methyl-2'-4'-bicyclic-cytidine, wherein the 2' and 4' positions of the sugar are bridged via a methylene, oU represents a 5-methyl-2'-MOE-uridine, and wherein * represents a phosphorothioate internucleoside linkage;

wherein $R^2$ comprises a Fab comprising a heavy chain comprising the amino acid sequence of SEQ ID NO: 19 and a light chain comprising the amino acid sequence of SEQ ID NO: 20;

wherein $R^1$ is covalently linked at attachment point A to $R^2$, wherein n1 is an integer representing the number of instances of $R^1$, and wherein each instance of $R^1$ is covalently linked to a different amino acid residue of the Fab.

2. The complex of claim 1, wherein each different amino acid residue is a lysine.

3. The complex of claim 1, wherein the heavy chain of the Fab comprises an N-terminal pyroglutamate.

4. The complex of claim 1, wherein n1 is 1-5.

5. A composition comprising the complex of claim 1.

6. The composition of claim 5, wherein the oligonucleotide is in a salt form.

7. The composition of claim 6, wherein the oligonucleotide is in a sodium salt form, potassium salt form, or magnesium salt form.

8. The composition of claim 5, wherein each different amino acid residue is a lysine.

9. The composition of claim 5, wherein the heavy chain of the Fab comprises an N-terminal pyroglutamate.

10. The composition of claim 5, wherein the composition is formulated for intravenous administration.

11. A method of reducing DMPK expression in a subject, the method comprising administering to the subject an effective amount of a composition comprising the complex of claim 1.

12. A method of treating myotonic dystrophy in a subject, the method comprising administering to the subject an effective amount of a composition comprising the complex of claim 1.

13. The method of claim 12, wherein the subject has an expansion of a disease-associated repeat of a DMPK allele that is associated with myotonic dystrophy.

14. The method of claim 13, wherein the disease-associated repeat comprises repeating units of a CTG trinucleotide sequence.

15. The method of claim 11, wherein each different amino acid residue is a lysine.

16. The method of claim 11, wherein the heavy chain of the Fab comprises an N-terminal pyroglutamate.

17. The method of claim 11, wherein the composition is formulated for intravenous administration.

18. The method of claim 11, wherein the subject is human.

19. The method of claim 12, wherein each different amino acid residue is a lysine.

20. The method of claim 12, wherein the heavy chain of the Fab comprises an N-terminal pyroglutamate.

21. The method of claim 12, wherein the composition is formulated for intravenous administration.

22. The method of claim 12, wherein the subject is human.

23. The composition of claim 5, wherein the average value of n1 of complexes of the composition is in the range of 0.5 to 5.

24. The composition of claim 5, wherein the average value of n1 of complexes of the composition is in the range of 0.8 to 2.

* * * * *

```
                         SEQUENCE LISTING


Sequence total quantity: 26
SEQ ID NO: 1            moltype = AA  length = 9
FEATURE                 Location/Qualifiers
REGION                  1..9
                        note = Synthetic
source                  1..9
                        mol_type = protein
                        organism = synthetic construct
SEQUENCE: 1
GYSITSGYY                                                      9

SEQ ID NO: 2            moltype = AA  length = 7
```

-continued

```
FEATURE                Location/Qualifiers
REGION                 1..7
                       note = Synthetic
source                 1..7
                       mol_type = protein
                       organism = synthetic construct
SEQUENCE: 2
ITFDGAN                                                            7

SEQ ID NO: 3           moltype = AA  length = 12
FEATURE                Location/Qualifiers
REGION                 1..12
                       note = Synthetic
source                 1..12
                       mol_type = protein
                       organism = synthetic construct
SEQUENCE: 3
TRSSYDYDVL DY                                                      12

SEQ ID NO: 4           moltype = AA  length = 6
FEATURE                Location/Qualifiers
REGION                 1..6
                       note = Synthetic
source                 1..6
                       mol_type = protein
                       organism = synthetic construct
SEQUENCE: 4
QDISNF                                                             6

SEQ ID NO: 5           moltype =   length =
SEQUENCE: 5
000

SEQ ID NO: 6           moltype = AA  length = 9
FEATURE                Location/Qualifiers
REGION                 1..9
                       note = Synthetic
source                 1..9
                       mol_type = protein
                       organism = synthetic construct
SEQUENCE: 6
QQGHTLPYT                                                          9

SEQ ID NO: 7           moltype = AA  length = 6
FEATURE                Location/Qualifiers
REGION                 1..6
                       note = Synthetic
source                 1..6
                       mol_type = protein
                       organism = synthetic construct
SEQUENCE: 7
SGYYWN                                                             6

SEQ ID NO: 8           moltype = AA  length = 16
FEATURE                Location/Qualifiers
REGION                 1..16
                       note = Synthetic
source                 1..16
                       mol_type = protein
                       organism = synthetic construct
SEQUENCE: 8
YITFDGANNY NPSLKN                                                  16

SEQ ID NO: 9           moltype = AA  length = 10
FEATURE                Location/Qualifiers
REGION                 1..10
                       note = Synthetic
source                 1..10
                       mol_type = protein
                       organism = synthetic construct
SEQUENCE: 9
SSYDYDVLDY                                                         10

SEQ ID NO: 10          moltype = AA  length = 11
FEATURE                Location/Qualifiers
REGION                 1..11
                       note = Synthetic
source                 1..11
                       mol_type = protein
```

```
                        organism = synthetic construct
SEQUENCE: 10
RASQDISNFL N                                                11

SEQ ID NO: 11           moltype = AA  length = 7
FEATURE                 Location/Qualifiers
REGION                  1..7
                        note = Synthetic
source                  1..7
                        mol_type = protein
                        organism = synthetic construct
SEQUENCE: 11
YTSRLHS                                                     7

SEQ ID NO: 12           moltype = AA  length = 8
FEATURE                 Location/Qualifiers
REGION                  1..8
                        note = Synthetic
source                  1..8
                        mol_type = protein
                        organism = synthetic construct
SEQUENCE: 12
GYSITSGY                                                    8

SEQ ID NO: 13           moltype =   length =
SEQUENCE: 13
000

SEQ ID NO: 14           moltype = AA  length = 8
FEATURE                 Location/Qualifiers
REGION                  1..8
                        note = Synthetic
source                  1..8
                        mol_type = protein
                        organism = synthetic construct
SEQUENCE: 14
SYDYDVLD                                                    8

SEQ ID NO: 15           moltype = AA  length = 7
FEATURE                 Location/Qualifiers
REGION                  1..7
                        note = Synthetic
source                  1..7
                        mol_type = protein
                        organism = synthetic construct
SEQUENCE: 15
SQDISNF                                                     7

SEQ ID NO: 16           moltype = AA  length = 6
FEATURE                 Location/Qualifiers
REGION                  1..6
                        note = Synthetic
source                  1..6
                        mol_type = protein
                        organism = synthetic construct
SEQUENCE: 16
GHTLPY                                                      6

SEQ ID NO: 17           moltype = AA  length = 119
FEATURE                 Location/Qualifiers
REGION                  1..119
                        note = Synthetic
source                  1..119
                        mol_type = protein
                        organism = synthetic construct
SEQUENCE: 17
QVQLQESGPG LVKPSQTLSL TCTVTGYSIT SGYYWNWIRQ PPGKGLEWIG YITFDGANNY  60
NPSLKNRVSI SRDTSKNQFS LKLSSVTAED TATYYCTRSS YDYDVLDYWG QGTTVTVSS   119

SEQ ID NO: 18           moltype = AA  length = 107
FEATURE                 Location/Qualifiers
REGION                  1..107
                        note = Synthetic
source                  1..107
                        mol_type = protein
                        organism = synthetic construct
SEQUENCE: 18
DIQMTQSPSS LSASVGDRVT ITCRASQDIS NFLNWYQQKP GQPVKLLIYY TSRLHSGVPS  60
RFSGSGSGTD FTLTISSLQP EDFATYYCQQ GHTLPYTFGQ GTKLEIK             107
```

-continued

```
SEQ ID NO: 19          moltype = AA  length = 227
FEATURE                Location/Qualifiers
REGION                 1..227
                       note = Synthetic
source                 1..227
                       mol_type = protein
                       organism = synthetic construct
SEQUENCE: 19
QVQLQESGPG LVKPSQTLSL TCTVTGYSIT SGYYWNWIRQ PPGKGLEWIG YITFDGANNY  60
NPSLKNRVSI SRDTSKNQFS LKLSSVTAED TATYYCTRSS YDYDVLDYWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHT                227

SEQ ID NO: 20          moltype = AA  length = 214
FEATURE                Location/Qualifiers
REGION                 1..214
                       note = Synthetic
source                 1..214
                       mol_type = protein
                       organism = synthetic construct
SEQUENCE: 20
DIQMTQSPSS LSASVGDRVT ITCRASQDIS NFLNWYQQKP GQPVKLLIYY TSRLHSGVPS  60
RFSGSGSGTD FTLTISSLQP EDFATYYCQQ GHTLPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 21          moltype = RNA  length = 16
FEATURE                Location/Qualifiers
misc_feature           1..16
                       note = Synthetic
source                 1..16
                       mol_type = other RNA
                       organism = synthetic construct
SEQUENCE: 21
cagcgcccac cagtca                                                  16

SEQ ID NO: 22          moltype = DNA  length = 16
FEATURE                Location/Qualifiers
misc_feature           1..16
                       note = Synthetic
source                 1..16
                       mol_type = other DNA
                       organism = synthetic construct
SEQUENCE: 22
tgactggtgg gcgctg                                                  16

SEQ ID NO: 23          moltype = AA  length = 760
FEATURE                Location/Qualifiers
source                 1..760
                       mol_type = protein
                       organism = Homo sapiens
SEQUENCE: 23
MMDQARSAFS NLFGGEPLSY TRFSLARQVD GDNSHVEMKL AVDEEENADN NTKANVTKPK  60
RCSGSICYGT IAVIVFFLIG FMIGYLGYCK GVEPKTECER LAGTESPVRE EPGEDFPAAR  120
RLYWDDLKRK LSEKLDSTDF TGTIKLLNEN SYVPREAGSQ KDENLALYVE NQFREFKLSK  180
VWRDQHFVKI QVKDSAQNSV IIVDKNGRLV YLVENPGGYV AYSKAATVTG KLVHANFGTK  240
KDFEDLYTPV NGSIVIVRAG KITFAEKVAN AESLNAIGVL IYMDQTKFPI VNAELSFFGH  300
AHLGTGDPYT PGFPSFNHTQ FPPSRSSGLP NIPVQTISRA AAEKLFGNME GDCPSDWKTD  360
STCRMVTSES KNVKLTVSNV LKEIKILNIF GVIKGFVEPD HYVVVGAQRD AWGPGAAKSG  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QNVKHPVTGQ FLYQDSNWAS KVEKLTLDNA  540
AFPFLAYSGI PAVSFCFCED TDYPYLGTTM DTYKELIERI PELNKVARAA AEVAGQFVIK  600
LTHDVELNLD YERYNSQLLS FVRDLNQYRA DIKEMGLSLQ WLYSARGDFF RATSRLTTDF  660
GNAEKTDRFV MKKLNDRVMR VEYHFLSPYV SPKESPFRHV FWGSGSHTLP ALLENLKLRK  720
QNNGAFNETL FRNQLALATW TIQGAANALS GDVWDIDNEF                        760

SEQ ID NO: 24          moltype = DNA  length = 2859
FEATURE                Location/Qualifiers
source                 1..2859
                       mol_type = genomic DNA
                       organism = Homo sapiens
SEQUENCE: 24
aggggggctg gaccaagggg tggggagaag gggaggaggc ctcggccggc cgcagagaga  60
agtggccaga gaggcccagg ggacagccag ggacaggcag acatgcagcc agggctccag  120
ggcctggaca ggggctgcca ggccctgtga caggaggacc ccgagccccc ggcccgggga  180
ggggccatgg tgctgcctgt ccaacatgtc agccgaggtg cggctgaggc ggctccagca  240
gctggtgttg gacccgggct tcctggggct ggagcccctg ctcgaccttc tcctgggcgt  300
ccaccaggag ctgggcgcct ccgaactggc ccaggacaag tacgtggccg acttcttgca  360
```

-continued

```
gtgggcggag cccatcgtgg tgaggcttaa ggaggtccga ctgcagaggg acgacttcga  420
gattctgaag gtgatcggac gcggggcgtt cagcgaggta gcggtagtga agatgaagca  480
gacgggccag gtgtatgcca tgaagatcat gaacaagtgg gacatgctga agaggggcga  540
ggtgtcgtgc ttccgtgagg agagggacgt gttggtgaat ggggaccggc ggtggatcac  600
gcagctgcac ttcgccttcc aggatgagaa ctacctgtac ctggtcatgg agtattacgt  660
gggcggggac ctgctgacac tgctgagcaa gtttggggag cggattccgg ccgagatggc  720
gcgcttctac ctggcggaga ttgtcatggc catagactcg gtgcaccggc ttggctacgt  780
gcacagggac atcaaacccg acaacatcct gctggaccgc tgtggccaca tccgcctggc  840
cgacttcggc tcttgcctca agctgcgggc agatggaacg gtgcggtcgc tggtggctgt  900
gggcacccca gactacctgt cccccgagat cctgcaggct gtgggcggtg ggcctgggac  960
aggcagctac gggcccgagt gtgactggtg ggcgctgggt gtattcgcct atgaaatgtt  1020
ctatgggcag acgcccttct acgcggattc cacggcggag acctatggca agatcgtcca  1080
ctacaaggag cacctctctc tgccgctggt ggacgaaggg gtccctgagg aggctcgaga  1140
cttcattcag cggttgctgt gtcccccgga gacacggctg ggccggggtg gagcaggcga  1200
cttccggaca catcccttct tctttggcct cgactgggat ggtctccggg acagcgtgcc  1260
ccccttaca ccggatttcg aaggtgccac cgacacatgc aacttcgact tggtggagga  1320
cgggctcact gccatggaga cactgtcgga cattcgggaa ggtgcgccgc taggggtcca  1380
cctgcctttt gtgggctact cctactcctg catggccctc agggacagtg aggtcccagg  1440
ccccacaccc atggaactgg aggccgagca gctgcttgag ccacacgtgc aagcgcccag  1500
cctggagccc tcggtgtccc cacaggatga aacagctgaa gtggcagttc cagcggctgt  1560
ccctgcggca gaggctgagg ccgaggtgac gctgcgggag ctccaggaag ccctggagga  1620
ggaggtgctc acccggcaga gcctgagccg ggagatggag gccatccgca cggacaacca  1680
gaacttcgcc agtcaactac gcgaggcaga ggctcggaac cgggacctag aggcacacgt  1740
ccggcagttg caggagcgga tggagttgct gcaggcagag ggagccacag ctgtcacggg  1800
ggtccccagt ccccgggcca cggatccacc ttcccatcta gatggccccc cggccgtggc  1860
tgtgggccag tgcccgctgg tggggccagg ccccatgcac cgccgccacc tgctgctccc  1920
tgccagggtc cctaggcctg gcctatcgga ggcgctttcc ctgctcctgt tcgccgttgt  1980
tctgtctcgt gccgccgccc tggctgcat tgggttggtg gcccacgccg gccaactcac  2040
cgcagtctgg cgccgcccag gagccgcccg cgctccctga accctagaac tgtcttcgac  2100
tccgggggccc cgttggaaga ctgagtgccc ggggcacggc acagaagccg cgcccaccgc  2160
ctgccagttc acaaccgctc cgagcgtggg tctccgccca gctccagtcc tgtgatccgg  2220
gcccgccccc tagcggccgg ggagggaggg gccgggtccg cggccggcga acggggctcg  2280
aagggtcctt gtagccggga atgctgctgc tgctgctgct gctgctgctg ctgctgctgc  2340
tgctgctgct gctgctgctg ctggggggat cacagaccat ttctttcttt cggccaggct  2400
gaggccctga cgtggatggg caaactgcag gcctgggaag gcagcaagcc gggccgtccg  2460
tgttccatcc tccacgcacc cccacctatc gttggttcgc aaagtgcaaa gctttcttgt  2520
gcatgacgcc ctgctctggg gagcgtctgg cgcgatctct gcctgcttac tcgggaaatt  2580
tgcttttgcc aaacccgctt tttcggggat cccgcgcccc cctcctcact tgcgctgctc  2640
tcggagcccc agccggctcc gcccgcttcg gcggtttgga tatttattga cctcgtcctc  2700
cgactcgctg acaggctaca ggacccccaa caaccccaat ccacgttttg gatgcactga  2760
gaccccgaca ttcctcggta tttattgtct gtccccacct aggaccccca cccccgaccc  2820
tcgcgaataa aaggccctcc atctgcccaa agctctgga                        2859
```

```
SEQ ID NO: 25          moltype = DNA  length = 2683
FEATURE                Location/Qualifiers
source                 1..2683
                       mol_type = genomic DNA
                       organism = Mus musculus
SEQUENCE: 25
gaactggcca gagagaccca agggatagtc agggacgggc agacatgcag ctagggttct  60
ggggcctgga caggggcagc caggccctgt gacgggaaga ccccgagctc cggcccgggg  120
aggggccatg gtgttgcctg cccaacatgt cagccgaagt gcggctgagg cagctccagc  180
agctggtgct ggacccaggc ttcctgggac tggagcccct gctcgacctt ctcctgggcg  240
tccaccagga gctgggtgcc tctcacctag cccaggacaa gtatgtggcc gacttcttgc  300
agtgggtgga gcccattgca gcaaggctta aggaggtccg actgcagagg gatgattttg  360
agattttgaa ggtgatcggg cgtggggcgt tcagcgaggt agcggtggtg aagatgaaac  420
agacgggcca agtgtatgcc atgaagatta tgaataagtg ggacatgctg aagagaggcg  480
aggtgtcgtg cttccgggaa gaaagggatg tattagtgaa aggggaccgg cgctggatca  540
cacagctgca ctttgccttc caggatgaga actacctgta cctggtcatg gaatactacg  600
tgggcgggga cctgctaacg ctgctgagca agtttgggga gcggatcccc gccgagatgg  660
ctcgcttcta cctggccgag attgtcatgg ccatagactc cgtgcaccgg ctgggctacg  720
tgcacaggga catcaaacca gataacattc tgctggaccg atgtgggcac attcgcctgg  780
cagacttcgg ctcctgcctc aaactgcagc ctgatggaat ggtgaggtcg ctggtggctg  840
tgggcacccc ggactacctg tctcctgaga ttctgcaggc cgttggtgga gggcctgggg  900
caggcagcta cgggccagag tgtgactggt gggcactggg cgtgttcgcc tatgagatgt  960
tctatgggca gacccccttc tacgcggact ccacagccga gacatatgcc aagattgtgc  1020
actacaggga acacttgtcg ctgccgctgg cagacacagt tgtccccgag gaagctcagg  1080
acctcattcg tgggctgctg tgtcctgctg agataaggct aggtcgaggt ggggcagact  1140
tcgagggtgc cacggacaca tgcaatttcg atgtggtgga ggaccggctc actgccatgg  1200
tgagcggggg cggggagacg ctgtcagaca tgcaggaaga catgcccctt ggggtgcgcc  1260
tgcccttcgt gggctactcc tactgctgca tggccttcag agacaatcag gtcccggacc  1320
ccacccctat ggaactagag gccctgcagt tgcctgtgtc agacttgcaa gggcttgact  1380
tgcagccccc agtgtcccca ccggatcaag tggctgaaga ggctgaccta gtggctgtcc  1440
ctgcccctgt ggctgaggca gagaccacgg taacgctgca gcagctccag gaagccctgg  1500
aagaagaggt tctcacccgg cagagcctga gccgcgagct ggaggccatc cggaccgcca  1560
accagaactt ctccagccaa ctacaggagg ccgaggtccg aaaccgagac ctggaggcgc  1620
atgttcggca gctacaggaa cggatggaga tgctgcaggc cccaggagcc gcagccatca  1680
cgggggtccc cagtccccgg gccacggatc caccttccca tctagatggc cccccggccg  1740
tggctgtggg ccagtgcccg ctggtggggc caggccccat gcaccgccgt cacctgctgc  1800
```

-continued

```
tccctgccag gatccctagg cctggcctat ccgaggcgcg ttgcctgctc ctgttcgccg  1860
ctgctctggc tgctgccgcc acactgggct gcactgggtt ggtggcctat accggcggtc  1920
tcaccccagt ctggtgtttc ccgggagcca ccttcgcccc ctgaacccta agactccaag  1980
ccatctttca tttaggcctc ctaggaaggt cgagcgacca gggagcgacc caaagcgtct  2040
ctgtgcccat cgcgcccccc cccccccccc accgctccgc tccacacttc tgtgagcctg  2100
ggtccccacc cagctccgct cctgtgatcc aggcctgcca cctggcggcc ggggagggag  2160
gaacagggct cgtgcccagc accoctggtt cctgcagagc tggtagccac cgctgctgca  2220
gcagctgggc attcgccgac cttgctttac tcagccccga cgtggatggg caaactgctc  2280
agctcatccg atttcacttt ttcactctcc cagccatcag ttacaagcca taagcatgag  2340
ccccctattt ccagggacat cccattccca tagtgatgga tcagcaagac ctctgccagc  2400
acacacggag tctttggctt cggacagcct cactcctggg ggttgctgca actccttccc  2460
cgtgtacacg tctgcactct aacaacggag ccacagctgc actccccct cccccaaagc  2520
agtgtgggta tttattgatc ttgttatctg actcactgac agactccggg acccacgttt  2580
tagatgcatt gagactcgac attcctcggt atttattgtc tgtccccacc tacgacctcc  2640
actcccgacc cttgcgaata aaatacttct ggtctgccct aaa                    2683
```

```
SEQ ID NO: 26          moltype = DNA  length = 19841
FEATURE                Location/Qualifiers
source                 1..19841
                       mol_type = genomic DNA
                       organism = Homo sapiens
SEQUENCE: 26
tttcctactt gaagcctgac gtagtaaaga tcgggggagg gttagacaga tacagtggtc  60
cccaaccatt ttggcaccag ggactggtct tatggaagac agtttttcca cagactgttg  120
gggggatggt tttgggatga aaccgttctg cctctgatca tcaggtgtta gattctaata  180
aggagcgcac acctagatcc ctcgcatgca tagttcatgg tggggttcgc actcttacga  240
ggattgaatg gtgcgctgct ccggtaggag gctgggctca ggctgtaatg cctgctcgcc  300
caccactcac ctcctgctgc atggcctggt tcctaacagg ccacggacca ctactgttcc  360
atggcccgga ggttgaggac cccgagatac aggacaattc tgtggcaagc aggactgtcc  420
cctcgccaaa gatgggacat cgaggctcct tggagcaccc tgtggccacc ttgcagcagc  480
ctctgtttcc ccatgtttcc atgacctggt gtccatctgt cttcccccagt ttgggagctt  540
ctctccgagg aggacctggg cctggtgtgg cacctgctgt gtgagcgggg ccatgtccaa  600
cggccttctt ggggactttg ggtcggggag aagttctgcc tgggttttac tgccttctcc  660
caaccccaca ctgtctcccc tggcagcggt tgatcgacaa gaccaaggtg acatatctga  720
agtggctgcc tgagtcggag agcctgttcc tggcatcaca cgccagtggc cacctgtacc  780
tgtacaacgt cagccacccc tgcgcctcgg ccccgcccca gtacagcctg ctgaagcagg  840
gcgagggctt ctctgtctat gctgccaaga gcaaggcacc ccgcaacccg ctggccaagt  900
gggcggtggg tgaggggccc ctcaacgagt tcgccttctc gcccgatggc cggcacctgg  960
cctgtgtgag ccaggatggc tgcctgcgcg tcttccactt cgactccatg ctcctgcgtg  1020
ggctcatgaa gagctacttt ggggcctgc tgtgtgtgtg ctggagccct gacggccgct  1080
acgtggtgac gggtggcgaa gatgacctgg tcaccgtgtg gtccttcacc gagggccgcg  1140
tggtggctcg aggccatggc cacaagtcct gggtcaacgc tgtggccttt gacccctaca  1200
ccacaagggc agaggaggcg gcgacagcag ccggtgctga tggggagcgg agcggcgaag  1260
aggaggagga ggagcccgag gctgcgggca caggctcggc cgggggcgcc ccgctctctc  1320
cactgcccaa ggctggctcc attacttacc gctttggctc ggcgggccag gacacgcagt  1380
tctgcctgtg ggacctcact gaagacgtgc tctacccgca cccccccctg gcccgcaccc  1440
gcaccctccc tggcacacct ggcaccacgc caccggccgc cagcagctcg aggggtggcg  1500
agcctggccc aggcccccctg cctcgctcgc tgtcccgctc caacagtctc ccgcacccag  1560
ctggcggggg caaggcgggc ggcccgggtg tggcggcaga gcctggcaca ccattcagca  1620
ttggccgctt cgccacgctc acactgcagg agcggcggga ccgggggca gagaaggagc  1680
acaagcgcta ccacagcctg ggcaacatca gccggggtgg cagtggcggc agtggcagtg  1740
gtggggagaa gcccagcggc cctgttcccc gcagccgcct ggacccgcc aaggtgctgg  1800
gcactgcgct gtgcccgcgc atccacgagg tgcccctgct ggagcccctt gtgtgcaaga  1860
agatcgccca ggagcggctc acagtcctcc tgttcctgga ggactgcatc atcactgcct  1920
gccaggaggg cctcatctgc acctgggccc ggccgggcaa ggcggtgagt ggccccacac  1980
cagcctgccg gggacctggc aggacctttc gtgggaagag gcaggcattg gcagagagag  2040
ggctttgttg ctgtcacagc ctctggctcc gtggggtgag gggaagccag ggaaatctta  2100
gtgtctcagt acaagacctc tcagatcctt agagtgaggg ggtctagccc taggcagcag  2160
gcagcagaaa gaggggtggg tgtgagagcc agctaggaat tggggcatcc aaggctggcc  2220
gtctgaaggg cagcagatgg gccccacatg gccaggtctt actgcctgtc actcgaacca  2280
gaatctattt ctgttgaaca tctgtttttt aaatcgtgaa actttttga gtacttcagg  2340
ccaaaactag gggcgagctc aagcctgtgg gcatggctgc cagcctgggt ctgggactca  2400
ggatctgagc ctcctgctga aggcacaggc tgggaatccc aggcctgggt tccagtccca  2460
ctccctctgt gaccctggac aagtcactgc cccctctgac ctccaactca tcacctctta  2520
gaacagagcc tgtaggatgg gcagtgggtg gatgtgcttg cctcctgggt gggctgtggc  2580
gttgggaagg tcatagtagg cgaatcaggc ctggcatctt gtaagttcgg agctcgtctt  2640
gggtgtctca gcttcttagg gcttggactc agttgcccag ggtcctggag gccgtggctt  2700
ggttcctcag atcctcagtt ttggaatcgt agagtcctga gtccctagaa cttgagagca  2760
cagtctgagt gactcagagg caagagtggt gggatttggg gagtctggtt gagtcctaaa  2820
agagacccct ctgtctccgt agttcacaga cgaggagacc gaggcccaga caggggaagg  2880
aagttggccc aggtcaccca gcaagtcagt ggtagaggta ggactgtccc tgagttcttt  2940
ccccagcacc tcagggtccc tcccaagtta gaagggagct ccagtttccc cctcccctcc  3000
cacccttacc cttaccccat ggtctcactc aggatccgcc aaggactttg attattgcgt  3060
gaaagtgctg actgccagga caggaagcta gctaagatgc aagttcccag cctagagcag  3120
tggcctctgg ggggtctagg gcggacccaa gggcaaggcc agggtggcag cagctttggg  3180
gactctgggc tggctccctc cccttgacac tggctgaagc ccaggtggtc tctaacccct  3240
cccatctctc cctctcatct tccccagggc atctcctccc aaccaggcaa ctccccgagt  3300
ggcacagtgg tgtgaagcca tggatatcgg gcccccccaa ccccatgccc ccagcctcct  3360
agccataacc ctccctgctg acctcacaga tcaacgtatt aacaagacta accatgatgg  3420
```

-continued

```
atggactgct ccagtccccc cacctgcaca aaatttgggg gccccccaga ctggcccgga  3480
cacgggcgat gtaatagccc ttgtggcctc agccttgtcc cccacccact gccaagtaca  3540
atgacctctt cctctgaaac atcagtgtta ccctcatccc tgtccccagc atgtgactgg  3600
tcactcctgg ggagagactc cccgccccctg ccacaagagc cccaggtctg cagtgtgccc  3660
ctcagttgag tgggcagggc cgggggtggt ccagccctcg cccggccccc accccagctg  3720
cccttgctat tgtctgtgct tttgaagagt gttaaattat ggaagcccct caggttcctc  3780
cctgtcccgc aggacctctt atttatacta aagttccctg ttttctcagc gggtctgtcc  3840
ccttcggagg agatgatgta gaggacctgt gtgtgtactc tgtggttcta ggcagtccgc  3900
tttccccaga ggaggagtgc aggcctgctc ccagcccagc gcctcccacc ccttttcata  3960
gcaggaaaag ccggagccca gggagggaac ggacctgcga gtcacacaac tggtgaccca  4020
caccagcggc tggagcagga ccctcttggg gagaagagca tcctgcccgc agccagggcc  4080
cctcatcaaa gtcctcggtg ttttttaaat tatcagaact gcccaggacc acgtttccca  4140
ggccctgccc agctgggact cctcggtcct tgcctcctag tttctcaggc ctggccctct  4200
caaggcccag gcaccccagg ccggttggag gccccgactt ccactctgga gaaccgtcca  4260
ccctggaaag aagagctcag attcctcttg gctctcggag ccgcagggag tgtgtcttcc  4320
cgcgccaccc tccacccccc gaaatgtttc tgtttctaat cccagcctgg gcaggaatgt  4380
ggctccccgg ccaggggcca aggagctatt ttggggtctc gtttgcccag ggagggcttg  4440
gctccaccac tttcctcccc cagcctttgg gcagcaggtc acccctgttc aggctctgag  4500
ggtgcccccct cctggtcctg tcctcaccac cccttcccca cctcctggga aaaaaaaaaa  4560
aaaaaaaaaa aaaagctggt ataaagcaga gagcctgagg gctaaattta actgtccgag  4620
tcggaatcca tctctgagtc acccaagaag ctgccctggc ctcccgtccc cttcccaggc  4680
ctcaacccct ttctcccacc cagccccaac ccccagccct cacccccctag cccccagttc  4740
tggagcttgt cgggagcaag gggtggttg ctactgggtc actcagcctc aattggccct  4800
gtttcagcaa tgggcaggtt cttcttgaaa ttcatcacac ctgtggcttc ctctgtgctc  4860
taccttttta ttggggtgac agtgtgacag ctgagattct ccatgcattc cccctactct  4920
agcactgaag ggttctgaag ggccctggaa ggagggagct tggggggctg gcttgtgagg  4980
ggttaaggct gggaggcggg agggggctg gaccaagggg tggggagaag gggaggaggc  5040
ctcggccggc cgcagagaga agtggccaga gaggcccagg ggacagccag ggacaggcag  5100
acatgcagcc agggctccag ggcctggaca ggggctgcca ggccctgtga caggaggacc  5160
ccgagccccc ggcccgggga ggggccatgg tgctgcctgt ccaacatgtc agccgaggtg  5220
cggctgaggc ggctccagca gctggtgttg gacccgggct tcctggggct ggagcccctg  5280
ctcgaccttc tcctgggcgt ccaccaggag ctgggcgcct ccgaactggc ccaggacaag  5340
tacgtggccg acttcttgca gtggggtgag tgcctaccct cggggctcct gcagatgggg  5400
tgggggtggg gcaggagaca ggtctgggca cagaggcctg gctgttgggg gggcaggatg  5460
gcaggatggg catggggaga tcctcccatc ctggggctca gagtgtggac ctgggccctg  5520
gggcaacatt tctctgtcct atgccaccac tctggagggg cagagtaagg tcagcagagg  5580
ctagggtggc tgtgactcag agccatggct taggagtcac agcaggctag gctgccaaca  5640
gcctcccatg gcctctctgc accccgcctc agggtcaggg tcagggtcat gctgggagct  5700
ccctctccta ggaccctccc cccaaaagtg ggctctatgg ccctctcccc tggtttcctg  5760
tggcctgggg caagccagga gggccagcat ggggcagctg ccaggggcgc agccgacagg  5820
caggtgttcg gcgccagcct ctccagctgc cccaacaggt gcccaggcac tgggagggcg  5880
gtgactcacg cggccctgt gggagaacca gctttgcaga caggcgccac cagtgccccc  5940
tcctctgcga tccaggaggg acaactttgg gttcttctgg gtgtgtctcc ttcttttgta  6000
ggttctgcac ccaccccccac ccccagcccc aaagtctcgg ttcctatgag ccgtgtgggt  6060
cagccaccat tcccgccacc ccgggtccct gcgtccttta gttctcctgg cccagggcct  6120
ccaaccttcc agctgtccca caaaacccct tcttgcaagg gctttccagg gcctggggcc  6180
agggctggaa ggaggatgct tccgcttctg ccagctgcct tgtctgccca cctcctcccc  6240
aagcccagga ctcgggctca ctggtcactg gtttctttca ttcccagcac cctgcccctc  6300
tggccctcat atgtctggcc ctcagtgact ggtgtttggt ttttggcctg tgtgtaacaa  6360
actgtgtgtg acacttgttt cctgtttctc cgccttcccc tgcttcctct tgtgtccatc  6420
tctttctgac ccaggcctgg ttcctttccc tcctcctccc atttcacaga tgggaaggtg  6480
gaggccaaga agggccaggc cattcagcct ctggaaaaac cttctcccaa cctcccacag  6540
cccctaatga ctctcctggc ctccctttag tagaggatga agttgggttg gcagggtaaa  6600
ctgagaccgg gtggggtagg ggtctggcgc tcccgggagg agcactcctt ttgtggcccg  6660
agctgcatct cgcggcccct cccctgccag gcctggggcg ggggaggggg ccagggttcc  6720
tgctgcctta aaagggctca atgtcttggc tctctcctcc ctccccccgtc ctcagccctg  6780
gctggttcgt ccctgctggc ccactctccc ggaaccccccc ggaacccctc tctttcctcc  6840
agaacccact gtctcctctc cttccctccc ctcccatacc catccctctc tccatcctgc  6900
ctccacttct tccaccccccg ggagtccagg cctccctgtc cccacagtcc ctgagccaca  6960
agcctccacc ccagctggtc ccccacccag gctgcccagt ttaacattcc tagtcatagg  7020
accttgactt ctgagaggcc tgattgtcat ctgtaaataa ggggtaggac taaagcactc  7080
ctcctggagg actgagagat gggctggacc ggagcacttg agtctgggat atgtgaccat  7140
gctacctttg tctccctgtc ctgttccttc ccccagcccc aaatccaggg ttttccaaag  7200
tgtggttcaa gaaccacctg catctgaatc tagaggtact ggatacaacc ccacgtctgg  7260
gccgttaccc aggacattct acatgagaac gtgggggtgg ggccctggct gcacctgaac  7320
tgtcacctgg agtcagggtg gaaggtggaa gaactgggtc ttatttcctt ctccccttgt  7380
tctttagggt ctgtccttct gcagactccg ttaccccacc ctaaccatcc tgcacaccct  7440
tggagccctc tgggccaatg ccctgtcccg caaagggctt ctcaggcatc tcacctctat  7500
gggagggcat ttttggcccc cagaacctta cacggtgttt atgtggggaa gcccctggga  7560
agcagacagt cctagggtga agctgagagg cagagagaag gggagacaga cagagggtgg  7620
ggctttcccc cttgtctcca gtgccctttc tggtgaccct cggttctttt cccccaccac  7680
ccccccagcg gagcccatcg tggtgaggct taaggaggtc cgactgcaga gggacgactt  7740
cgagattctg aaggtgatcg gacgcggggc gttcagcgag gtaagccgaa ccgggcggga  7800
gcctgacttg actcgtggtg ggcggggcat aggggttggg gcggggcctt agaaattgat  7860
gaatgaccga gccttagaac ctagggctgg gctggaggcg gggcttggga ccaatgggcg  7920
tggtgtggca ggtggggcgg ggccacggct gggtgcagaa gcgggtggag ttgggtctgg  7980
gcgagccctt ttgttttccc gccgtctcca ctctgtctca ctatctcgac ctcaggtagc  8040
ggtagtgaag atgaagcaga cggccaggt gtatgccatg aagatcatga acaagtggga  8100
catgctgaag aggggcgagg tgaggggctg ggcggacgtg gggggctttg aggatccgcg  8160
```

-continued

```
ccccgtctcc ggctgcagct cctccgggtg ccctgcaggt gtcgtgcttc cgtgaggaga  8220
gggacgtgtt ggtgaatggg gaccggcggt ggatcacgca gctgcacttc gccttccagg  8280
atgagaacta cctggtgagc tccgggccgg ggtgactagg aagagggaca agagcccgtg  8340
ctgtcactgg acgaggaggt ggggagagga agctctagga ttgggggtgc tgcccggaaa  8400
cgtctgtggg aaagtctgtg tgcggtaaga gggtgtgtca ggtggatgag gggccttccc  8460
tatctgagac ggggatggtg tccttcactg cccgtttctg gggtgatctg ggggactctt  8520
ataaagatgt ctctgttgcg gggggtctct tacctggaat gggataggtc ttcaggaatt  8580
ctaacggggc cactgcctag ggaaggagtg tctgggacct attctctggg tgttgggtgg  8640
cctctgggtt ctctttccca gaacatctca gggggagtga atctgcccag tgacatccca  8700
ggaaagtttt tttgtttgtg tttttttttg aggggcgggg gcgggggccg caggtggtct  8760
ctgatttggc ccggcagatc tctatggtta tctctgggct ggggctgcag gtctctgccc  8820
aaggatgggg tgtctctggg aggggttgtc ccagccatcc gtgatggatc agggcctcag  8880
gggactacca accacccatg acgaacccct tctcagtacc tggtcatgga gtattacgtg  8940
ggcggggacc tgctgacact gctgagcaag tttggggagc ggattccggc cgagatggcg  9000
cgcttctacc tggcggagat tgtcatggcc atagactcgg tgcaccggct tggctacgtg  9060
cacaggtggg tgcagcatgg ccgaggggat agcaagcttg ttccctggcc gggttcttgg  9120
aaggtcagag cccagagagg ccagggcctg gagagggacc ttcttggttg gggcccaccg  9180
gggggtgcct gggagtaggg gtcagaactg tagaagccct acaggggcgg aacccgagga  9240
agtggggtcc caggtggcac tgcccggagg ggcggagcct ggtgggacca cagaagggag  9300
gttcatttat cccacccttc tcttttcctc cgtgcaggga catcaaaccc gacaacatcc  9360
tgctggaccg ctgtggccac atccgcctgg ccgacttcgg ctcttgcctc aagctgcggg  9420
cagatggaac ggtgagccag tgccctggcc acagagcaac tggggctgct gatgagggat  9480
ggaaggcaca gagtgtggga gcgggactgg atttggaggg gaaaagaggt ggtgtgaccc  9540
aggcttaagt gtgcatctgt gtggcggagt attagaccag gcagagggag gggctaagca  9600
tttggggagt ggttggaagg agggcccaga gctggtgggc ccagaggggt gggcccaagc  9660
ctcgctctgc tccttttggt ccaggtgcgg tcgctggtgg ctgtgggcac cccagactac  9720
ctgtccccccg agatcctgca ggctgtgggc ggtgggcctg ggacaggcag ctacgggccc  9780
gagtgtgact ggtgggcgct gggtgtattc gcctatgaaa tgttctatgg gcagacgccc  9840
ttctacgcgg attccacggc ggagacctat ggcaagatcg tccactacaa ggtgagcacg  9900
gccgcaggga gacctggcct ctcccggtag gcgctcccag gctatcgcct cctctccctc  9960
tgagcaggag cacctctctc tgccgctggt ggacgaaggg gtccctgagg aggctcgaga  10020
cttcattcag cggttgctgt gtcccccgga gacacggctg ggccggggtg gagcaggcga  10080
cttccggaca catcccttct tctttggcct cgactgggat ggtctccggg acagcgtgcc  10140
cccctttaca ccggatttcg aaggtgccac cgacacatgc aacttcgact tggtggagga  10200
cgggctcact gccatggtga gcgggggcgg ggtaggtacc tgtggcccct gctcggctgc  10260
gggaacctcc ccatgctccc tccataaagt tggagtaagg acagtgccta ccttctgggg  10320
tcctgaatca ctcattcccc agagcacctg ctctgtgccc atctactact gaggacccag  10380
cagtgaccta gacttacagt ccagtggggg aacacagagc agtcttcaga cagtaaggcc  10440
ccagagtgat cagggctgag acaatggagt gcagggggtg gggactcct gactcagcaa  10500
ggaaggtcct ggagggcttt ctggagtggg gagctatctg agctgagact tggagggatg  10560
agaagcagga gaggactcct cctcccttag gccgtctctc ttcaccgtgt aacaagctgt  10620
catggcatgc ttgctcggct ctgggtgccc ttttgctgaa caatactggg gatccagcac  10680
ggaccagatg agctctggtc cctgccctca tccagttgca gtctagagaa ttagagaatt  10740
atggagagtg tggcaggtgc cctgaaggga agcaacagga tacaagaaaa aatgatgggg  10800
ccaggcacgg tggctcacgc ctgtaacccc agcaatttgg caggccgaag tgggtggatt  10860
gcttgagccc aggagttcga gaccagcctg ggcaatgtgg tgagaccccc gtctctacaa  10920
aaatgtttta aaaattggtt gggcgtggtg gcgcatgcct gtatactcag ctactaggt  10980
ggccgacgtg ggcttgagcc caggaggtca aggctgcagt gagctgtgat tgtgccactg  11040
cactccagcc tgggcaacgg agagagactc tgtctcaaaa ataagataaa ctgaaattaa  11100
aaaataggct gggctggccg ggcgtggtgg ctcacgcctg taatctcagc actttgggag  11160
gccgaggcgg gtggatcacg aggtcaggag atcgagacca tcttggctaa cacggtgaaa  11220
ccccatctct cctaaaaata caaaaaatta gccaggcgtg gtggcgggcg cctgtagtcc  11280
cagctactca ggaggctgag gcaggagaat ggcgtgaacc cgggaggcag agtttgcagt  11340
gagccgagat cgtgccactg cactccagcc tgggcgacag agcgagactc tgtctcagaa  11400
aaaaaaaaaa aaaaaaaaaa aaataggctg gaccgcggcc gggcgctgtg gctcatgcct  11460
gtaatcccag cactttggga gtccaaggcc ggtgggtcat gagatcagga gttttgagac  11520
taggctggcc aacacggtga aaccccgtct ctactaaaaa tacaagaaaa ttagctgggt  11580
gtggtctcgg gtgcctgtaa ttccagttac tggggaagct gaggcaggag aattgcttga  11640
acctgggagg cagagtttgc agtgagccaa gatcatgcca ctacactcca gtctgggtga  11700
cagagtgaga ctctgtctca aaaaaaaaaa aaaaaaaaag ggttgggcaa ggtggttcac  11760
gcctgtaatc ccagaacttt gggaggctga ggcaggcaga tcactggaag tcaggagttc  11820
aagaccagcc tggccaacat ggtgaaaccc tgtgtctact aaaaatacaa aatttagcca  11880
ggcttggtgg cgtatgcctg taatgccagc tactcaggag gctgaggcag gagaatcgct  11940
tgattgaacc tgggaggcag agtttgcagt gggctggggt tgtgccactg cactctaggc  12000
tgggagacag caagactcca tctaaaaaaa aaaaacagaa ctgggctggg cacagtggct  12060
tatatttgta atcccagcac tttgggaggc tgaggttgga ggactgcttg agcccagagt  12120
ttgggactac aacagctgag gtaggcggat cacttgaggt cagaagatgg agaccagcct  12180
ggccagcgtg gcgaaacccc gtctctacca aaaatataaa aaattagcca ggcgtggtag  12240
agggcgcctg taatctcagc tactcaggac gctgaggcag gagaatcgcc tgaacctggg  12300
aggcggaggt tgcagtgagc tgagattgca ccactgcact ccagcctggg taacagagcg  12360
agactccgta tcaaagaaaa agaaaaaaga aaaaatgctg gaggggccac tttagataag  12420
ccctgagttg gggctggttt ggggggaaca tgtaagccaa gatcaaaaag cagtgagggg  12480
cccgccctga cgactgctgc tcacatctgt gtgtcttgcg caggagacac tgtcggacat  12540
tcgggaaggt gcgccgctag gggtccacct gccttttgtg ggctactcct actcctgcat  12600
ggccctcagg taagcactgc cctggacggc ctccaggggc cacgaggctg cttgagcttc  12660
ctgggtcctg ctccttggca gccaatggag ttgcaggatc agtcttggaa ccttactgtt  12720
ttgggcccaa agactcctaa gaggccagag ttggaggacc ttaaattttc agatctatgt  12780
acttcaaaat gttagattga attttaaaac ctcagagtca cagactgggc ttcccagaat  12840
cttgtaacca ttaactttta cgtctgtagt acacagagcc acaggacttc agaacttgga  12900
```

-continued

```
aaatatgaag tttagacttt tacaatcagt tgtaaaagaa tgcaaattct ttgaatcagc  12960
catataacaa taaggccatt taaaagtatt aatttaggcg ggccgcggtg gctcacgcct  13020
gtaatcctag cactttggga ggccaaggca ggtggatcat gaggtcagga gatcgagacc  13080
atcctggcta acacggtgaa accccgtctc tactaaaaat acaaaaaaat tagccgggca  13140
tggtggcggg cgcttgcggt cccagctact tgggaggcga ggcaggagaa tggcatgaac  13200
ccgggaggcg gagcttgcag tgagccgaga tcatgccact gcactccagc ctgggcgaca  13260
gagcaagact ccgtctcaaa aaaaaaaaaa aaaaagtatt tatttaggcc gggtgtggtg  13320
gctcacgcct gtaattccag tgctttggga ggatgaggtg ggtggatcac ctgaggtcag  13380
gagttcgaga ccagcctgac caacgtggag aaacctcatc tctactaaaa aacaaaatta  13440
gccaggcgtg gtggcatata cctgtaatcc cagctactca ggaggctgag gcaggagaat  13500
cagaacccag gagggggagg ttgtggtgag ctgagatcgt gccattgcat tccagcctgg  13560
gcaacaagag tgaaacttca tctcaaaaaa aaaaaaaaaa aagtactaat ttacaggctg  13620
ggcatggtgg ctcacgcttg gaatcccagc actttgggag gctgaagtgg acggattgct  13680
tcagcccagg agttcaagac cagcctgagc aacataatga gaccctgtct ctacaaaaaa  13740
ttgaaaaaat cgtgccaggc atggtggtct gtgcctgcag tcctagctac tcaggagtct  13800
gaagtaggag aatcacttga gcctggagtt tgaggcttca gtgagccatg atagattcca  13860
gcctaggcaa caaagtgaga cctggtctca acaaaagtat taattacaca aataatgcat  13920
tgcttatcac aagtaaatta gaaaatacag ataaggaaaa ggaagttgat atctcgtgag  13980
ctcaccagat ggcagtggtc cctggctcac acgtgtactg acacatgttt aaatagtgga  14040
gaacaggtgt ttttttggtt tgttttttc cccttcctca tgctactttg tctaagagaa  14100
cagttggttt tctagtcagc ttttattact ggacaacatt acacatacta taccttatca  14160
ttaatgaact ccagcttgat tctgaaccgc tgcggggcct gaacggtggg tcaggattga  14220
acccatcctc tattagaacc caggcgcatg tccaggatag ctaggtcctg agccgtgttc  14280
ccacaggagg gactgctggg ttggagggga cagccacttc ataccccagg gaggagctgt  14340
ccccttccca cagctgagtg gggtgtgctg acctcaagtt gccatcttgg ggtcccatgc  14400
ccagtcttag gaccacatct gtggaggtgg ccagagccaa gcagtctccc catcaggtcg  14460
gcctccctgt cctgaggccc tgagaagagg ggtctgcagc ggtcacatgt caagggagga  14520
gatgagctga ccctagaaca tgggggtctg gaccccaagt ccctgcagaa ggtttagaaa  14580
gagcagctcc caggggccca aggccaggag aggggcaggg cttttcctaa gcagaggagg  14640
ggctattggc ctacctggga ctctgttctc ttcgctctgc tgctcccctt cctcaaatca  14700
ggaggtcttg gaagcagctg cccctaccca caggccagaa gttctggttc tccaccagag  14760
aatcagcatt ctgtctccct ccccactccc tcctcctctc cccagggaca gtgaggtccc  14820
aggccccaca cccatggaac tggaggccga gcagctgctt gagccacacg tgcaagcgcc  14880
cagcctggag ccctcggtgt ccccacagga tgaaacagta agttggtgga ggggaggggg  14940
tccgtcaggg acaattggga gagaaaaggt gagggcttcc cgggtggcgt gcactgtaga  15000
gccctctagg gacttcctga acagaagcag acagaaacca cggagagacg aggttacttc  15060
agacatggga cggtctctgt agttacagtg gggcattaag taagggtgtg tgtgttgctg  15120
gggatctgag aagtcgatct ttgagctgag cgctggtgaa ggagaaacaa gccatggaag  15180
gaaaggtgcc aagtggtcag gcgagagcct ccagggcaaa ggccttgggc aggtgggaat  15240
cctgatttgt tcctgaaagg tagtttggct gaatcattcc tgagaaggct ggagaggcca  15300
gcaggaaaca aaacccagca aggccttttg tcgtgagggc attagggagc tggagggatt  15360
ttgagcagca gagggacata ggttgtgtta gtgtttgagc accagccctc tggtccctgt  15420
gtagatttag aggaccagac tcagggatgg ggctgaggga ggtagggaag ggagggggct  15480
tggatcattg caggagctat ggggattcca gaaatgttga ggggacggag gagtagggga  15540
taaacaagga ttcctagcct ggaaccagtg cccaagtcct gagtcttcca ggagccacag  15600
gcagccttaa gcctggtccc catacacagg ctgaagtggc agttccagcg gctgtccctg  15660
cggcagaggc tgaggccgag gtgacgctgc gggagctcca ggaagccctg gaggaggagg  15720
tgctcacccg gcagagcctg agccgggaga tggaggccat ccgcacggac aaccagaact  15780
tcgccaggtc gggatcgggg ccggggccgg ggccgggatg cgggccggtg gcaacccttg  15840
gcatcccctc tcgtccggcc cggacggact caccgtcctt acctccccac agtcaactac  15900
gcgaggcaga ggctcggaac cgggacctag aggcacacgt ccggcagttg caggagcgga  15960
tggagttgct gcaggcagag ggagccacag gtgagtccct catgtgtccc cttccccgga  16020
ggaccgggag gaggtgggcc gtctgctccg cggggcgtgt atagacacct ggaggaggga  16080
agggacccac gctggggcac gccgcgccac cgccctcctt cgcccctcca cgcgccctat  16140
gcctctttct tctccttcca gctgtcacgg gggtccccag tccccgggcc acggatccac  16200
cttcccatgt aagaccccct tctttcccct gcctcagacc tgctgcccat tctgcagatc  16260
ccctccctgg ctcctggtct ccccgtccag atatagggct caccctacgt ctttgcgact  16320
ttagagggca gaagcccttt attcagcccc agatctccct ccgttcaggc ctcaccagat  16380
tccctccggg atctccctag ataacctccc caacctcgat tcccctcgct gtctctcgcc  16440
ccaccgctga gggctgggct gggctccgat cgggtcacct gtcccttctc tctccagcta  16500
gatggccccc cggccgtggc tgtgggccag tgcccgctgg tggggccagg ccccatgcac  16560
cgccgccacc tgctgctccc tgccagggta cgtccggctg cccacgcccc cctccgccgt  16620
cgcgccccgc gctccacccg cccccttgcca cccgcttagc tgcgcatttg cggggctggg  16680
cccacggcag gagggcggat cttcgggcag ccaatcaaca caggccgcta ggaagcagcc  16740
aatgacgagt tcggacggga ttcgaggcgt gcgagtggac taacaacagc tgtaggctgt  16800
tggggcgggg gcggggcgca gggaagagtg cgggcccacc tatgggcgta ggcggggcga  16860
gtcccaggag ccaatcagag gcccatgccg ggtgttgacc tcgccctctc cccgcaggtc  16920
cctaggcctg gcctatcgga ggcgctttcc ctgctcctgt tcgccgttgt tctgtctcgt  16980
gccgccgccc tgggctgcat tgggttggtg gcccacgccg gccaactcac cgcagtctgg  17040
cgccgcccag gagccgcccg cgctccctga accctagaac tgtcttcgac tccggggccc  17100
cgttggaaga ctgagtgccc ggggcacggc acagaagccg cgcccaccgc ctgccagttc  17160
acaaccgctc cgagcgtggg tctccgccca gctccagtcc tgtgatccgg gcccgccccc  17220
tagcggccgg ggagggaggg gccgggtccg cggccggcga acggggctcg aagggtcctt  17280
gtagccggga atgctgctgc tgctgctgct gctgctgctg ctgctgctgc tgctgctgct  17340
gctgctgctg ctggggggat cacagaccat ttctttcttt cggccaggct gaggccctga  17400
cgtggatggg caaactgcag gcctgggaag gcagcaagcc gggccgtccg tgttccatcc  17460
tccacgcacc cccacctatc gttggttcgc aaagtgcaaa gctttcttgt gcatgacgcc  17520
ctgctctggg gagcgtctgg cgcgatctct gcctgcttac tcgggaaatt tgcttttgcc  17580
aaacccgctt tttcggggat cccgcgcccc cctcctcact tgcgctgctc tcggagcccc  17640
```

-continued

```
agccggctcc gcccgcttcg gcggtttgga tatttattga cctcgtcctc cgactcgctg  17700
acaggctaca ggacccccaa caaccccaat ccacgttttg gatgcactga gaccccgaca  17760
ttcctcggta tttattgtct gtccccacct aggaccccca cccccgaccc tcgcgaataa  17820
aaggccctcc atctgcccaa agctctggac tccacagtgt ccgcggtttg cgttgtgggc  17880
cggaggctcc gcagcgggcc aatccggagg cgtgtggagg cggccgaagg tctgggagga  17940
gctagcggga tgcgaagcgg ccgaatcagg gttgggggag gaaaagccac ggggcggggc  18000
tttggcgtcc ggccaatagg agggcgagcg ggccacccgg aggcaccgcc cccgcccagc  18060
tgtggcccag ctgtgccacc gagcgtcgag aagagggggc tgggctggca gcgcgcgcgg  18120
ccatcctcct tccactgcgc ctgcgcacgc cacgcgcatc cgctcctggg acgcaagctc  18180
gagaaaagtt gctgcaaact ttctagcccg ttccccgccc ctcctcccgg ccagacccgc  18240
ccccccctgcg gagccgggaa ttccgagggg cggagcgcag gccgagatgg ggaatgtggg  18300
ggcctgcaga ggaccctgga gacggaggcg tgcagaagct cagtctcggg gcggaggctt  18360
cgcgccctta gtcctcctgg acggcccgtt accttctgcg ttgtcccgat ggggaaactg  18420
aggccctgag ccagaagcac acgctggggg gaggcagaaa gcgcggccag aggcggaggg  18480
aaaacaaagg gagaatcaca gacagacggg agggggacgg acacacacaa ggggacagag  18540
acccgagtgg agagctggat ctcgccttcc cggcgtgggg cgcagggtcg gccagaaaga  18600
agatcgagaa gagcggggag tgggggcgaa aagggggac aggtggggga ggaggctggg  18660
gaaagcccga gggaggaaga gagggaggga ggaacttccc aaagttgcaa aacatggcta  18720
ccttgcctgc ggagccgagc gcggggccgg cggctggggg ggaggcggtg gcggcggcgg  18780
cggcgaccga agaggaggag gaggaagcgc gccagctctt gcagactttg caggcggccg  18840
agggtgaggc ggcggcggcg gccggggccg gggcgggcgc agcggctgcg ggagctgagg  18900
gcccgggatc cccgggcgtc cccgggtcgc cccccgaggc cgcttccgaa ccgcccacgg  18960
gcctccgctt ctcgcccgag caggtggcgt gcgtctgcga ggcgctgctc caggcgggcc  19020
acgccggccg cttgagccgc ttcctgggcg cactgccccc ggccgagcgc ctacgtggca  19080
gcgacccggt gttgcgcgcg cgggccctgg tggccttcca gcggggcgag tacgccgagc  19140
tctaccggct actcgagagc cgccccttcc ccgccgccca ccacgccttc ctgcaggacc  19200
tctacctgcg cgcgcgctac catgaggccg agcgggcccg cggccgcgcg cttggcgcag  19260
tggacaagta tcgactgcgc aagaagttcc cgctgcccaa gaccatctgg gacggcgagg  19320
agacagtcta ctgcttcaag gagcgctccc gcgcagcgct caaggcctgc taccgcggca  19380
accgctaccc cacgccggac gagaagcgcc gcctggccac actcaccggc ctgtcgctca  19440
cgcaggtcag caactggttc aagaaccggc gacagcgcga ccggaccggg gccggaggcg  19500
gcgcgccctg caagaggtga ggggcctcgg gcggcgcaag tccagctctc ccggggacat  19560
cccgtccacc agccctcttc ccccgtgccc actgctgggg ccggcgcgcc gaggtcctcg  19620
gacatctccc gggaccagct cacaatctca ggcgcccgcg gggcgcgggg actaagtgtg  19680
gacgggacag gcacccgccc gggccctctc cccgcacgcg tctcctcttc cagcggctcc  19740
attccgagct ccttcccaaa tcccatcggt gttggggaat cacactgcgg ggggcactag  19800
agggactgag gaaaaaggac agggcctgtg gccactccac t                      19841
```